US006898299B1

(12) United States Patent
Brooks

(10) Patent No.: US 6,898,299 B1
(45) Date of Patent: May 24, 2005

(54) METHOD AND SYSTEM FOR BIOMETRIC RECOGNITION BASED ON ELECTRIC AND/OR MAGNETIC CHARACTERISTICS

(76) Inventor: Juliana H. J. Brooks, 5689 Walnut View Blvd., Columbus, OH (US) 43230

( * ) Notice: Subject to any disclaimer, the term of this patent is extended or adjusted under 35 U.S.C. 154(b) by 0 days.

(21) Appl. No.: 09/396,112

(22) Filed: Sep. 15, 1999

Related U.S. Application Data

(63) Continuation-in-part of application No. 09/151,581, filed on Sep. 11, 1998, now Pat. No. 6,507,662.

(51) Int. Cl.[7] .................................................. G06K 9/00
(52) U.S. Cl. ..................... 382/115; 600/506; 340/5.52; 340/5.82
(58) Field of Search .................. 382/115, 118, 382/124–126, 128; 902/3–6; 235/379, 380, 381, 382; 73/579, 585, 587; 128/746, 920, 630, 647, 660.01; 600/559, 506; 340/5.2, 5.52, 5.82, 5.53

(56) References Cited

U.S. PATENT DOCUMENTS

| | | |
|---|---|---|
| 3,557,777 A | 1/1971 | Cohen |
| 3,639,905 A | 2/1972 | Yaida et al. |
| 4,227,071 A | 10/1980 | Tomyn |

(Continued)

FOREIGN PATENT DOCUMENTS

DE     195 47 818 A1    6/1997    ........... G07C/11/00

OTHER PUBLICATIONS

Star Micronics: Star Card chosen in Roxburgh ID application for corporate branding initiative. http://www.elibrary.com, M2 Communications, Ltd., Dec. 9, 1998.
Could plastic kill cash at last? (the advent of the newly-developed Mondex plastic payment system). http://www.elibrary.com, The chartered Institute of Management Accountants (UK), Dec. 9, 1998.
Surfaces and Displays. http://Nicholas.www.media.mit.edu, WIRED Ventures Ltd., vol. 5.01, Dec. 2, 1998.
Towards a Cashless Society: Electronic Wallets. http://wwwcordis.lu/esprit, Dec. 3, 1998.
NetPay Payment System. http://www.maithean.com, Maithean Secure Electronic Commerce Solutions, Dec. 3, 1998.

(Continued)

*Primary Examiner*—Vikkram Bali
(74) *Attorney, Agent, or Firm*—David A. Greenlee

(57) ABSTRACT

A method and apparatus for authenticating an individual living organism by recognizing a unique internal electric and/or magnetic and/or acoustic characteristic, which comprises a biometric signature, involve presenting a body part to a sensing device that senses the signature. The sensed presented biometric signature is compared to a known biometric signature to authenticate the individual. This authentication can then be used to authorize any of a wide variety of actions by the individual, such as accessing equipment or an area, or to perform actions, such as conducting financial transactions. A card having sensors is used to sense the biometric signature which is read by a card reader and sent to a local or remote reader for biometric signature comparison.

54 Claims, 140 Drawing Sheets

U.S. PATENT DOCUMENTS

| | | | |
|---|---|---|---|
| 4,524,692 A | | 6/1985 | Rodvelt |
| D283,405 S | | 4/1986 | Yuen |
| D290,817 S | | 7/1987 | Yuen |
| 4,926,368 A | | 5/1990 | Morita et al. |
| 4,935,962 A | | 6/1990 | Austin |
| 4,972,099 A | | 11/1990 | Amano et al. |
| 5,077,804 A | | 12/1991 | Richard |
| 5,245,329 A | | 9/1993 | Gokcebay |
| 5,310,035 A | | 5/1994 | Dobransky, Jr. et al. |
| 5,337,043 A | | 8/1994 | Gokcebay |
| 5,420,405 A | | 5/1995 | Chasek |
| 5,453,601 A | | 9/1995 | Rosen |
| 5,455,407 A | | 10/1995 | Rosen |
| 5,521,362 A | | 5/1996 | Powers |
| 5,529,307 A | | 6/1996 | Chang |
| 5,544,255 A | | 8/1996 | Smithies et al. |
| 5,559,504 A | * | 9/1996 | Itsumi et al. ............... 340/5.53 |
| 5,561,446 A | | 10/1996 | Montlick |
| 5,567,276 A | | 10/1996 | Boehm et al. |
| 5,644,727 A | | 7/1997 | Atkins |
| 5,647,017 A | | 7/1997 | Smithies et al. |
| 5,687,254 A | | 11/1997 | Poon et al. |
| 5,704,355 A | | 1/1998 | Bridges |
| 5,715,314 A | | 2/1998 | Payne et al. |
| 5,719,950 A | | 2/1998 | Osten et al. |
| 5,724,424 A | | 3/1998 | Gifford |
| 5,724,524 A | | 3/1998 | Hunt et al. |
| 5,768,423 A | | 6/1998 | Aref et al. |
| 5,787,187 A | | 7/1998 | Bouchard et al. ............ 382/115 |
| 5,799,087 A | | 8/1998 | Rosen |
| 5,801,367 A | | 9/1998 | Asplund et al. ............. 235/384 |
| 5,802,497 A | | 9/1998 | Manasse |
| 5,807,257 A | | 9/1998 | Bridges |
| 5,818,955 A | | 10/1998 | Smithies et al. |
| 5,832,089 A | | 11/1998 | Kravitz et al. |
| 6,507,662 B1 | * | 1/2003 | Brooks ....................... 382/115 |

OTHER PUBLICATIONS

Café: <http://www.digicash.com/products/projects/café.html>. http://intertrader.com, Digital Money Online, Dec. 3, 1998.

An electrophoretic ink for all–printed reflective electronic displays. Nature, vol. 394, Jul. 16, 1998, pp. 253–255.

Mutant bacteria, electronic ink and paper under development—Offbeat technologies may hold key to displays. EETIMES–Issue 1022. http://www.techweb.com, CMP Media Inc., Dec. 3, 1998.

Poulos, M et al: "Neural Network Based Person Identification Using EEG Features", Phoenix, AZ, Mar. 15–10, 1999, New York, NY IEEE, US, pp. 1117–1120.

* cited by examiner

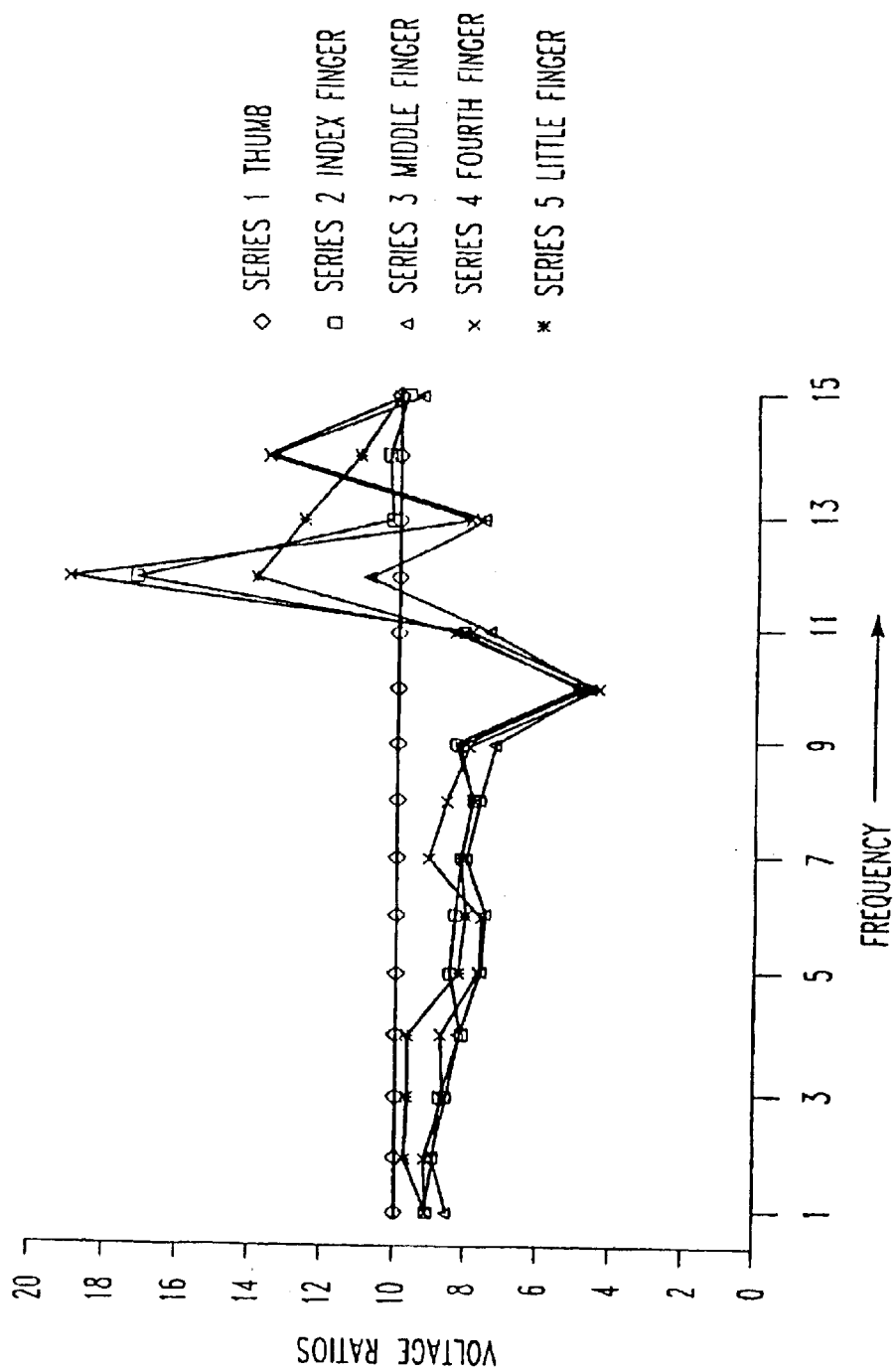

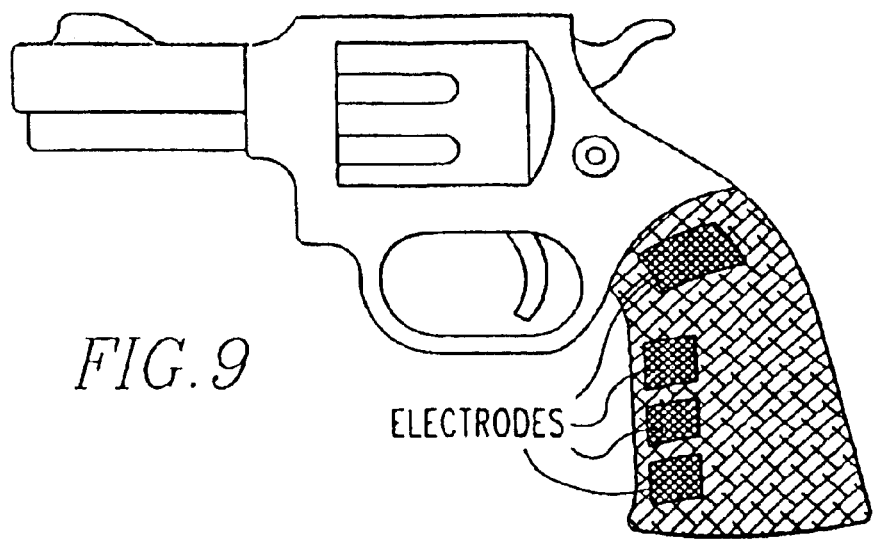
FIG.9　ELECTRODES
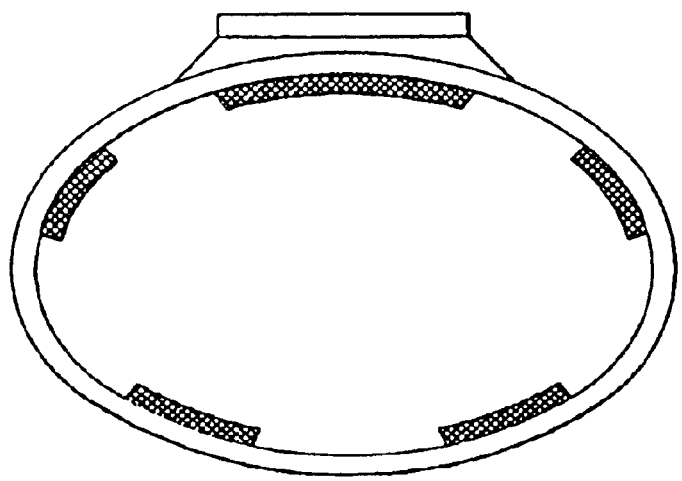
FIG10

DETECTOR CAN BE A PHASE SENSITIVE DETECTOR

POWER SUPPLY REGULATORS

U₃ = LT1058CN
HANDPIECE AMPLIFIER 1 THROUGH 4

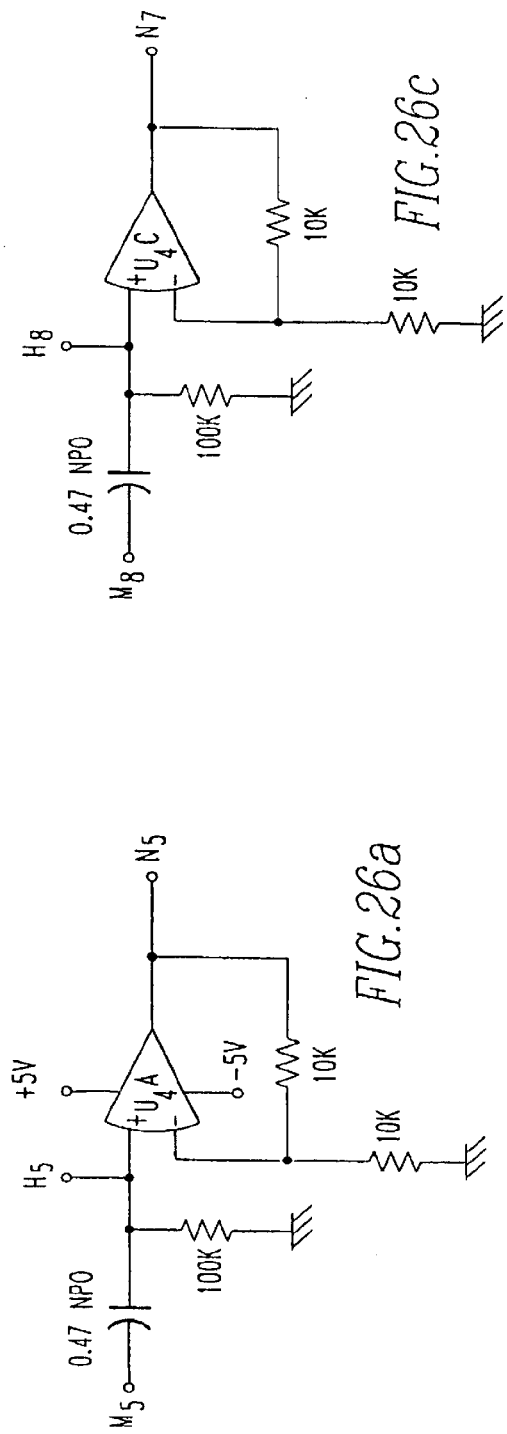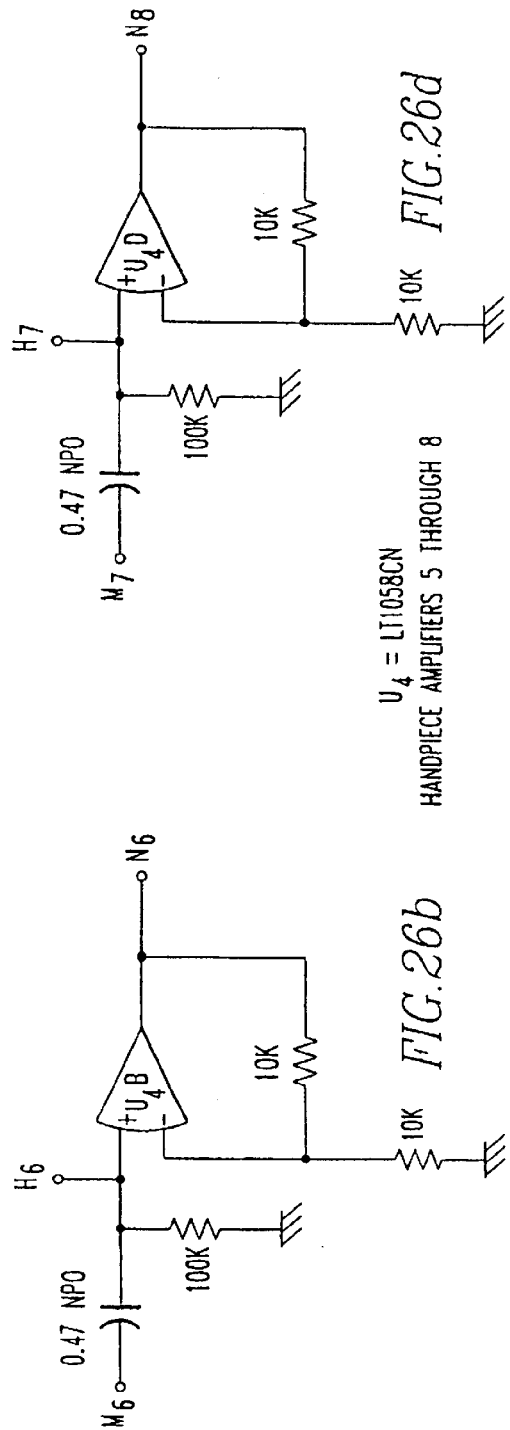

OUTPUT MUX LOAD RESISTORS

SIGNAL DETECTOR & ANALOG TO DIGITAL CONVERTER

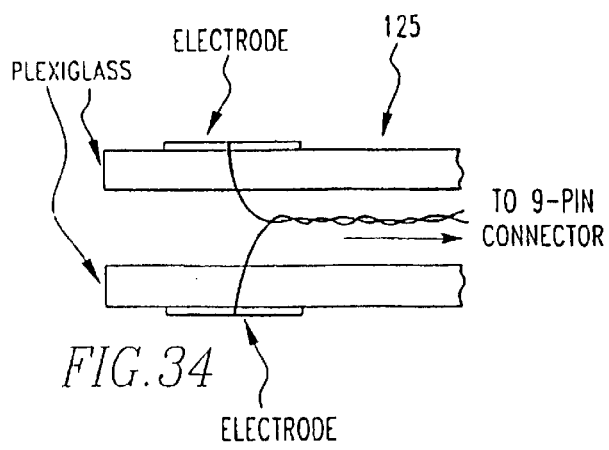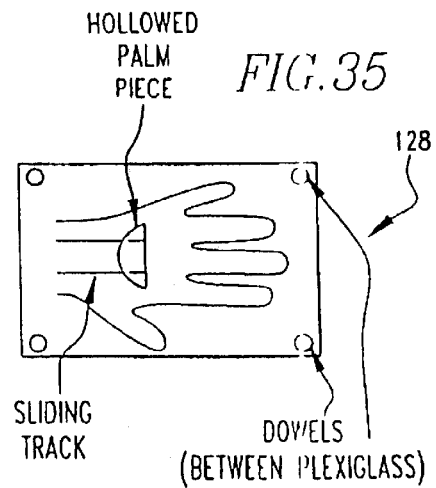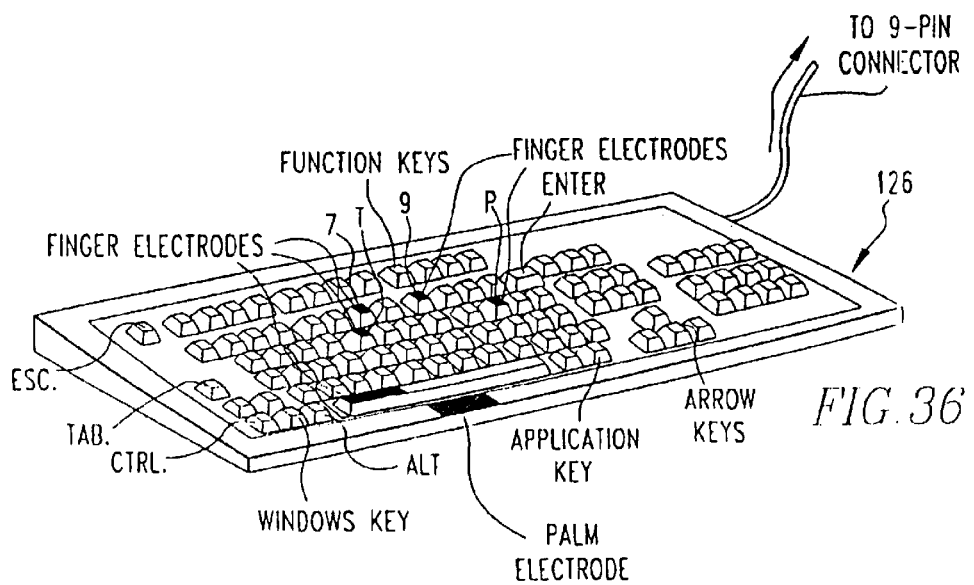

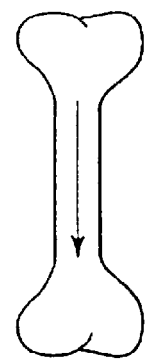
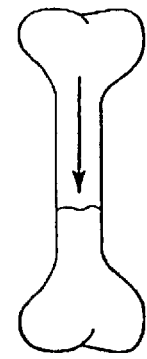
FIG.59          FIG.60
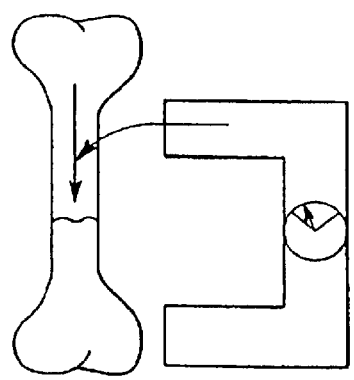
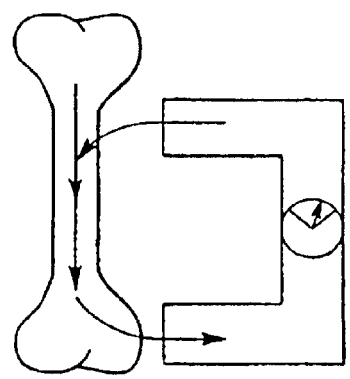
FIG.61          FIG.62

1. NON-CONDUCTIVE RIM
2. CONDUCTIVE ELECTRODE
3. NON-CONDUCTIVE DIVIDER
4. CONNECTOR TO ANALYZER
5. CONNECTOR TO GENERATOR

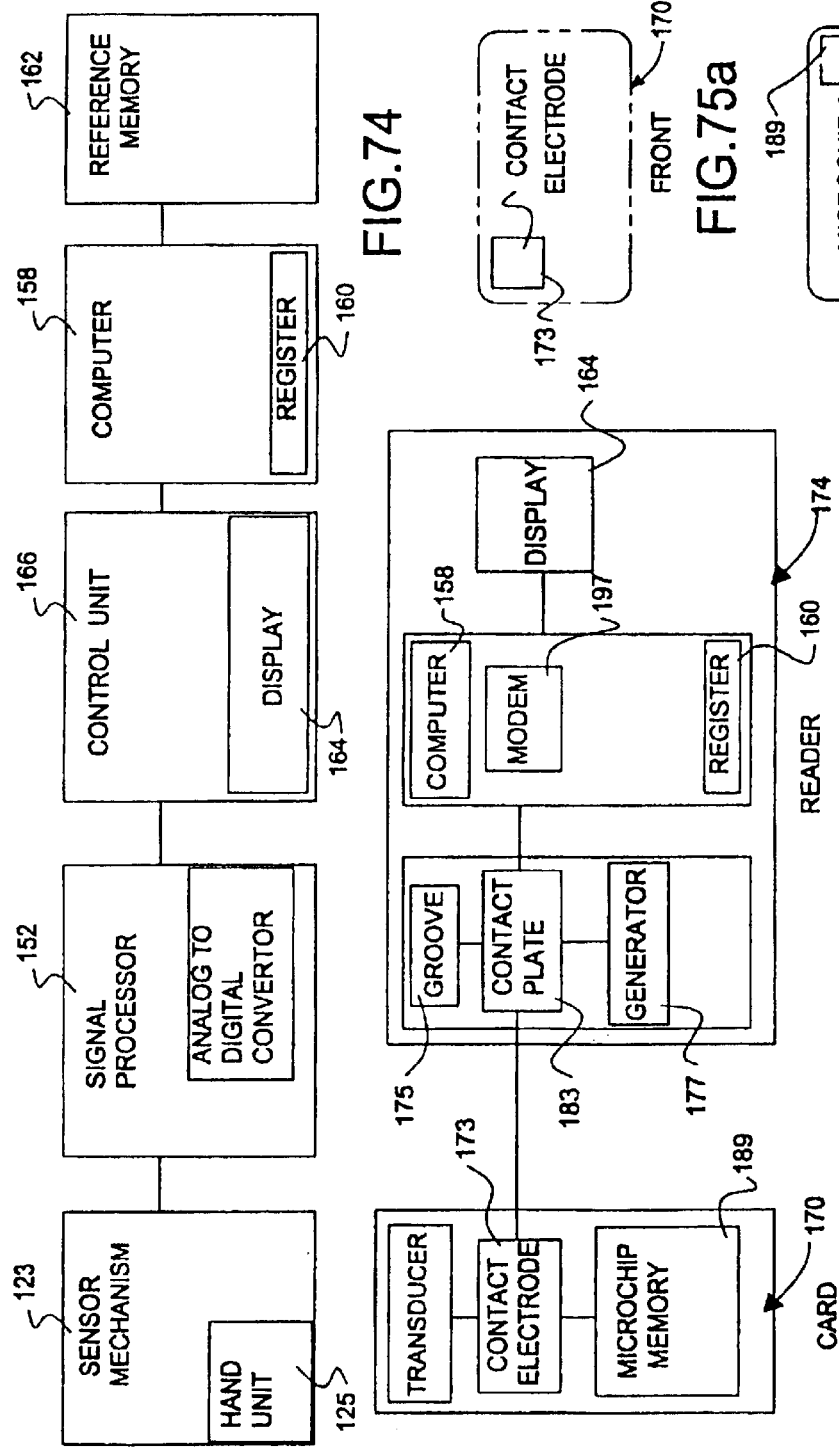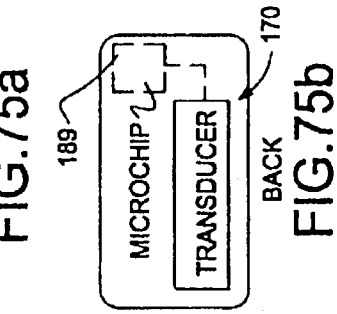

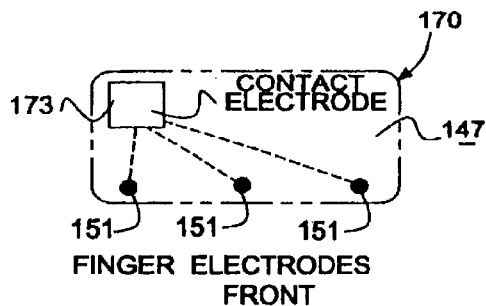
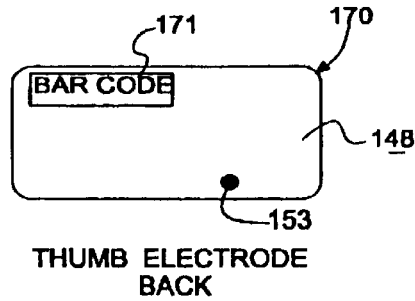
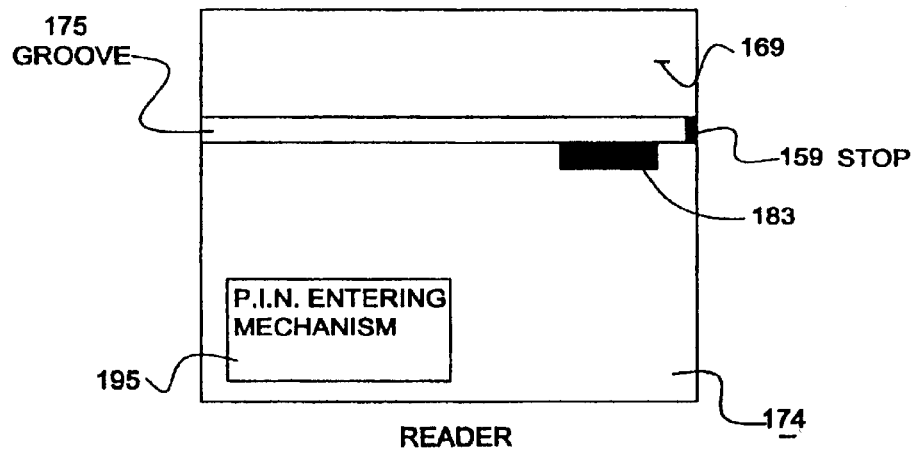
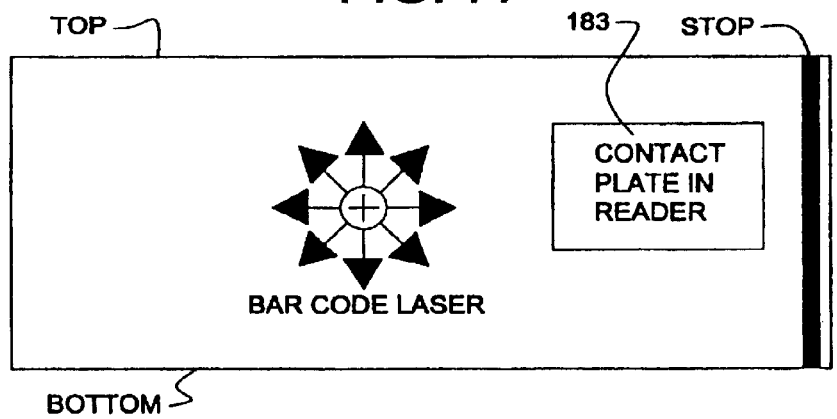

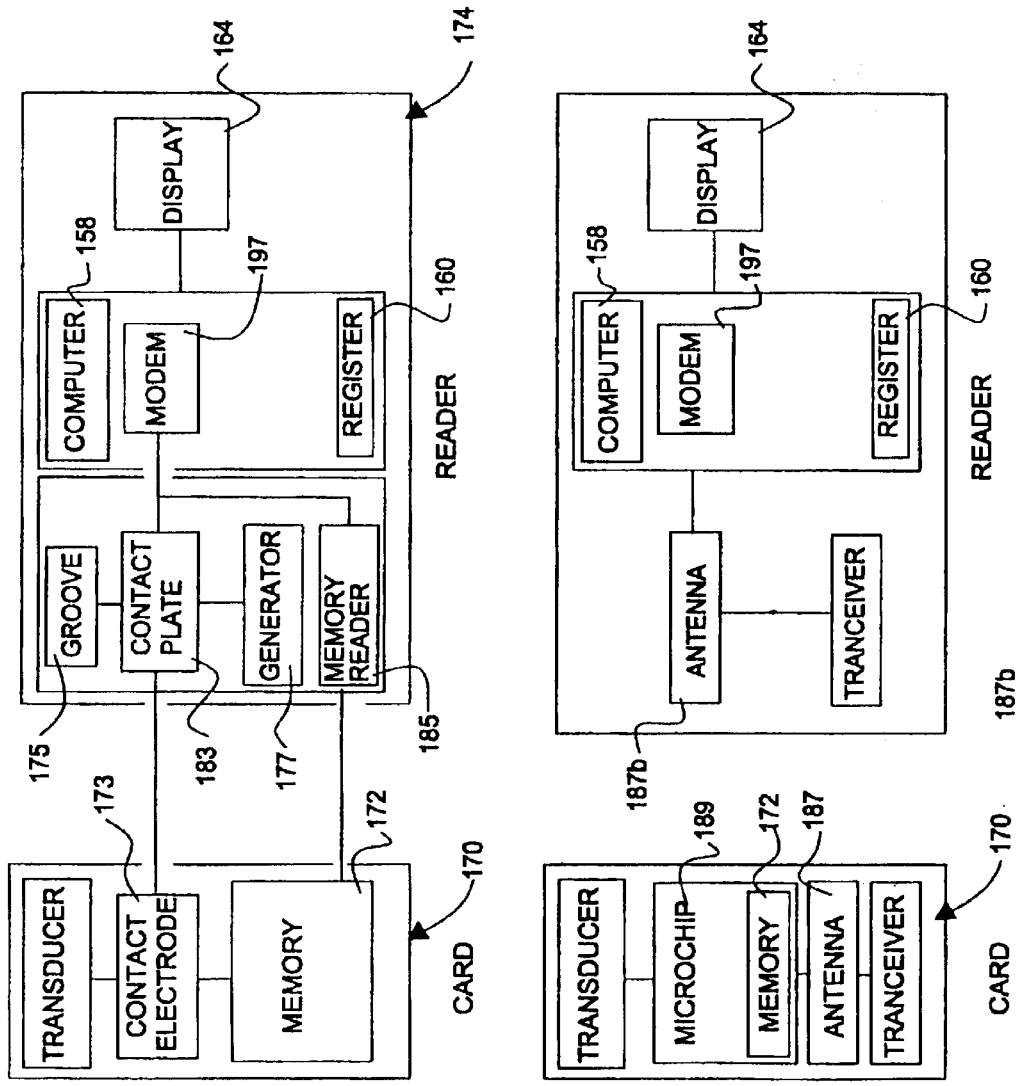

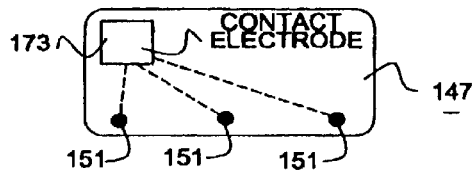
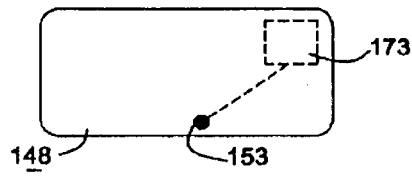
FIG.82  FIG.83
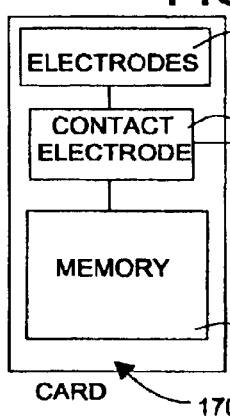
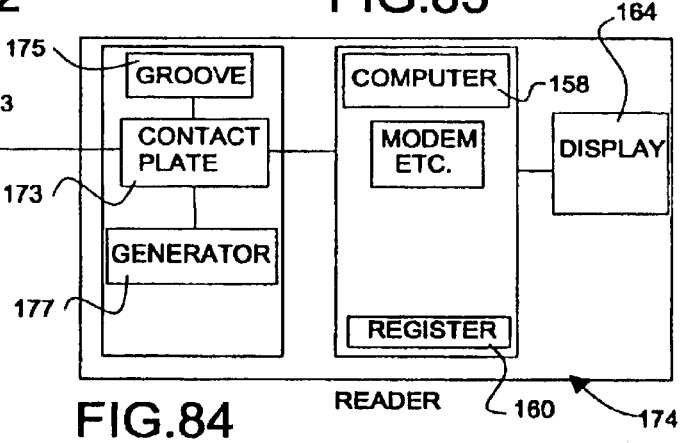
FIG.84
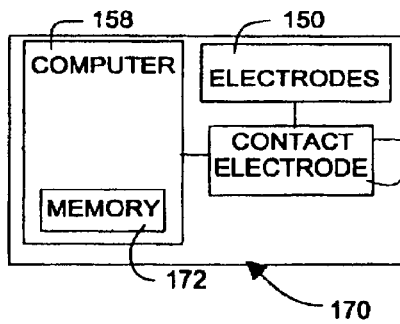
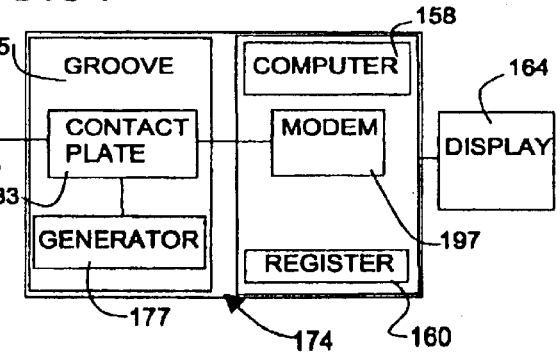
FIG.85
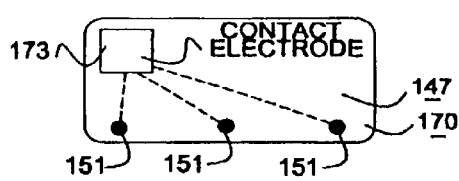
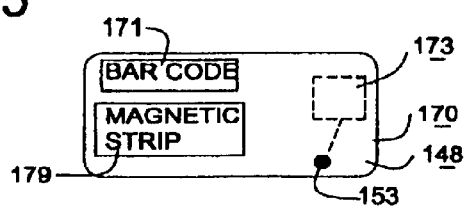
FIG.86  FIG.87

TOUCHLESS PAYPHONE

RECESSED SENSOR UNIT IN LAP-TOP COMPUTOR

RECESSED FLAP SENSOR UNIT IN LAP-TOP COMPUTER

— FLAP SENSOR UNIT

— HINGE

SPRING / HINGE MECHANISM
ELECTRIC FIELD DETECTOR
CONTACT PLATES
E.N. TRANSMITTER
SPRINGS
CONNECTION OF CONTACT PLATE AND E.N. TRANSMITTER

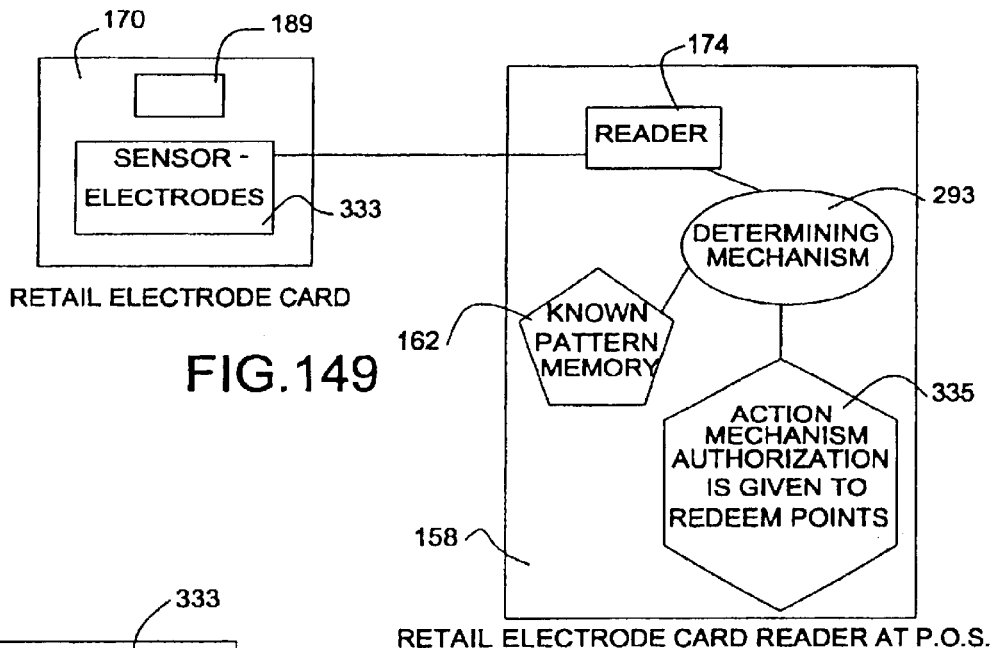
FIG.149
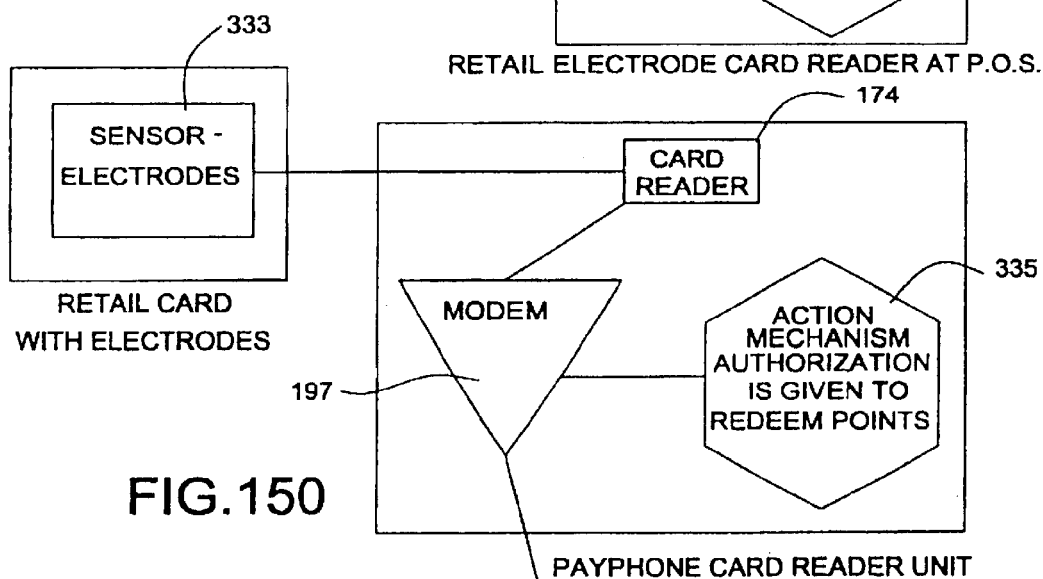
FIG.150
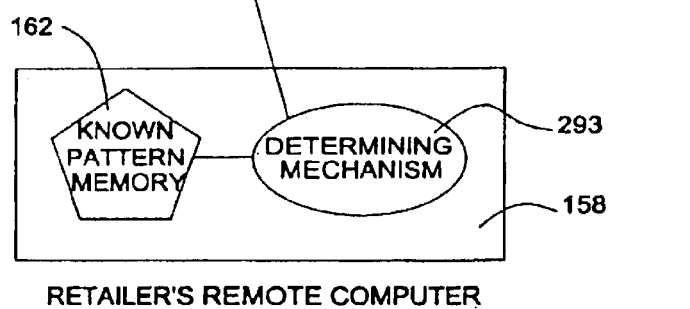

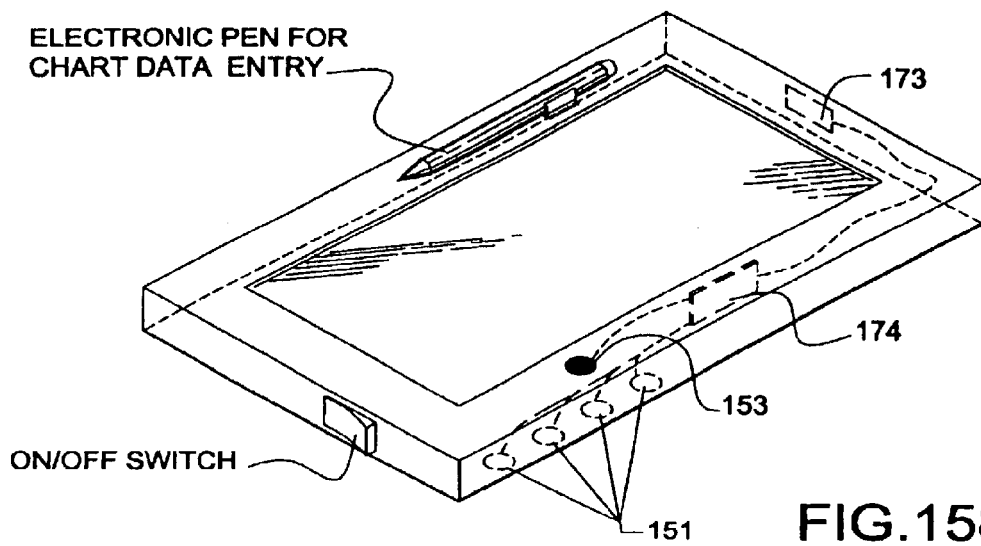
FIG.158b
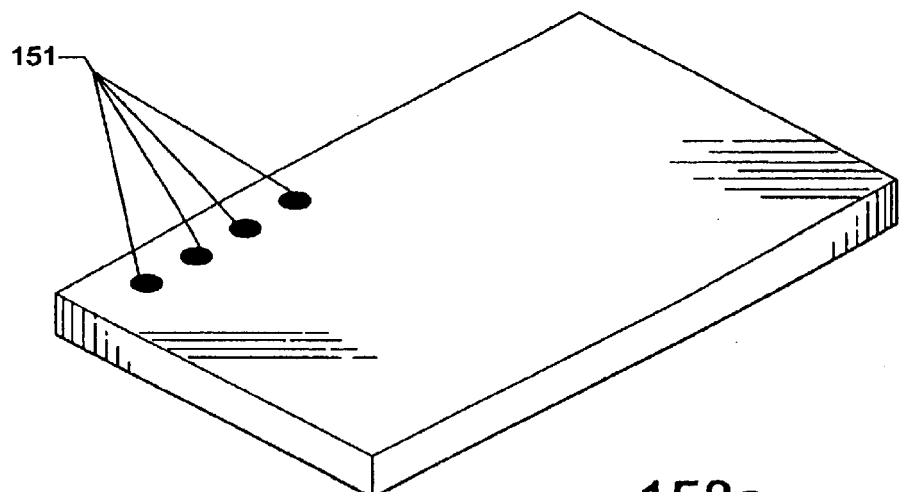
158c

PIEZOELECTRIC MATERIAL FOR ACOUSTIC SENSORS

— MOLDED ACOUSTIC SENSOR

EN TRANSMITTER

PRESSURE ACTIVATED ACOUSTIC SENSOR

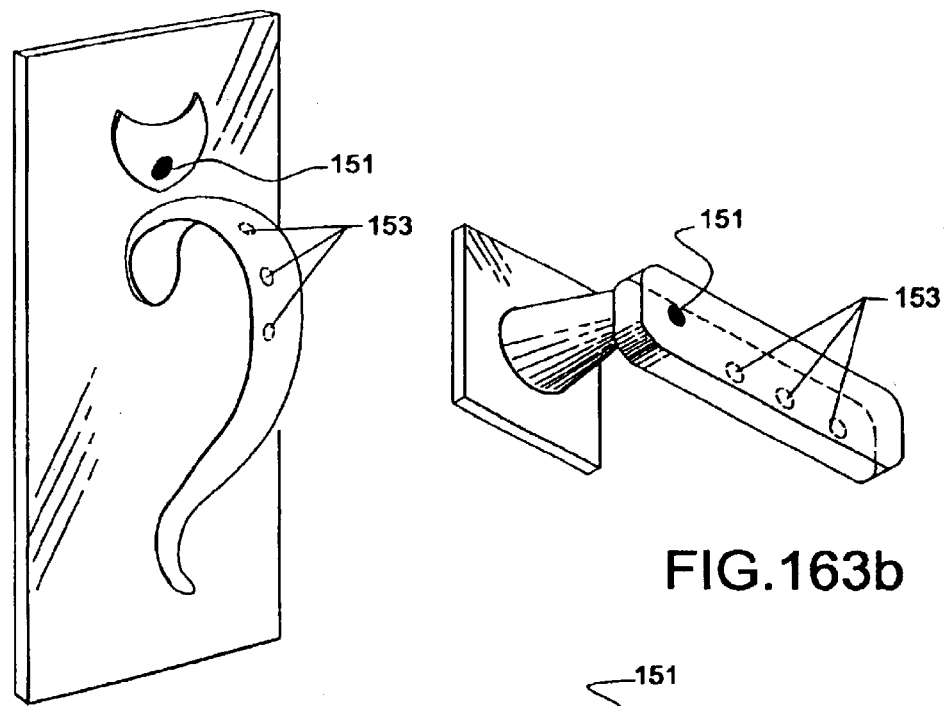
FIG.163b
FIG.163a
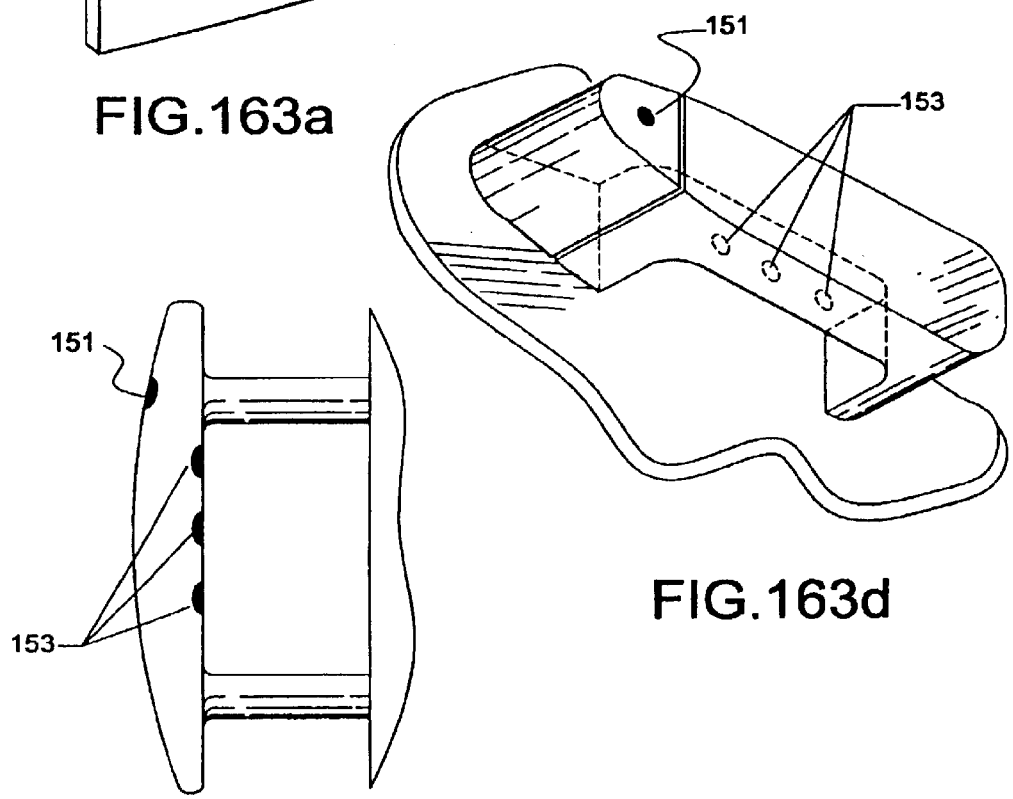
FIG.163d
FIG.163c

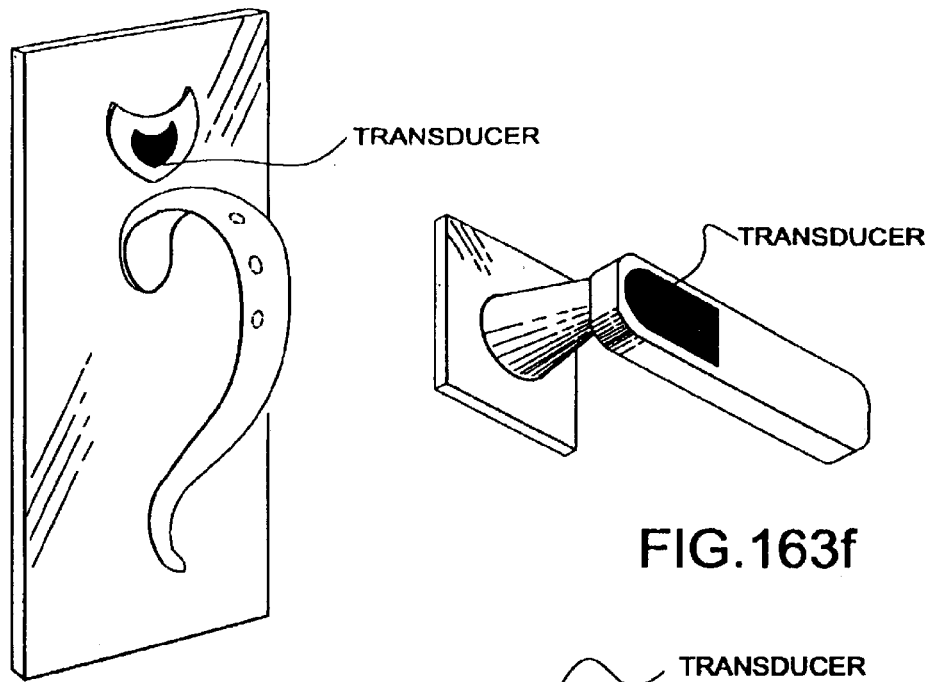
FIG.163e
FIG.163f
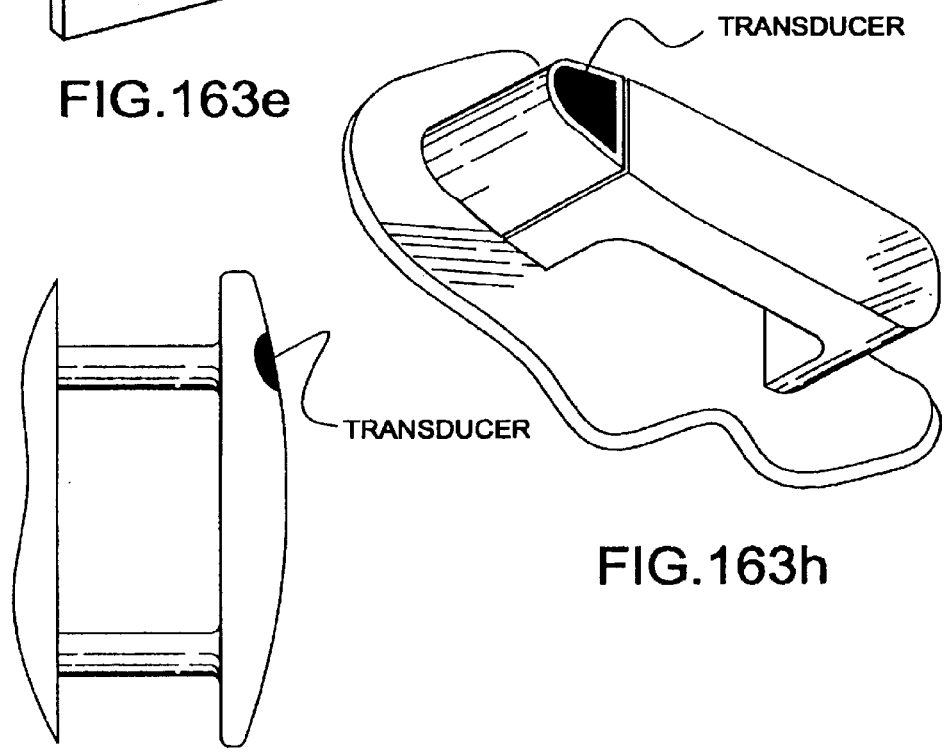
FIG.163g
FIG.163h

COMPOSITE BIOMETRIC LOCK

MULTIPLE BIOMETRIC LOCK

OPTIONAL BIOMETRIC LOCK
BIOMETRIC DOOR HANDLE

OPTIONAL BIOMETRIC LOCK

RESTRICTED DATABASE ACCESS UNIT ON SIDE OF MONITOR

PORTABLE READER UNIT CARRIED BY GUARDS

DRUG CABINET HANDPIECE / LOCK MECHANISM

BIOMETRIC DOOR HANDLE

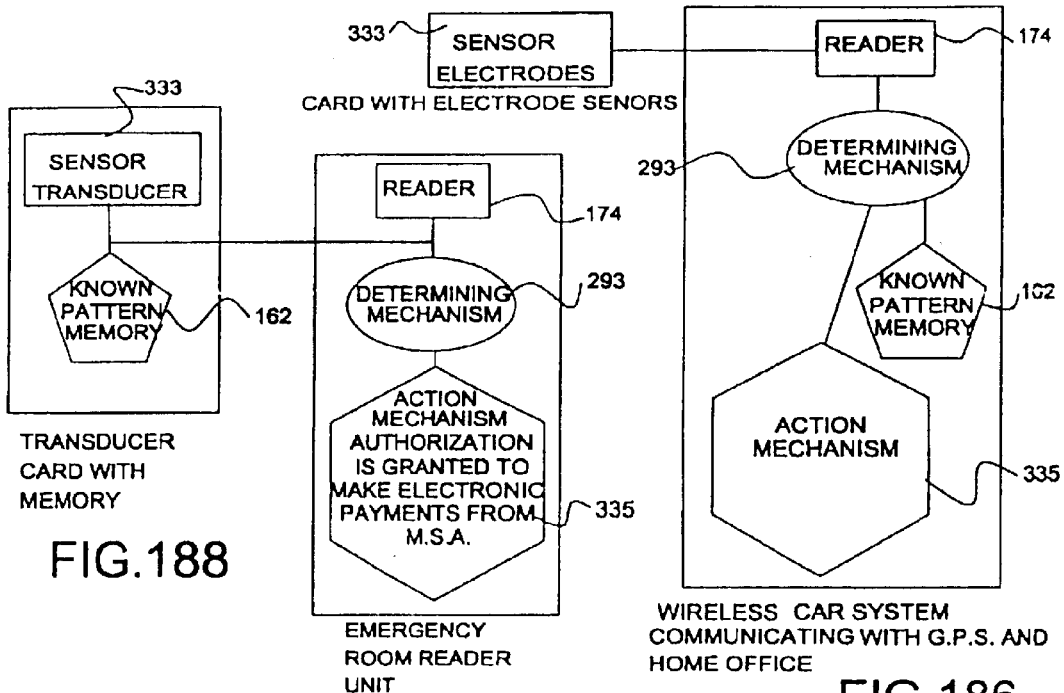
FIG.188
FIG.186
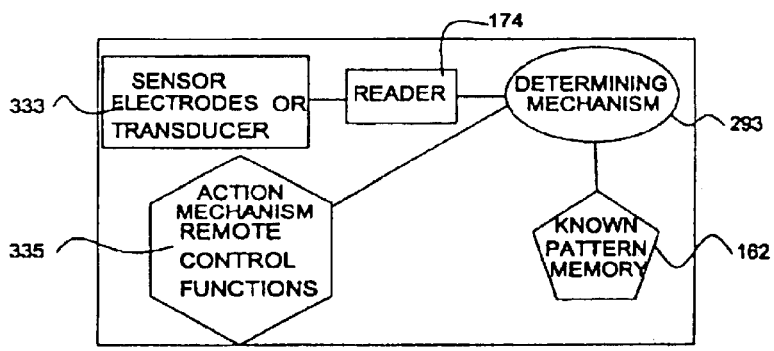
FIG.187
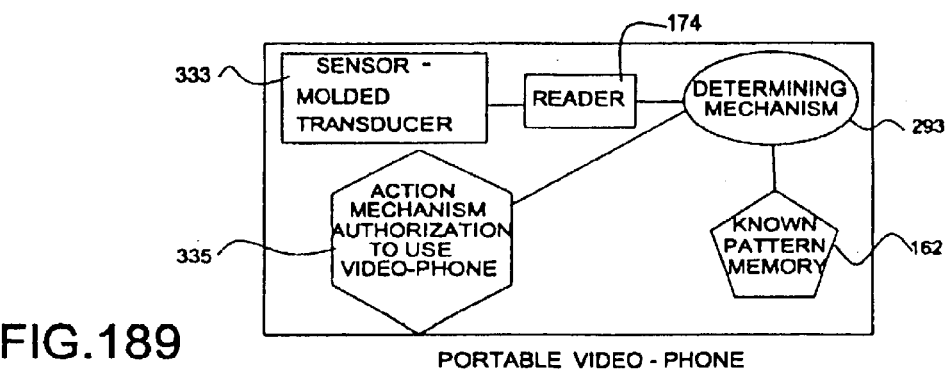
FIG.189

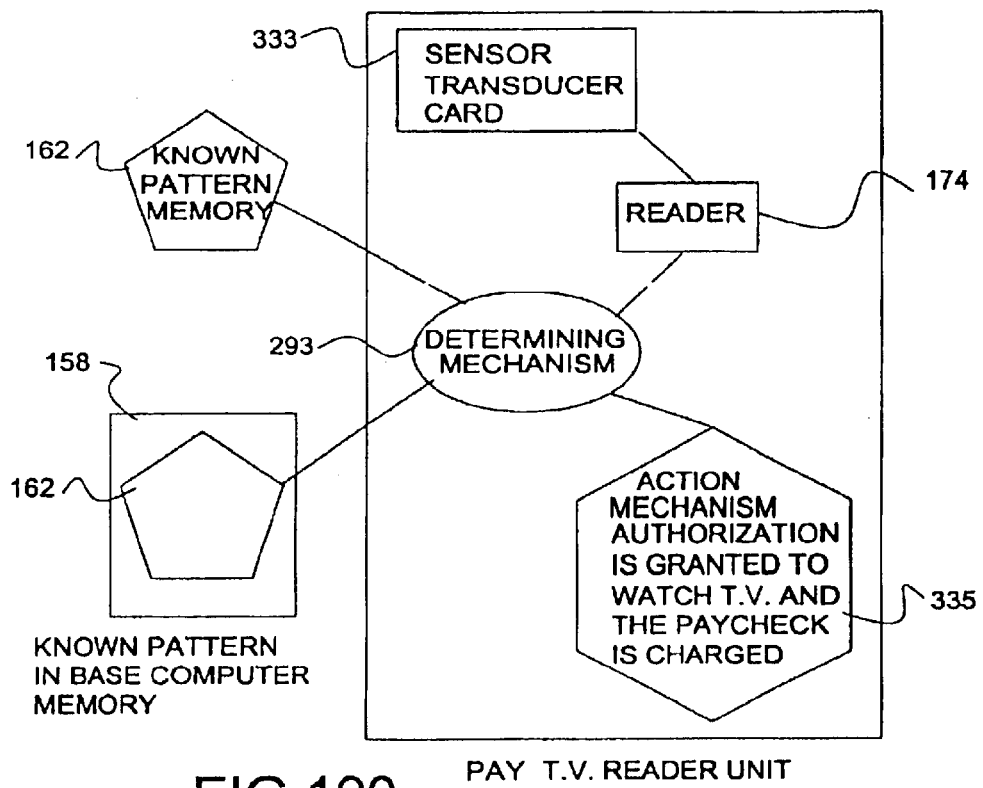
FIG.190  PAY T.V. READER UNIT
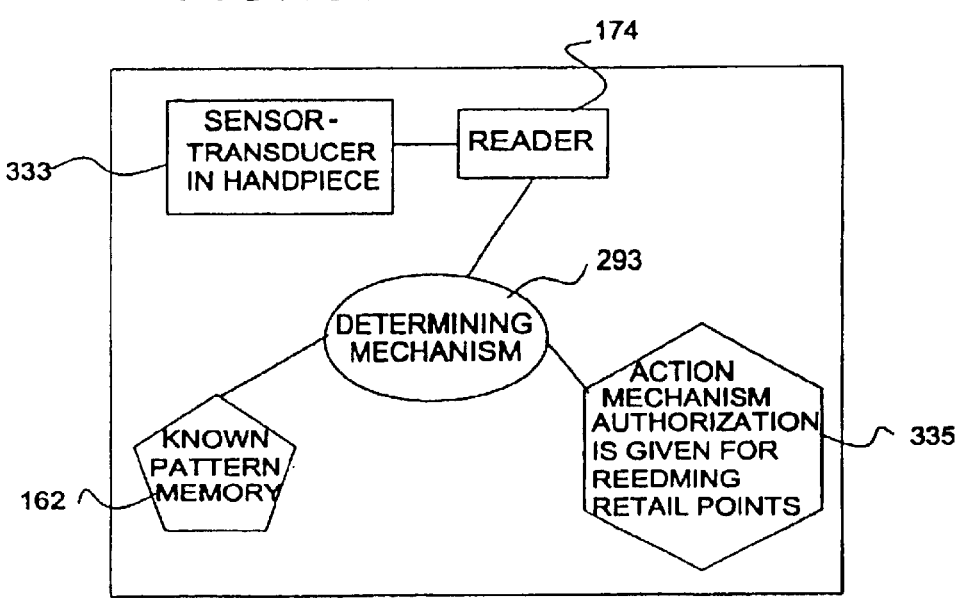
FIG.191  ACOUSTIC HANDPIECE AT CASH REGISTER

READER UNIT COMMUNICATING WITH MOUSE

BANK A.T.M. ACCESS COMPUTER

WIRELESS CAR SYSTEM COMMUNICATING WITH G.P.S. AND HOME OFFICE

READER UNIT ATTACHED TO FELON'S TELEPHONE

MECHANISM FOR RECOGNIZING A BIOMETRIC SIGNATURE OF AN INDIVIDUAL FROM ENERGY EMITTED BY THE INDIVIDUAL.

ALLOWING AN ACTION MECHANISM

FIG.200

OPTIONAL MULTIPLE BIOMETRIC LOCK

METHOD AND SYSTEM FOR BIOMETRIC RECOGNITION BASED ON ELECTRIC AND/OR MAGNETIC CHARACTERISTICS

CROSS-REFERENCE TO RELATED APPLICATIONS

This application is a continuation-in-part of application Ser. No. 09/151,581, filed Sep. 11, 1998, now U.S. Pat. No. 6,507,662.

BACKGROUND OF INVENTION

1. Field of the Invention

The present invention relates generally to the detection of unique energy characteristics of an individual living organism. More specifically, the present invention relates to biometric recognition of an organism based on a biometric signature of the individual acquired by sensing unique electric and/or magnetic and/or acoustic properties of the individual by sensors with unique characteristics. Recognition of the individual in this manner enables the individual to perform an action

2. Description of the Related Art

Security methods based on memory data encoded into magnetic cards, such as personal identification numbers or passwords, are widely used in today's business, industrial, and governmental communities. With the increase in electronic transactions and verification, there has been an increase in lost or stolen cards, and forgotten, shared, or observed identification numbers or passwords. Because the magnetic cards offer little security against fraud or theft, there has been a movement toward developing more secure methods of automated recognition based on unique, externally detectable, personal physical anatomic characteristics, such as fingerprints, iris pigment patterns, and retina prints, or external behavior characteristics, such as writing style and voice patterns. Known as biometrics, such techniques are effective in increasing the reliability of recognition systems by identifying a person by characteristics unique to that individual. Some representative techniques include fingerprint recognition, focusing on external personal skin patterns, hand geometry, concentrating on personal hand shape and dimensions, retina scanning, defining a person's unique blood vessel arrangement in the retina of the eye, voice verification, distinguishing an individual's distinct sound waves, and signature verification.

Uses of biometric recognition applications include regulating physical access to restricted areas or devices, and access to computer systems which contain sensitive information used by various governmental, private and public organizations. Additionally, law enforcement applications include home incarceration, parole programs, and physical access into jails or prisons. Also, U.S. government entitlement programs rely on such a system, the Automated Fingerprint Identification System (AFIS), for access to deter fraud.

Biometric recognition can be used in an "identification mode", in which the biometric system identifies a person from an entire enrolled population by searching a population database for a match. A biometric recognition system can also be used in a "verification mode", in which the system authenticates a person's claimed identity by comparing previously enrolled patterns of biometric data. In many present biometric applications there is little margin for any inaccuracy in either the identification mode or the verification mode.

Current commercially available biometric methods and systems are limited because they use only externally visible distinguishing characteristics for identification, e.g. fingerprints, iris patterns, hand geometry and blood vessel patterns. The most widely used biometric method is fingerprinting, which is plagued by several problems, including false negative identifications due to dirt, moisture and grease on the print being scanned. Additionally, some individuals have insufficient detail of the print ridge pattern due to trauma or a wearing down of the ridge structure. More importantly, some individuals are reluctant to have their fingerprint patterns memorialized because of the ever-decreasing privacy of personal information.

Other techniques currently in use include iris pigment patterns and retina scanning, which are currently being introduced in many bank systems. However, these are controversial because of the unknown health risks of subjecting eyes to electromagnetic radiation.

Another limitation of current biometric recognition systems is the relative ease with which external physical features can be photographed, copied or lifted. The ease of copying of external characteristics enables unauthorized duplication of fingerprints, eye scans, and other biometric patters. With the advancement of cameras, videos, lasers and synthetic polymers, technology is available to produce a counterfeit human body part with the requisite unique physical patterns and traits of a particular individual. In high-level security systems, which require verification of a presented unique skin or body part for entry, a counterfeit model could be produced, thereby allowing unauthorized entry into a secured facility. As these duplication capabilities become more sophisticated, less costly and more available, there is a greater need to verify whether the body part offered for identification purposes is a counterfeit reproduction or even the severed, lifeless body part of an authorized individual.

U.S. Pat. No. 5,719,950 suggests that verifying an exterior specific characteristic of an individual, such as a fingerprint, in correlation with a non-specific characteristic, such as oxygen level in the blood, can verify the identity of a person. This method may be effective, but still relies on exterior characteristics for verification of the individual. However, this invention is directed to apparatus and a method for utilizing unique internal characteristics for verification of the identity and viability of an individual. Also, the equipment required by that patent is complicated by having dual operations, which introduce more variables to be checked before identity is verified. This complication is obviated in this invention by using a single sensor to conduct both operations.

Current biometric systems are also limited in size. For example, a fingerprint scanner must be at least as big as the fingerprint it is scanning. Other limitations include the lack of moldability and flexibility of some systems, which prevents incorporation into flexible and moving objects. Finally, the complex scanning systems used in current biometric identification methods are expensive, which prevents their widespread use.

Accordingly, there is a need for more automated and reliable biometric recognition methods and systems, which use non-visible physical characteristics that are not easily copied, photographed, or duplicated. This would eliminate concerns regarding fingerprints that are unidentifiable due to dirt, grease, moisture or external surface deterioration, potential risks involved in eye scanning, costly instrumentation that depends on external characteristics, and the possibility of deceiving a system through use of an artificial reproduction of a unique external characteristic.

SUMMARY OF INVENTION

The present invention pertains to an apparatus for authenticating an individual living organism by recognition of the individual organism's identity. The apparatus comprises a sensing mechanism for sensing unique internal electric and/or magnetic and/or acoustic properties of the organism, and a mechanism for recognizing the organism. In one application, this authentication enables authorization of an action by the individual.

The present invention pertains to a method for authenticating an individual living organism by recognition of an individual organism's identity. The method comprises the steps of sensing unique internal electric and/or magnetic and/or acoustic properties of the organism, and recognizing the organism from the property. In one application, this authentication enables authorization of an action by the individual.

As used herein, "unique internal characteristic" means a characteristic that cannot be seen by visual inspection of or through the outer integument, or surface, of the organism.

The present invention pertains to a method and apparatus for verifying the identity and viability of an individual organism by identifying a non-specific characteristic, such as blood oxygen level, combined with a unique internal characteristic of the organism, such as an electric and/or magnetic and/or acoustic characteristic.

The apparatus preferably comprises a sensing mechanism having a contact area of less than 2.0 $cm^2$ to identify an attribute of the organism. The sensing mechanism produces a signal corresponding to the attribute, which is sent to the recognizing mechanism. The sensing mechanism preferably has a thickness of less than 0.2 cm.

The apparatus includes a mechanism for recognizing the organism from the attribute with an accuracy of greater than one in one billion. The sensing mechanism is preferably moldable into a shape having a non-flat surface. The electrodes can be concave, flat, convex, or a combination thereof, enabling molding into numerous shapes for inclusion in various devices. Characteristics of an individual organism can be detected by its unique electrical and/or magnetic properties.

I. These properties can be measured
  A. Using any mechanism which uses a DC, AC, electric field, magnetic field, and/or EM field.
  B. Using touch and/or touchless methods.
  C. By positioning the organism in relation to the applied energy
    1. as part of an energy flow
    2. interrupts an energy flow
    3. responds to an energy field by generating its own energy flow
    4. using induced currents.
  D. For a single body segment or for multiple segments. Multiple segments can be compared with each other, i.e., a measured segment from the left hand can be compared to a measured segment on the right hand.
  E. Using one or more frequencies.
  F. Using one or more waveform shapes.
  G. Generating 3 or more dimensional matrices.
  H. Using unique sensors.
  I. To an accuracy of one in one billion or greater.
  J. Detecting energy emitted by the organism.

II. An individual organism can be recognized by its electrical and/or magnetic properties using any of the mechanisms described in I. Although the absolute measurements of these properties may vary from day to day, the relative ratios of these measurements will remain constant enough to derive a unique biometric pattern.

III. Diagnostic characteristics of an organism can be detected by its electrical and/or magnetic properties. The method of positioning the organism in relation to applied energy as part of an energy flow, interrupting the energy flow, and detecting emitted energy is described in the prior art. However, this invention is based on the new discovery that an organism responds to an energy field by generating its own energy flow, such as an induced current. Induced currents can be used to measure the electrical and/or magnetic properties of an organism to determine diagnostic characteristics such as:
  A. Presence or absence of bone trauma
  B. Presence or absence of tumors
  C. Presence or absence of toxins
  D. Levels of metabolites.

The present invention pertains to an apparatus for identifying electric and/or magnetic properties of an individual living organism comprising a sensing mechanism for sensing the electric and/or magnetic properties and a mechanism for forming matrices of sensed properties having at least four dimensions.

The present invention pertains to a method for sensing an induced current in an individual living organism comprising the steps of inducing current in the organism and detecting the current induced in the organism. This method can be used to diagnose a fracture or break in a bone.

The present invention pertains to an apparatus for sensing an induced current in an individual living organism comprising a mechanism for inducing current in the organism and a mechanism for detecting the induced current. This apparatus can be used to diagnose a bone fracture or break.

The apparatus of this invention comprises a mechanism for transmitting electric and/or magnetic energy into the organism and a mechanism for receiving the electric and/or magnetic energy after it has passed through the organism.

The present invention pertains to methods and apparatus for authorizing actions by an individual using a computer. The method comprises the steps of sensing a non-visible attribute of an individual, recognizing the individual, and authorizing an action by the individual. The non-visible attribute amounts to a biometric signature. The present invention pertains to an apparatus for authorizing an action. The apparatus comprises a mechanism for recognizing a biometric signature of an individual, and a mechanism for allowing or enabling the action.

These actions can include computer, database or program access, TV channel access, communications access, access to financial accounts, conducting financial transactions (e.g. paying bills, charging purchases, accessing ATM machines, transferring funds, buy/sell stocks/bonds/mutual funds), location access (e.g. vault, safe, room, building, compound, etc.), political access (e.g. passport, visa, membership, etc.) unlocking a lock, equipment access/maintenance/operation (e.g. gambling machines, vehicles, medical equipment, weapons), automatic cost charging (e.g. tolls, transportation fares, entry fees, retail purchases, etc.), library book/recording/video loan, video or other rental, bank safe deposit box access, or any other situation where it is necessary to establish the identity of an individual to authorize an action.

The apparatus can comprise a contact card having sensors, which an individual touches to generate a biometric signature, and a card reader for recognizing the individual from the biometric signature. The card reader can include a touchless electric field sensor for measuring induced current in the individual to obtain the biometric signature. The card can have a memory which stores a known biometric signature, and the recognizing mechanism can have a reader for obtaining the known biometric signature from the card.

The apparatus can include a memory stick storing a known biometric signature and account information of the individual, and a memory stick reader connected to the recognizing mechanism. The presented and read biometric signature of the individual is compared to the known biometric signature in the memory stick.

The apparatus can include a driver's license having a known biometric signature of the individual and sensors for obtaining the biometric signature of the individual to enable law enforcement officials to verify the cardholder's identity.

The apparatus can include an identification card having the biometric signature of the individual, and a microprocessor.

The apparatus can include a time clock, having a memory with an account of the individual.

The apparatus can include a biometric glove for obtaining the biometric signature of the individual, and electronic records which are accessed by the individual as long as the individual wears the biometric glove and the recognizing mechanism recognizes the individual.

The apparatus can include a touch electrode wrist band that is worn by the individual, and a portable recognizing mechanism to which the wrist bank communicates to provide the biometric signature of the individual to the recognizing mechanism.

The apparatus can include a forehead mounted headset having (1) sensors for obtaining a biometric signature to obtain medical records from a database via a receiver, (2) virtual screen glasses, having see through mode which allows the individual to view actual reality and virtual records at the same time through the glasses, and (3) a transmitter for transmitting the biometric signature to the recognizing mechanism.

The apparatus can include a vehicle having a door handle and steering wheel, either or both of which have biometric sensors.

The apparatus can include a remote controller having biometric sensors and the recognizing mechanism for recognizing the biometric signature of the individual and allowing the controller to transmit a control signal.

The apparatus can include an ankle band with biometric sensors and a transmitter which transmits the biometric signature of the individual obtained from the sensor.

The apparatus can include a flip-up sensor mounted on a device to be controlled (e.g. vehicle, weapon, machine), or a sensor molded into the surface of the device (e.g. gun handle/stock, steering wheel, door handle).

The present invention pertains to a method for authenticating an individual including the steps of touching sensors of a card by the individual to generate a biometric signature of the individual, reading the card with a reader, and recognizing the individual from the biometric signature.

The sensors can sense acoustic characteristics, or electric, or magnetic, or combinations of these characteristics of the individual to generate a biometric signature.

The present invention pertains to a method for monitoring, comprising the steps of obtaining a biometric signature of an individual via a touchless mechanism having a sensor mechanism sensing an electric and/or magnetic characteristic of the individual, and transmitting the signature along with to a mechanism ID, to a remote site to monitor the location of the individual. To track this location as the individual moves, the method includes transmitting a GPS signal.

Further objects, advantages and features of this invention may be more readily ascertained by reference to the following detailed description of preferred embodiments, taken in reference to the attached drawings, in which:

BRIEF DESCRIPTION OF THE DRAWINGS

FIG. 4 is a representative graph of voltage measurement values plotted against multi-frequencies;

FIGS. 6a–6f are charts of subjects regarding impedance and digits;

FIG. 9 is an illustration showing the biometric recognition system of the present invention incorporated into the hand piece of a firearm;

FIG. 10 is an illustration showing the biometric recognition system incorporated into a wrist watchband;

FIGS. 24–33 are circuit diagrams for a hand piece or mouse for sensing electric or magnetic properties;

FIG. 34 is a schematic view of a side view of a hand unit;

FIG. 35 is a schematic top view of a hand unit;

FIG. 36 is a schematic view of a keyboard having electrodes;

FIG. 59 depicts a bone with an arrow representing normal current in a bone;

FIG. 60 depicts a bone having a fracture or break with current interrupted due to the fracture or break;

FIG. 61 is a schematic with a galvanometer at 0 current reading of induced current in a bone having a fracture or break;

FIG. 62 is a schematic with a galvanometer showing normal induced current in a healthy bone;

FIG. 74 is a schematic of an alternative apparatus for charging a purchase;

FIG. 74a is a schematic of a smart card and reader of an acoustic biometric system;

FIG. 75 is a schematic of a first side of a contact card with bar code;

FIG. 75a is a schematic the front of an acoustic smart card;

FIG. 75b is a schematic of the back the card of FIG. 75;

FIG. 76 is a side view of a contact card with bar code;

FIG. 77 is a top view of a reader for a contact card with bar code;

FIG. 77a is a schematic of a card and reader of an acoustic biometric system;

FIG. 78 is a side view of a reader groove for a contact card with bar code;

FIG. 78a is a schematic of a contactless acoustic smart card and reader of an acoustic biometric system;

FIG. 82 is a side view of a contact card with sensors;

FIG. 83 is a view of the other side the card of FIG. 82;

FIG. 84 is a schematic of a contact card and a reader for the contact card, both having embedded microchips;

FIG. 85 is a schematic of a contact card with microprocessor and a reader for a contact card with microprocessor;

FIG. 86 is a side view of a contact card with bar code and magnetic strip;

FIG. 87 is a view of the other side of the card of FIG. 86;

FIG. 123 is a schematic of wristbands for a video arcade;

FIGS. 124 and 124a are schematics of a utility box;

FIG. 125 is a schematic of a home electric meter having a sensor card reader;

FIG. 126 is a schematic of a home electric meter with touchless magnetic sweep hand sensors;

FIG. 127 is a schematic of a subway commuter hand piece, where data is communicated to subway computer for comparison;

FIG. 128 is a schematic of a turnpike commuter unit with acoustic, biometric and infrared transmitter;

FIG. 129 is a schematic of a bus unit with electrode stored-value smart card;

FIGS. 130 and 131 are schematics of payphone units;

FIG. 131a is a perspective view of an electrode payphone;

FIG. 131b is a rear view of the payphone of FIG. 131a;

FIG. 132 is a schematic of a touchless microwave phone;

FIG. 132a is a perspective view of the payphone of FIG. 132;

Figure 133:
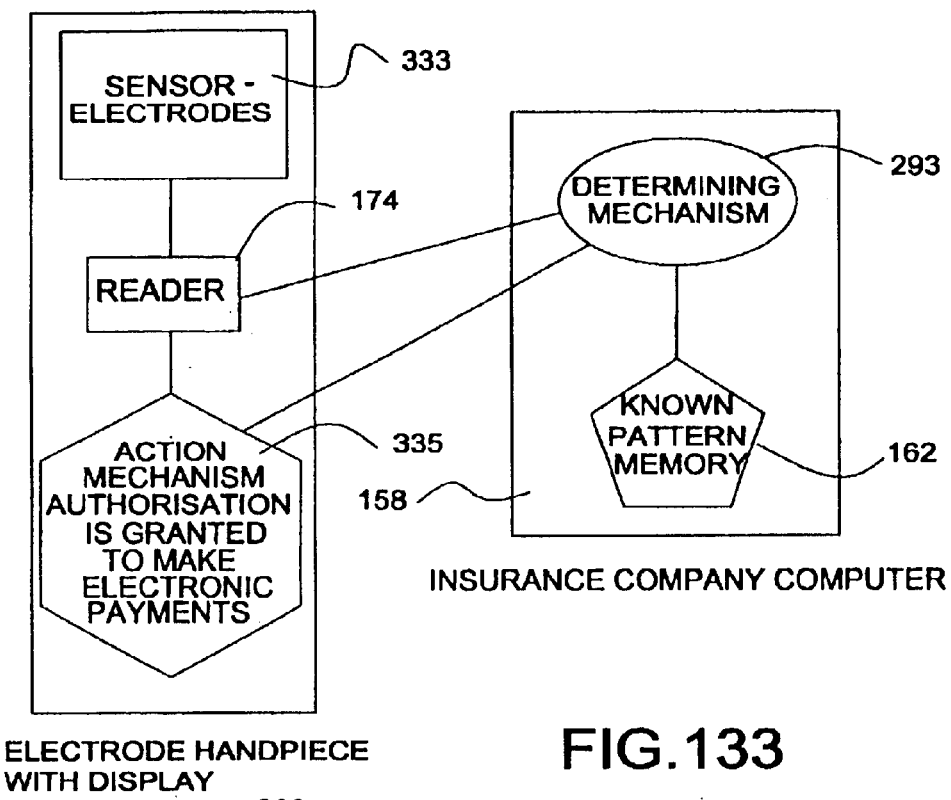
Figure 134:
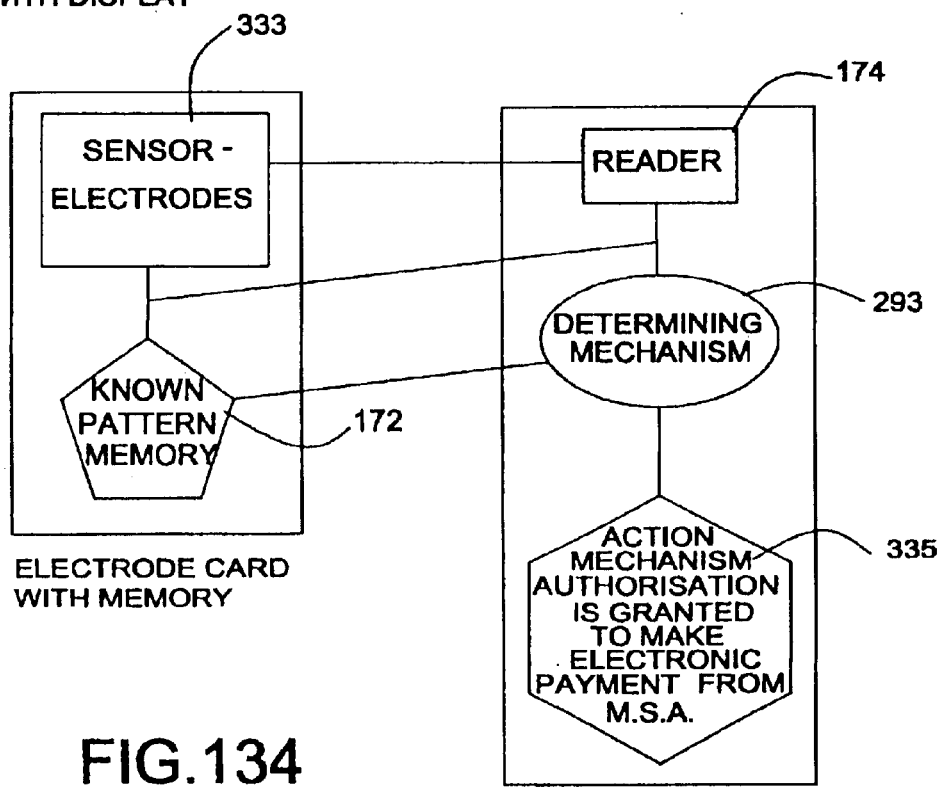
Figure 135:
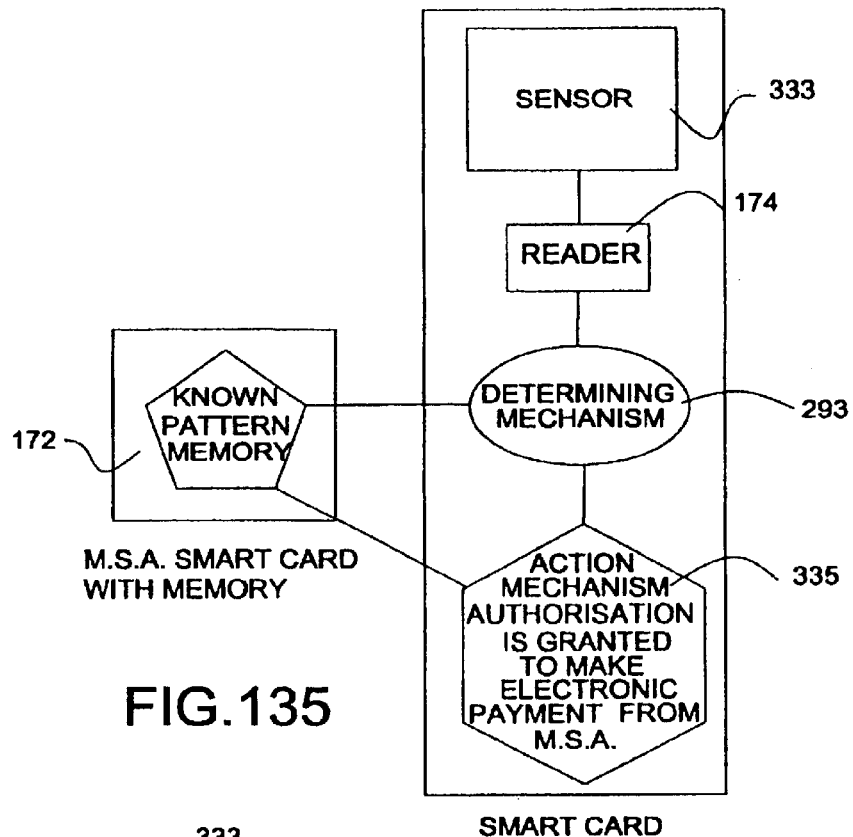
Figure 136:
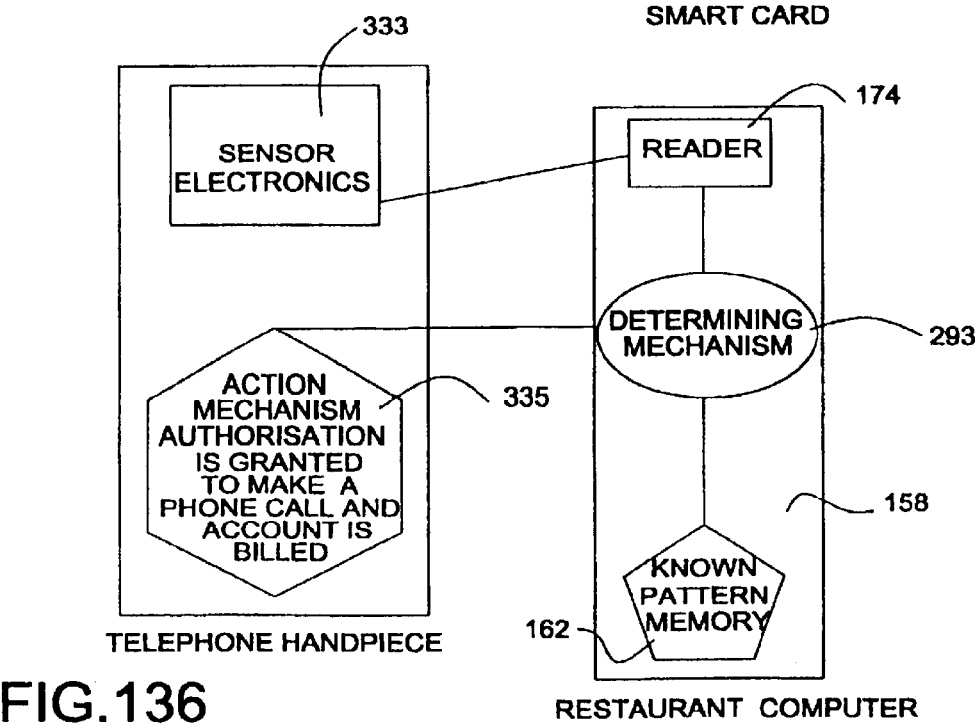
Figure 137:
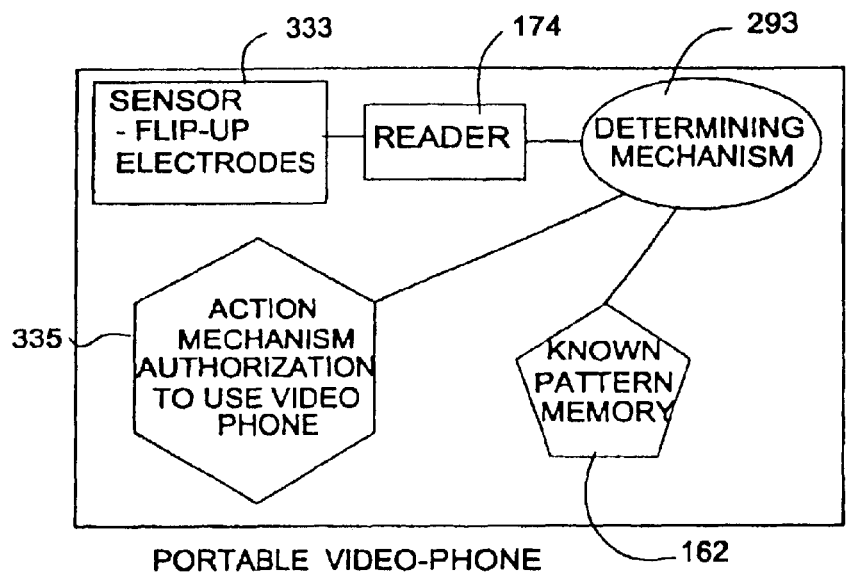
Figure 138:
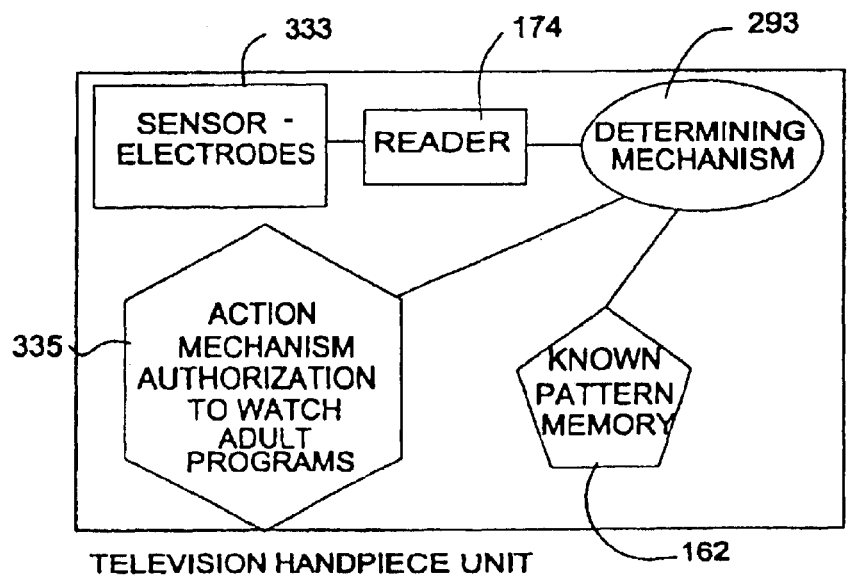
Figure 138A:
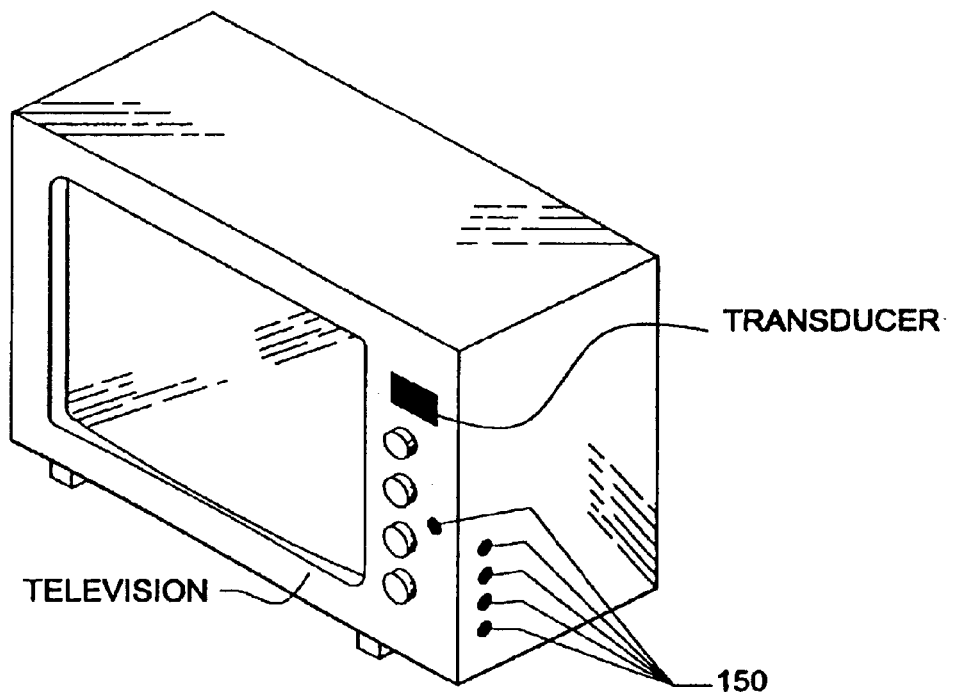
Figure 138B:
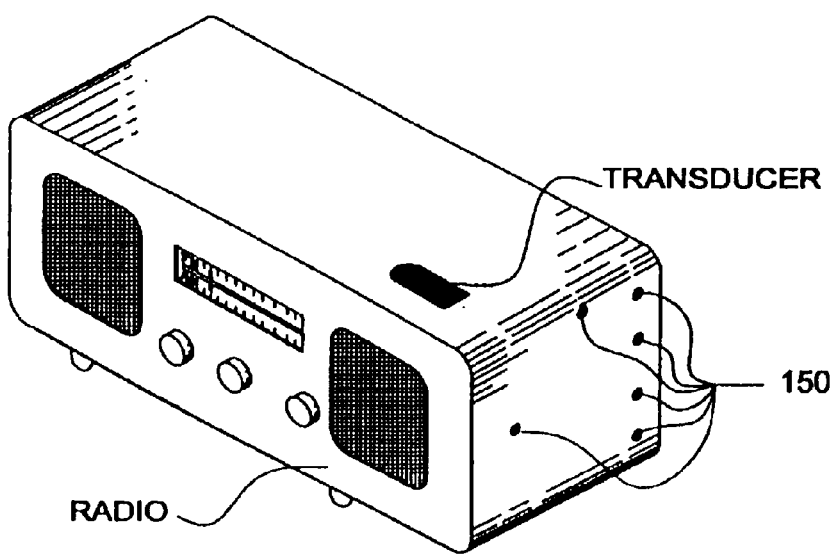
Figure 139:
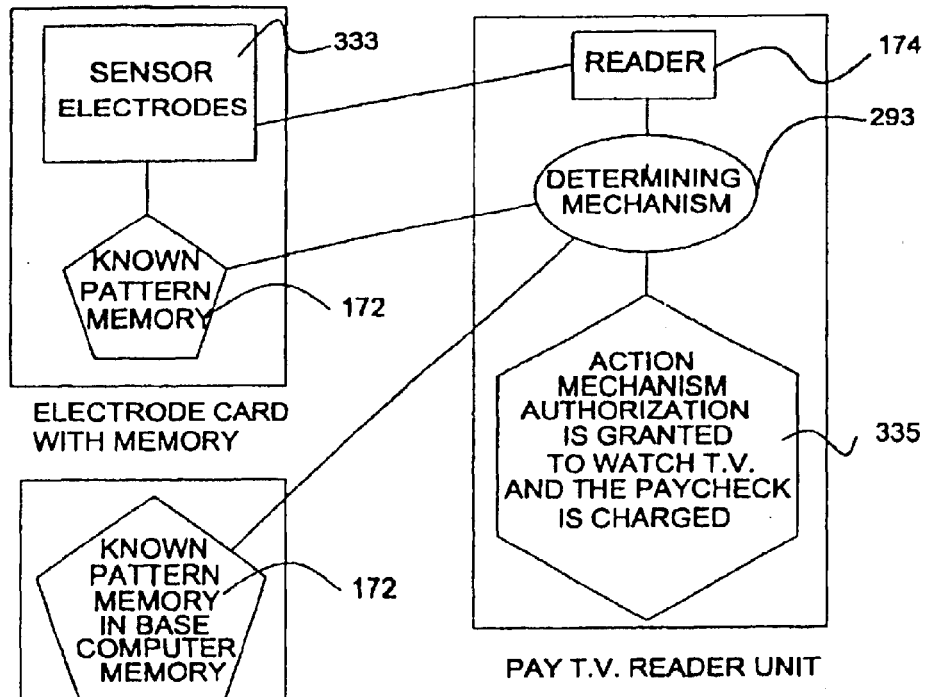
Figure 140:
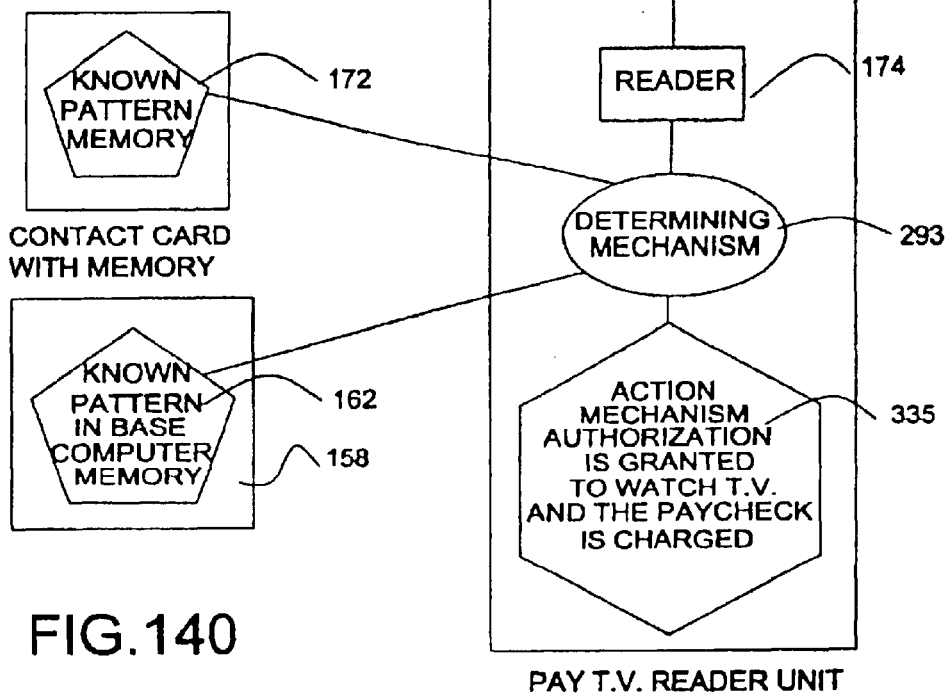
Figure 141:
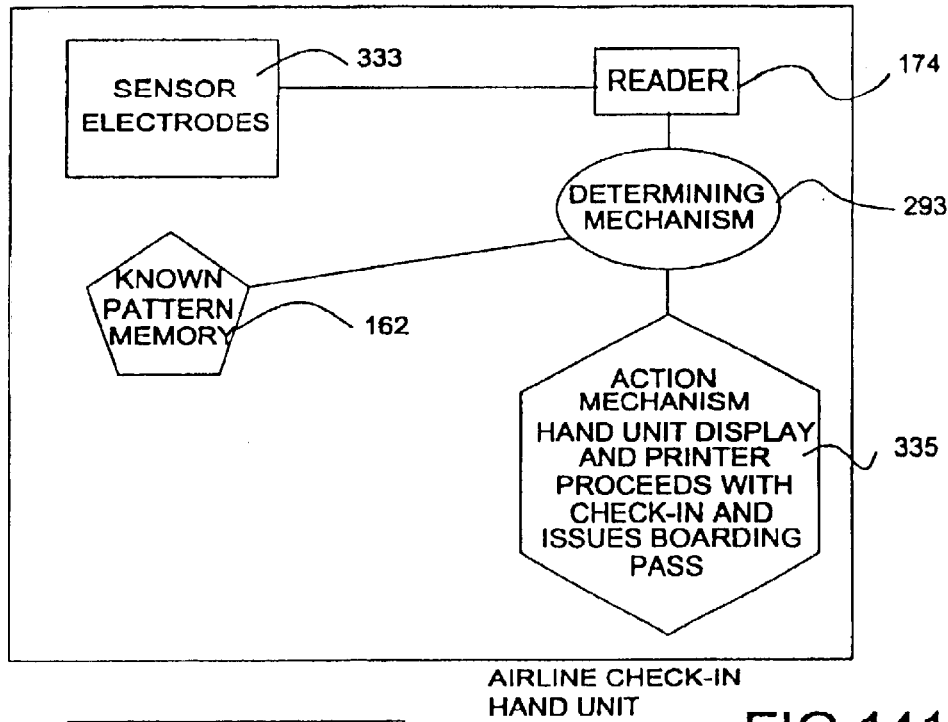
Figure 142:
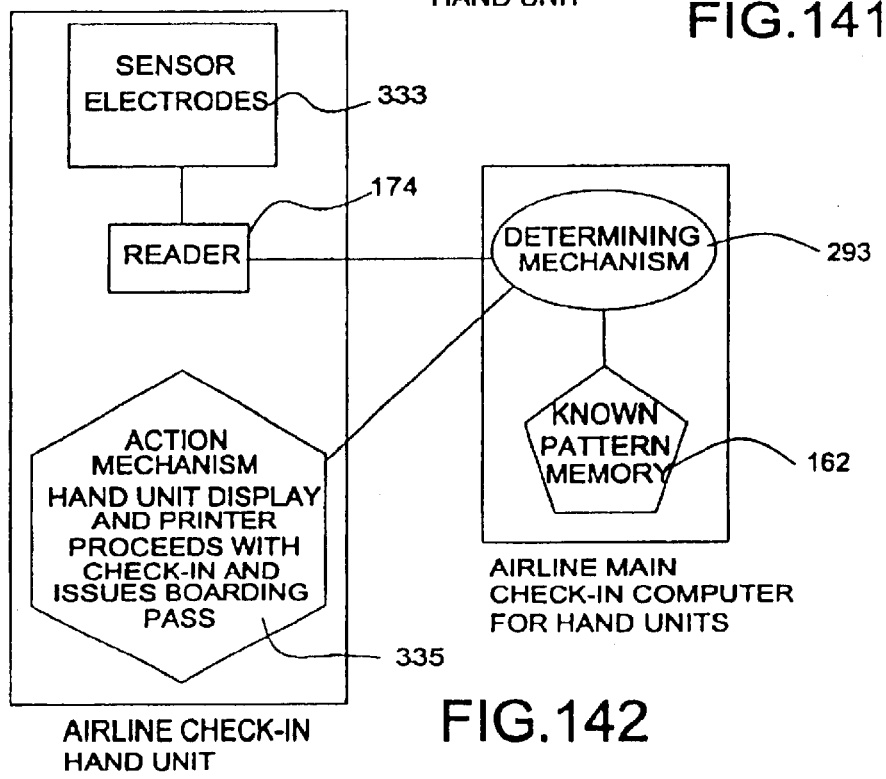
Figure 143:
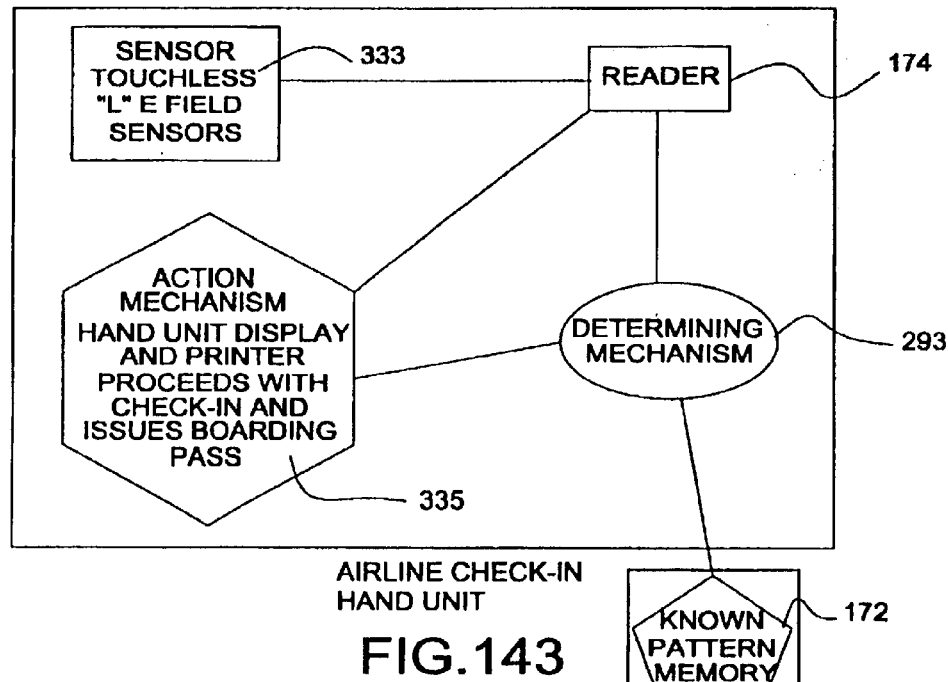
Figure 144:
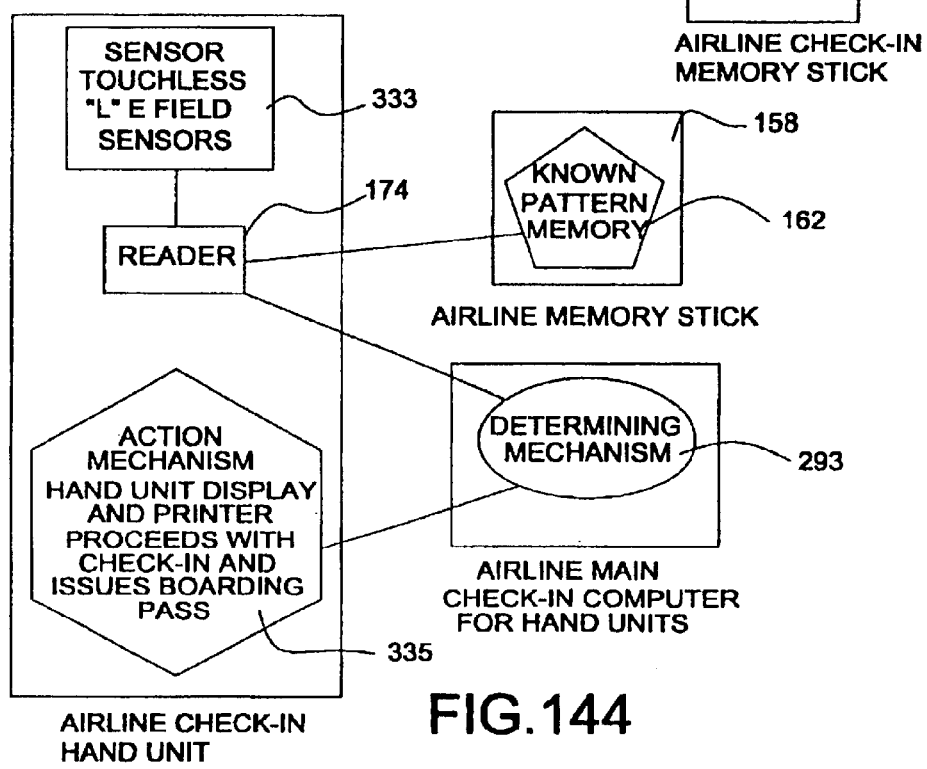
Figure 145:
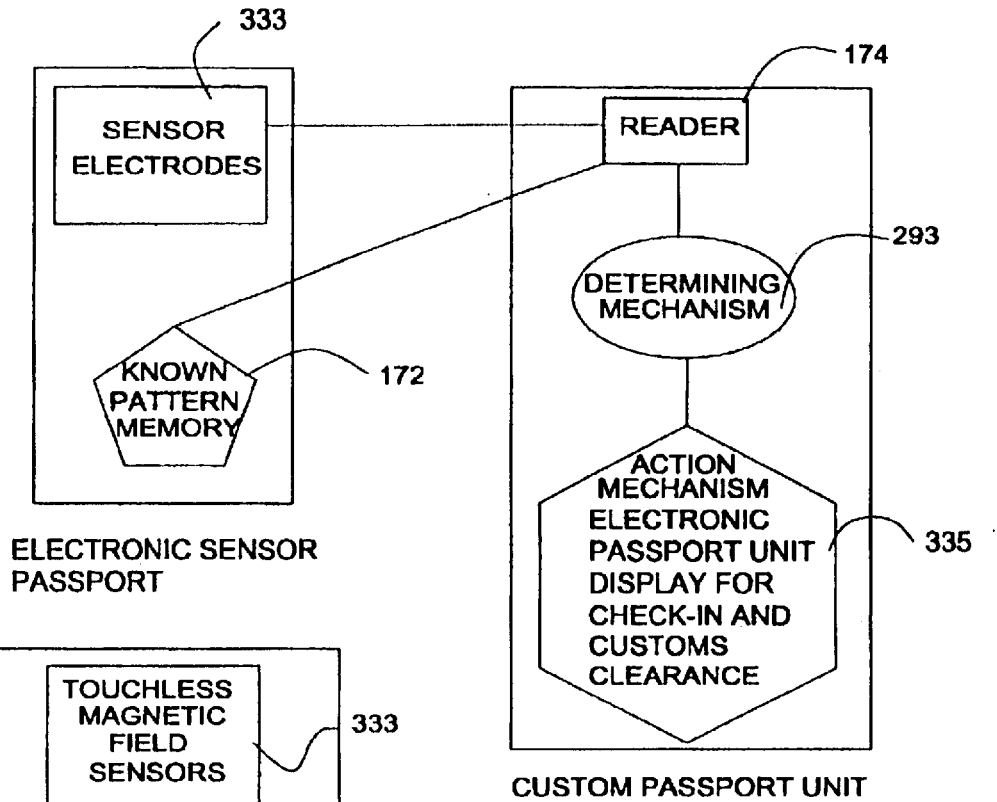
Figure 146:
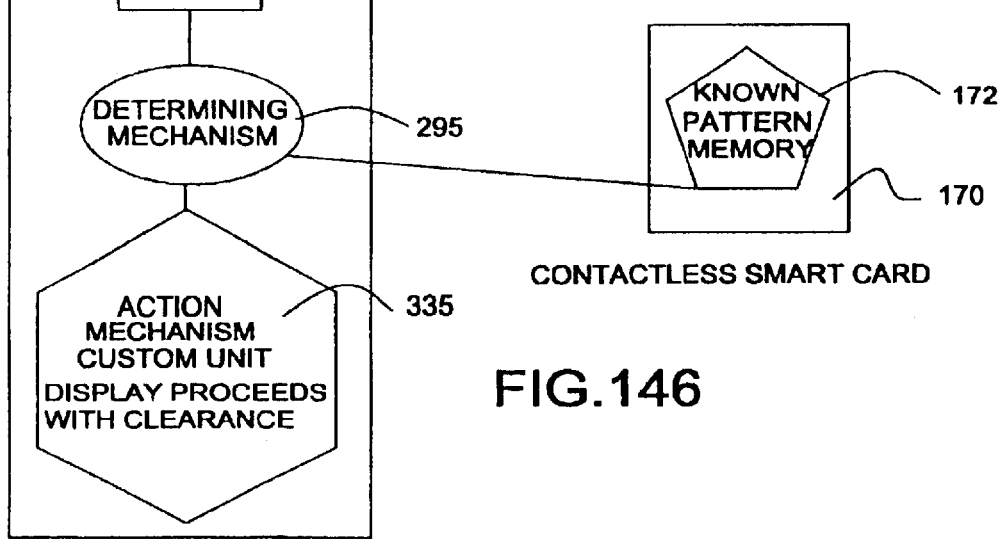
Figure 147:
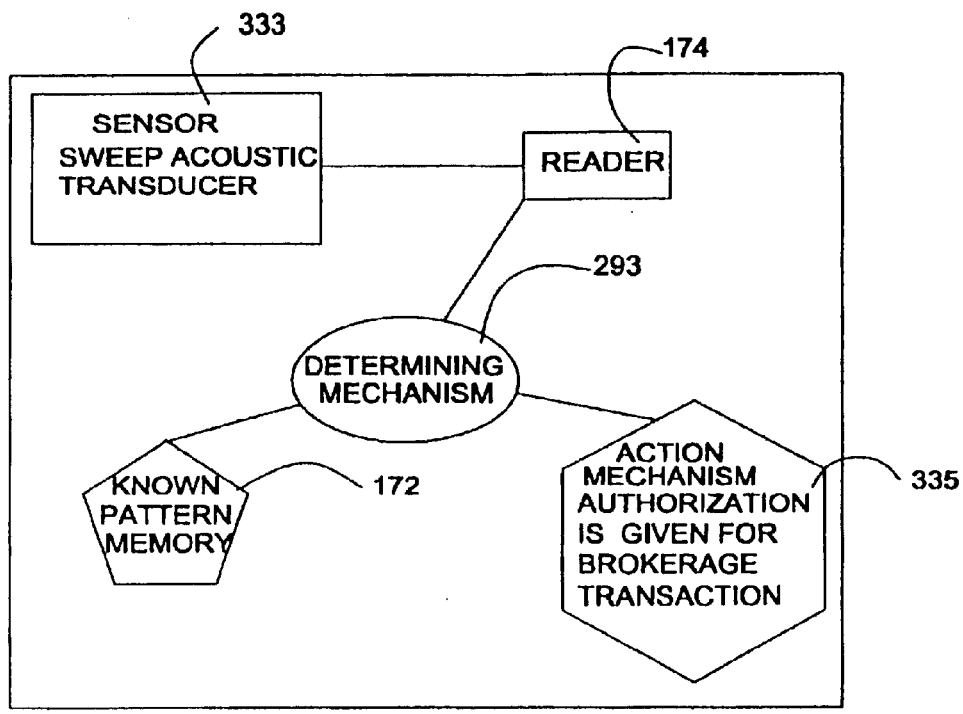
Figure 148:
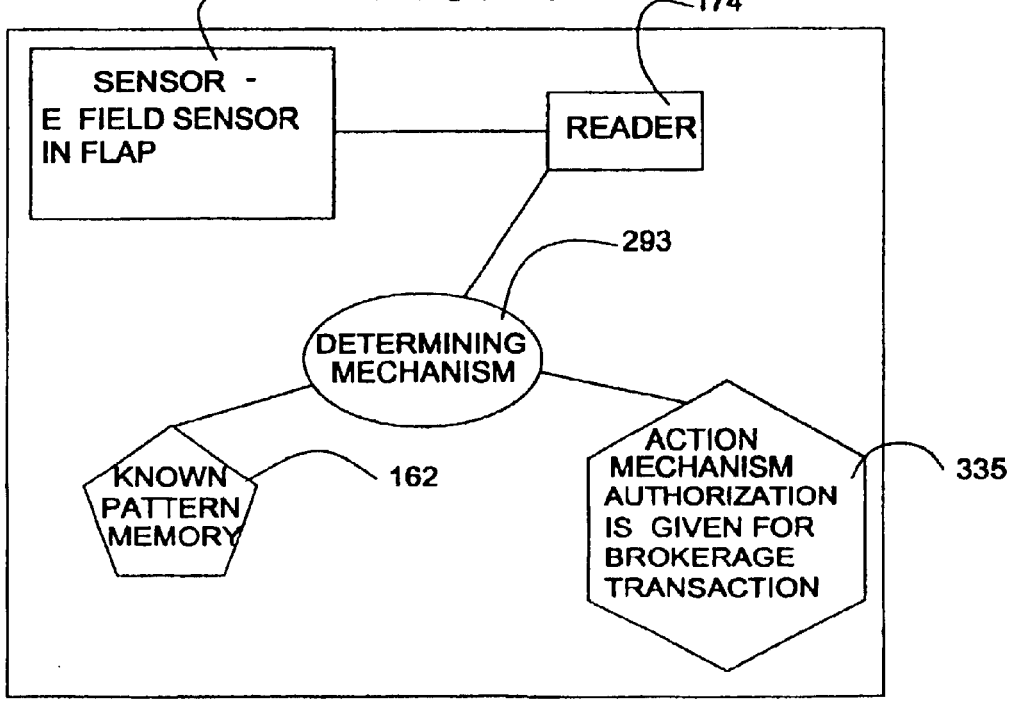
Figure 148A:
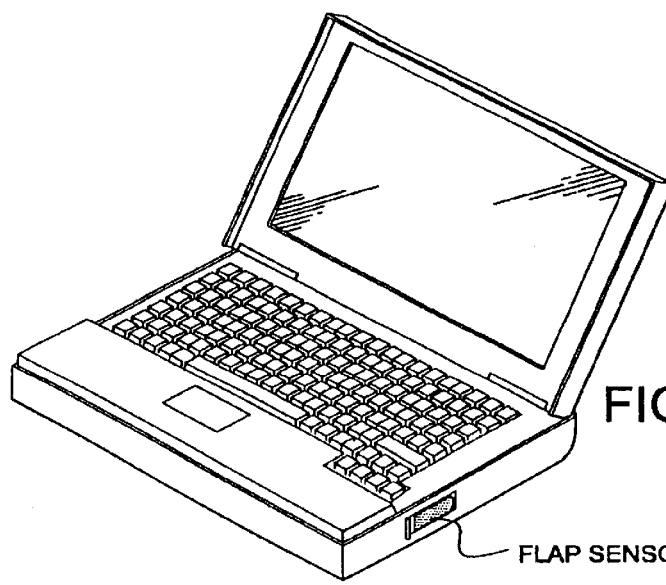
Figure 148B:
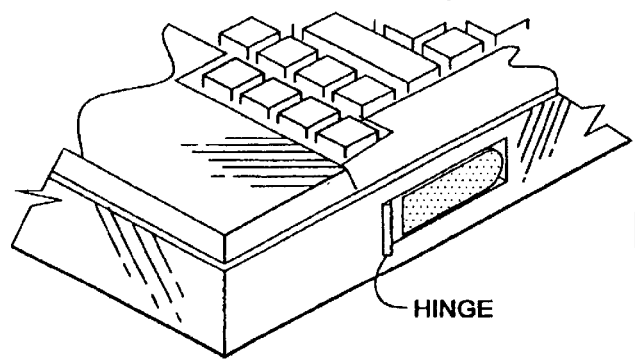
Figure 148C:
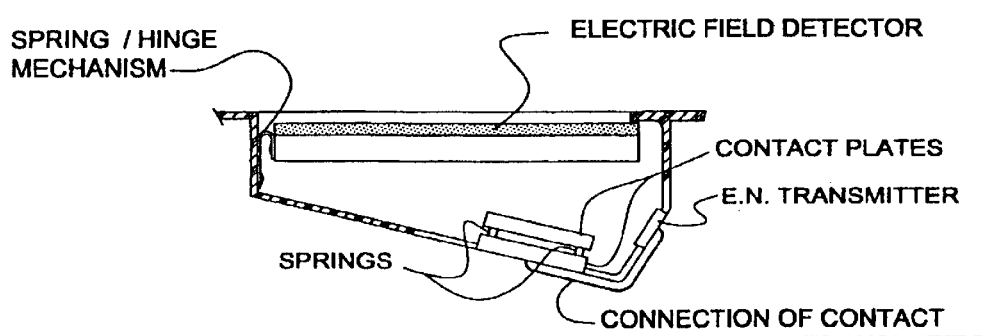
Figure 151:
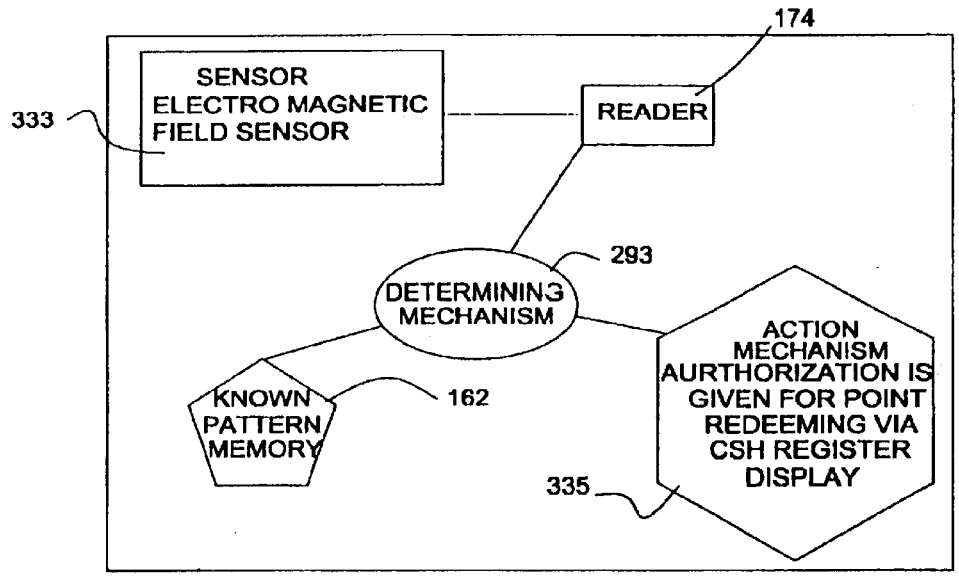
Figure 152:
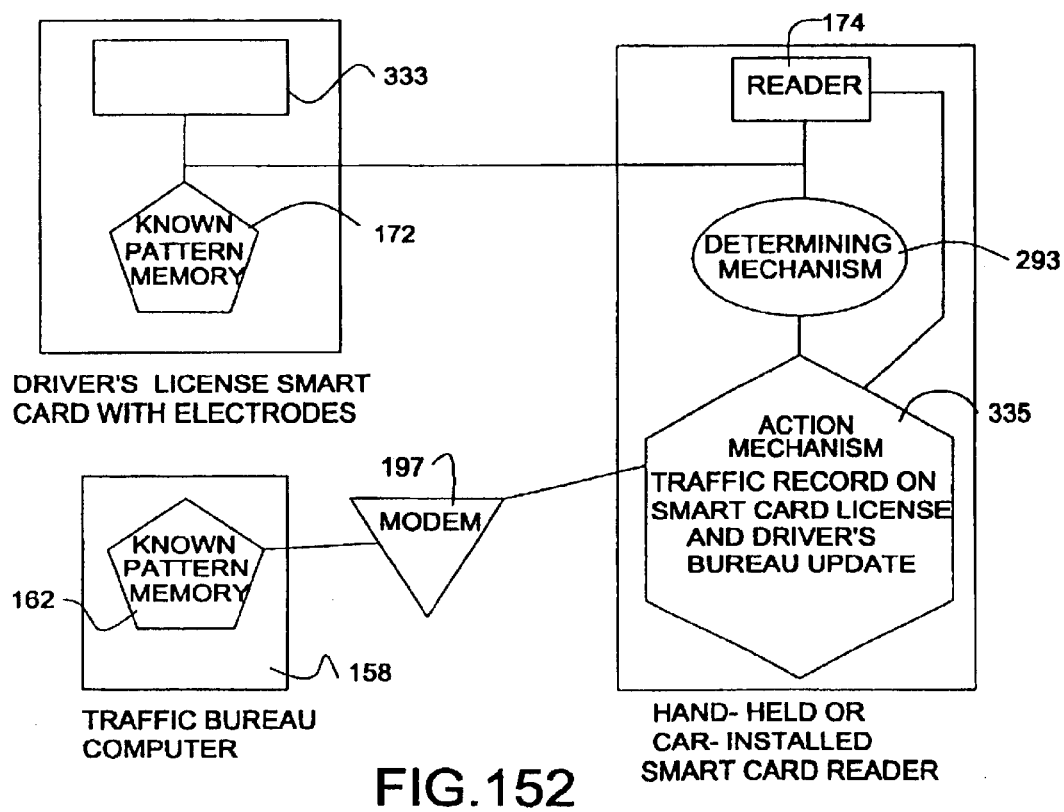
Figure 153:
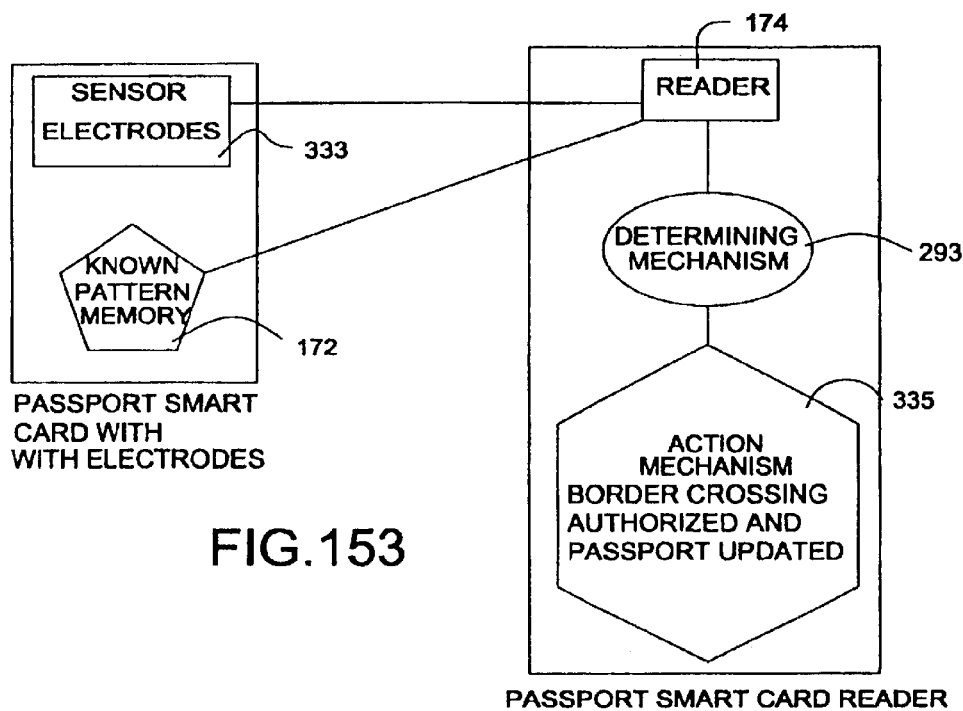
Figure 154:
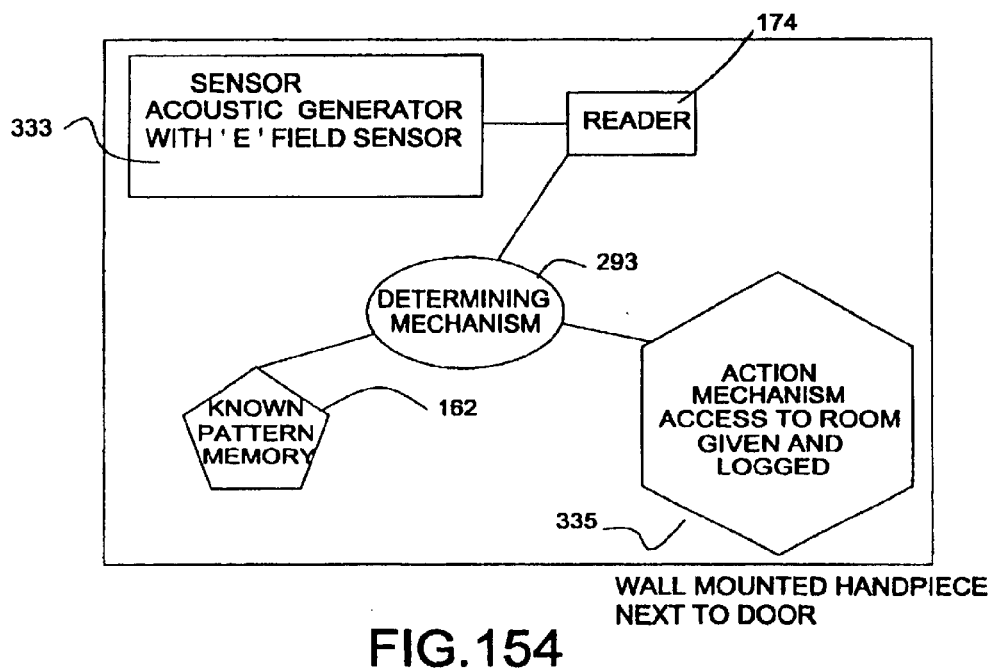
Figure 155:
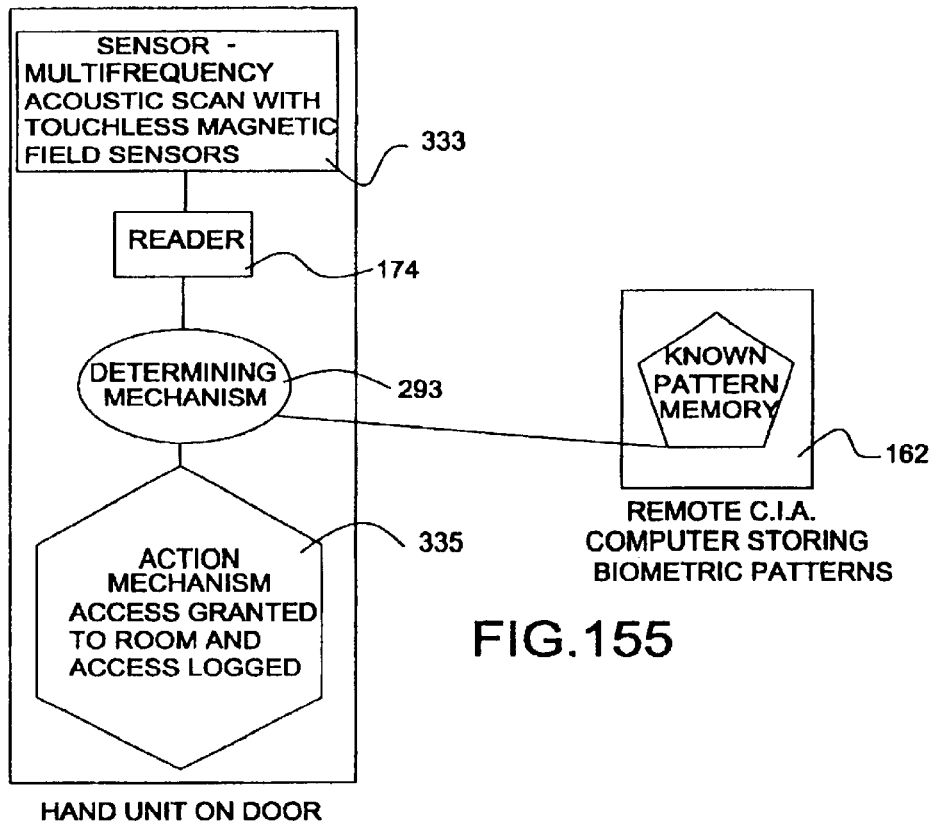
Figure 156:
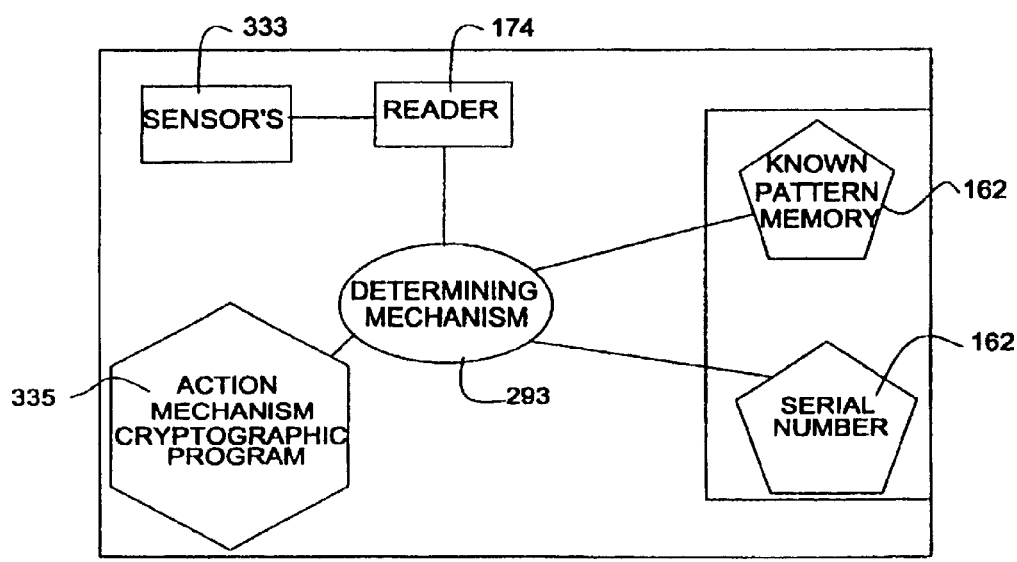
Figure 157:
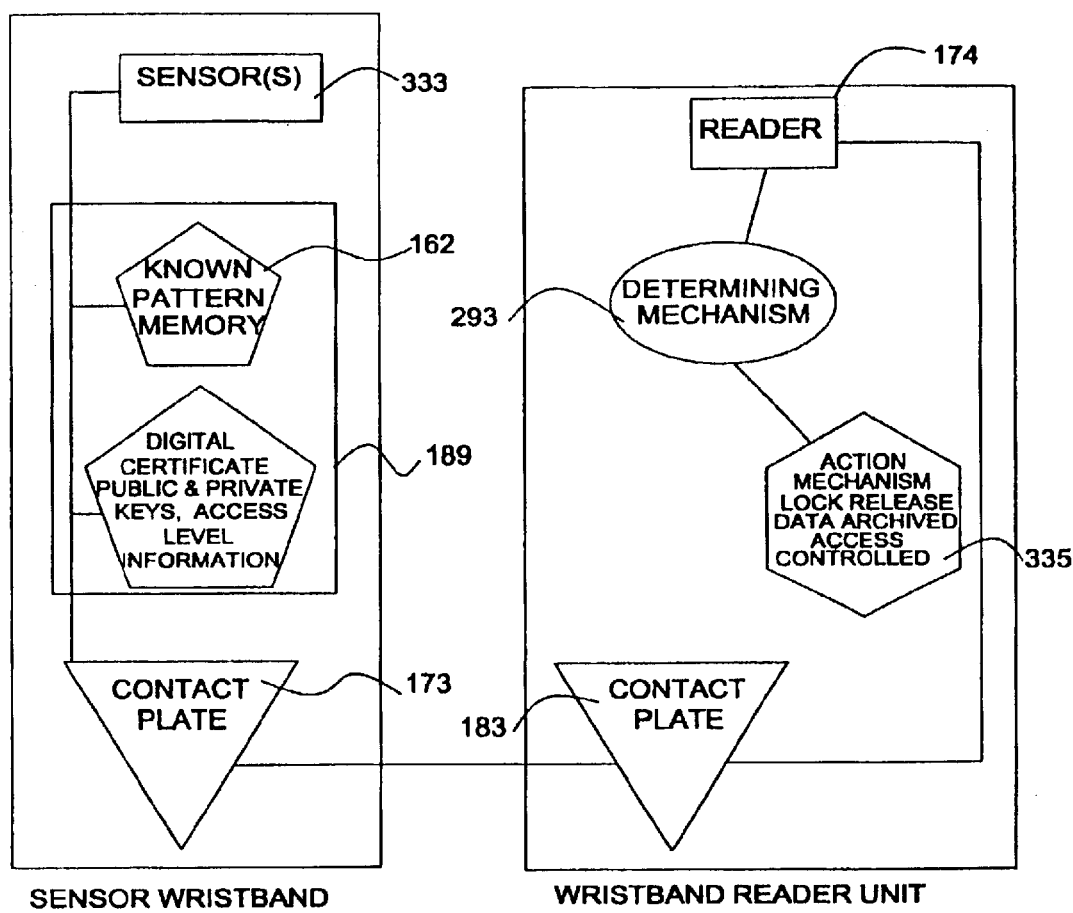
Figure 158:
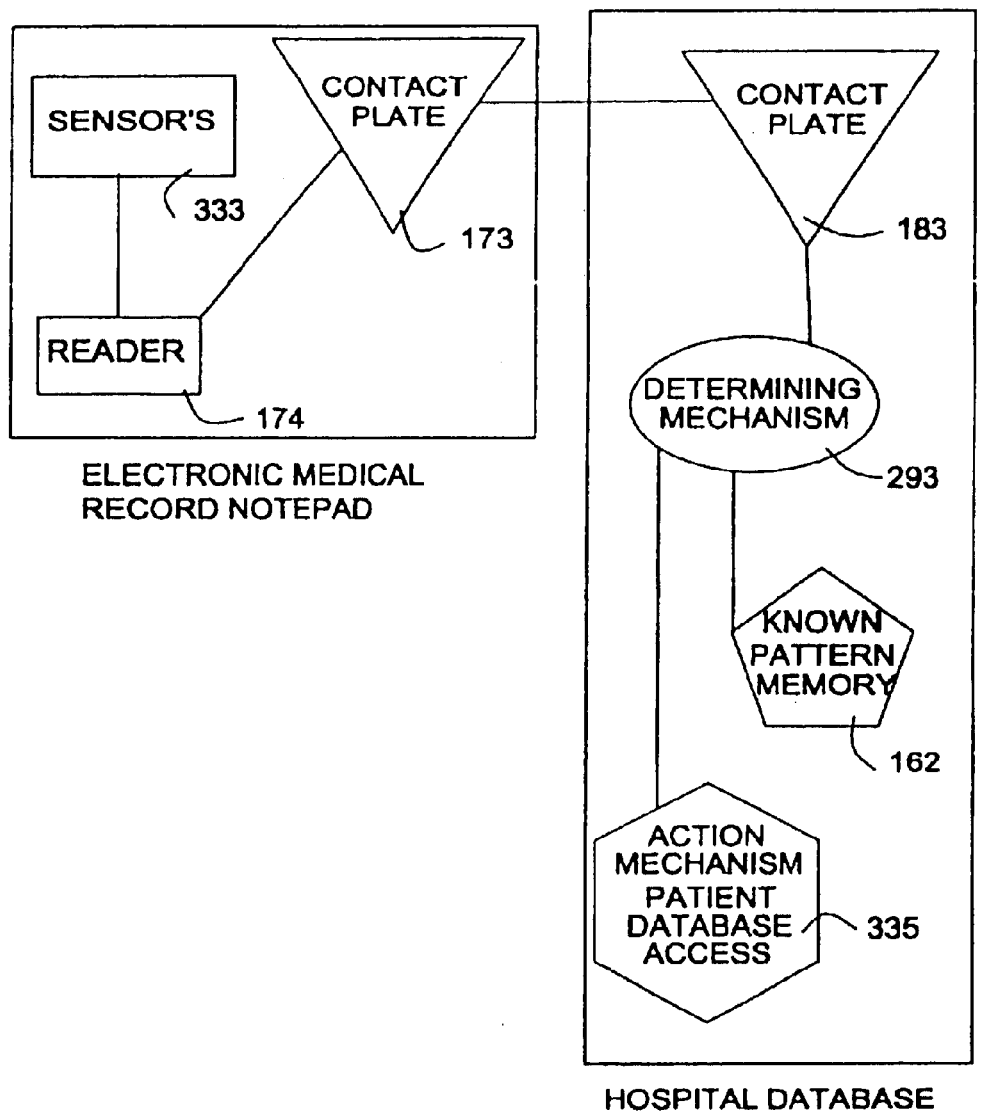
Figure 159:
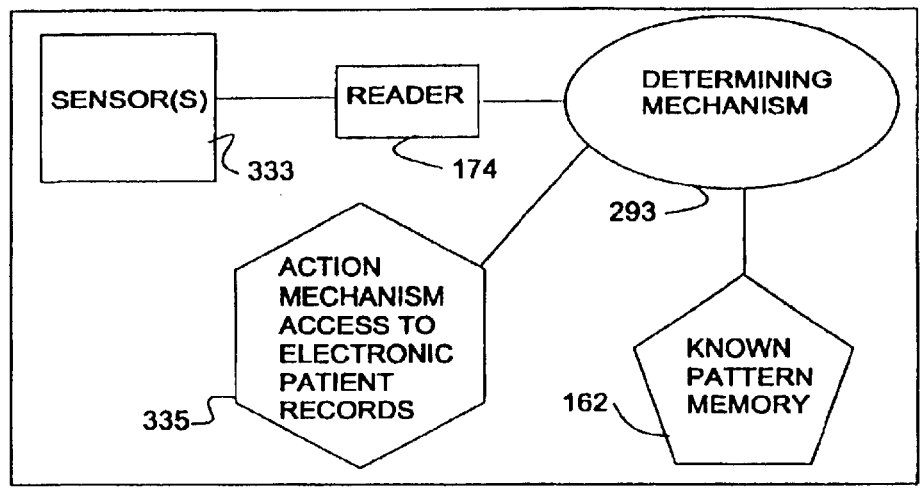
Figure 160:
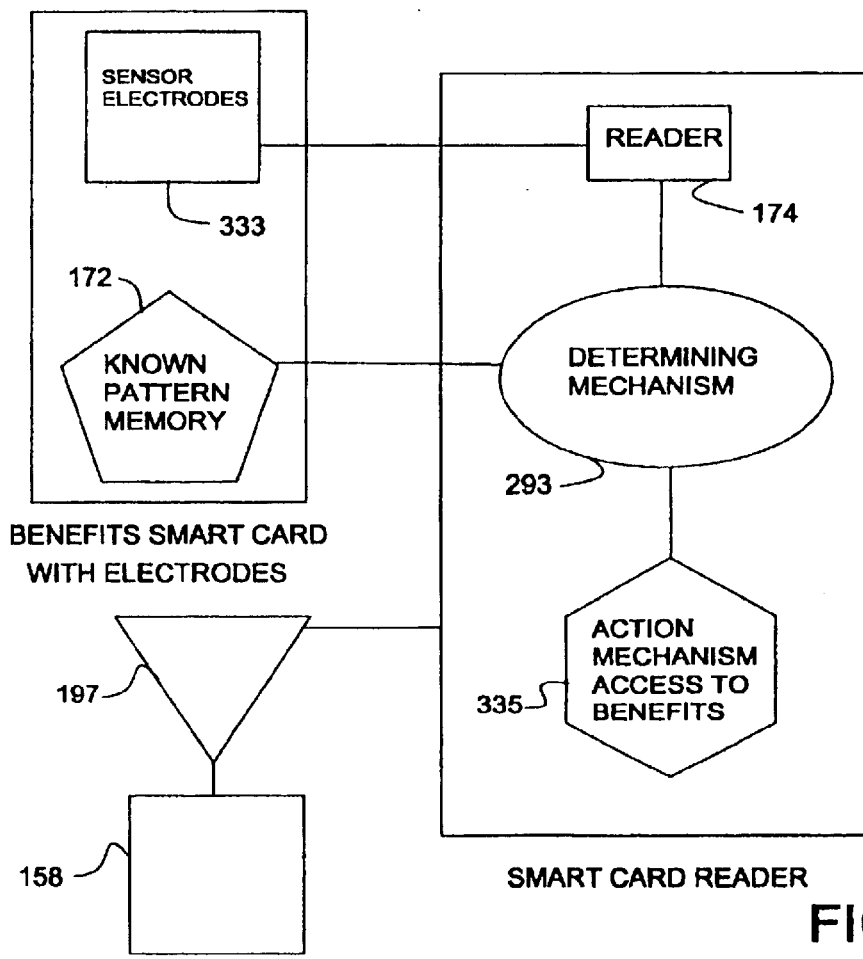
Figure 161:
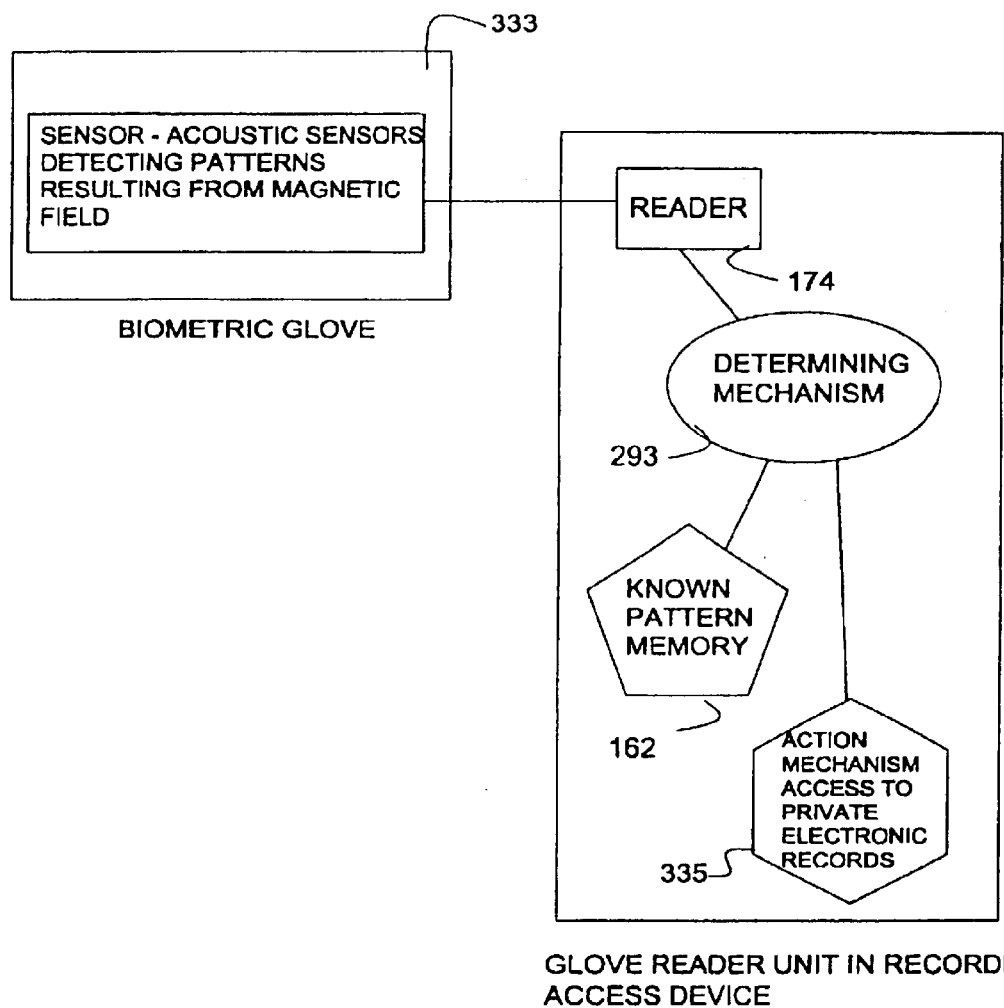
Figure 161A:
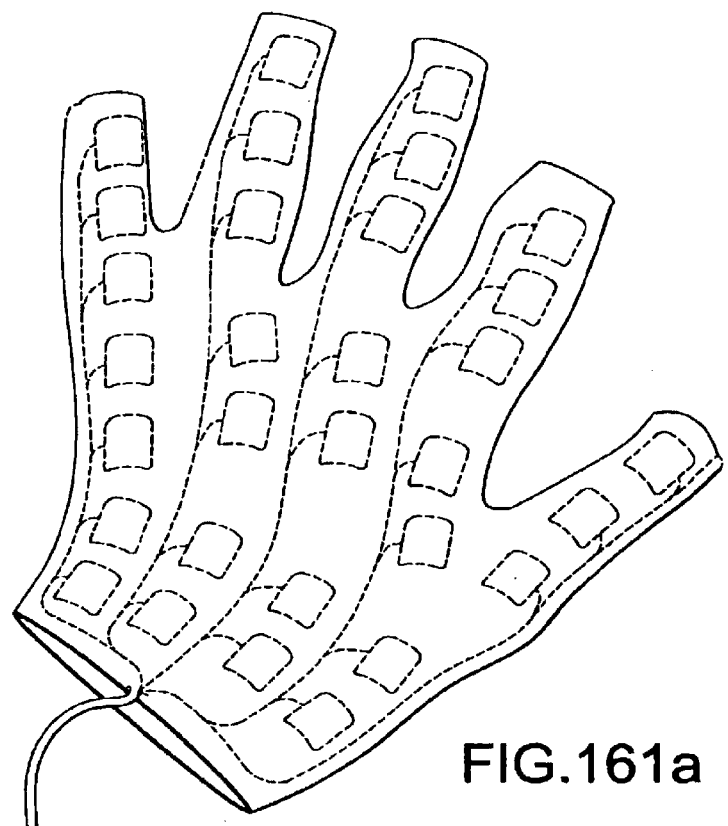
Figure 161B:
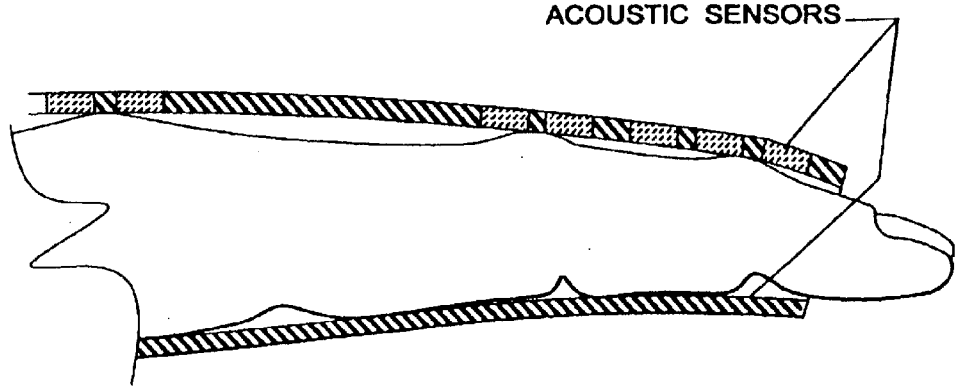
Figure 162:
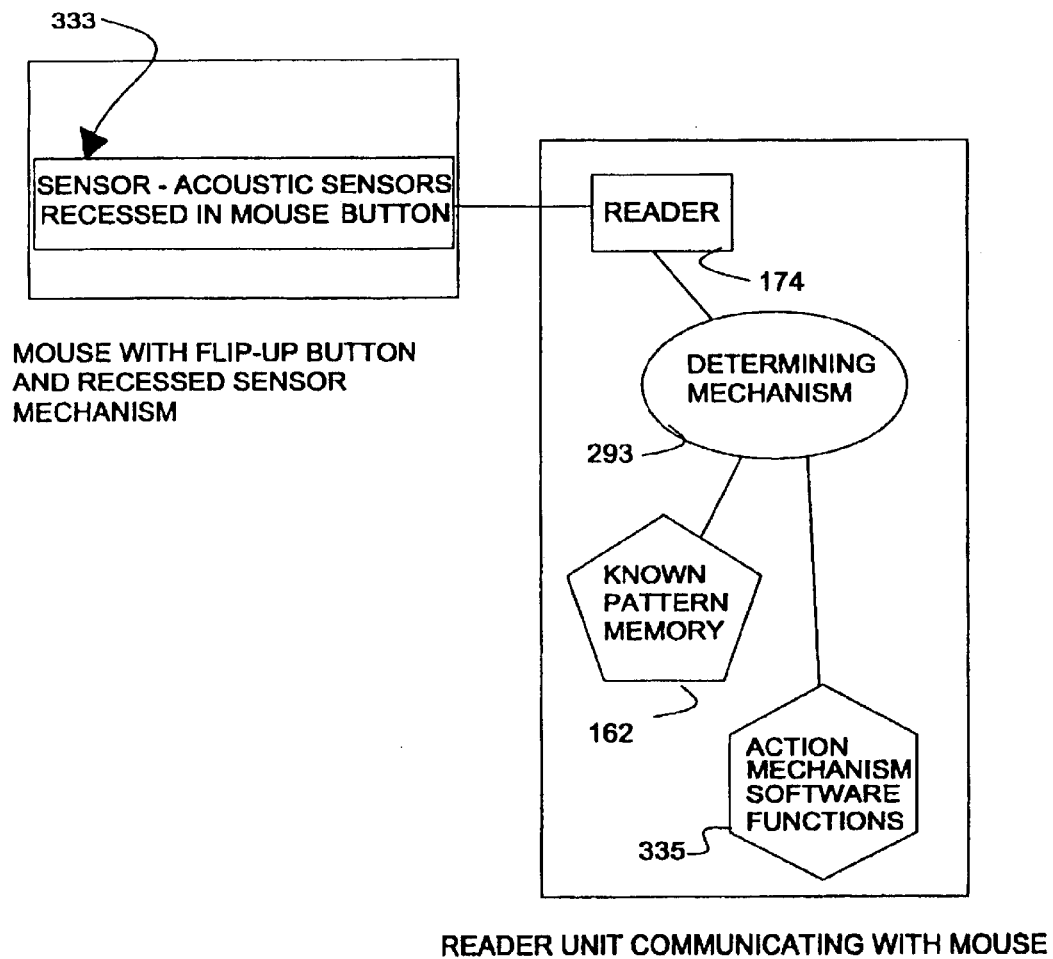
Figure 162A:
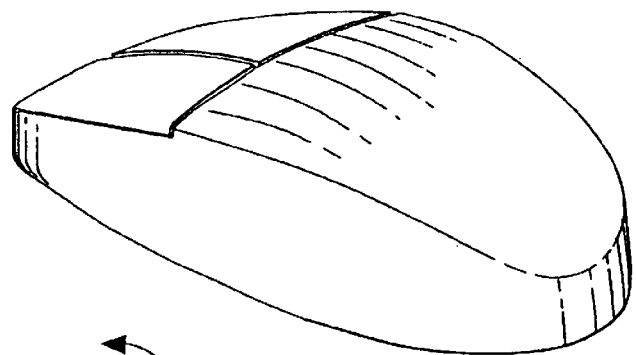
Figure 162B:
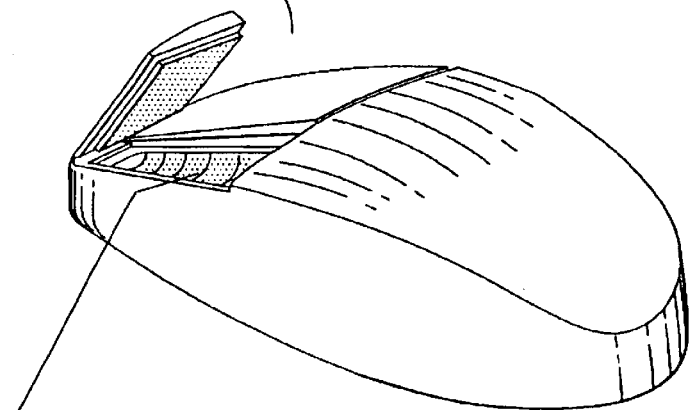
Figure 162C:
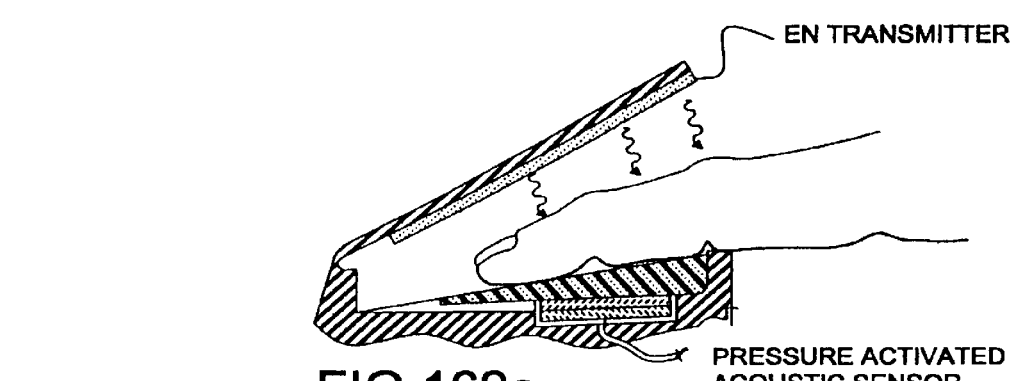
Figure 163:
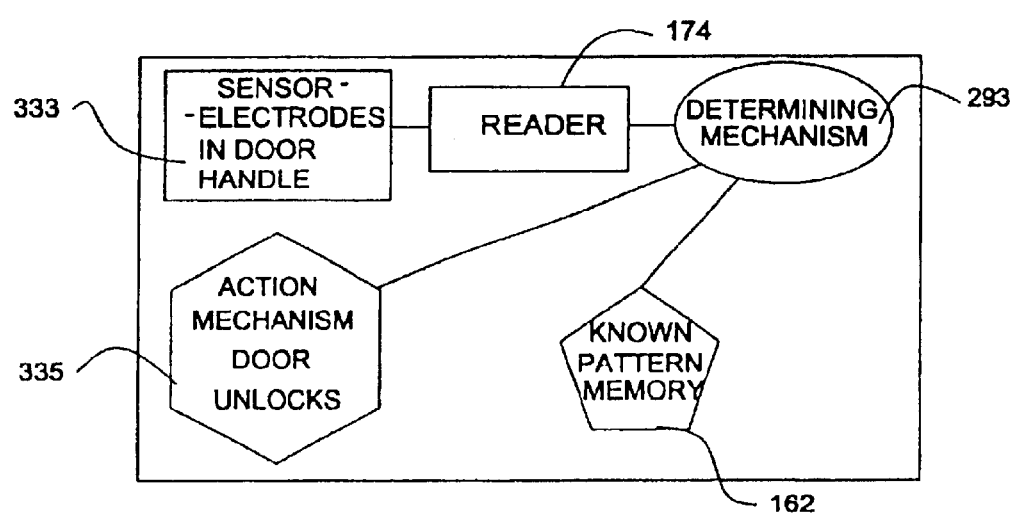
Figure 164:
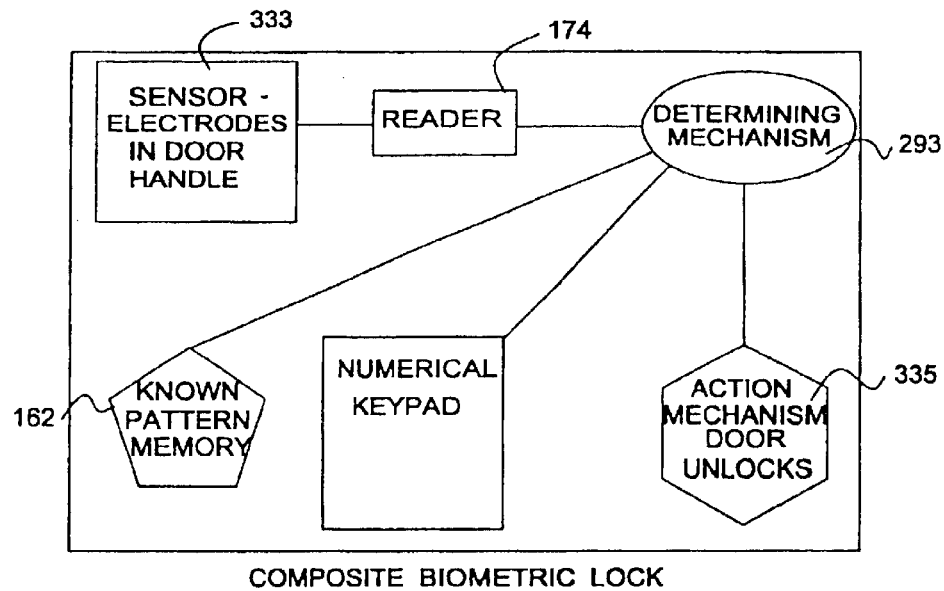
Figure 165:
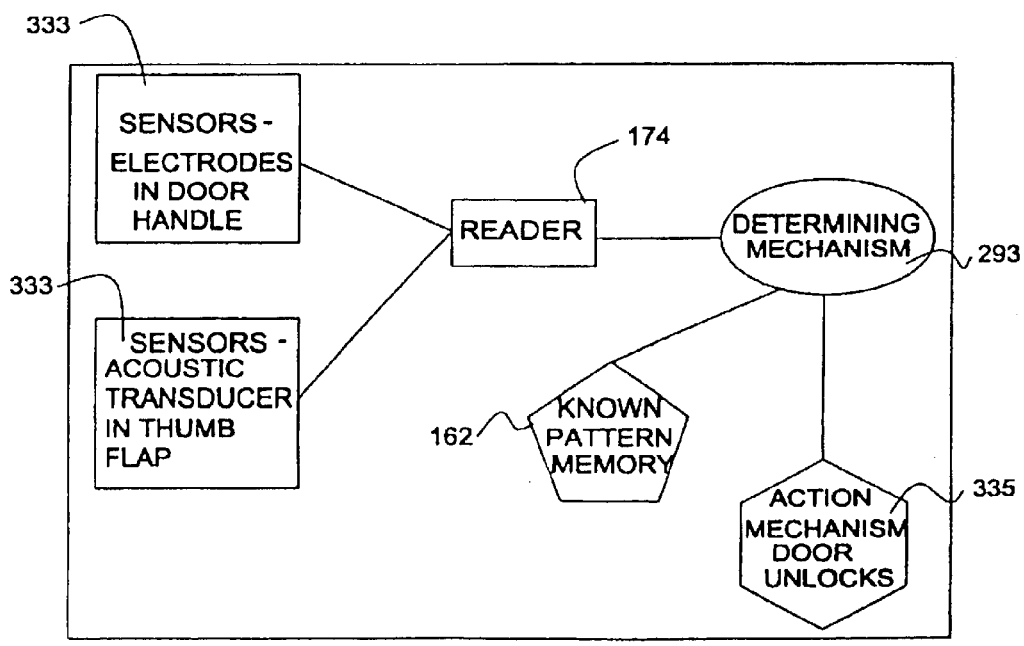
Figure 166:
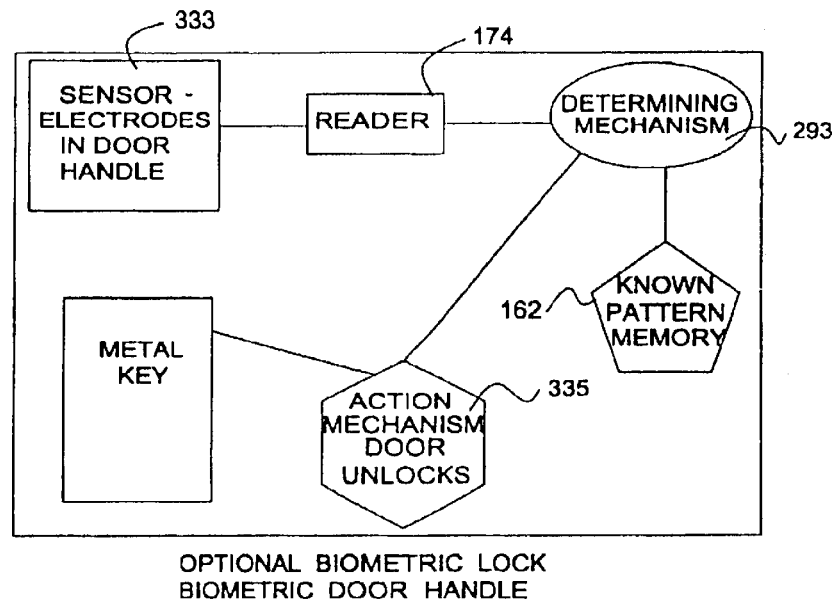
Figure 167:
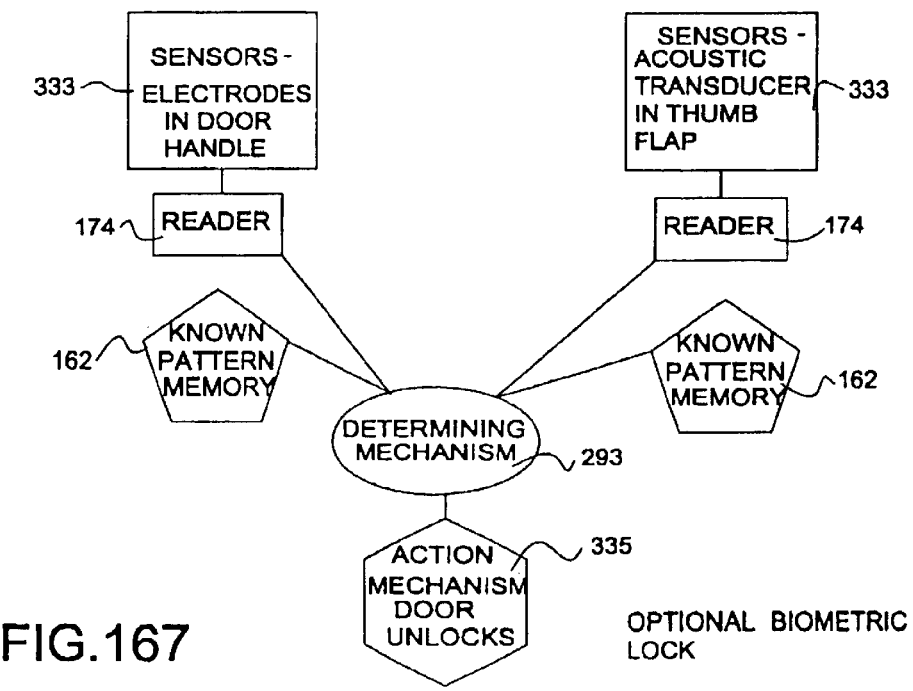
Figure 168:
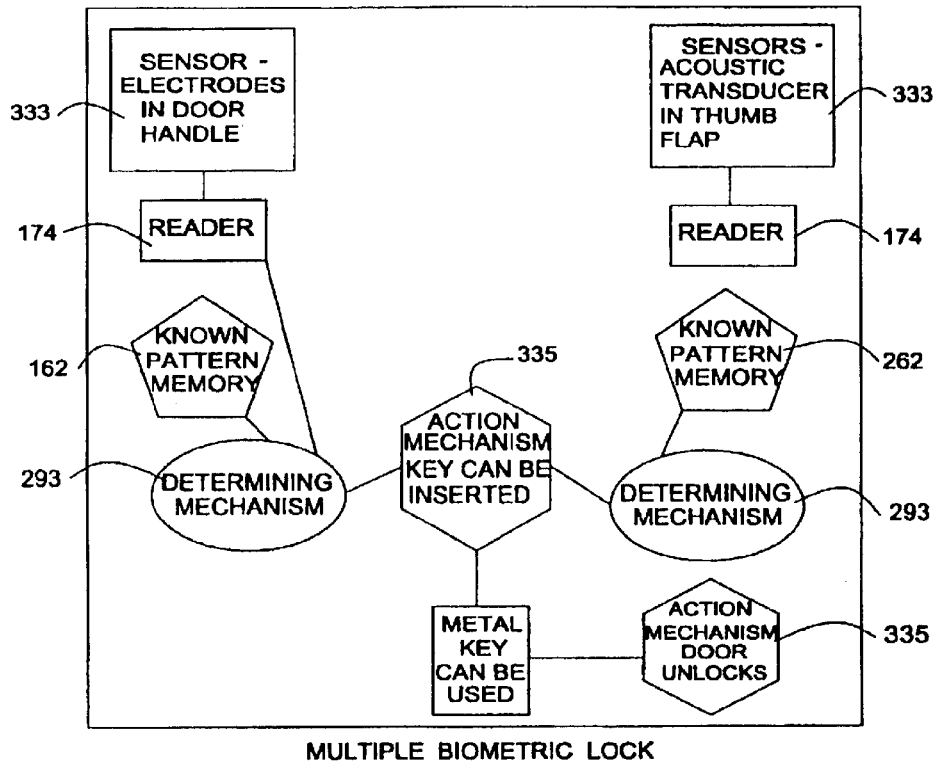
Figure 169:
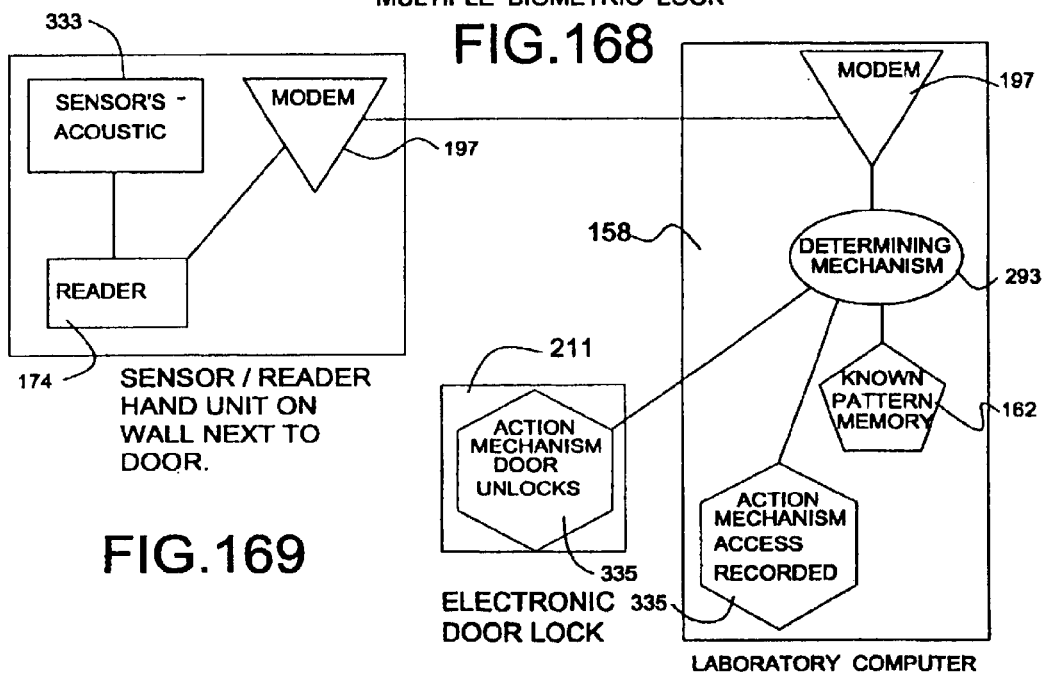
Figure 170:
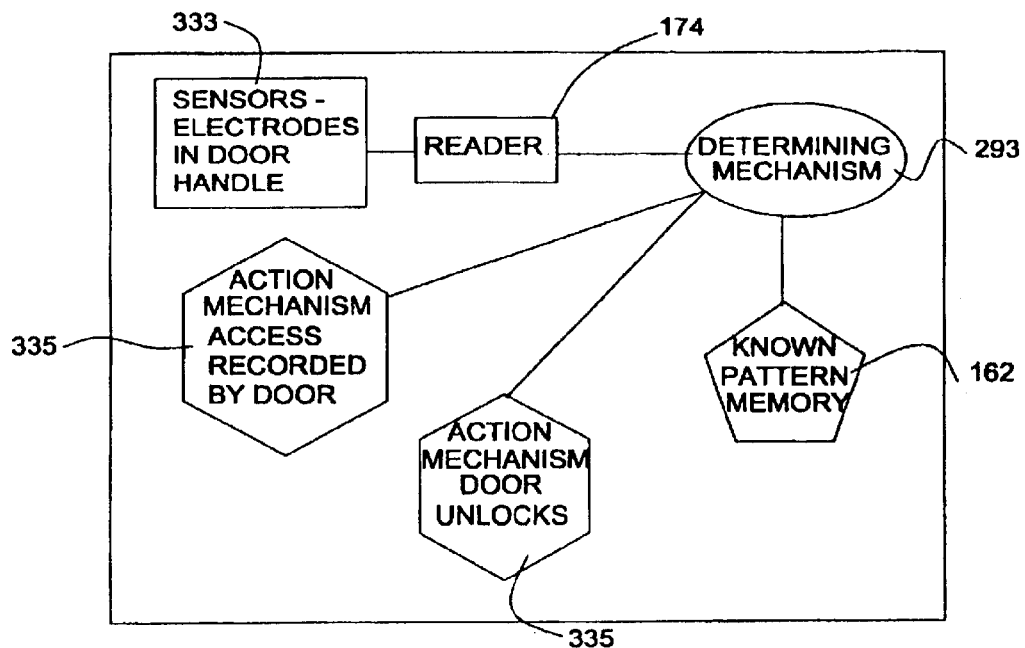
Figure 170A:
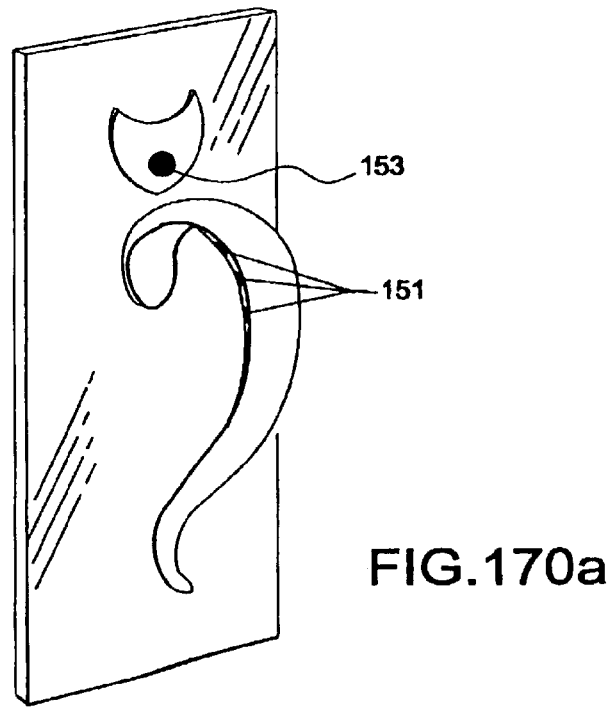
Figure 171:
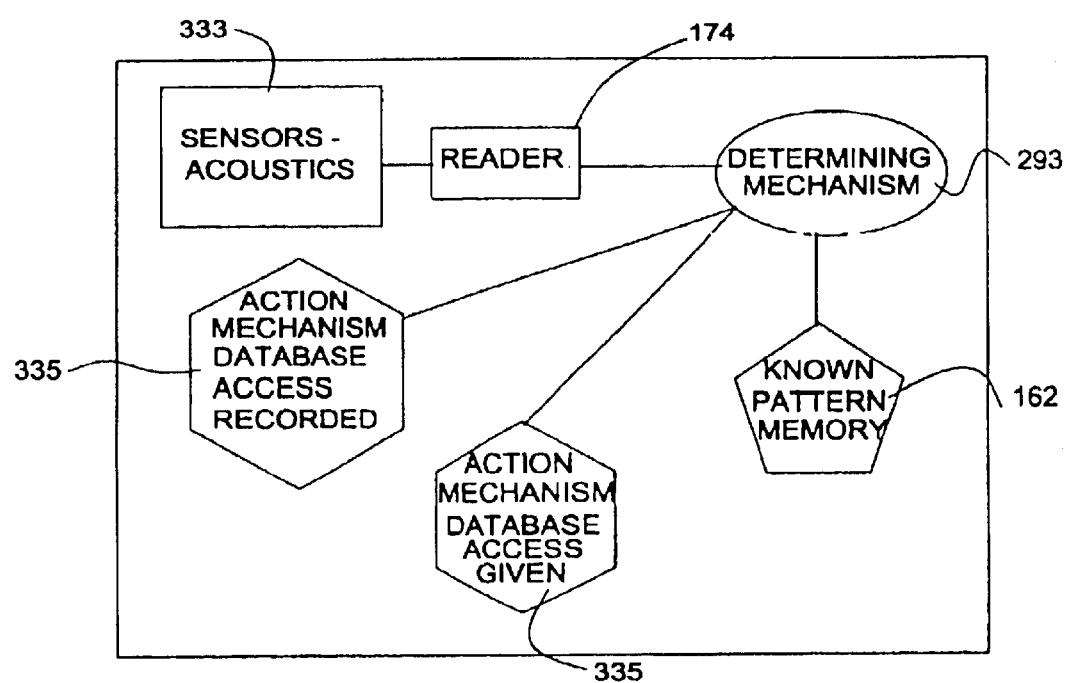
Figure 171A:
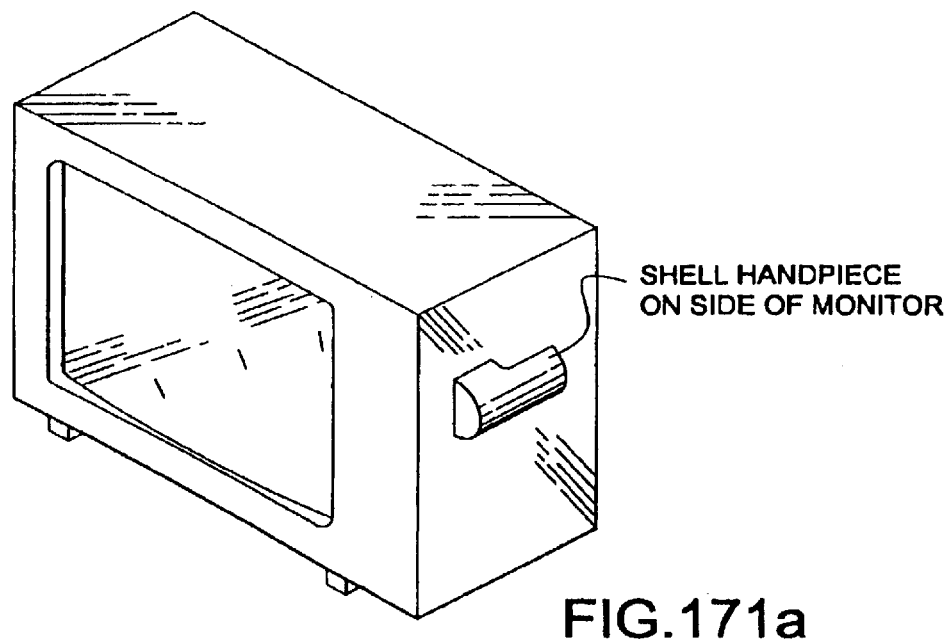
Figure 171B:
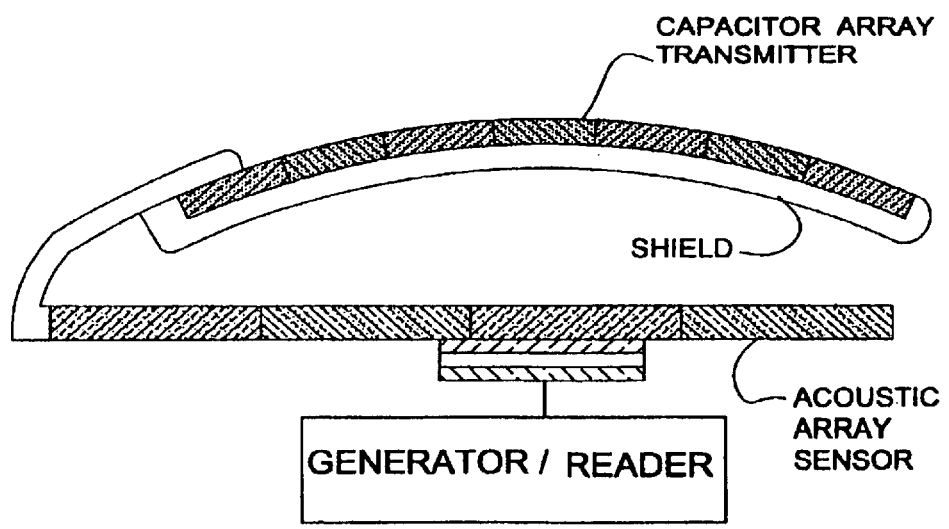
Figure 172:
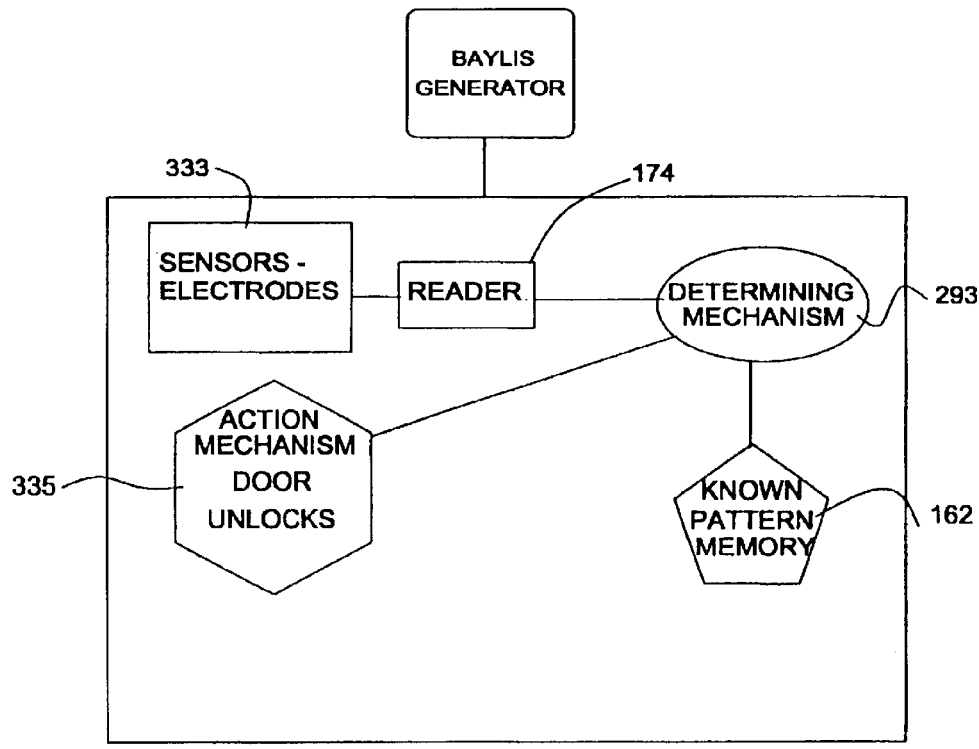
Figure 173:
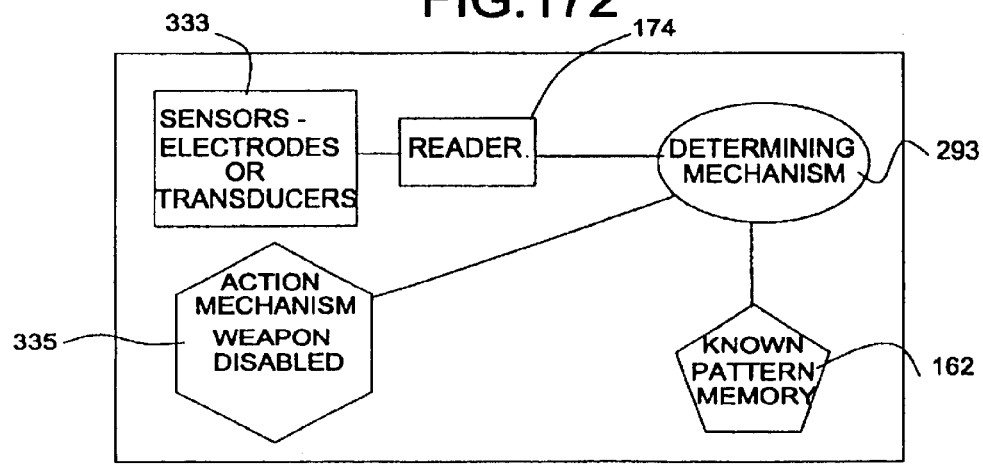
Figure 174:
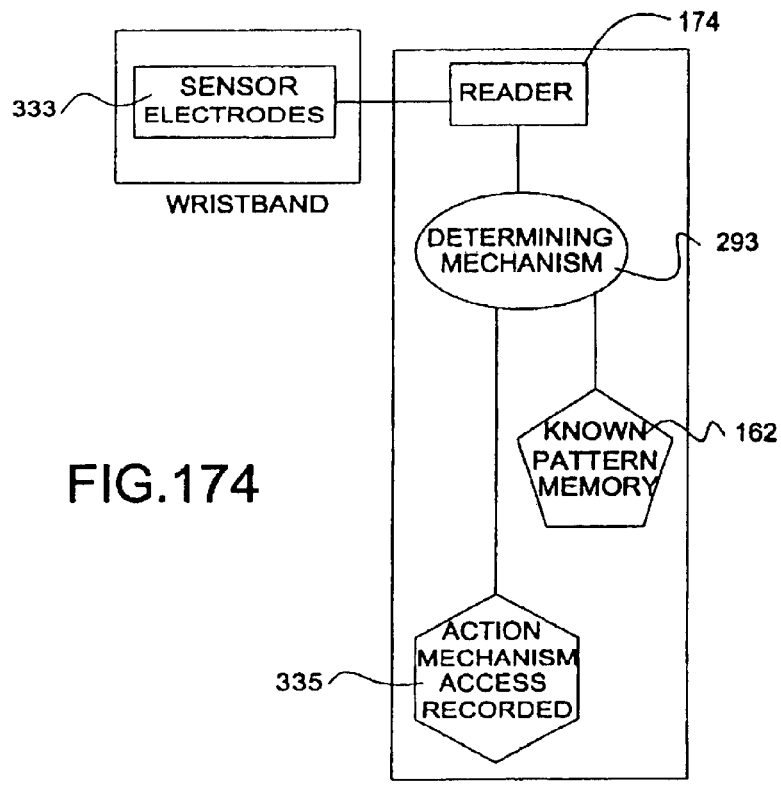
Figure 175:
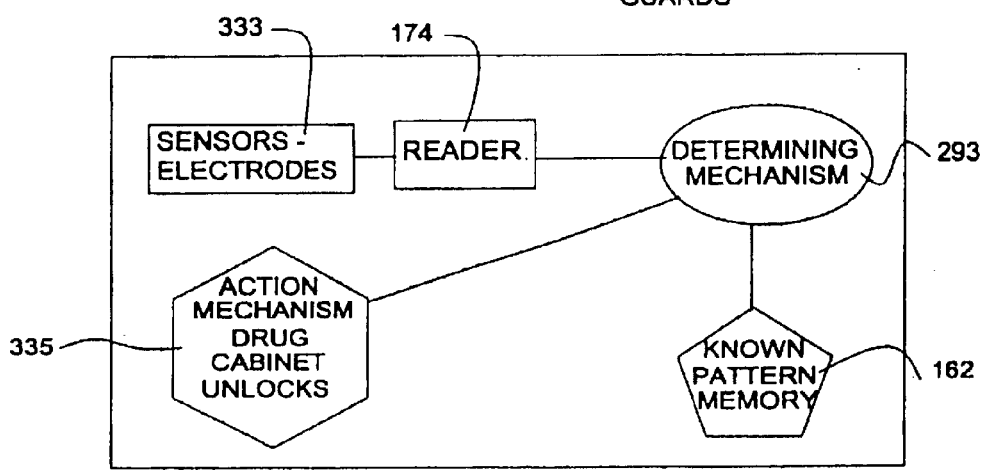
Figure 176:
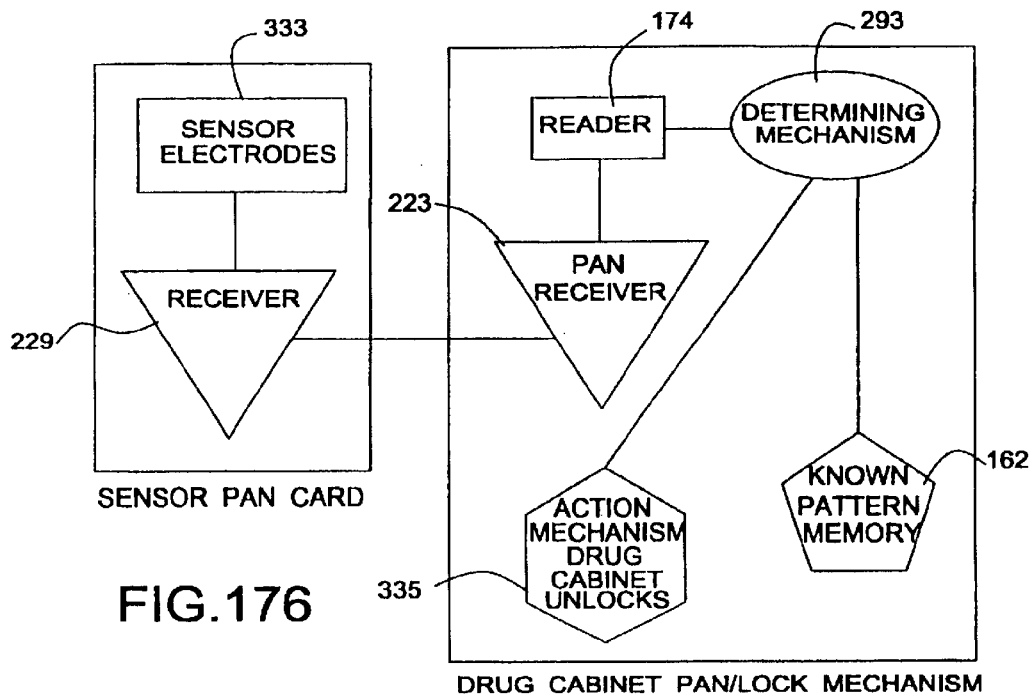
Figure 177:
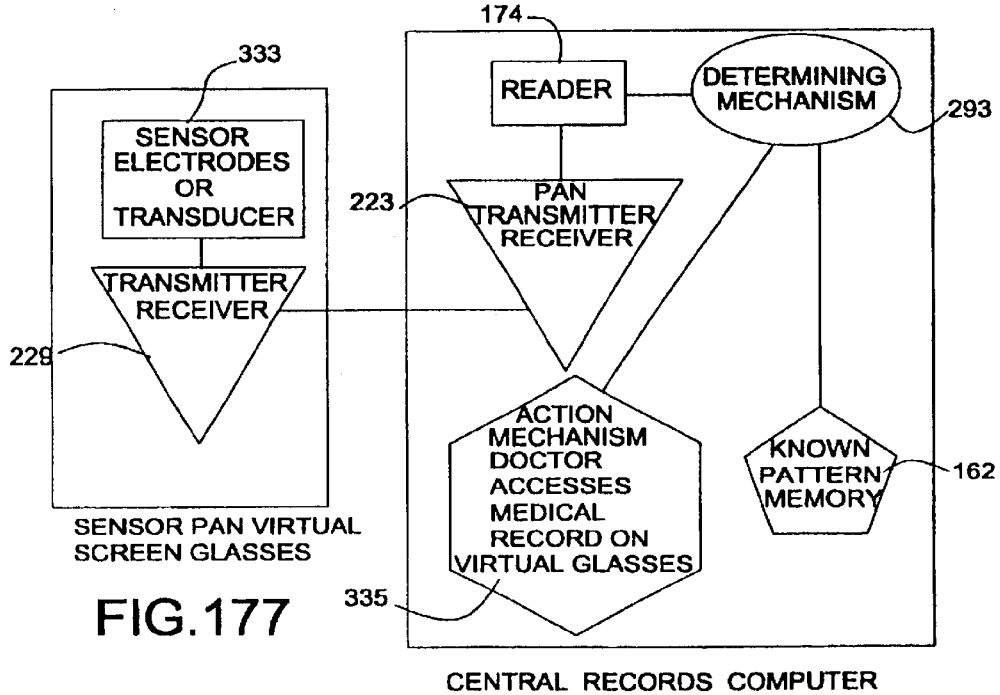
Figure 177A:
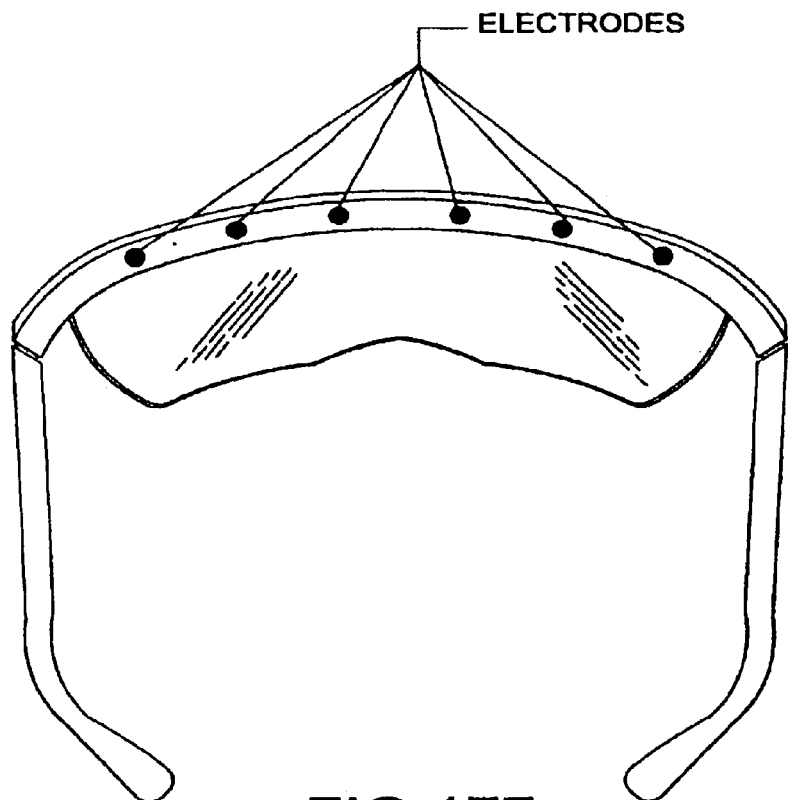
Figure 177B:
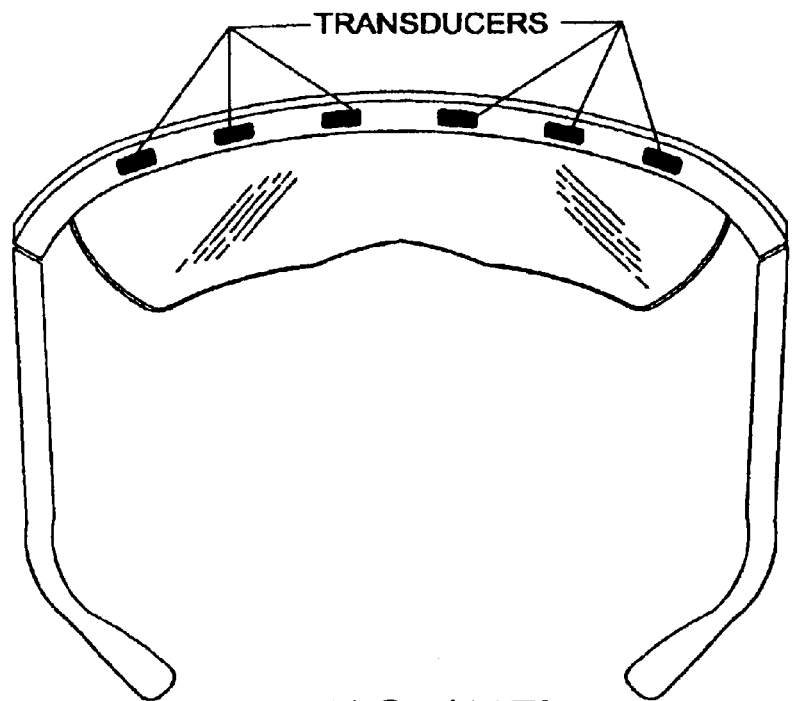
Figure 178:
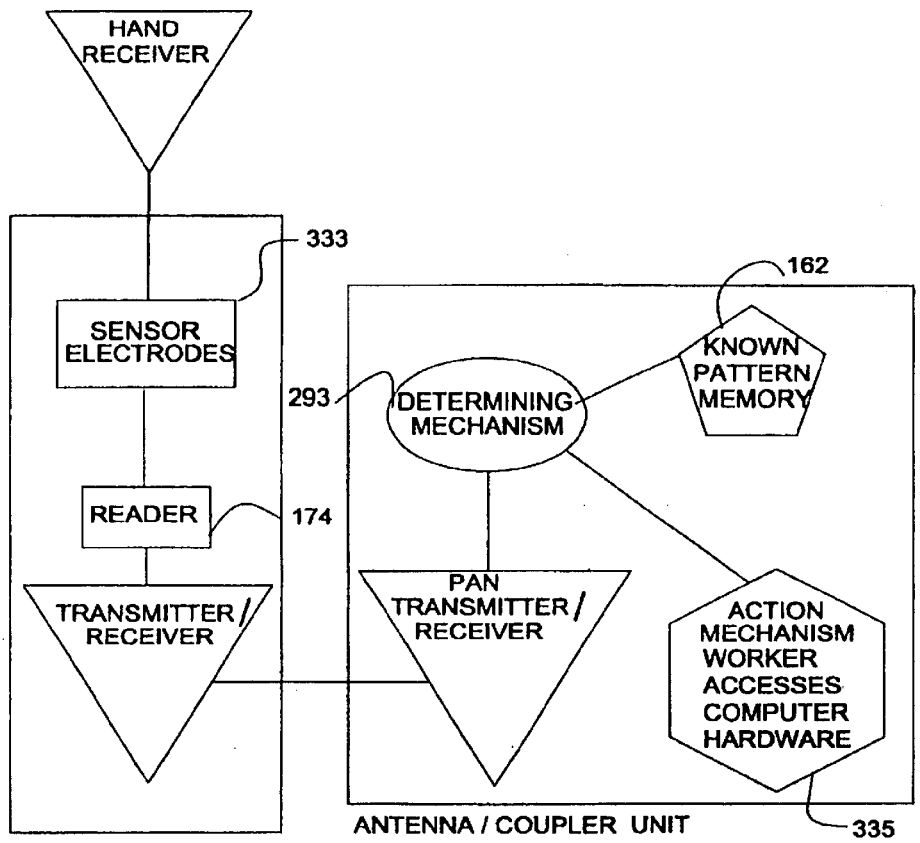
Figure 178A:
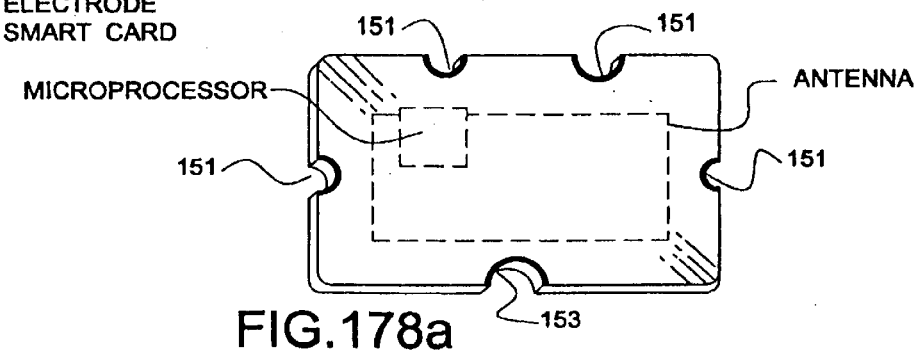
Figure 179:
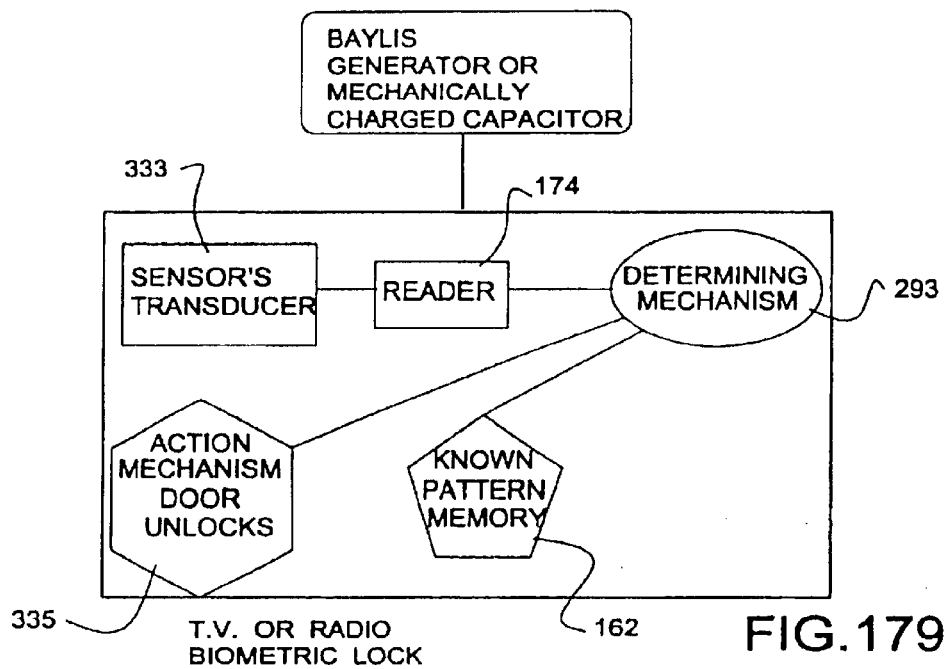
Figure 180:
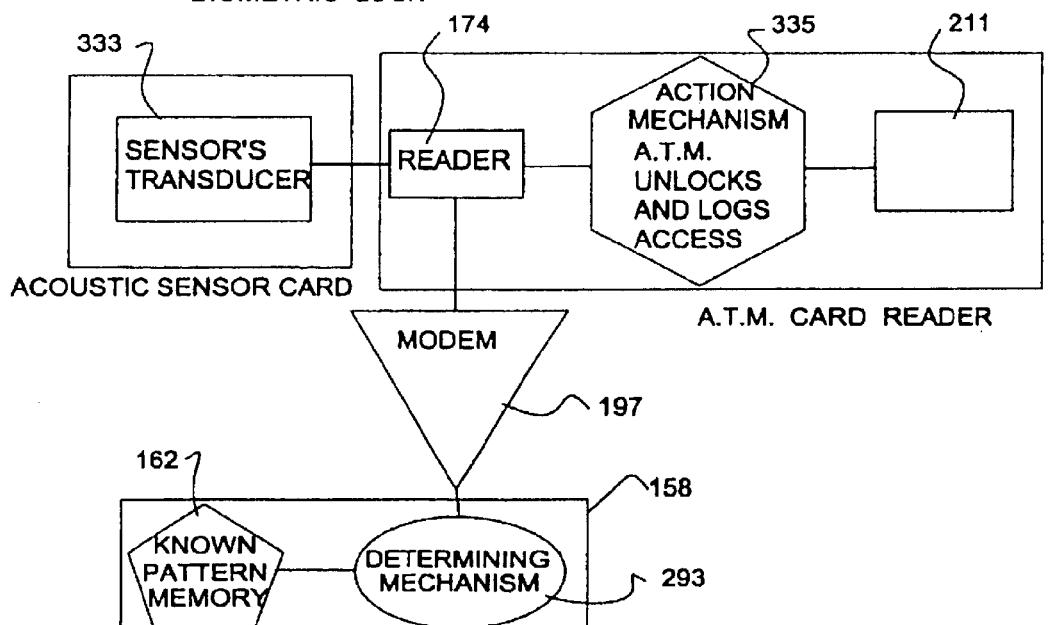
Figure 181:
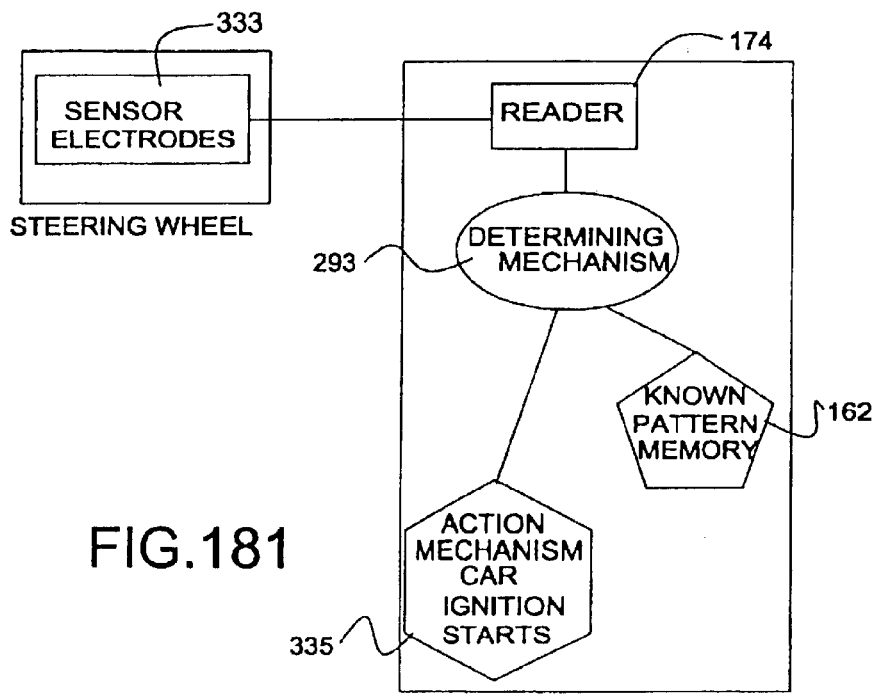
Figure 182:
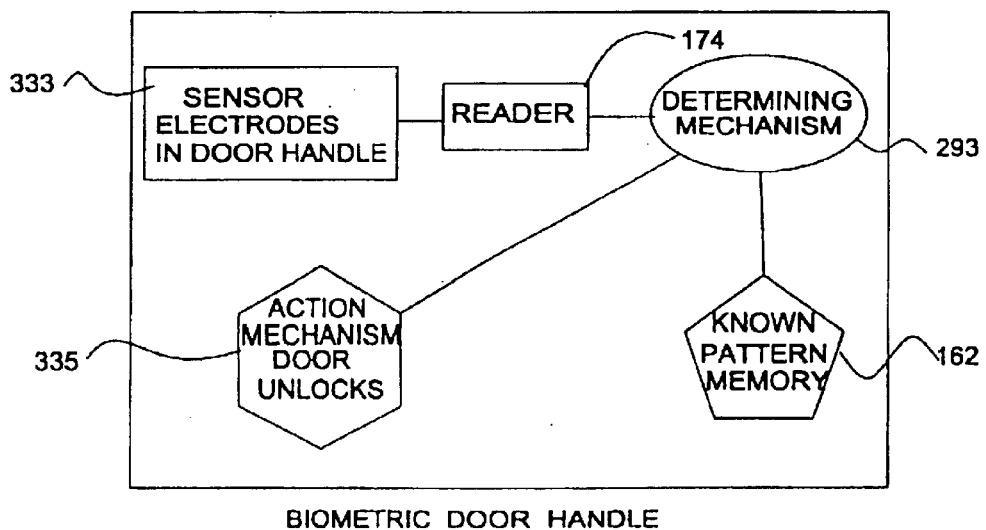
Figure 182A:
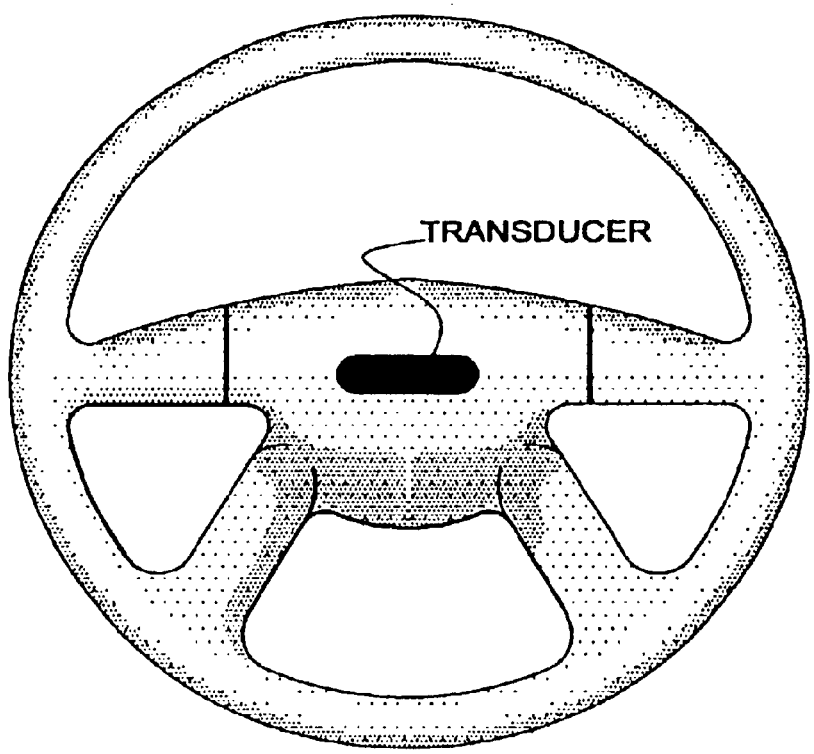
Figure 182B:
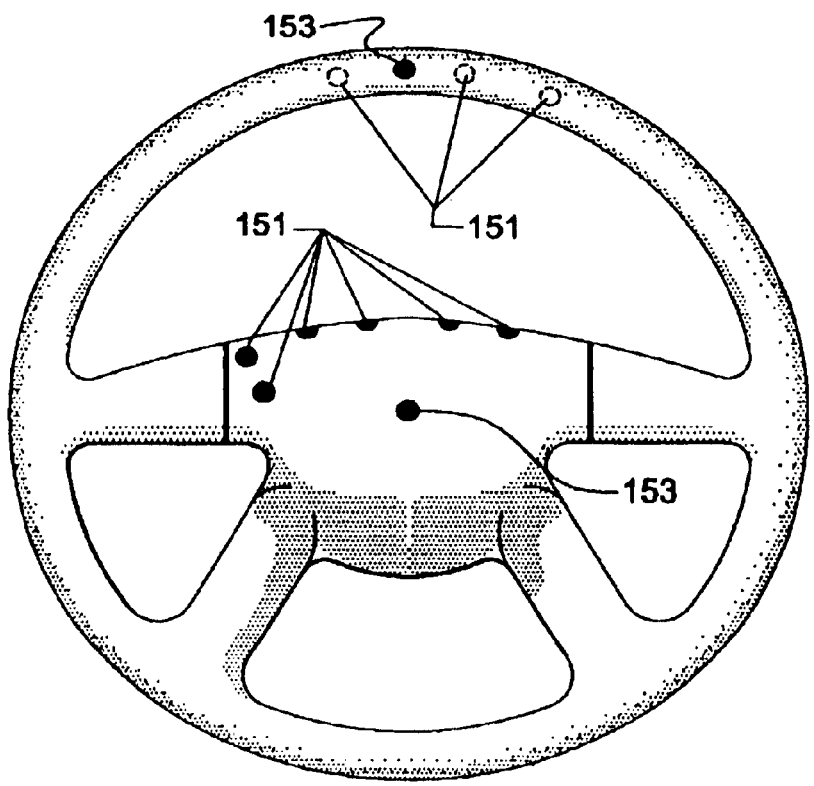
Figure 183:
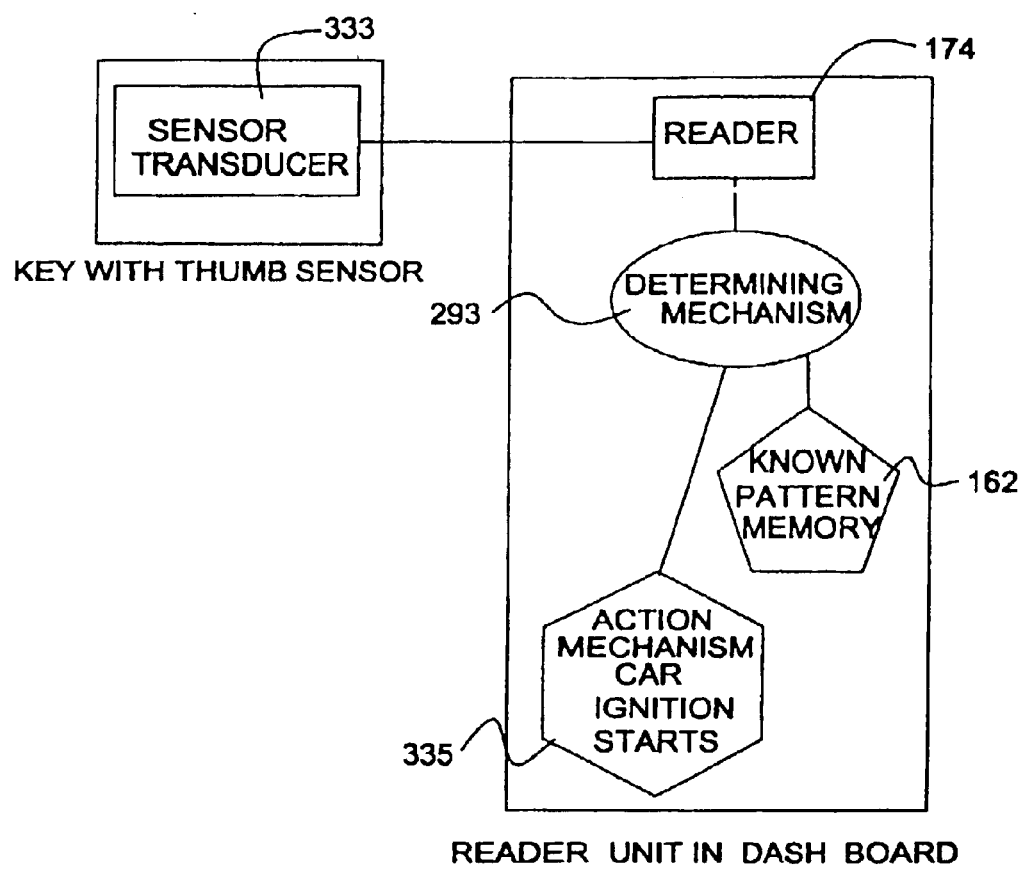
Figure 183A:
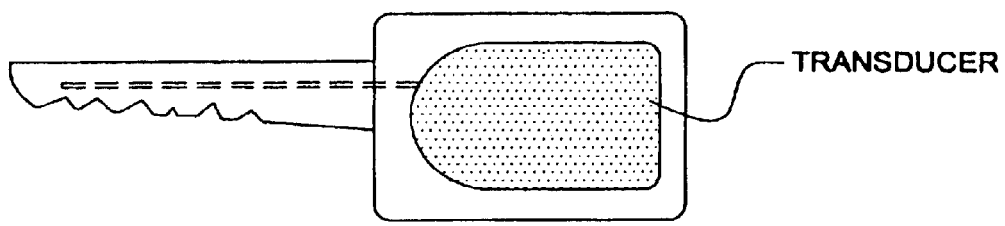
Figure 183B:
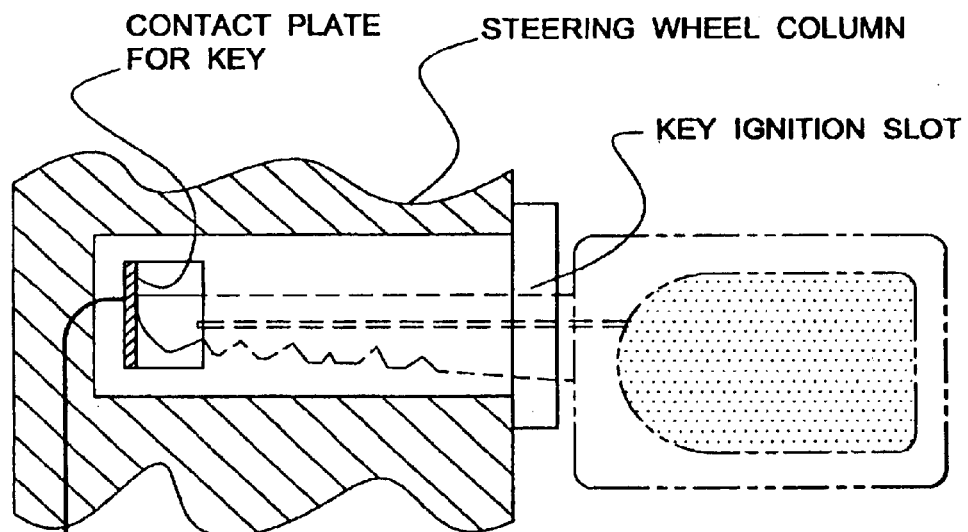
Figures 184, 185:
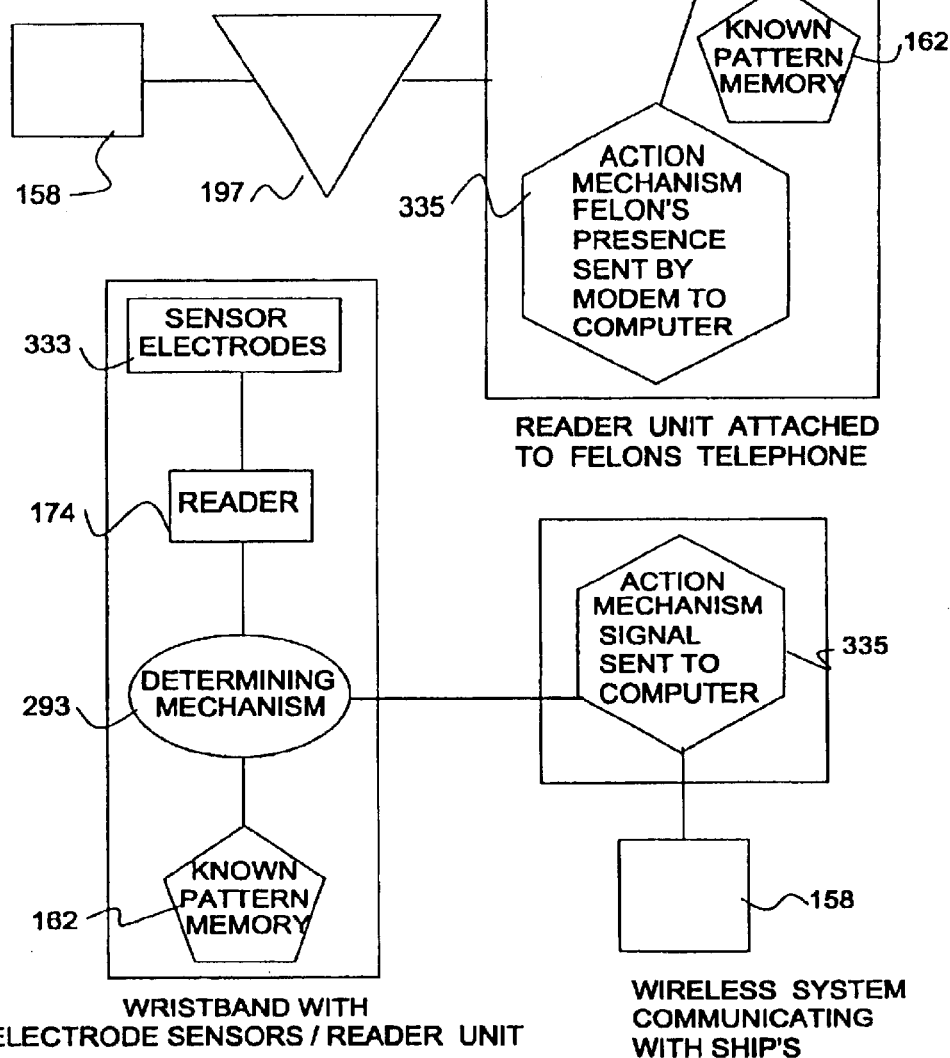
Figure 185A:
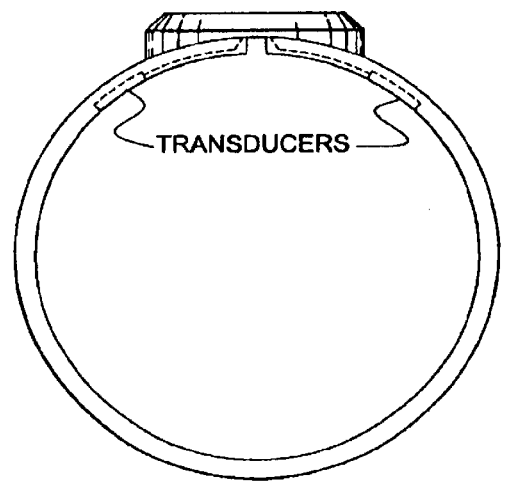
Figure 185B:
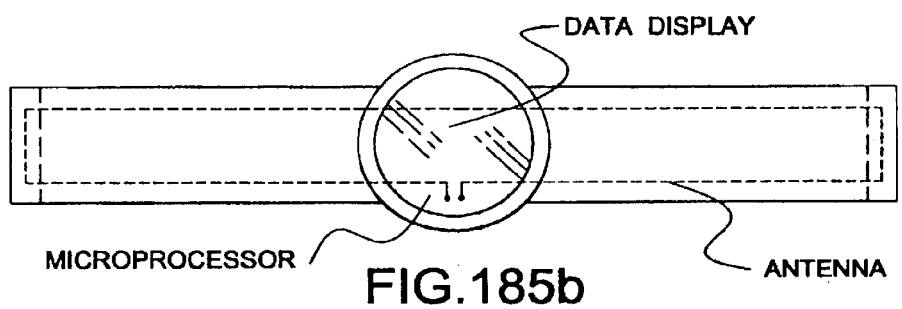
Figure 185C:
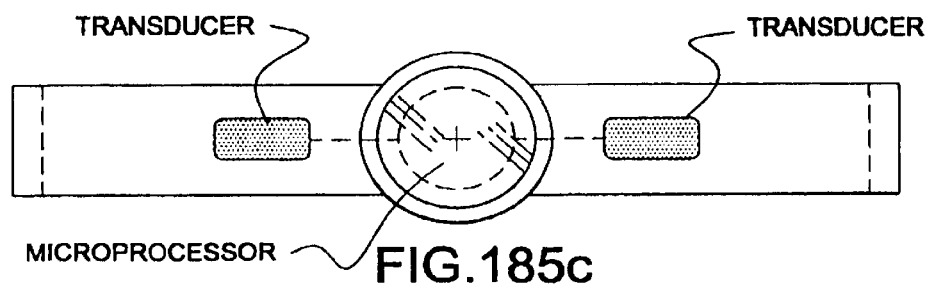
Figure 185D:
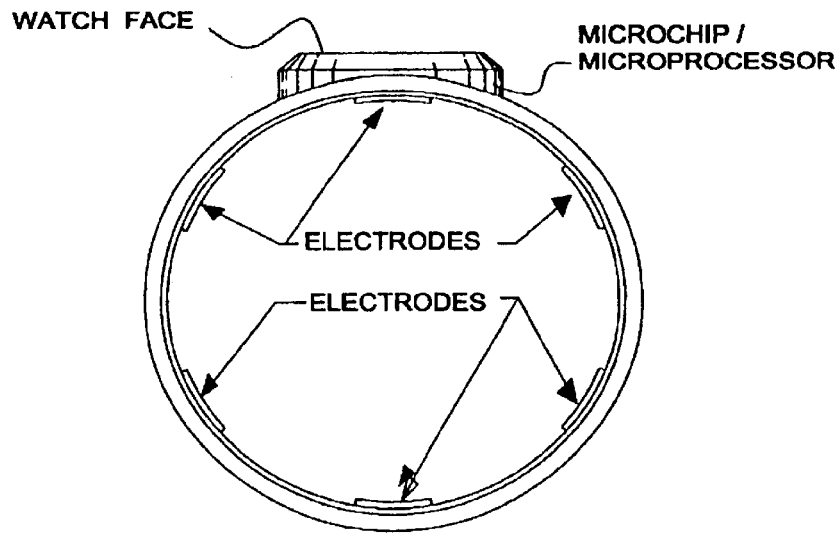
Figure 185E:
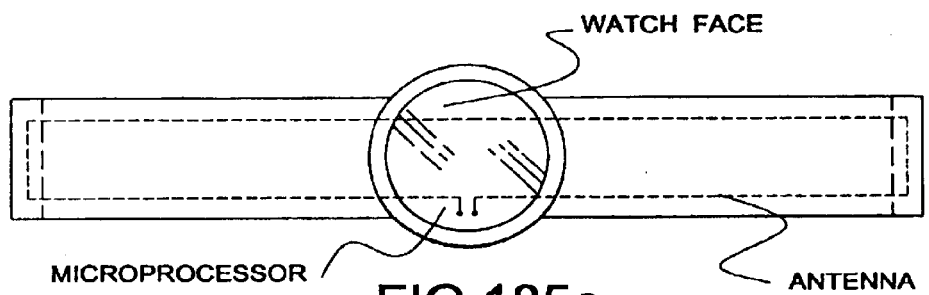
Figure 185F:
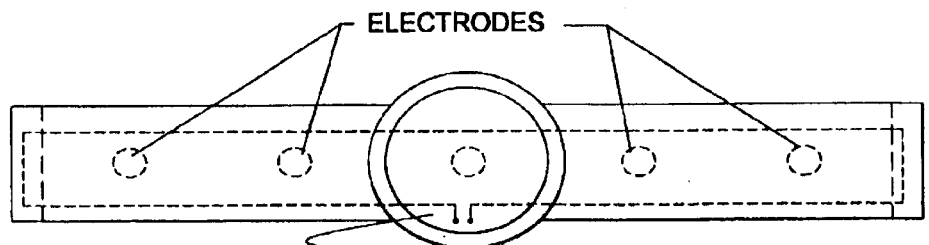
Figure 192:
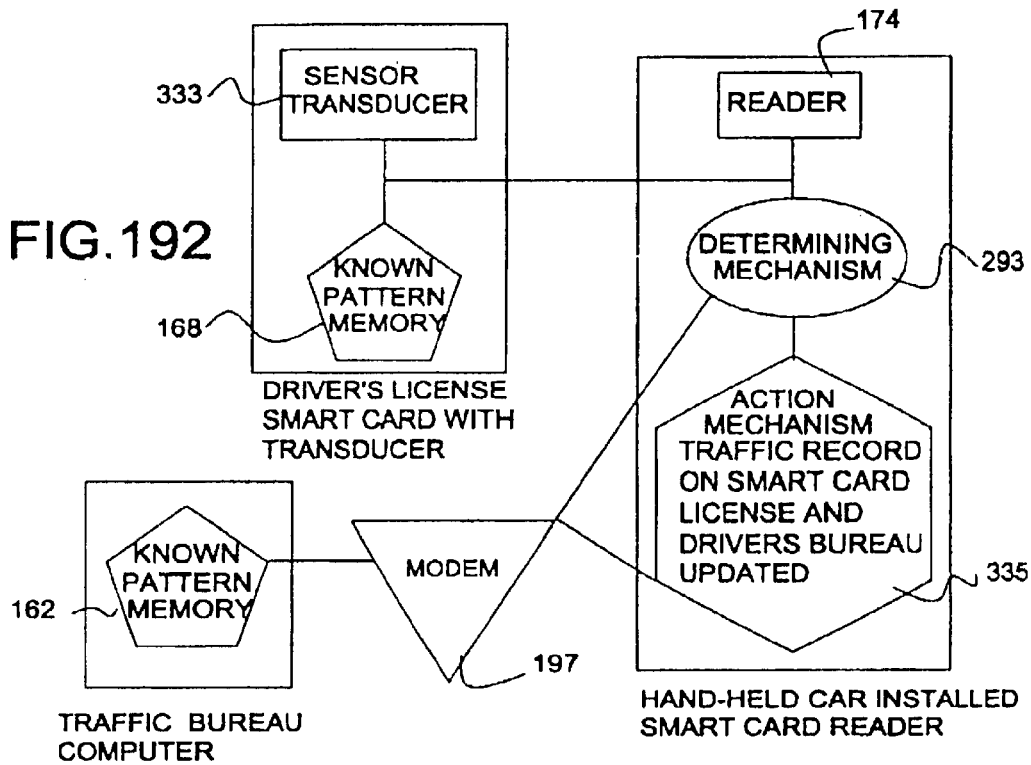
Figure 193:
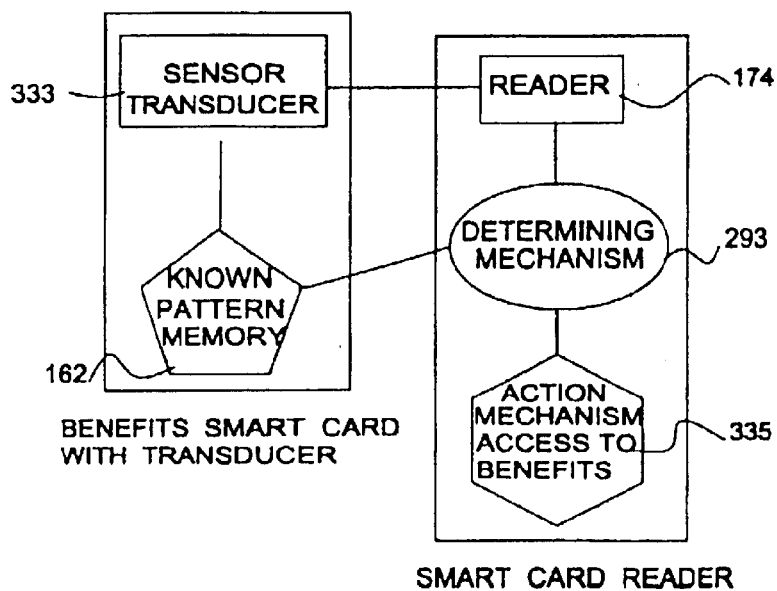
Figure 194:
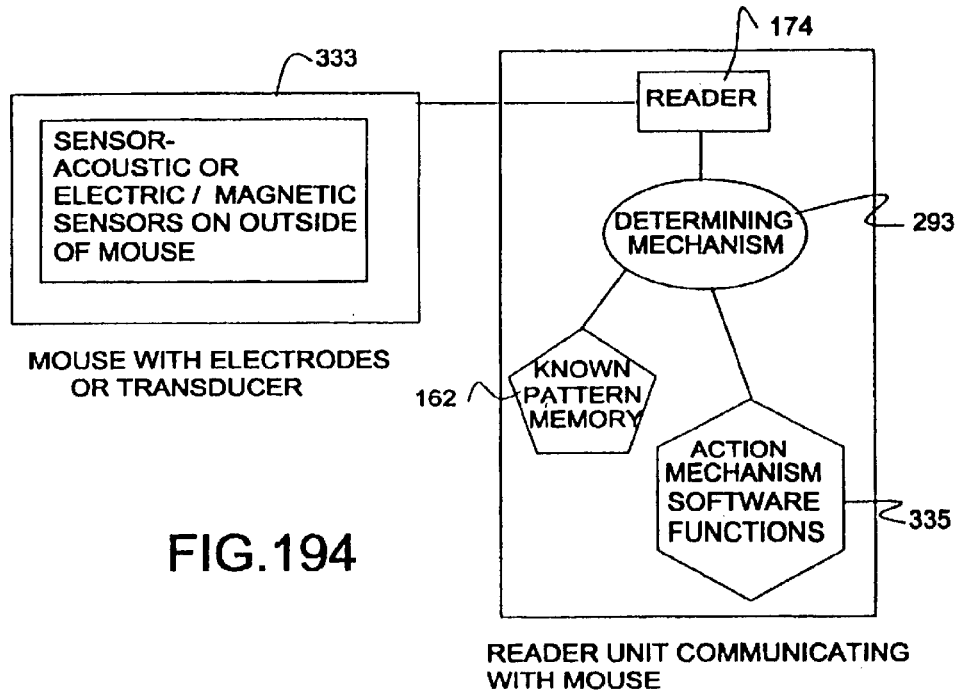
Figure 195:
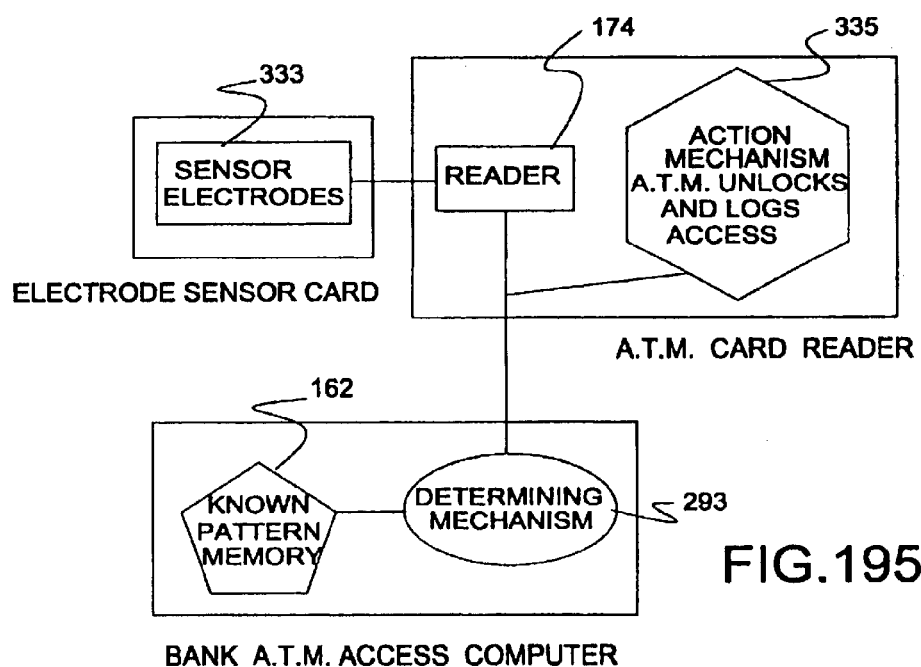
Figure 196:
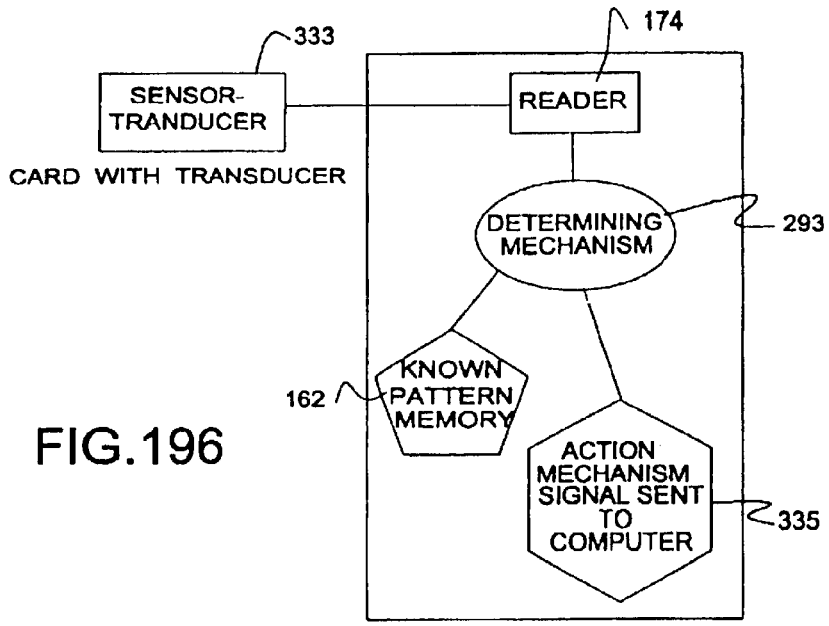
Figure 197:
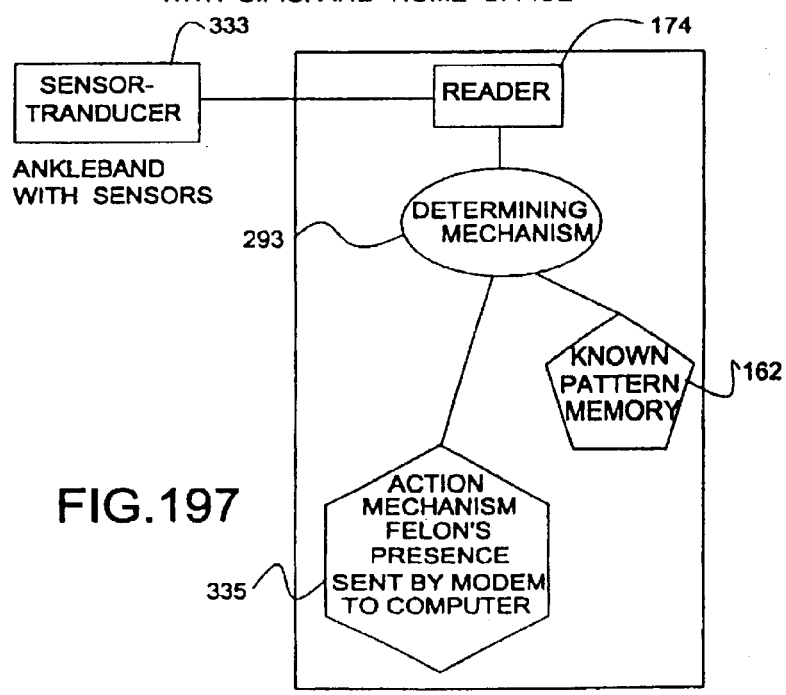
Figure 198:
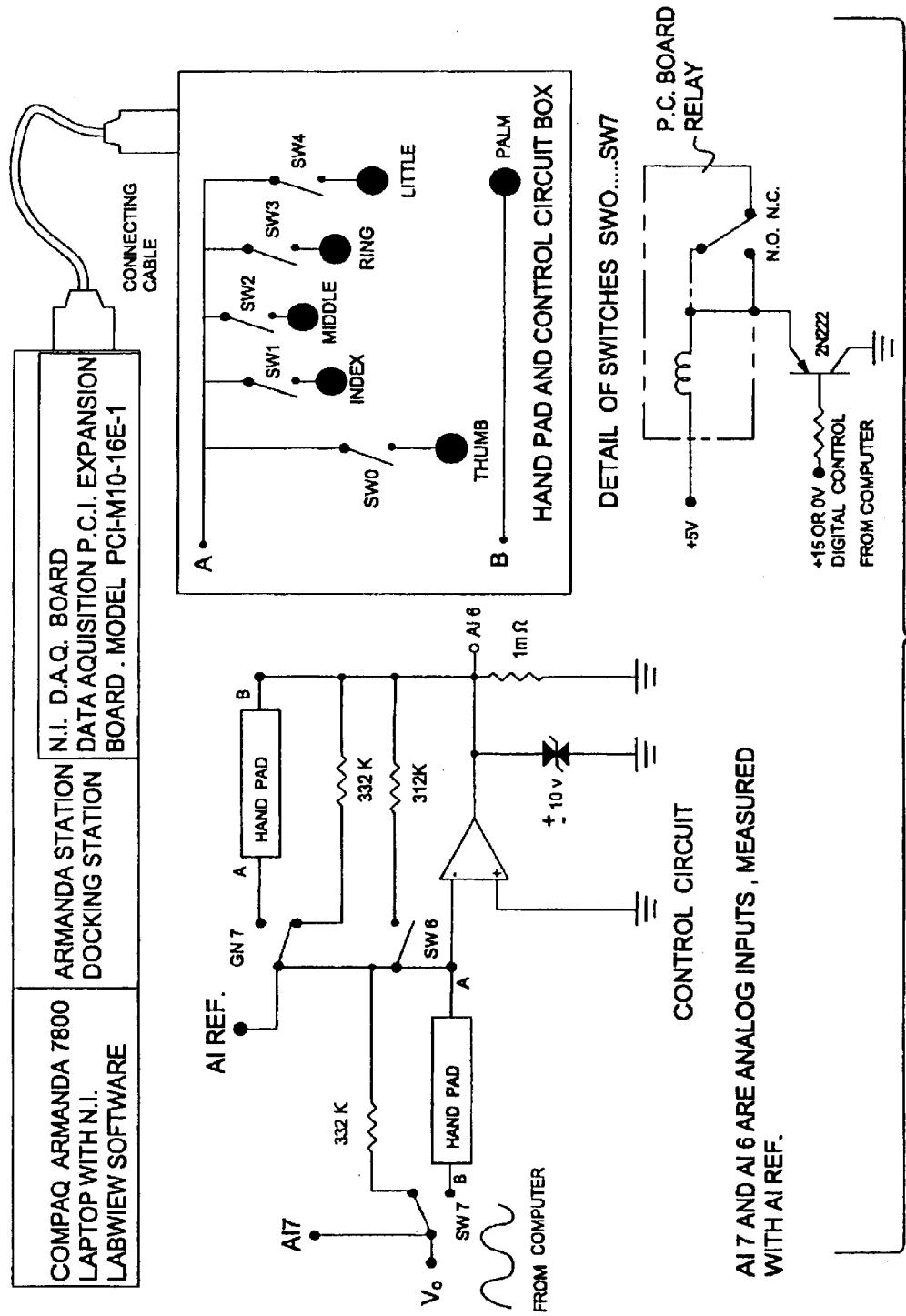
Figure 199:
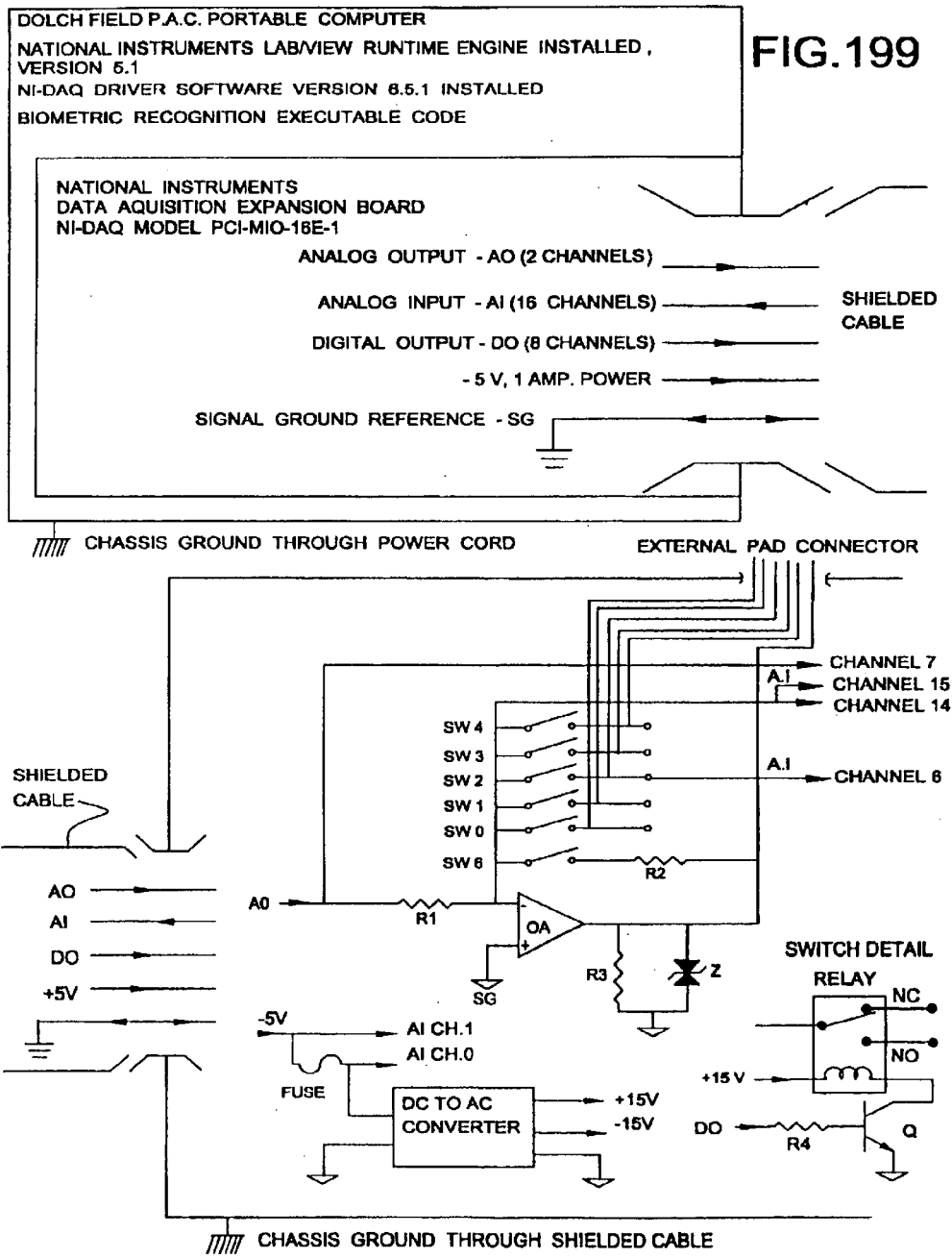
Figure 201:
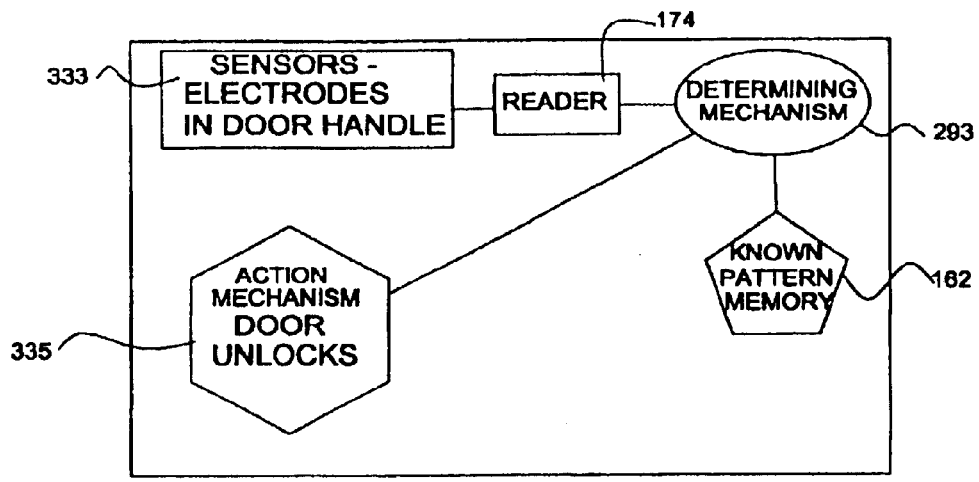
Figure 202:
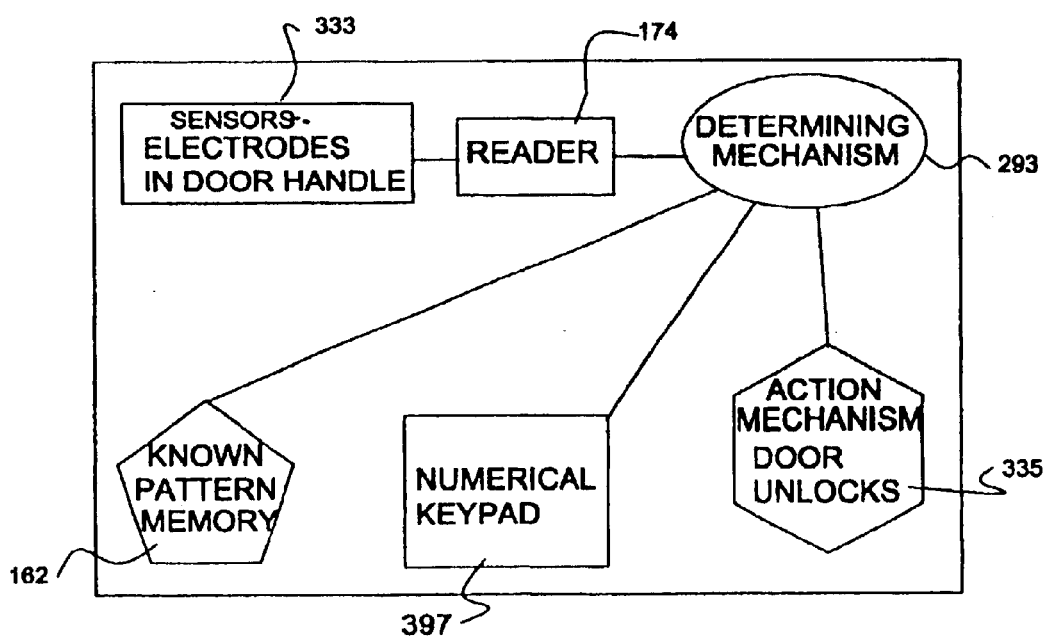
Figure 203:
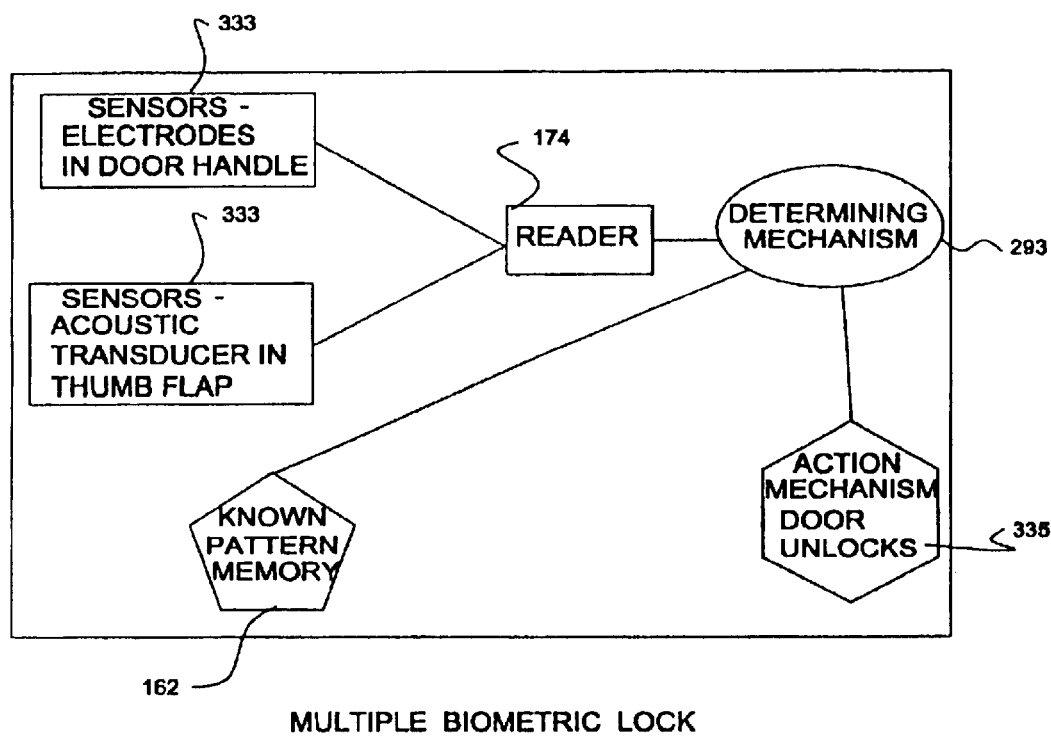
Figure 204:
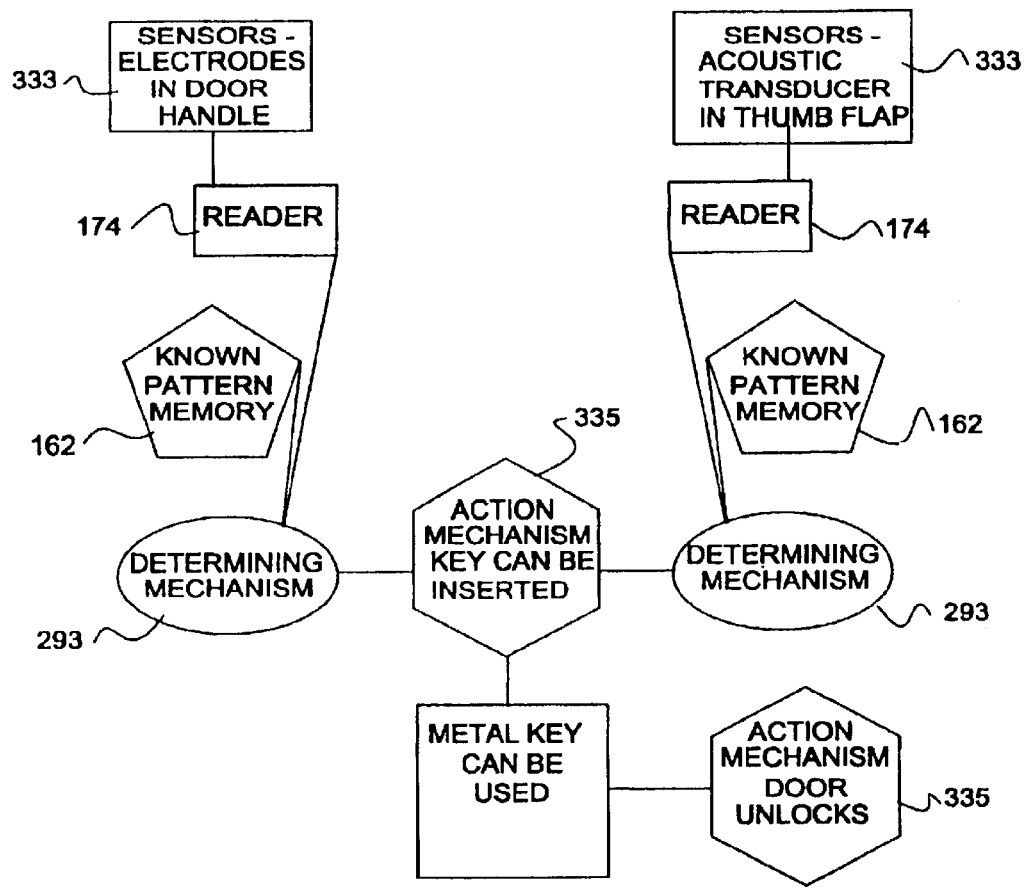
Figure 205:
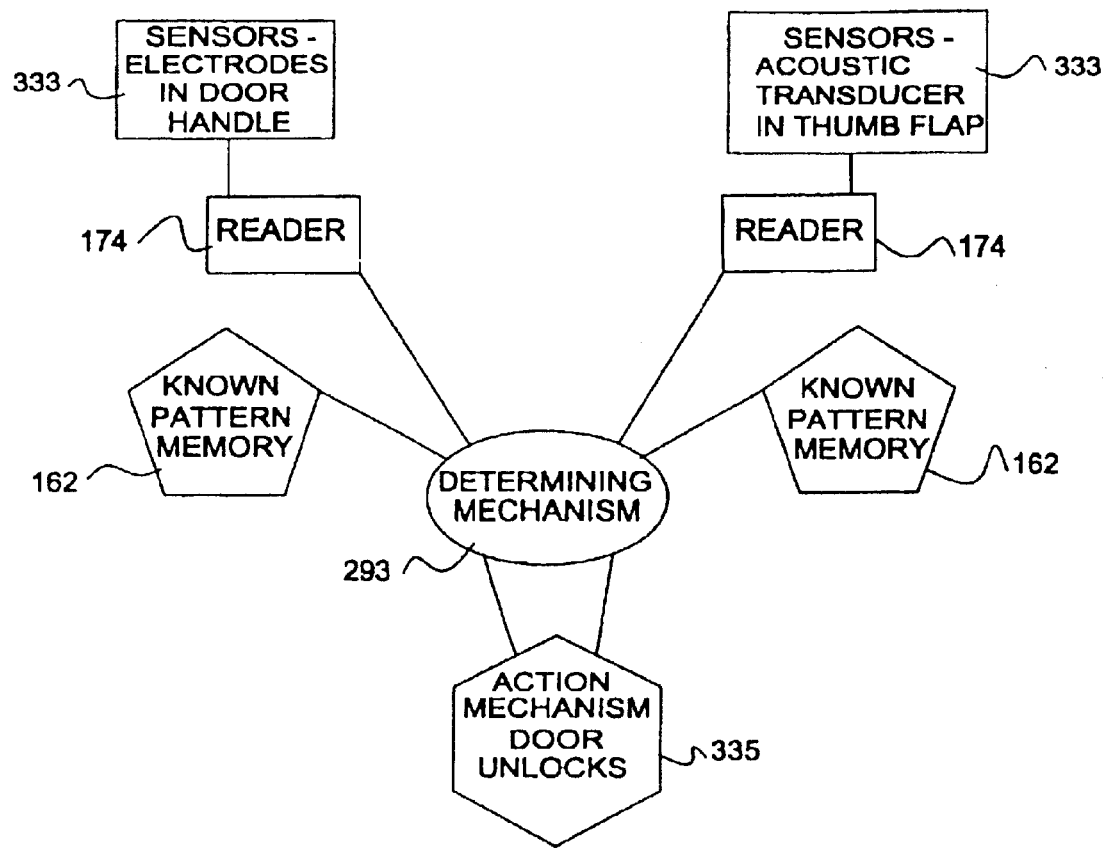
Figure 206:
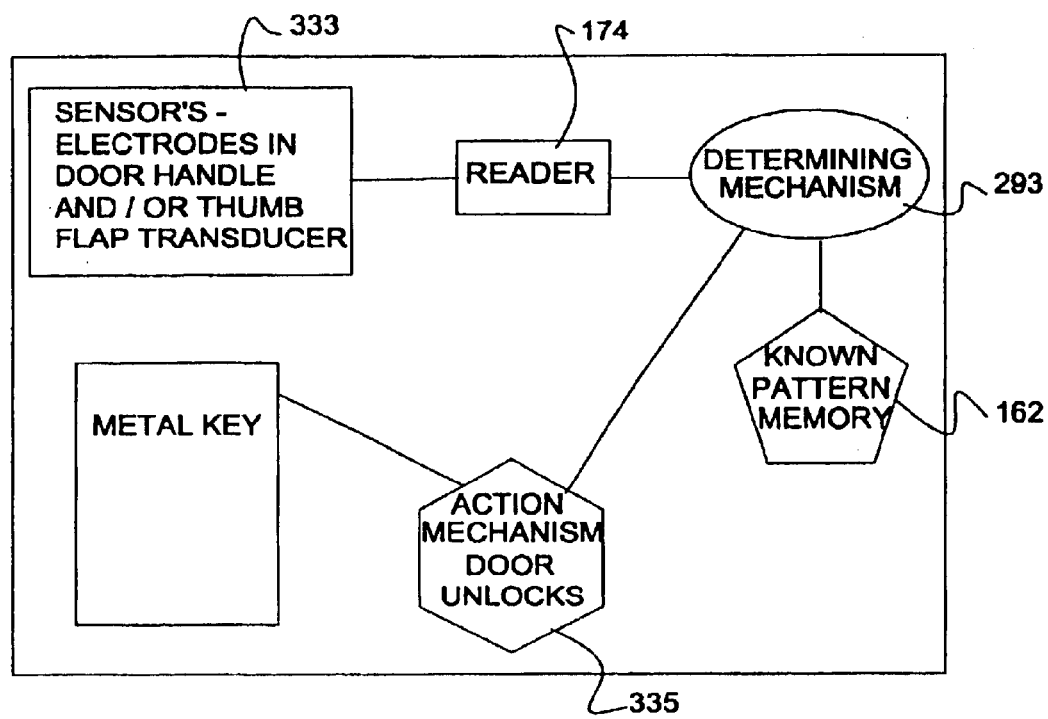

FIG. 133 is a schematic of a unit for electronic payment authorization;

FIG. 134 is a schematic of an MSA electrode card and reader;

FIG. 135 is a schematic of an MSA smart card, which stores account and biometric information, and a reader;

FIG. 136 is a schematic of a portable electrode telephone;

FIG. 137 is a schematic of a portable video phone with flip-up electrode sensor;

FIG. 138 is a schematic of a television lock-out hand piece unit;

FIG. 138a is a perspective view of a television with a biometric lock;

FIG. 138b is a perspective view of a radio having a biometric lock;

FIG. 139 is a schematic of a pay-TV electrode card;

FIG. 140 is a schematic of a pay-TV touchless electric field sensor/reader and contact card with memory, FIG. 141 is a schematic of an airline check-in hand unit;

FIG. 142 is a schematic of an airline remote check-in hand unit;

FIG. 143 is a schematic of an airline touchless check-in hand unit and memory stick;

FIG. 144 is a schematic of an airline touchless remote check-in hand unit with memory stick;

FIG. 145 is a schematic of a customs electronic/sensor passport unit;

FIG. 146 is a schematic of a customs touchless and contactless electronic passport;

FIG. 147 is a schematic of a brokerage wireless PC transaction unit;

FIG. 148 is a schematic of a brokerage wireless PC transaction unit;

FIG. 148a is a perspective view of a lap-top computer having a sensor unit;

FIG. 148b is an enlarged view of the FIG. 148a sensor unit;

FIG. 148c is a side view of the FIG. 148b sensor unit;

FIG. 149 is a schematic of a retail electrode card unit used for redeemable points;

FIG. 150 is a schematic of a remote version of the retail electrode card unit of FIG. 149;

FIG. 151 is a schematic of a retail electrode card unit having a touchless;

FIG. 152 is a schematic of a smart card driver's license;

FIG. 153 is a schematic of a smart car passport;

FIG. 154 is a schematic of a computer room access unit;

FIG. 155 is a schematic of a security room access unit;

FIG. 156 is a schematic of a sensor smart identification card;

FIG. 157 is a schematic of an employee access monitoring and time tracking unit;

FIG. 158 is a schematic of an electronic medical record notepad;

FIGS. 158a and 158b are perspective views of an electronic medical record notepad;

FIG. 159 is a schematic of a smart sensor wristband;

FIG. 160 is a schematic of a social services card;

FIG. 161 is a schematic of a biometric glove;

FIGS. 161a and 161b are perspective views of a biometric glove;

FIG. 162 is a schematic of a software licensing unit;

FIGS. 162a and 162b are schematic views of a mouse having sensors, while FIG. 162c is an enlarged side view of the mouse sensor, FIG. 163 is a schematic of a discrete biometric lock;

FIGS. 163a, 163b, 163c and 163d are schematics of door handles with electrode sensors;

FIGS. 163e, 163f, 163g and 163h are schematics of door handles with acoustic sensors;

FIG. 164 is a schematic of a composite biometric lock;

FIG. 165 is a schematic of a multiple biometric lock;

FIG. 166 is a schematic of an optional biometric lock;

FIG. 167 is a schematic of another optional biometric lock;

FIG. 168 is a schematic of another multiple biometric lock;

FIG. 169 is a schematic of a laboratory access unit;

FIG. 170 is a schematic of a door handle electrode;

FIG. 170a is a perspective view of a door handle with electrodes;

FIG. 171 is a schematic of a restricted database access unit;

FIG. 171a is a perspective view of a monitor having a restricted access database mounting a shell hand piece; while FIG. 171b is a side view of the shell hand piece;

FIG. 172 is a schematic of a remote site entry door lock unit without power grid electricity;

FIG. 173 is a schematic of a weapon security device;

FIG. 174 is a schematic of a closed property access unit;

FIG. 175 is a schematic of a drug cabinet access unit;

FIG. 176 is a schematic of a drug cabinet access unit with PAN cards;

FIG. 177 is a schematic of medical record access unit having a forehead biometric sensing unit;

FIGS. 177a and 177b are top views of two forms of a sensor virtual screen glasses sensing units;

FIG. 178 is a schematic of a computer hardware access unit;

FIG. 178a is a top view of a scalloped electrode card;

FIG. 179 is a schematic of a portable TV or radio unit;

FIG. 180 is a schematic of an ATM hardware access unit;

FIG. 181 is a schematic of a vehicle steering wheel unit;

FIG. 182 is a schematic of a vehicle door access unit;

FIGS. 182a and 182b are front views of biometric vehicle steering wheel units;

FIG. 183 is a schematic of a vehicle sensor key access unit;

FIG. 183a is a side view of a vehicle sensor key;

FIG. 183b is a side view of a vehicle sensor key reader,

FIG. 184 is a schematic of an ankleband house arrest unit;

FIG. 185 is a schematic of a shipboard crew locator system;

FIGS. 185a, 185b and 185c are views of a contactless acoustic band unit;

FIGS. 185d, 185e and 185f are views of a contactless electrode watch unit;

FIG. 186 is a schematic of a GPS locator/verification unit;

FIG. 187 is a schematic of a remote control biometric unit;

FIG. 188 is a schematic of an MSA transducer card reader;

FIG. 189 is a schematic of a portable video phone with molded transducer;

FIG. 190 is a schematic of a pay-TV transducer card reader;

FIG. 191 is a schematic of an acoustic hand piece at a cash register;

FIG. 192 is a schematic of a driver's license reader unit;

FIG. 193 is a schematic of a smart card reader;

FIG. 194 is a schematic of a mouse sensor,

FIG. 195 is a schematic of a card ATM reader-ATM computer;

FIG. 196 is a schematic of a card-wireless car system;

FIG. 197 is a schematic of an ankleband sensor;

FIGS. 198 and 199 are detailed schematics of hand piece electric circuits;

FIG. 200 is a block diagram of an alternative embodiment of an apparatus for authorizing an action;

FIG. 201 is a schematic of a discrete biometric lock system;

FIG. 202 is a schematic of a composite biometric lock system;

FIG. 203 is a schematic of a multiple biometric lock system;

FIG. 204 is a schematic of a composite multiple biometric lock system;

FIG. 205 is a schematic of an optional multiple biometric lock system;

FIG. 206 is a schematic of an optional composite biometric lock system; and

Figure 207:
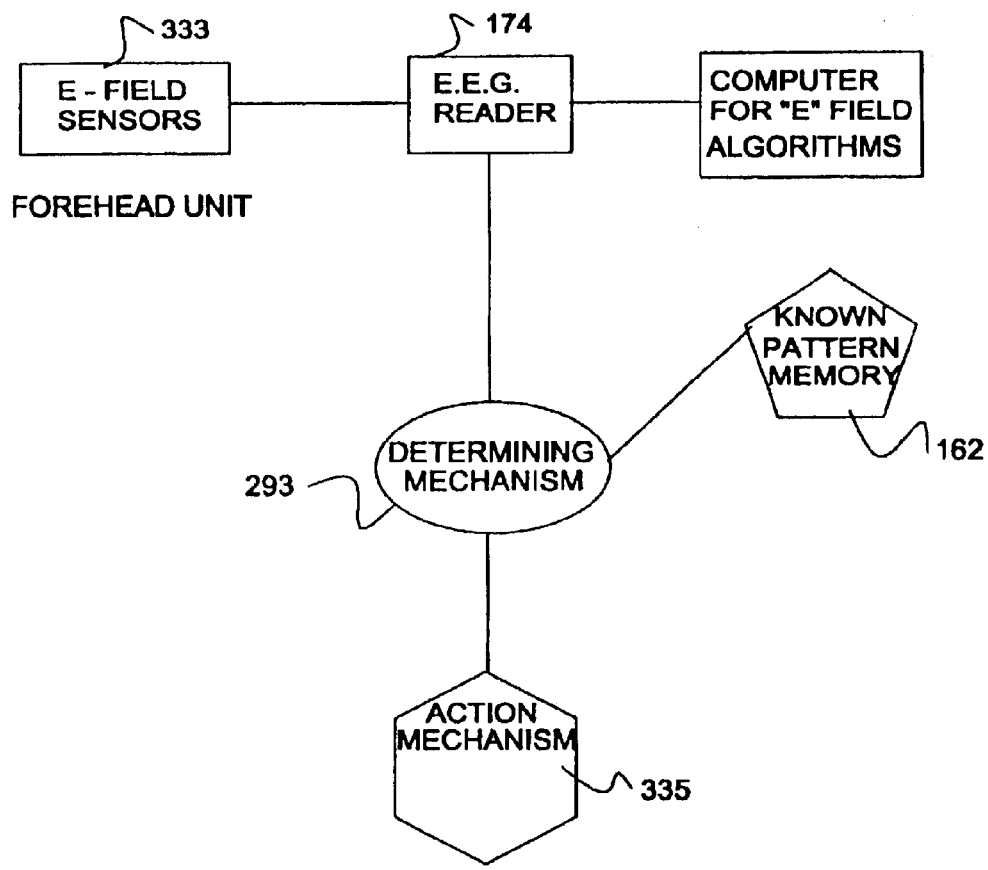

FIG. 207 is a schematic of another embodiment of an apparatus for authorizing an action.

DESCRIPTION OF PREFERRED EMBODIMENTS

The preferred embodiments of the present invention and their advantages are best understood by referring to FIGS. 1–11 of the drawings.

Before explaining the present invention in its best mode, a general explanation of electrical and magnetic properties will help to provide a better understanding of the invention. For purposes herein the term "field" includes, but is not limited to, waves, current, flux, resistance, potential, radiation or any physical phenomena including those obtainable or derivable from the Maxwell equations.

The electrical conductivity of a body segment of an individual organism depends upon a number of factors, including the length and cross-sectional area of a segment of tissue, and the composition of tissue, including lean and fatty tissue. There may be day-to-day variations in conductivity and other electrical measurements due to body weight adjustments and changes in body fluids and electrolyte composition, but the changes are fairly consistent through the different body segments being analyzed, because of the systemic physical characteristics of each organism. For instance, it is well known, in regard to clinical impedance measurements, that the impedance variations in a subject due to physiological changes, are smaller than the variability among normal subjects.

When measuring electrical and/or magnetic properties of an individual for biometric recognition purposes, whether applying energy by the contact method or by the non-contact method, several different measurements may be utilized, such as impedance, resistance, reactance, phase angle, current, or voltage differential across a measured body segment. For instance, impedance is a function of two components, i.e. the resistance of the tissue to the flow of current and reactance, which is additional opposition to the current due to the capacitant effect of membranes, tissue interfaces, and other biocapacitant tissue.

Many bioimpedance measurements in the prior art depend on the assumption that the relationship of body composition, such as body fluid and tissue mass, is dynamic, and that fluctuations occur. As fluids increase in the tissue, the bioimpedance signal decreases in value, because the segment being measured has an increase in conductive potential due to the increase in fluid volume. Increases in segmental fluid volume will decrease bioimpedance values. Decreases in segmental fluid will decrease the conductive potential and thus increase the bioimpedance value. However, it been found that the daily fluctuation in bioempedence value is consistent systemically through the body, and that the overall ratio between impedance values taken from different segments of a body part will remain constant.

Figure 1:
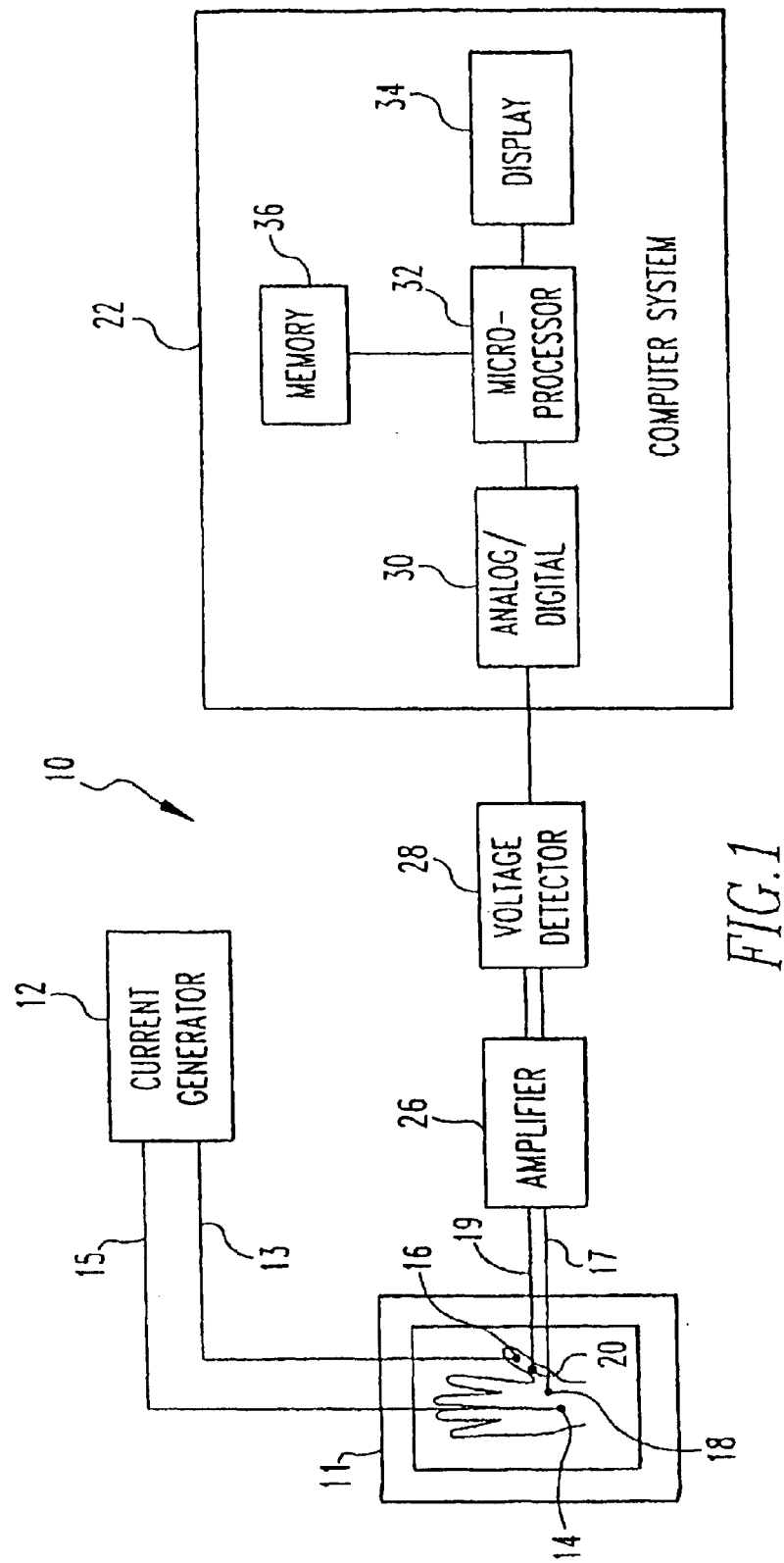
FIG. 1 is a block diagram illustrating one preferred embodiment of the present invention.

Referring now to the drawings, FIG. 1 illustrates an electrical current applied directly to the presented body part of a tested individual through surface contacting electrodes to generate a biometric pattern. A biometric recognition system 10 is a device which measures the electric and/or magnetic properties of a body segment by applying an input electrical signal in the form of a constant magnitude current to the body segment tissue and measuring the resulting voltage. Since R=V/I, the measured voltage yields either a relative or calculated resistance. The voltage or resistance pattern is unique for an individual.

According to this invention, a constant magnitude voltage signal is applied to the body part, and the resulting current is measured by a voltage detector 28 to determine the bioelectrical characteristics of the tested segment of the presented body part.

The contact system described below uses a constant magnitude alternating (AC) current source, although direct current (DC) may be used, especially in devices that use an internal battery for a power source. If DC is used in the contact system, an oscillator is used to convert DC to AC. The system 10 comprises a current generator 12 that is connected to excitation electrodes 14, 16, positioned on a presented body part (i.e. body part presented for analysis), such as the hand shown in FIGS. 1 and 3. System 10 further comprises an analyzer 22 that is connected and receives an output voltage signal from receiver electrodes 18 and 20. The analyzer 22 receives the voltage output signal produced by a flow of current between electrodes 18 and 20 in response to the current flowing from current generator 12. Current generator 12 is a current source for generating a constant magnitude current. The identification system of the present invention may utilize a continuous, constant magnitude current or a periodic, constant magnitude current.

Periodic signals may include sinusoidal, square wave, ramp and saw tooth. Generally, the constant current magnitude ranges from about 1 microamp to 4 milliamps. Preferably, the signal frequency ranges from about 40 Hz to about 400 MHZ, which is a frequency magnitude range within accepted risk standards for electrically susceptible human organisms. The present invention may utilize a single, predetermined frequency or multiple, variable frequencies within the above range. It should be noted that any frequency other than the described above may also be used in the present invention so long as electrical and/or magnetic properties of the tissue can be measured accurately. A disadvantage of using frequencies below 40 Hz is that the measurements take longer fractions of a second to complete. This lengthens the overall time required to obtain a biometric pattern.

Each different frequency used has a different effect in the body segment, because of membrane physiology, and tissue structure and composition, with accompanying changes in capacitance and inductance. When using multiple frequencies during testing, the output signals provide a unique biometric measurement pattern that is predictive of the tested individual. This is also true for changing waveform, angular frequency, capacitance and inductance at a singular frequency.

Figure 2:
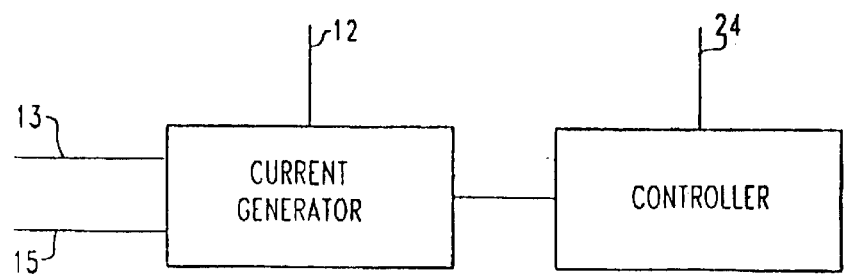
FIG. 2 is a block diagram illustrating a periodic controller connected to a current generator.

If a periodic, constant magnitude current is preferred, current generator 12 may be connected to a controller 24 which is capable of generating periodic output signals to control the current generator, as shown in FIG. 2.

The output signal of current generator 12 is transmitted to excitation electrodes 14 and 16 through respective connectors 15 and 13. For purposes of illustration, FIG. 1 shows a tetrapolar electrode placement comprising two excitation electrodes 14 and 16 that are active for injecting the current, while two passive electrodes 18 and 20 detect the resultant signal. It is contemplated that a bipolar setup comprising only two electrodes (one excitation and one passive) may be utilized, especially in systems having minimum surface area for placement of the electrodes.

In the tetrapolar electrode system of FIG. 1, the first excitation electrode 14 is positioned on the palm heel of the hand, while the second excitation electrode 16 is positioned on the palmar tip of the thumb. Similar electrode pairs may be placed and spaced a sufficient distance from each other to provide a drop in voltage on the remaining four fingers, so that the hand will have a least five distinct segments to be tested. Of course other electrode configurations may also be used with the present method.

The present invention preferably uses the tetrapolar setup of electrodes, which is more effective in overcoming the inconsistencies that may occur in the impedance measurement values caused by external contact resistance. External resistance may change significantly with certain specific changes in physical conditions, such as varying skin moisture content. These changes are minimized by using a tetrapolar electrode system. The tetrapolar electrode system is preferred because it eliminates both electrode polarization and contact resistance effects between the electrodes and the body part being measured. Contact resistance is variable with the motion of the subject and creates motion artifacts which interfere with measurement of electrical parameters of the body. By applying the current to the tested individual through one pair of electrodes and measuring voltage differences through another pair of electrodes, the contact resistance and the inherent voltage drop are eliminated from the voltage measurement. The path the energy takes is not critical, except that it should approximate the path taken for obtaining the reference pattern.

It should be understood that in some systems of the present invention, the injection of current and the sensing of the voltage may be accomplished with two electrodes for the bioelectric measurements. However, with the bipolar setup, the measured voltages are the voltage drops along the current pathway that include both the internal impedance and the boundary contact impedance. The voltage drop across the contact impedance can be significant compared with the voltage drop across the internal impedance. To overcome this problem when using a two-electrode system, a compound electrode may be used. A compound electrode is a single electrode that incorporates an outer electrode to inject the current and an inner electrode to measure the voltage. A suitable compound electrode, for example, is disclosed by Ping Hua, 1993, Electrical Impedance Tomography, *IEEE Trans. Biomed. Eng.*, Jan. 40 (1), 29–34. It should be noted that tetrapolar or compound electrodes are not necessary, because switching can be used so that transmission and reception from the same electrode does not occur at the same time.

Since a variety of electrodes are commercially available and well known in the art, their structure and application will not be described in detail. Of particular utility are electrodes made of synthetic conductive polymers, including polyacetylene, polypyrrole, poly-3,4-ethylene dioxythiophene, conductive adhesive polymers, semiconducting polymers, conductive silicone rubbers, and conductive rubbers, all of which may be used to fabricate conductive inserts in a biometric recognition system, such as shown in FIGS. 7–10.

Exemplary unit 11, shown in FIG. 1, provides a surface for receiving a presented body part, such as a hand. This unit may be constructed so that the conductive electrodes are mounted on the flat surface of the holder or contact with the fingers, thumb and the palm heel.

Since bioelectrical measurements include the application or generation of current in the tested subject, the question of safety arises. The biometric system of this invention may use a transformer between the signal source generator and contacting electrodes to isolate the subject from potential electrical hazard. Any transformer that will transmit the required frequency associated with the constant current, but will not conduct 300 cycles, and preferably 60 cycles or higher, of voltage in current, may be utilized in this system.

Impedance to the current flow in the body segment generates a voltage difference or drop across the body segment. The amplitude of the voltage is modulated by changes in the body segment's electrical conductivity caused by differences in tissues and structures. Receiving electrodes 18 and 20, positioned between the excitation electrodes 14 and 16, are used to measure the voltage drop across the measured segment of the body part. The receiving electrodes are preferably the same types as used for excitation electrodes. A voltage signal proportional to the measured body segment's impedance is generated within the body segment and the voltage difference measured between electrode 18 and 20 is an alternating voltage produced in response to the constant magnitude alternating current. The voltage detector 28 may be any type well known to designers of electronic circuitry, such as a voltmeter, potentiometer and the like.

Voltage detector 28 can be of the type that detects the magnitude of the voltage signal and also detects the phase relationship between the alternating voltage and the alternating current producing the voltage. Therefore, both the resistive and reactive components of impedance may be measured. This type of detector is well known to electrical designers and often termed a synchronous detector, as shown in U.S. Pat. Nos. 3,871,359 and 5,063,937.

Before the voltage signal is received by the voltage detector 28, and depending on the strength of the signal, an amplifier 26 is connected between the signal received from the receiver electrodes 18 and 20 and voltage detector 28. A suitable amplifier will take a signal less than a millivolt and amplify it to volts, will produce a large voltage gain without significantly altering the shape or frequencies present, and will provide accurate measurements. Amplifiers of this type are well-known in the art.

A differential amplifier or other device is preferably used to remove background noise. This will require another electrode to be added to the bioimpedance system to serve as a common ground.

Figure 3:
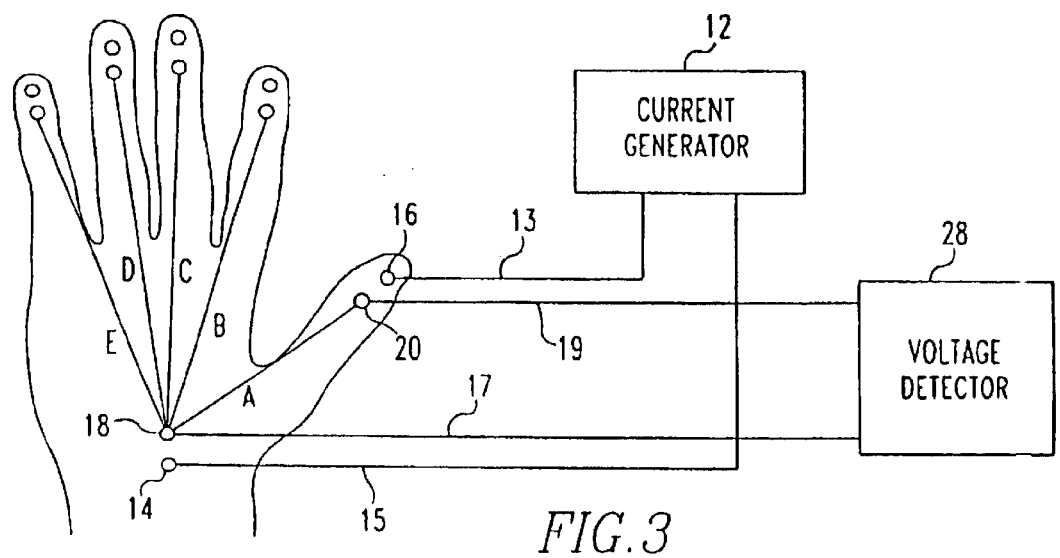
FIG. 3 is a pictorial representation of a hand attached to a biometric system of the present invention.
Figure 5A:
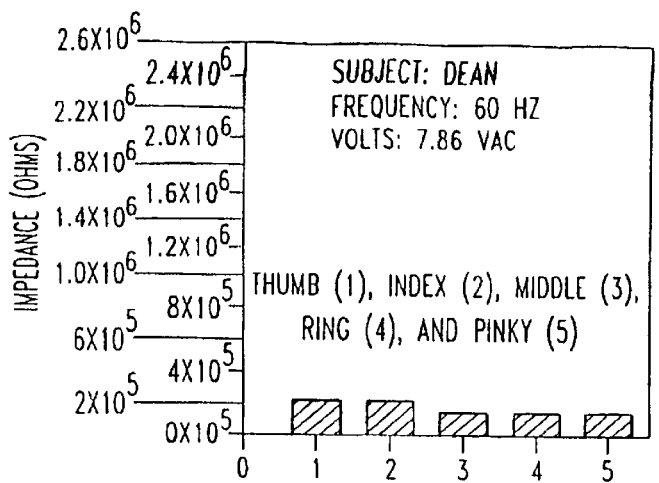
FIGS. 5a–5f are charts of subjects regarding impedance and digits.
Figure 5B:
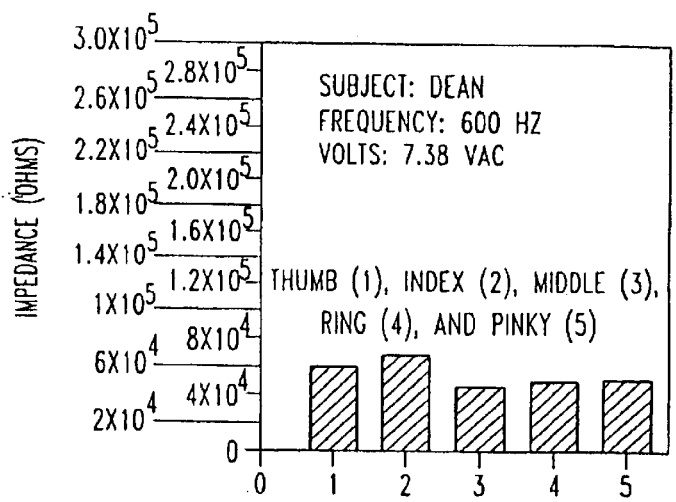
Figure 5C:
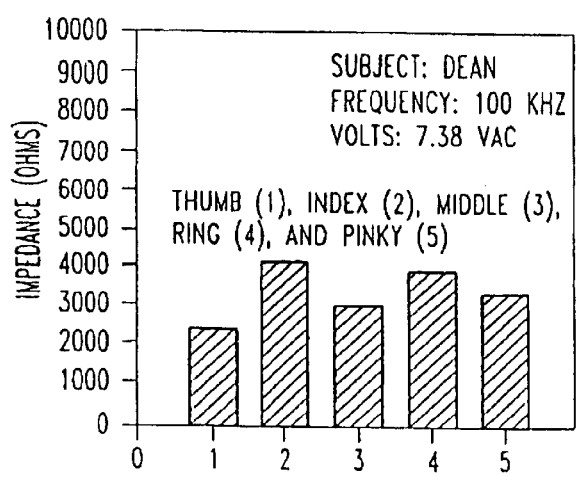
Figure 5D:
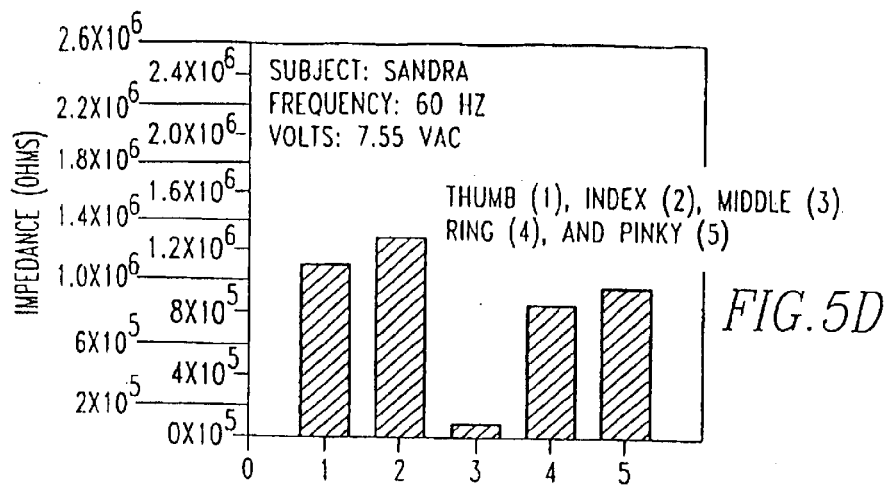
Figure 5E:
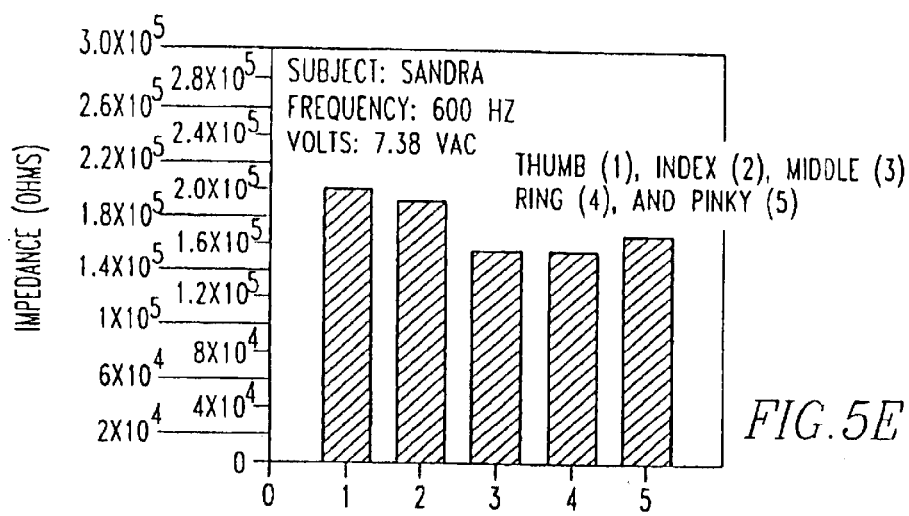
Figure 5F:
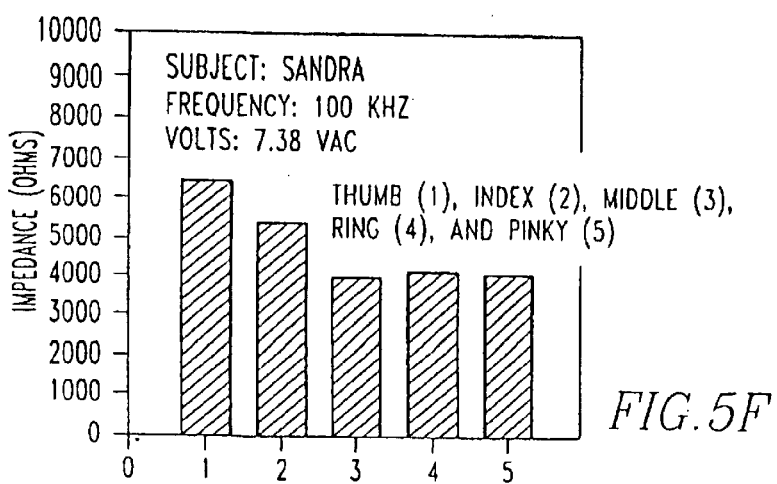
Figure 6A:
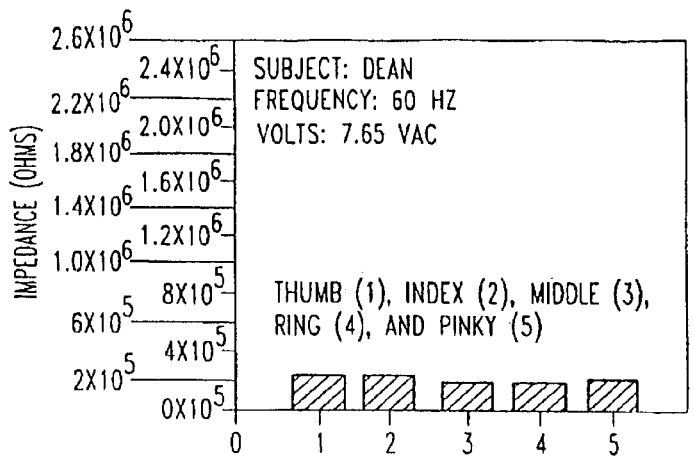
Figure 6B:
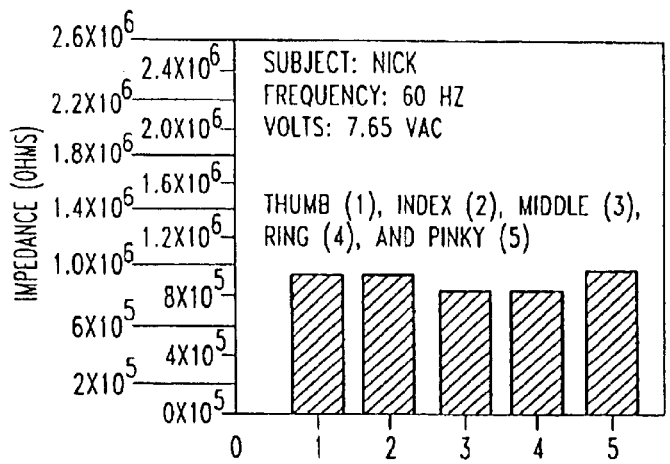
Figure 6C:
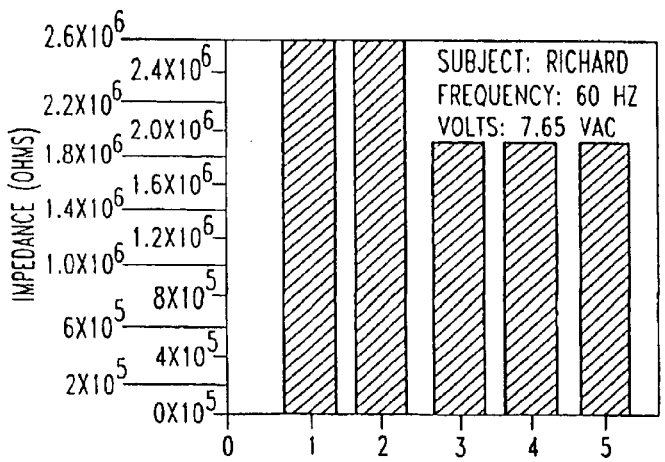
Figure 6D:
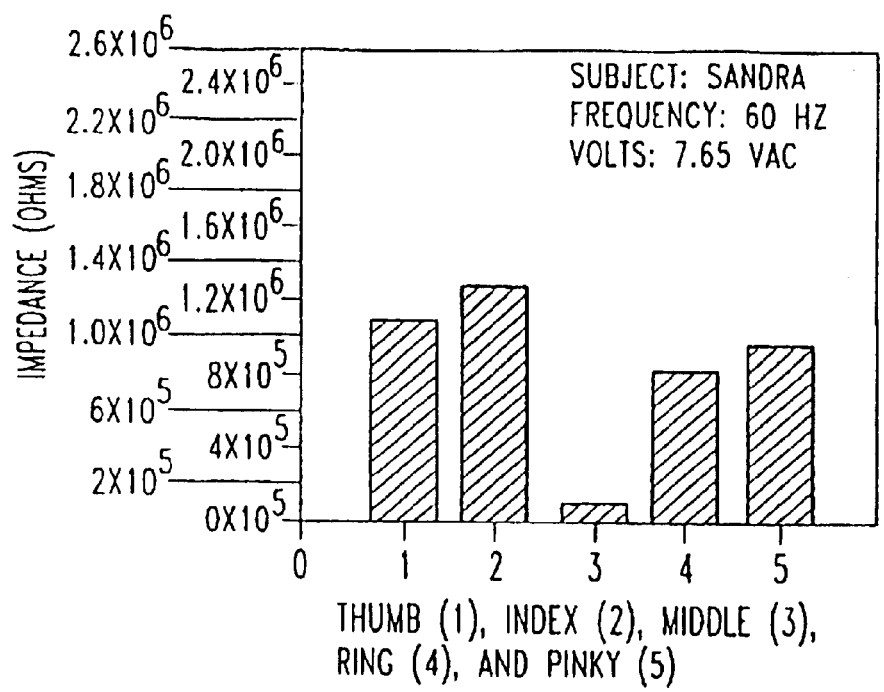
Figure 6E:
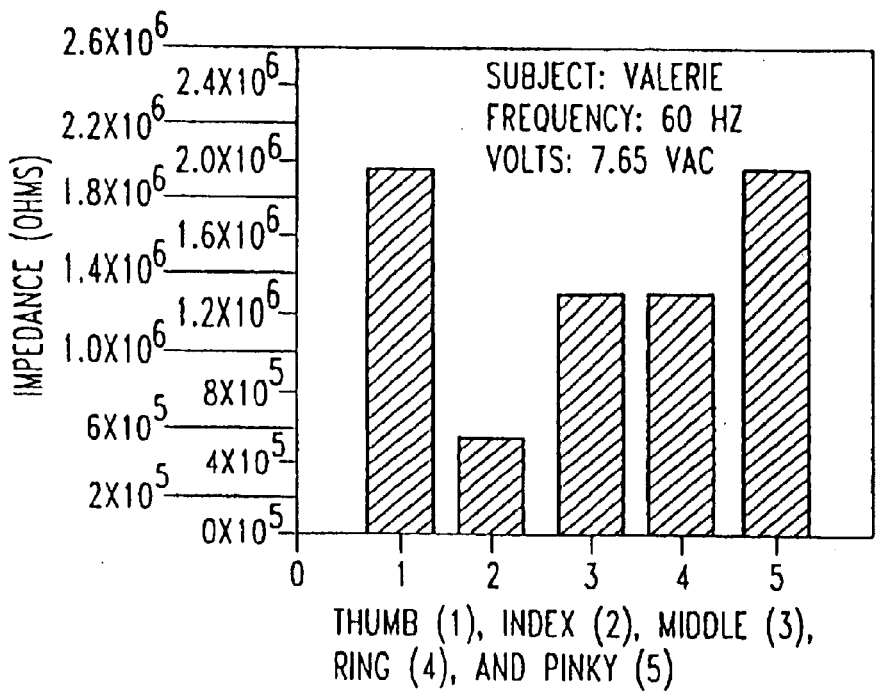

Once the voltage signal is measured, the signal is directed through an analog-to-digital converter 30, and the output digital signal is directed into a microprocessor 32, which automatically and instantaneously calculates impedance or any of the other bioelectrical characteristics of the body segment. Any general purpose computer or one capable of performing various mathematical operations on the voltage input information may be used in the present invention. A typical mathematical operation on the signal is the division of one impedance value by a subsequent detected impedance value from a second and subsequent tested segments of a body part to provide comparative ratios to establish a representative bioimpedance measurement pattern, as illustrated in FIG. 3. Here, the voltage difference in each of five different segments A, B, C, D, and E are detected, and a comparative ratio among these segments is determined by dividing one signal detected by a subsequent detected value. As an example A/A, B/A, C/A, D/A, and E/A are computed and the resultant values produce four comparative ratios for the tested body part to the thumb for a predetermined frequency. When measurements are taken on another day, the absolute measurements will most likely vary, although the ratios will remain relatively constant (to within 0.0–6.0%). If the frequency is changed, another set of comparative ratios can be determined for the same body part. When testing occurs at more frequencies, a larger set of comparative ratios are established, which can be used to provide a unique representative bioimpedance measurement pattern. FIG. 4 shows a set of the comparative ratios identified above, with series 1 (the thumb) set to 10. The frequencies measured were in Hz (on the horizontal axis 1–15):

10
20
50
100
200
500
1,000
2,000
5,000
10,000
20,000
50,000
100,000

200,000
500,000.

Frequency #10 (10,000 Hz) is an impedance resonance point for the thumb, while the fingers have resonance points at approximately 50,000 Hz.

FIGS. 5a–5f are charts of different tested individuals, showing impedance values for various fingers of the same individuals at different frequencies. FIGS. 6a–6f are charts of showing impedance values of the fingers of several tested individuals at the same frequency.

The computation of impedance values or any of the other bioelectrical and/or magnetic characteristics for each finger or other body segment for a plurality of frequencies can be plotted against the range of multi-frequencies to provide a representative bioelectric measurement pattern in the form of a unique curve for each finger. For example, FIG. 4 shows a plot for fingers A-E of FIG. 3 over a range of multiple frequencies.

The results of these computations are compared with a previously stored reference pattern stored in memory 36 to determine a match within an acceptable error range. Results from the comparison are displayed on display unit 34, which may be a digital display component of the microprocessor.

While a flat hand detector has been described, other embodiments of the described system and it elements may be used in other devices to gain access to or activate certain secure systems. For example, FIGS. 7, 8, 9, and 10 illustrate several contemplated setups and uses for the biometric recognition system of this invention which utilize unique electrical conductivity values of an individual.

Figure 7:
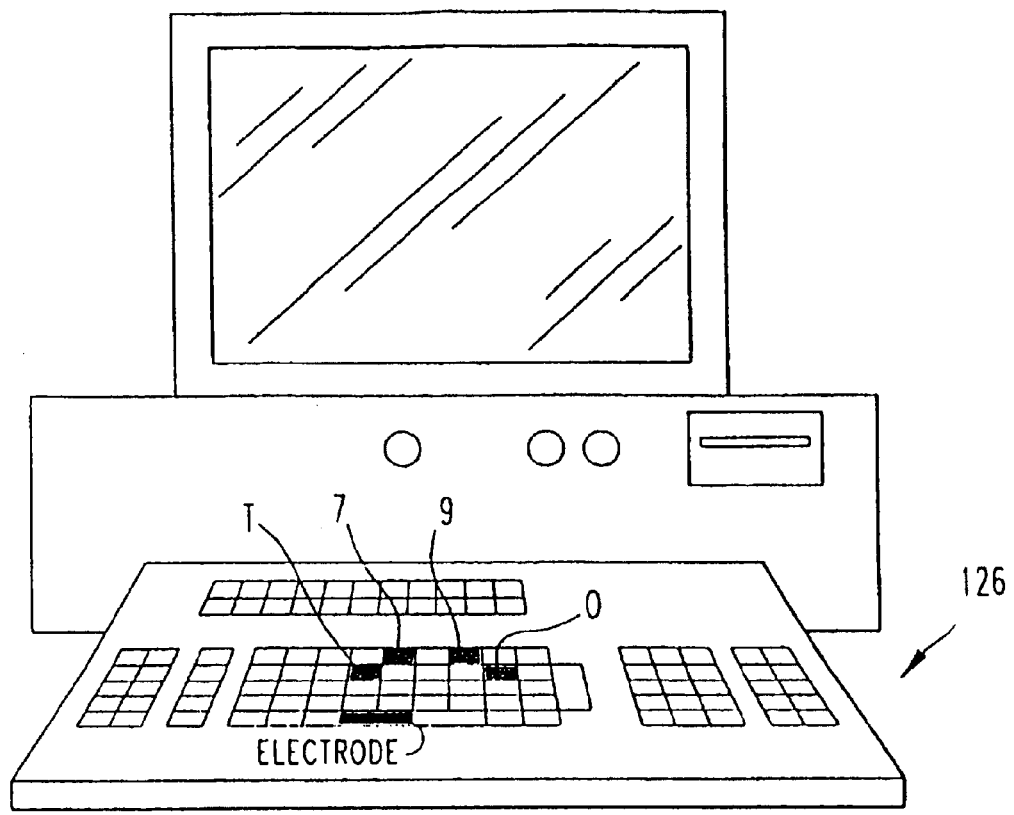
FIGS. 7 and 8 show alternative embodiments illustrating the biometric recognition system utilized in a keyboard and mouse.

FIG. 7 illustrates a computer keyboard having electrodes imbedded in specific keys for generating bioelectrical conductivity values, or biometric signature, which are compared to a stored signature. If the tested individual's bioelectrical pattern matches that of a stored signature, the user is authenticated and the computer is activated for user log on.

Figure 8:
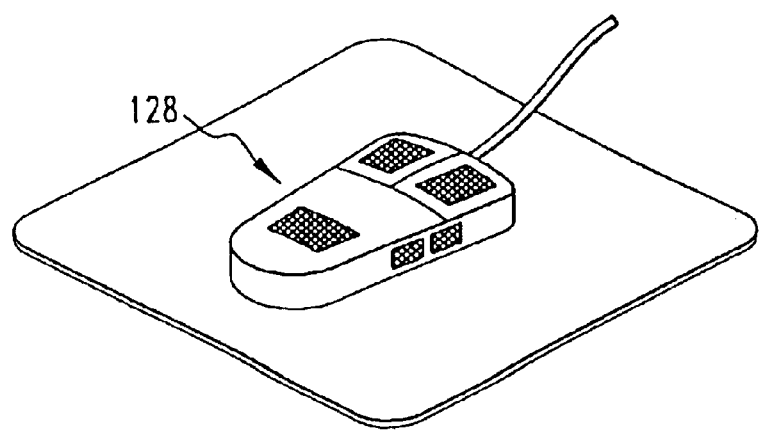

FIG. 8 illustrates using a microprocessor mouse to gain access to a restricted system. This system will recognize authorized users and prevent others from gaining access to the system.

FIG. 9 provides a system for authorizing use of a weapon such as a firearm to only a specific authorized user. If an unauthorized individual attempts to discharge the weapon, the system will not recognize the individual and will prevent activation of the firing mechanism.

FIG. 10 provides for a simple recognition system that provides an individual's biometric characteristic pattern or signature. The measurement electrodes are contained within a watchband so that conductivity and/or other electrical values are measured in the wrist of an individual. An auxiliary receiving system receives the pattern sent from the watchband and compares it to a stored pattern to verify the identity of the user. This device may be used to open an electronic door lock and replaces the need for a keypad or a remote control unit.

Figure 11:
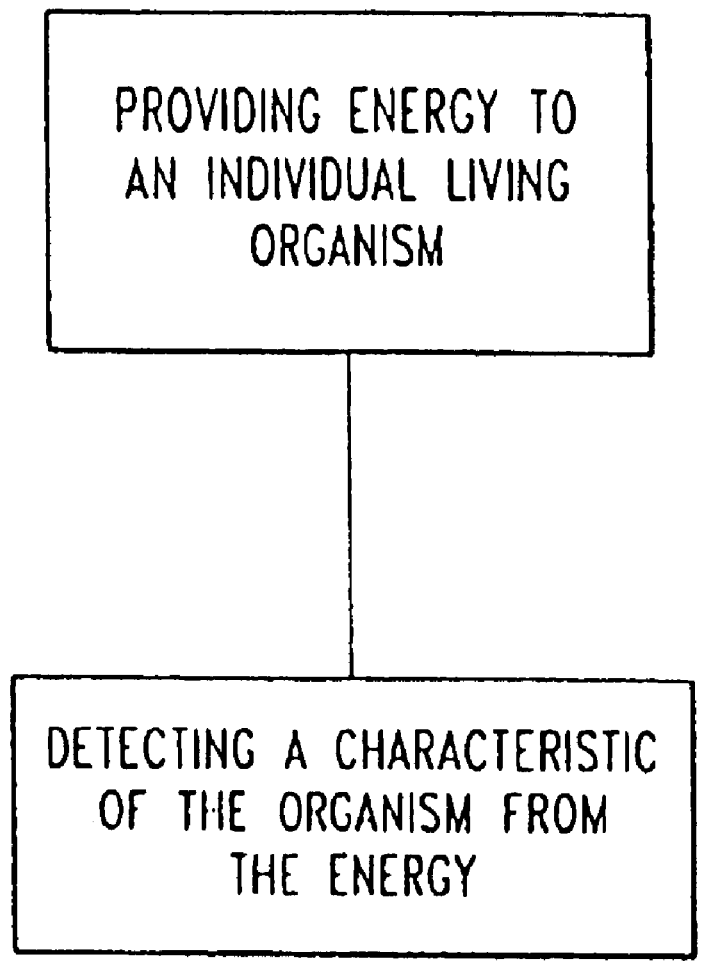
FIG. 11 is a flow chart of a method of the invention.

FIG. 11 is a flow chart of a biometric signature detecting method of the invention.

Figure 12A:
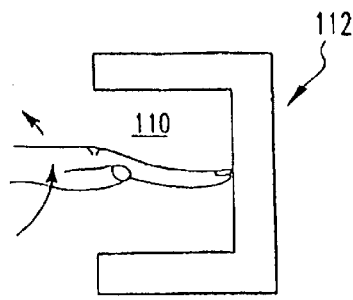
FIGS. 12a and 12b are side and overhead views of a non-contact apparatus for the interruption of an electric field of the present invention.
Figure 12B:
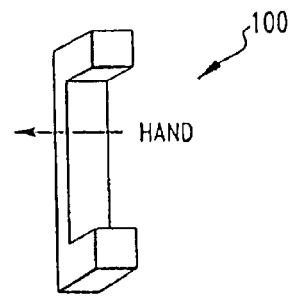
Figure 13:
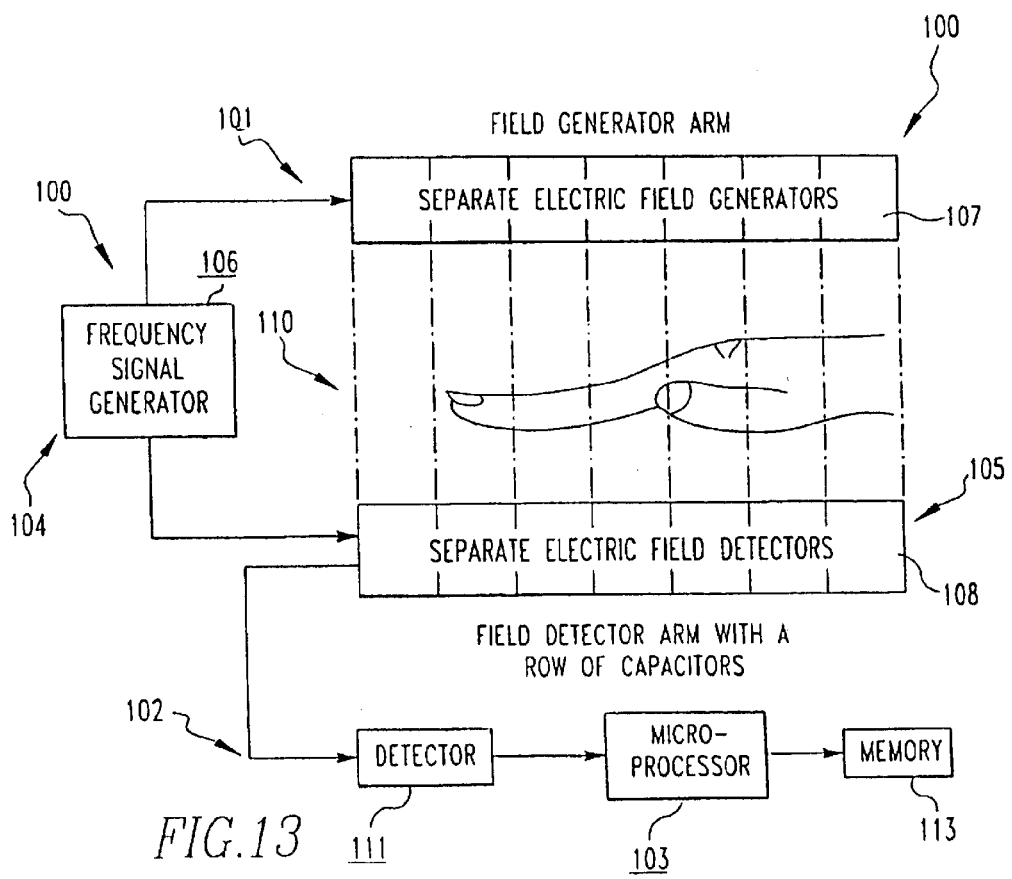
FIG. 13 is a schematic representation of an apparatus for sensing electric or magnetic properties of an organism.
Figure 14:
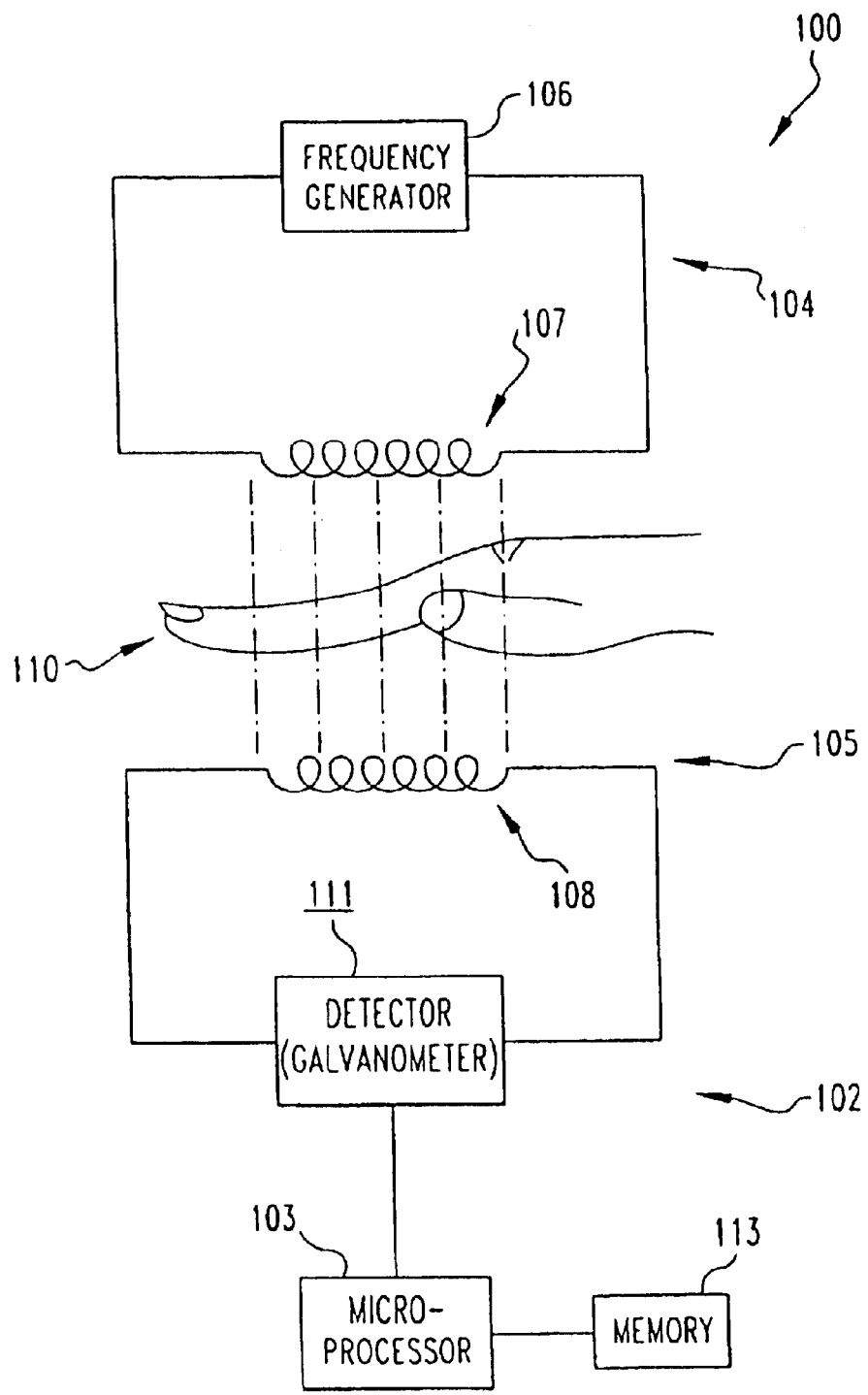
FIG. 14 is a schematic of an apparatus for sensing the magnetic properties of an organism.
Figure 15:
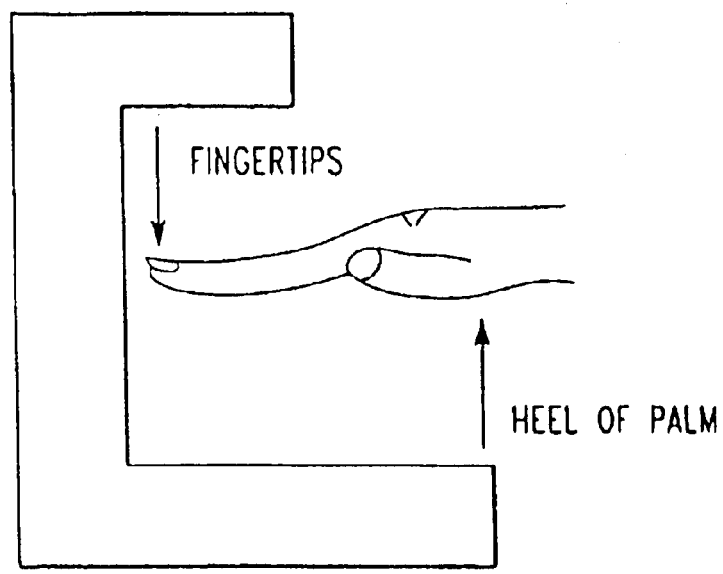
FIG. 15 is a schematic of an apparatus for inducing current longwise in an organism.
Figure 16:
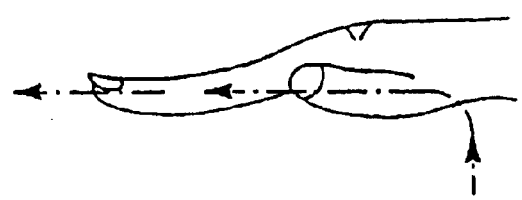
FIG. 16 is a schematic of the flow of induced current from the heel of the palm lengthwise to the finger tips.
Figure 17A:
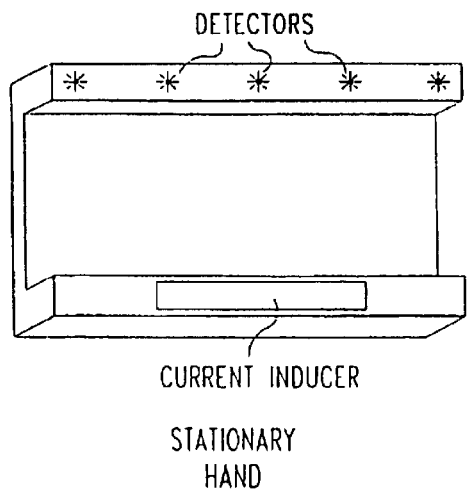
FIG. 17 is a schematic of an apparatus for the measurement of induced current in regard to a stationary hand.
Figure 17B:
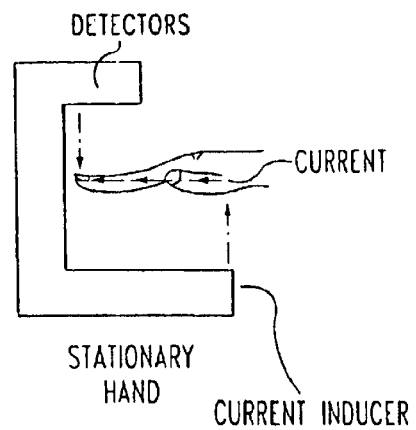
Figure 18A:
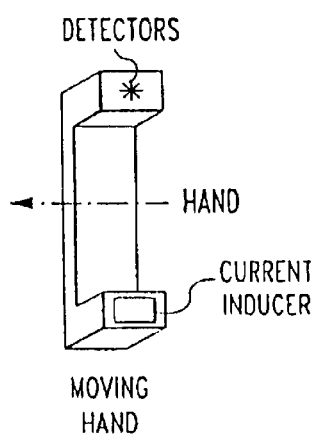
FIG. 18 is a schematic of an apparatus for the measurement of induced current in regard to a moving hand.
Figure 18B:
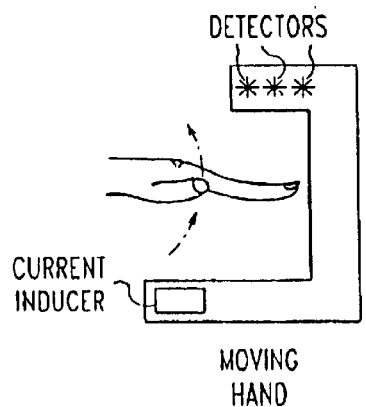
Figure 19:
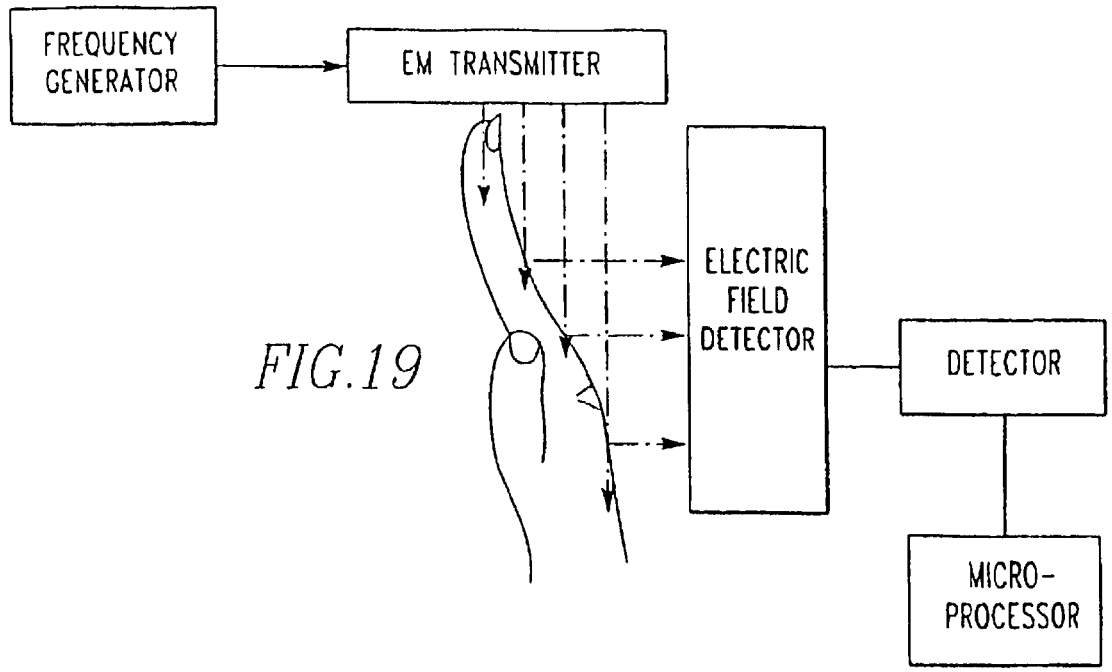
FIG. 19 is a schematic of an apparatus for inducing current using an electromagnetic field.
Figure 20:
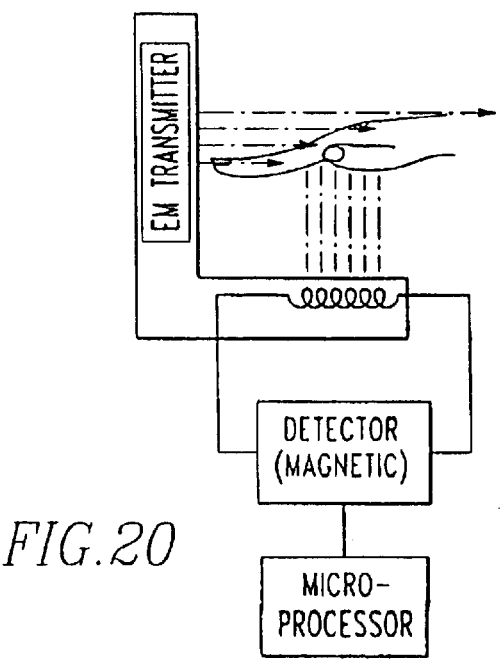
FIG. 20 is alternative embodiment of an apparatus for inducing current with an electric and/or magnetic field.

Referring to FIGS. 12, 13 and 14, an apparatus 100 for recognition of an individual living organism's identity comprises a sensing mechanism 101 for sensing electric and/or magnetic properties of the organism. The apparatus 100 comprises a mechanism 102 for recognizing the organism, which communicates with a sensing mechanism 101.

Preferably, recognizing mechanism 101 includes a microprocessor 103 having a known electric and/or magnetic property of the tested individual. Sensing mechanism 101 preferably includes a mechanism 104 for producing an electric field and/or magnetic field in the organism, and a mechanism 105 for receiving an electric field and/or magnetic field. Preferably, producing mechanism 104 includes a frequency generator 106, and receiving mechanism 105 includes an electric field receiver and/or magnetic field receiver 108 disposed adjacent to an electric or magnetic field transmitter 107. This defines a test zone 110 with the electric or magnetic field in which a hand or other body part of the tested individual is placed to sense the electric or magnetic properties of the individual. A detector 111 is connected to the electric or magnetic field receiver 108 and to the microprocessor 103. The detector mechanism preferably measures phase or amplitude or frequency or waveform of the electric or magnetic field that extends through the test zone. Apparatus 100 includes a housing 112 for transmitter 107 and receiver 108.

In operation, a conventional frequency generator is connected to a conventional electric and/or magnetic field transmitter. The frequency generator controls and drives the electric and/or magnetic field transmitter which produces an electric and/or magnetic field. Opposing the electric and/or magnetic field transmitter in one embodiment, is an electric and/or magnetic field receiver. Between the electric and/or magnetic field transmitter and the electric and/or magnetic field receiver is a test zone defined by the transmitter's and receiver's location. The test zone is where the tested individual places a body portion, such as a hand, in the electric and/or magnetic field between the transmitter an the receiver. The electric and/or magnetic field extends through the hand and the energy of the electric and/or magnetic field is affected in a unique way corresponding to the unique composition of the tested individual.

Detector 111 produces a signal corresponding to the electric field and/or magnetic field received by receiver 108 and provides the signal to microprocessor 103. Memory 1130f microprocessor 103 stores a known electric and/or magnetic and/and/or acoustic field signal for the individual organism. The stored signal is compared to the signal provided from detector 111 and, if substantially similar, a recognition signal is produced.

Detector 111 can measure phase, amplitude, frequency, waveform, etc., of the, electric and/or magnetic and/or acoustic field which extends through the body part of the individual in the test zone. Either an electric field by itself, or a magnetic field by itself or a combination of both, or an acoustic field can be used in the test zone. If frequency is used as the recognition characteristic, then preferably it is DC up to 500,000 Hertz. Use of current is preferably from 1–4 mAmp. Potential energy is preferably 0.1 to 15 volts. Waveforms of sine, ramped, square, or combinations thereof can be used. An electric field is preferably 20 to 700V/m$^2$. A magnetic field of between 100 mGauss to 10 Gauss is preferred.

Basically, the band or other presented body portion interrupts a steady electric and/or magnetic and/or acoustic field, and the detector measures the amount of interruption. Electric field measurements could be taken from the back of the hand straight through to the palmar surface, depending on how the transmitter and receiver are positioned. If the hand is swept through the test zone, straight through measurements would be obtained first for the thumb, and then for each of the fingers in sequence. This results in five sets of data. For use of a magnetic field, placement of the hand in the test zone would interrupt the current induced in the secondary coil from the magnetic flux created by the primary coil, as shown in FIG. 14.

The hand is used as an essential part of the current path. A current is induced by placement of the heel of the palm over a magnetic and/or electric and/or acoustic field, as shown in FIGS. 15, 16, 17 and 18, and the induced currents at the finger tips are detected, either with a magnetic and/or electric and/or acoustic field sensor.

In this invention, the presented body part is part of a circuit that is either electrically based, or magnetically based, or a combination of both, or is acoustically based, interferes or affects the energy in that circuit in a unique way. By knowing a priori information on how the presented body part interferes with or affects the energy in the circuit when tested, testing again under essentially the same conditions will produce test information that can be compared to the a priori information to either confirm or deny identity of the subject individual.

Figure 21:
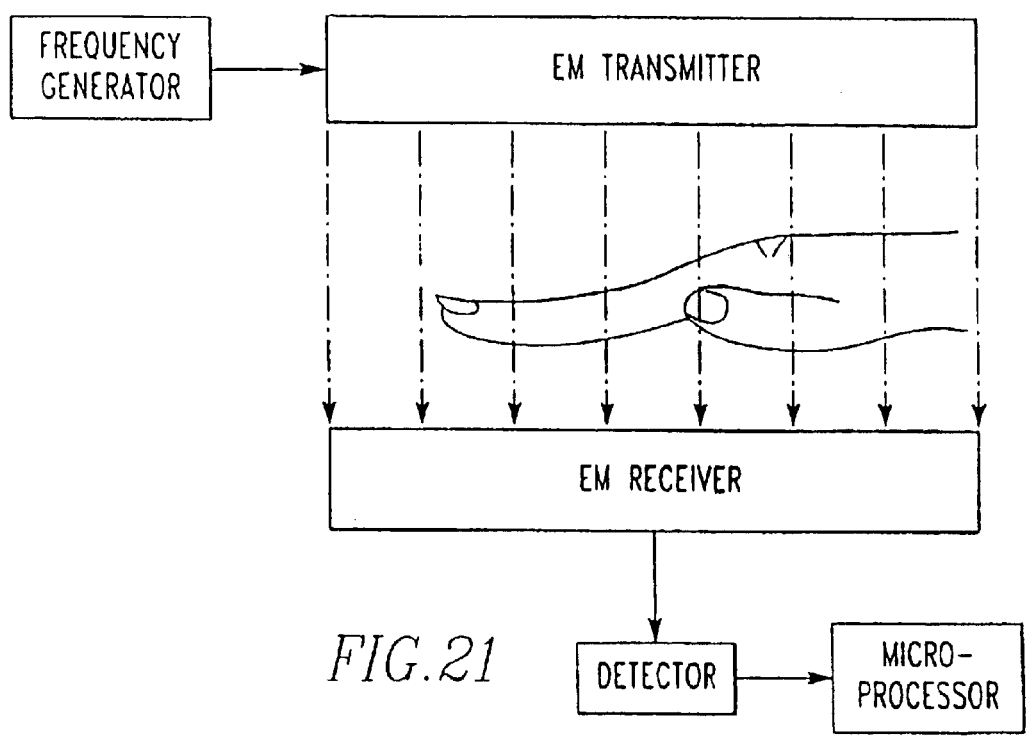
FIG. 21 is a schematic of an apparatus for sensing the interruption of an electromagnetic field.
Figure 22:
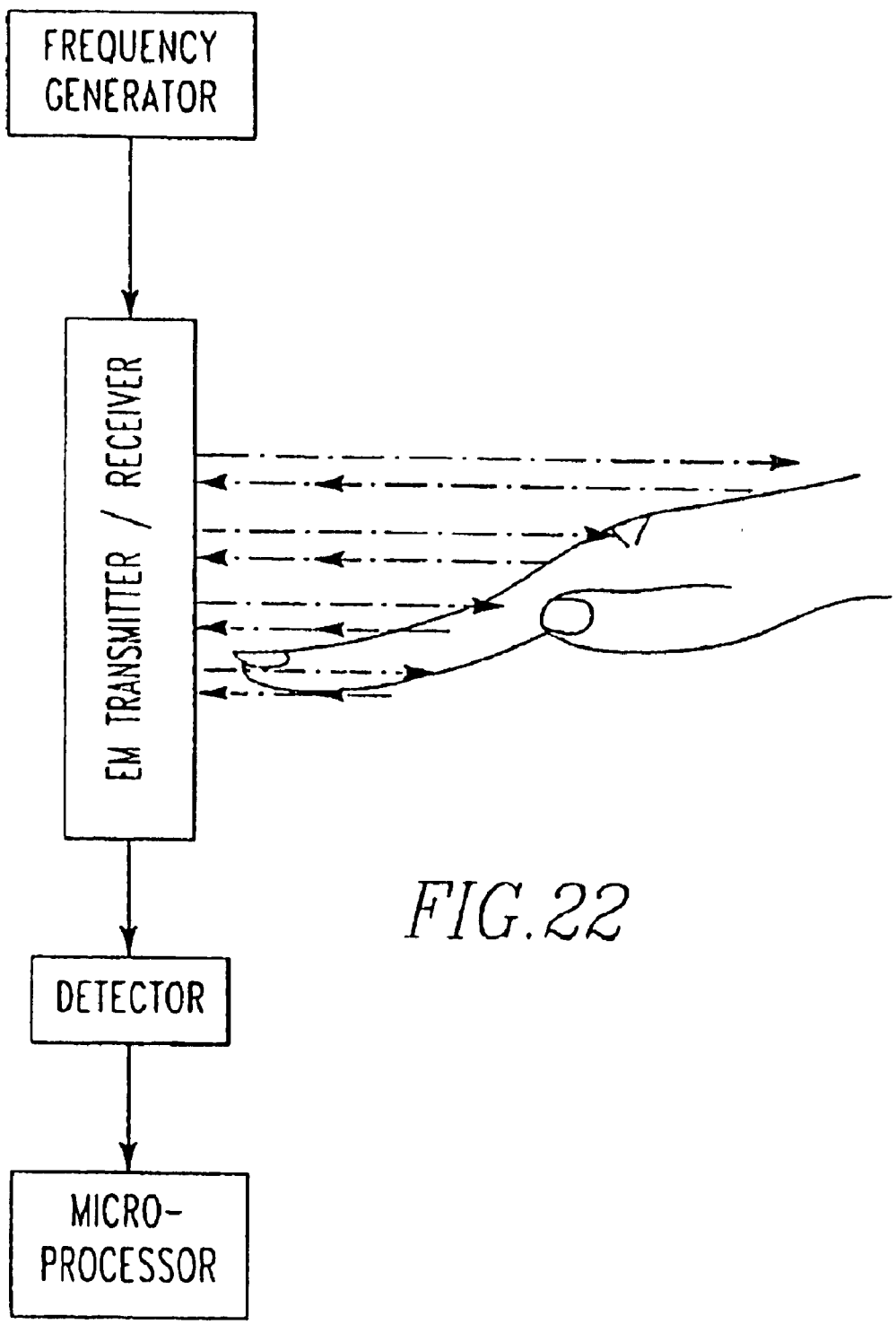
FIG. 22 is a schematic of sensing electric and/or magnetic properties via reflection of electromagnetic radiation.
Figure 23:
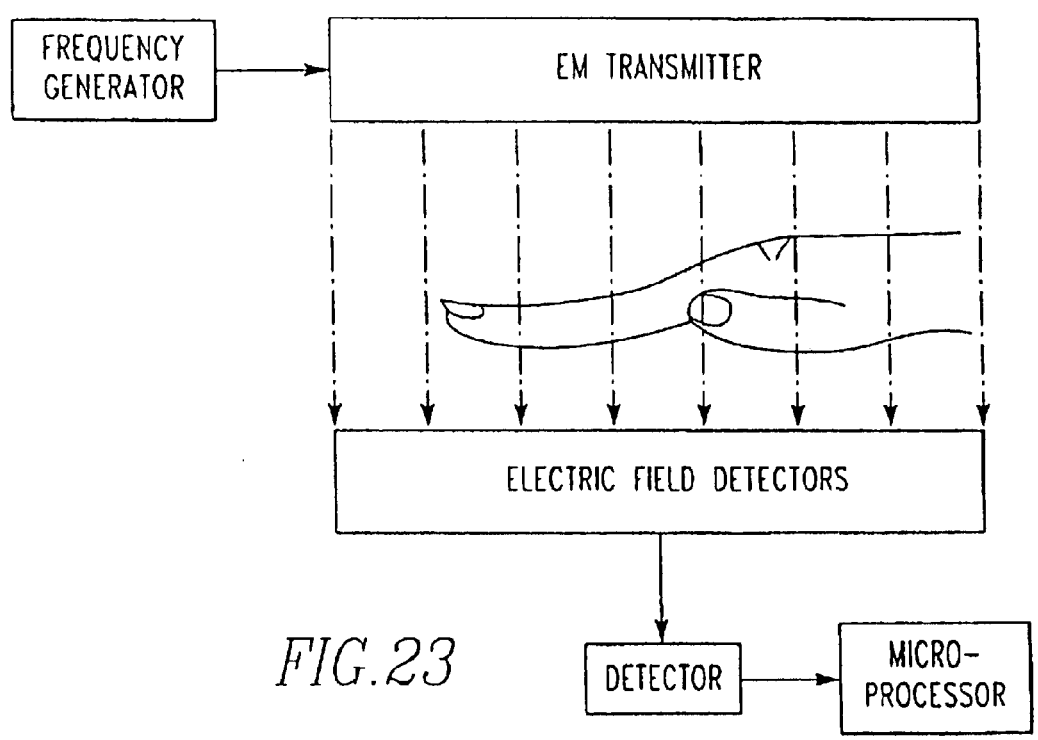
FIG. 23 is a schematic representation of an apparatus for measuring the interruption of an electromagnetic field by measuring only the electric field.
Figure 24:
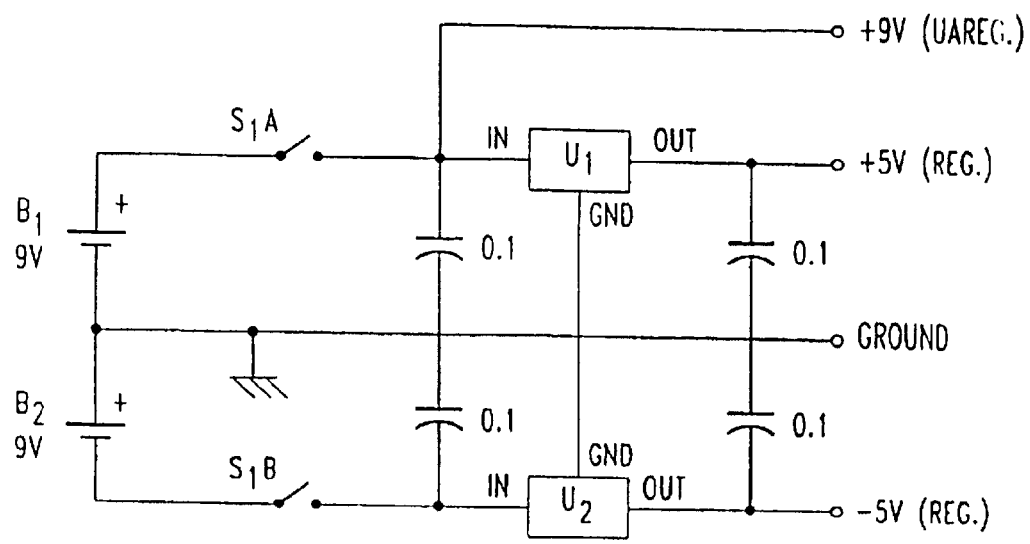
Figure 25A:
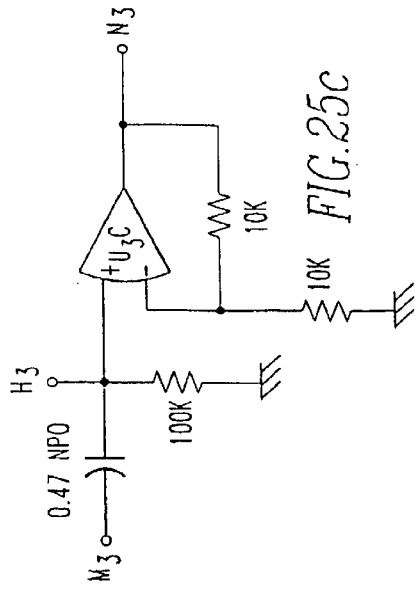
Figure 25B:
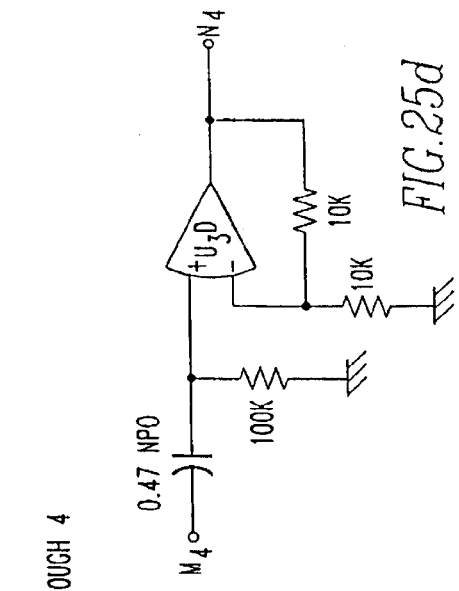
Figure 25C:
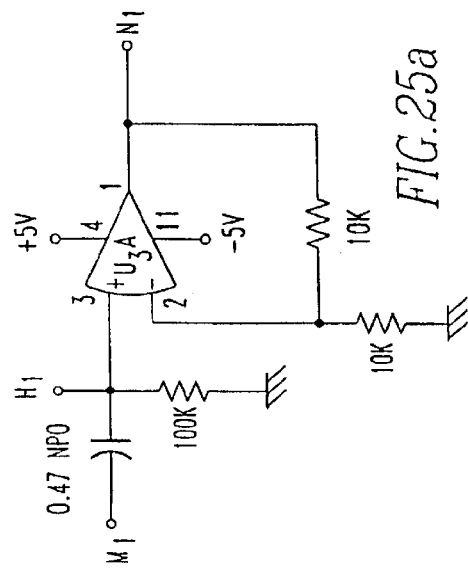
Figure 25D:
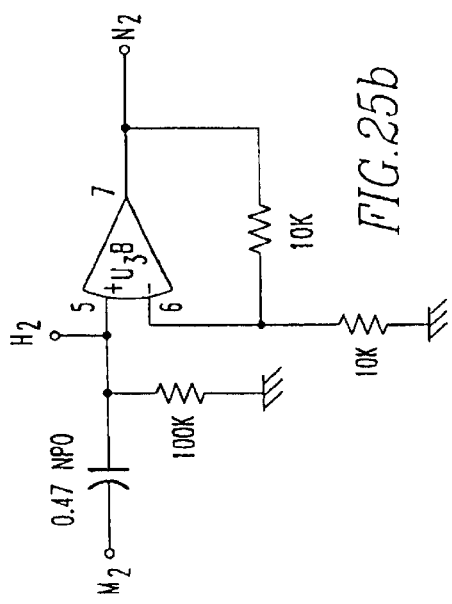
Figure 27:
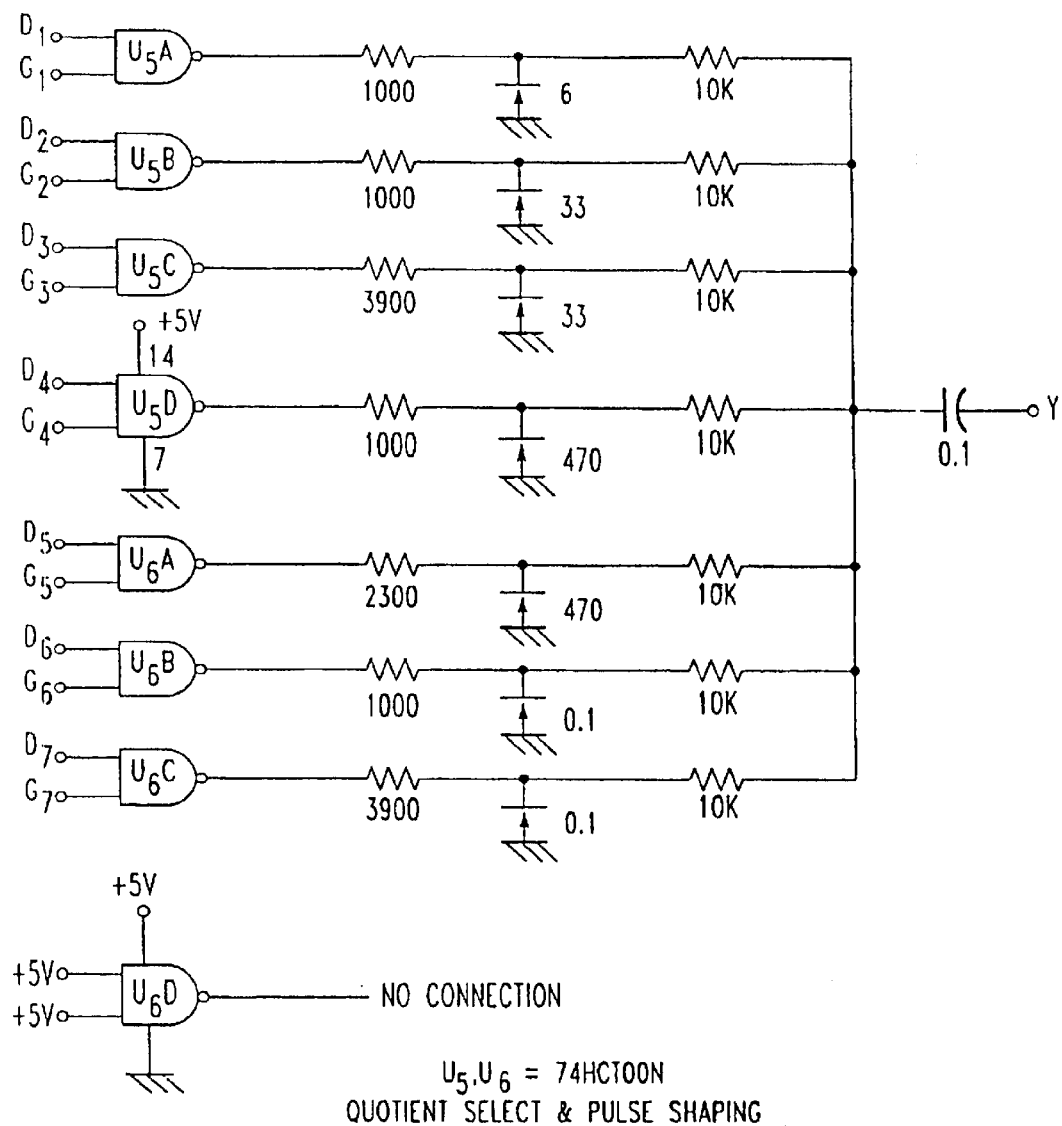
Figure 28:
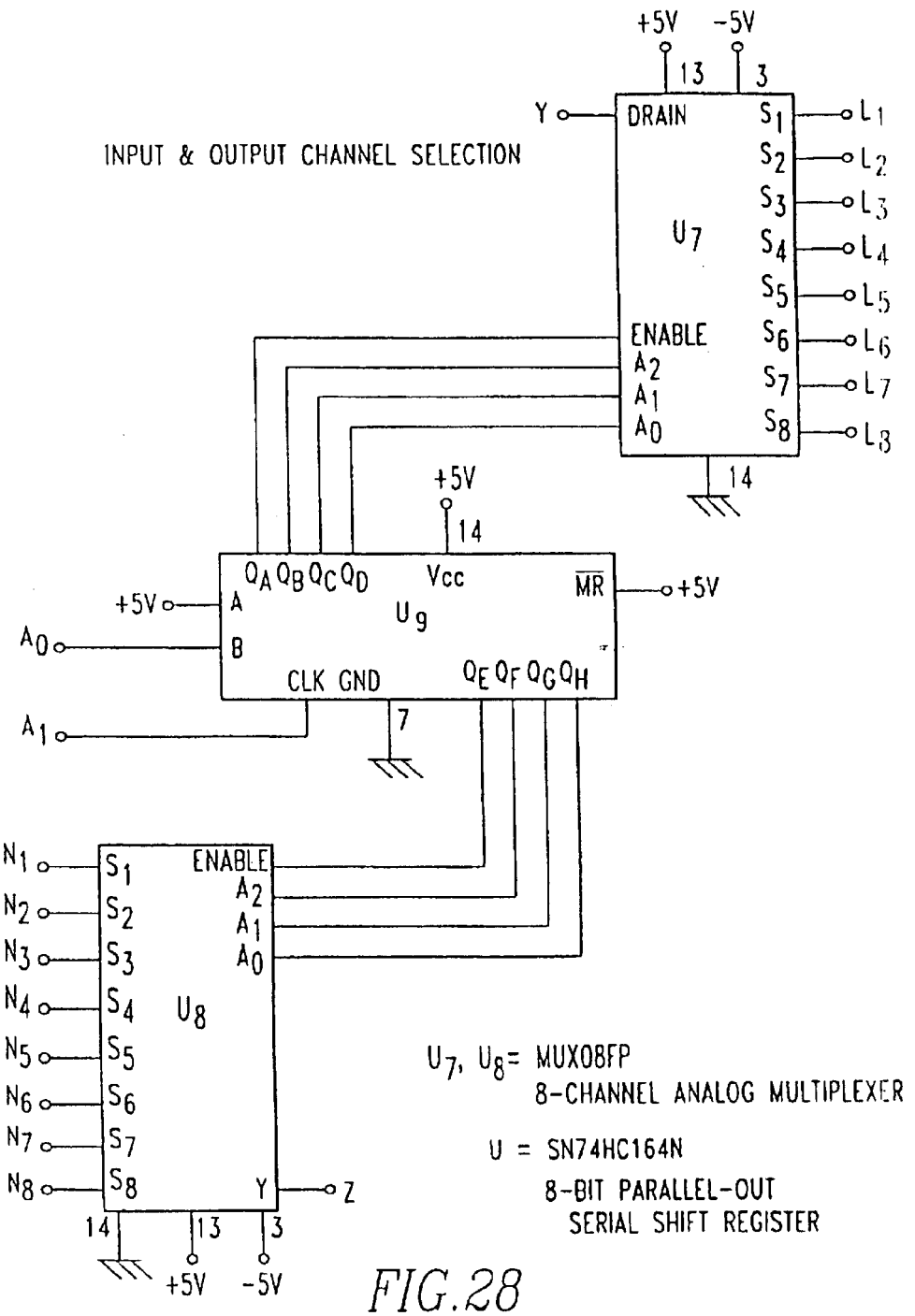
Figure 29:
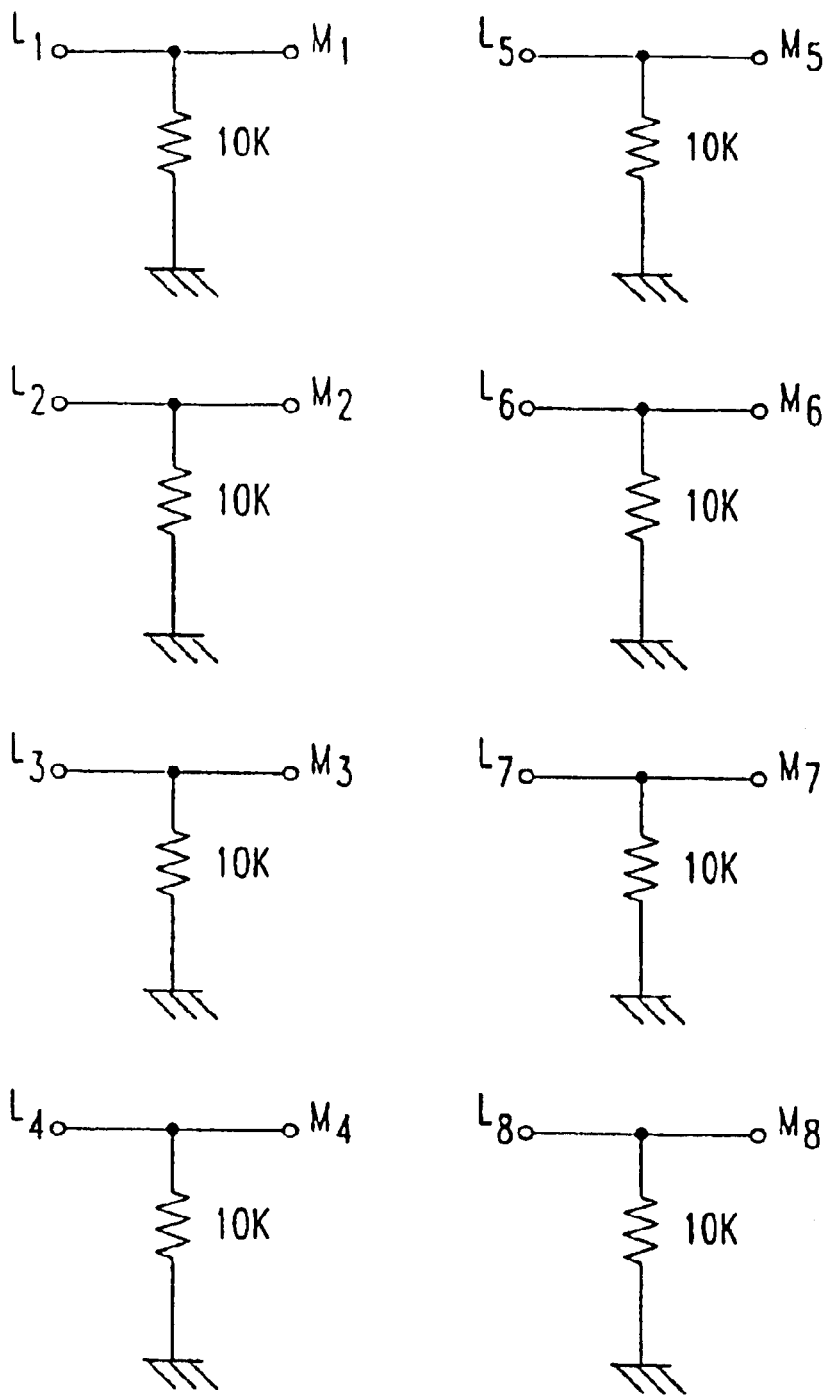
Figure 30:
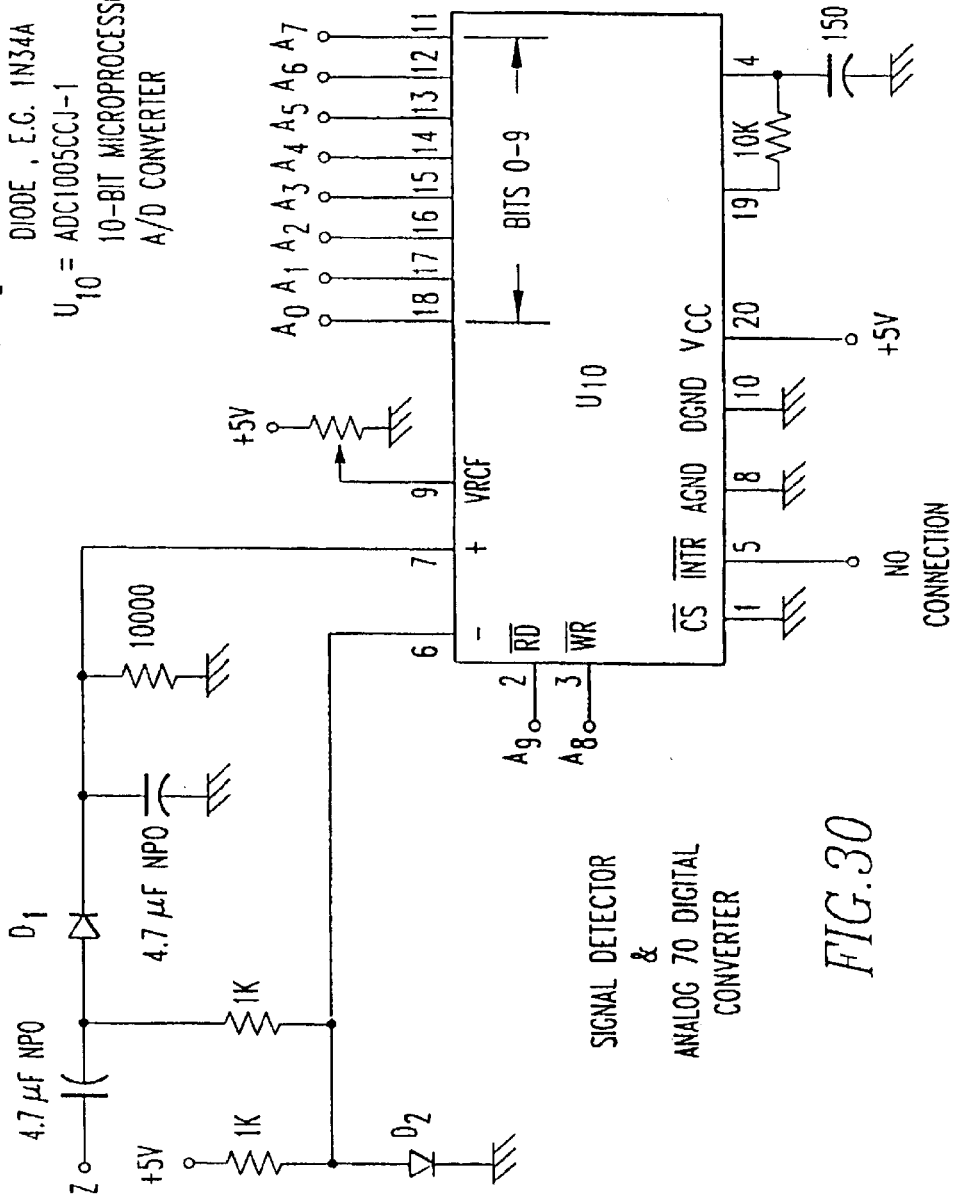
Figure 31:
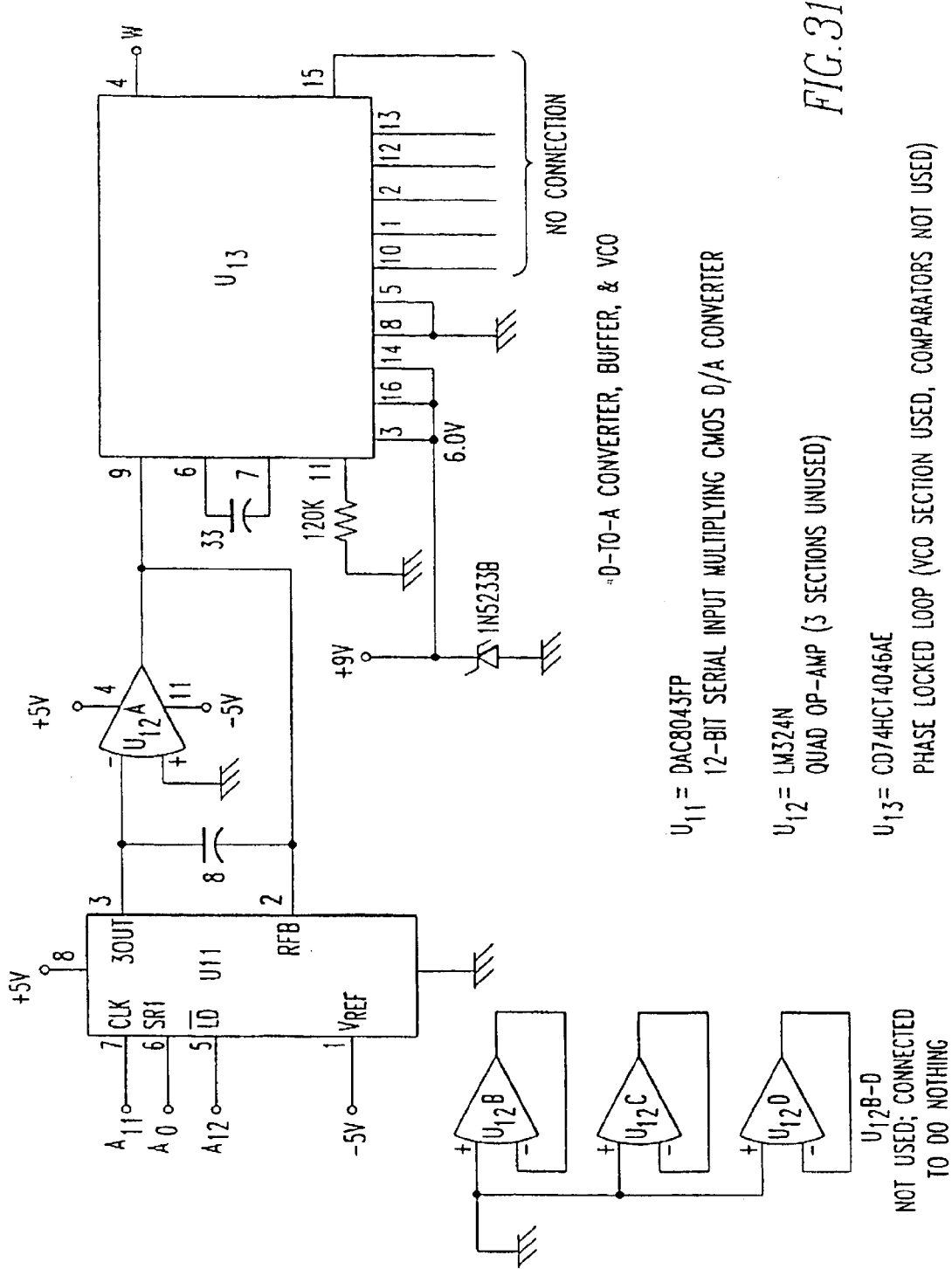
Figure 32:
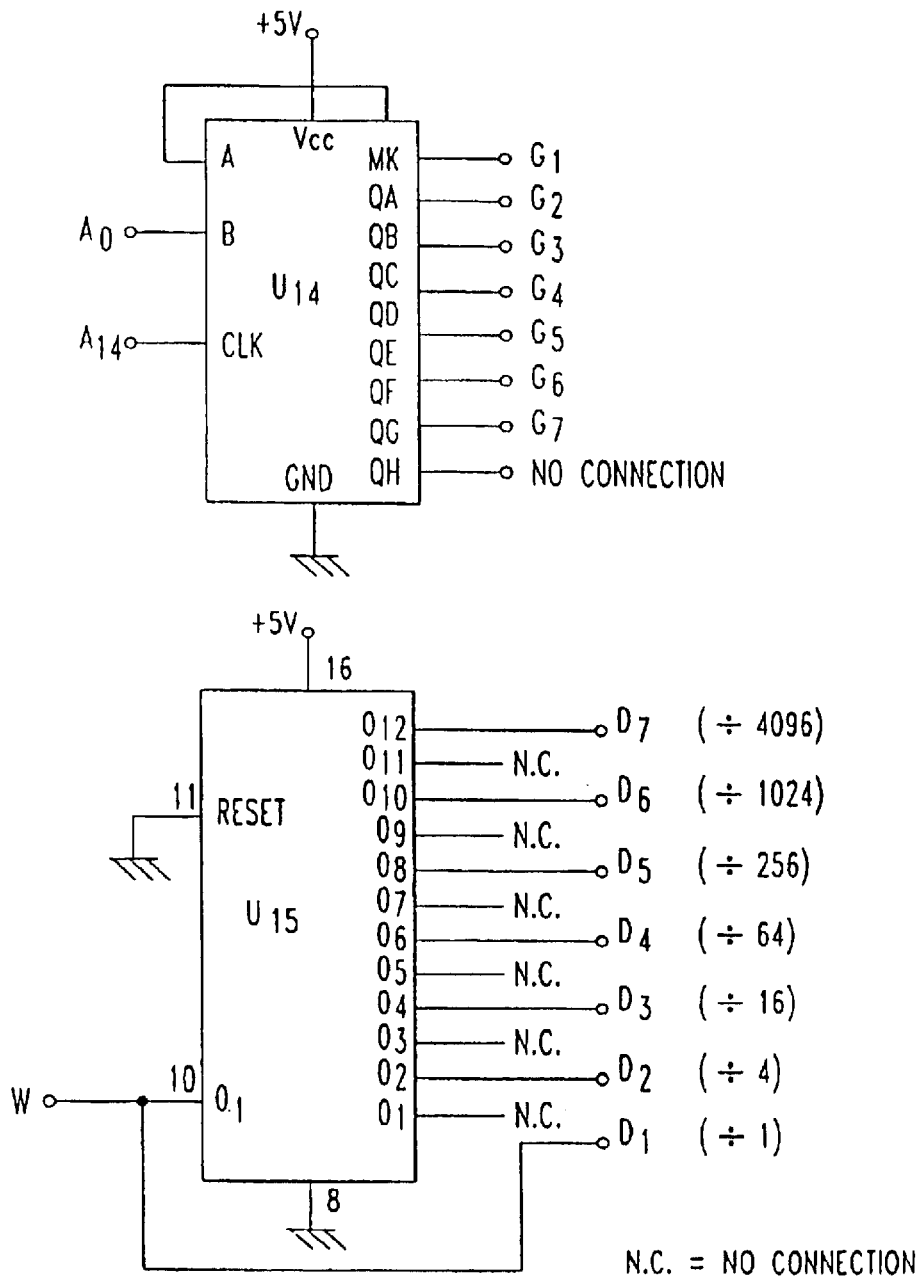

This identity test can be accomplished in many ways, such as a touch technique that measures the electrical properties of the presented body part, a touch technique which measures the magnetic properties of the body part, a touchless technique which measures the electric and/or magnetic properties using steady electrical and/or magnetic field interruption, as shown in FIGS. 12, 13, 14, and 21. Also useful are a touchless technique which measures the electric and/or magnetic properties using induced currents from an electric or magnetic field, as shown in FIGS. 15, 16, 17, 18, 20 and 22, or a touchless technique which measures the electric/magnetic field, as shown in FIG. 21, or a touchless method which measures the electric/magnetic properties by reflection of an electromagnetic field, as shown in FIG. 22, and where only one field is detected as shown in FIG. 23. Other techniques include a touchless technique which measures the electric and/or magnetic properties using induced current from an electromagnetic field can be used, or an acoustic field as shown in FIGS. 67–71. These are but some examples of the many ways electrical or magnetic properties of an individual can be determined for recognition purposes.

Touch apparatus for measuring these electric and/or magnetic properties of an organism comprises a sensing mechanism having a contact area of less than 2.0 cm² and has a contact area that is preferably less than 0.2 cm thick. In a preferred embodiment, a single acoustic transducer having about a 1.5 cm² surface area and a thickness of less than 0.2 cm was used to detect a biometric recognition pattern.

Figure 63:
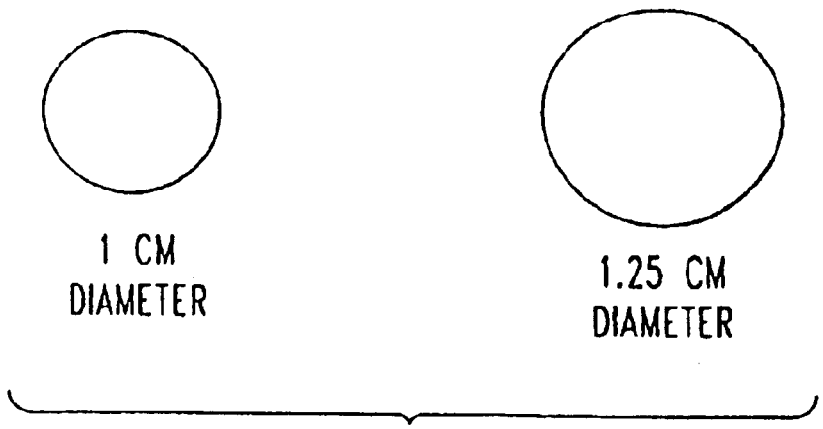
FIG. 63 depicts 1 cm and 1.25 cm diameter electrodes.
Figure 64:
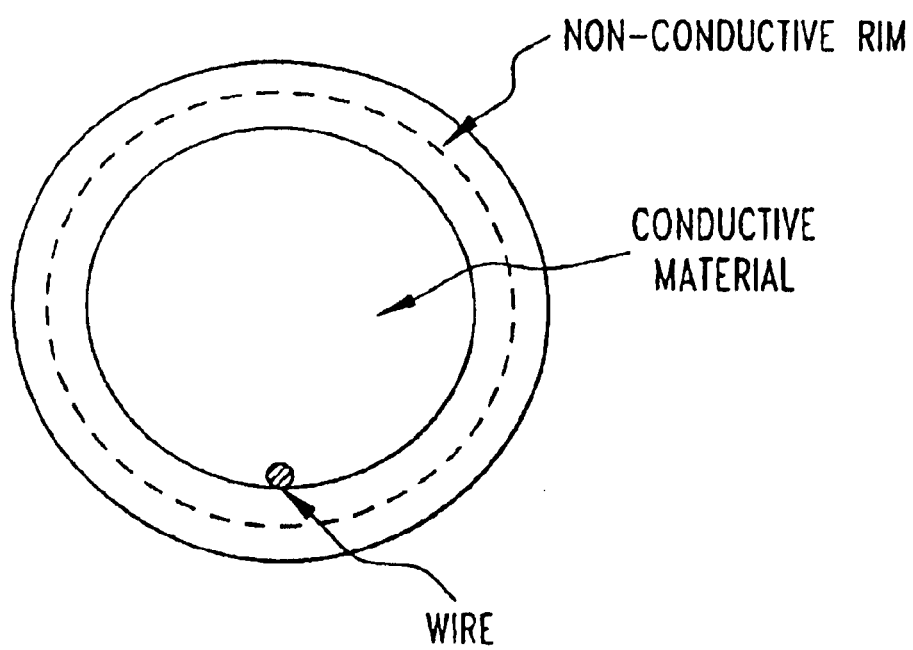
FIG. 64 is an enlarged sectional view of an electrode.
Figure 65:
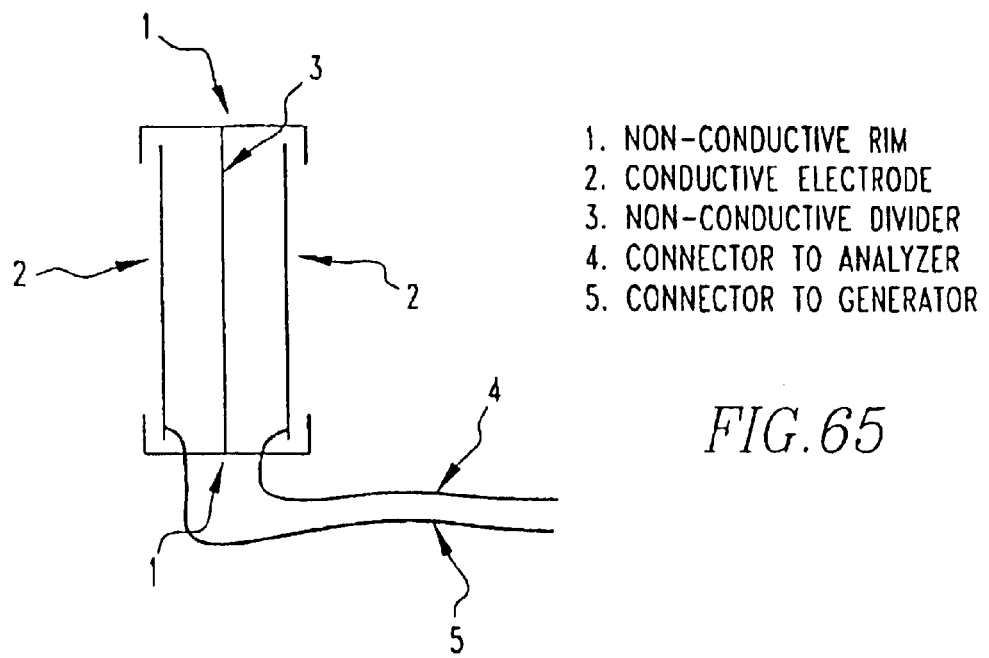
FIG. 65 is a side view of an electrode.
Figure 66:
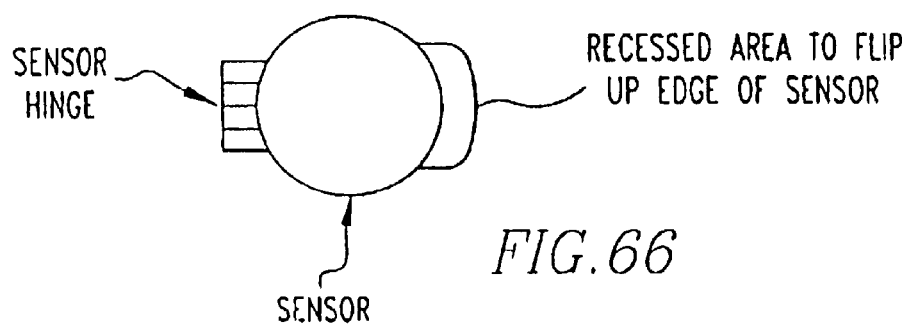
FIG. 66 shows a flip-up sensor.

FIG. 63 shows both a 1 cm diameter and a 1.25 cm diameter thin electrode for sequential grasping between the thumb and fingers. FIG. 64 shows a sectional view of the electrodes. FIG. 65 shows a side view of the electrodes. FIG. 66 shows a hinged flip-up sensor. This sensor can be as thin as the thickness of two pieces of metal foil and an insulator. It is hinge so that it is flush with a surface until it is used, when it is flipped up at right angles to the surface of the device mounting the sensor.

The present invention pertains to an apparatus for accurate recognition of an individual living organism's identity, to the exclusion of imposters, with an accuracy of greater than one in one billion. In this invention, 9 out of 10 imposters can be eliminated by testing with a single frequency scan. There are significant electric/magnetic pattern differences at least every 50 Hertz. Scanning from 50 Hertz up to 500,000 Hertz, will yield 10,000 significant patterns. If a different 9 out of 10 imposters are eliminated via testing at every different frequency, then an accuracy is attained of 1 in $1 \times 10^{10.000}$ people tested. The entire world population is only $8 \times 10^9$ power of people, rounding to 1 times $10^{10}$. Accordingly, an accuracy of 1,000 times the world's population is attained. However, we need only eliminate a different 9 out of 10 imposters at 10 different frequencies to be accurate for the entire world. The present invention is able to eliminate a different 9 out of 10 imposters for at least 25 different frequencies.

The present invention pertains to an apparatus which comprises a sensing mechanism that is moldable into a shape having a non-flat surface. The sensing mechanism can be concave, flat, convex, or a combination thereof, enabling molding for inclusion into devices of various shapes. The sensing mechanism only needs to contact the skin of the subject individual. Such a plastic piezoelectric film sensors can be purchased from the AMP Piezo Film Sensor Unit in Valley Forge, Pa. In addition, rigid acoustic transducers can be curved concave, or curved convex, or beveled or faceted surfaces can also be used.

The present invention pertains to a sensing mechanism which is flexible. The sensing mechanism can be made of rubber, plastic, metal, mineral or ceramic or composites. Because an electrode need only to be able to contact the skin of the subject individual, the electrode surface can be flexible and can be built into a watchband, jewelry or items of clothing, leather luggage, or plastic credit cards without any effect on the functionality of the article being attached with the flexible electrode.

For example, a plastic identity card with a name and picture of an individual can have a thumb electrode on one side and two or three finger electrodes on the other side. Operation is by grasping the electrodes and sliding the card into a reader, which reads the electric and/or magnetic pattern of the individual.

FIGS. 24–33 show the circuit diagrams for a preferred embodiment of the apparatus for recognition of a tested individual organism that can be connected to sensors or electrodes. Except as indicated, all decimal capacitance values are in pF, and all whole-number capacitances are in pF. All resistances values are in ohms.

The system contains a waveform-generation stage, a waveform-detection stage, and associated digital logic. The system allows up to 8 connections to a person for measurement.

The frequency range of the waveform-generation stage is approximately 75 Hz to 1.2 MHZ. To generate this signal, a voltage-controlled oscillator (U13) is used. The voltage used to tune the oscillator is generated by U11, a 12-bit D/A converter. This converter conveniently uses a serial input, so only 3 wires are required from the microcontroller to set the voltage output instead of the customary 12. The VCO tunes from approximately 300 kHz to 1.2 MHZ, a coverage range of approximately 1 to 4. Output from the VCO is approximately a square wave.

The VCO is fed into a 12-bit ripple counter, U15, in order to make lower frequencies available. The ripple counter is wired to divide the VCO output frequency by powers of 4; e.g., the output frequency is divided by 1, 4, 16, 256, 1024, or 4096. One of these outputs is selected by quad NAND gates U5 and U6. Each possible divisor is assigned to one input of its own NAND gate. The other input from each gate is set by the microcontroller to enable the correct divisor only. As the microcontroller has limited number of pins, a 8-bit parallel output serial shift register, U14, is used to reduce the number of connections required from 7 to 2 by allowing the NAND gate mask to be transmitted serially from the microcontroller.

As the D/A and VCO sections may exhibit some frequency drift over time, one of the divider outputs is connected to one of the microcontroller I/O pins. This permits the microcontroller, which contains a time reference which is locked to a ceramic resonator, to determine the actual VCO frequency for calibration purposes. The accuracy of this determination is limited by the resonator's tolerance and is 1% or better.

The outputs of the NAND gates are shaped with RC filters to limit the spectrum of the output waveform to what is intended. As square waves contain a very high-frequency component at the time of each state transition, the wave shapes are modified so that they are somewhat rounded. This ensures that the frequency being measured by the waveform-measurement stage is the frequency that was intended for measurement.

After the RC filters, the frequency-divided outputs are summed to a common point and passed through a capacitor to remove the DC bias. Note that only one output should be transmitted at a time (although it is possible to program the microprocessor to output multiple frequencies, this is not normal operation). The signal is fed, with the DC bias removed, to a CMOS analog multiplexer, U7, to distribute the signal to a point on the subject's hand; e.g., a finger or the wrist. The signal at this stage is approximately 1 volt peak to peak. U7, by the way, takes its address and enable inputs from another parallel output serial shift register, U9, for the same reasons that U14 is present elsewhere.

The waveform-measurement stage begins with a set of eight input amplifiers based on the LT1058 quad JFET input precision high-speed op-amp (U3, U4). It's pin-compatible with many other quad op-amps including the LM324. The LM324 cuts off around 20 kHz, and response past 1 MHZ is needed. The voltage gain is set at 2:1 but can be adjusted by altering resistor values. The issue is enduring that sensitivity is adequate without overloading the analog MUX inputs on U8. The full output of the waveform-generation stage will be on one of the MUX pins, while the low level at another pin is being routed to the detector.

The CMOS analog multiplexer, U8, is used to route the signal from the appropriate hand connection (e.g., finger or wrist) to the detector. The address and enable inputs for this MUX also come from U9. A half-wave diode detector is used to rectify the AF or RF signal and provide a DC level that is usable by the A/D converter. Because the diode has a forward voltage drop of around 0.3 V, a 0.3 V bias voltage is used to keep the diode at the threshold of conduction for small signal detection. The bias voltage is generated by reference to an identical diode.

The A/D converter, U10, is microprocessor compatible meaning that its outputs can be switched to high impedance. This permits the same connections to be used for other purposes. Of the eight output pins, seven are dedicated to the A/D converter, but one doubles as the data pin, for the serial input chips are not clocked during A/D transfers to the microcontroller. To further complicate things, the ten A/D output bits are stuffed into eight wires, so that two wires read two bits each. This is accomplished by initiating two read cycles from the microcontroller.

Figure 33:
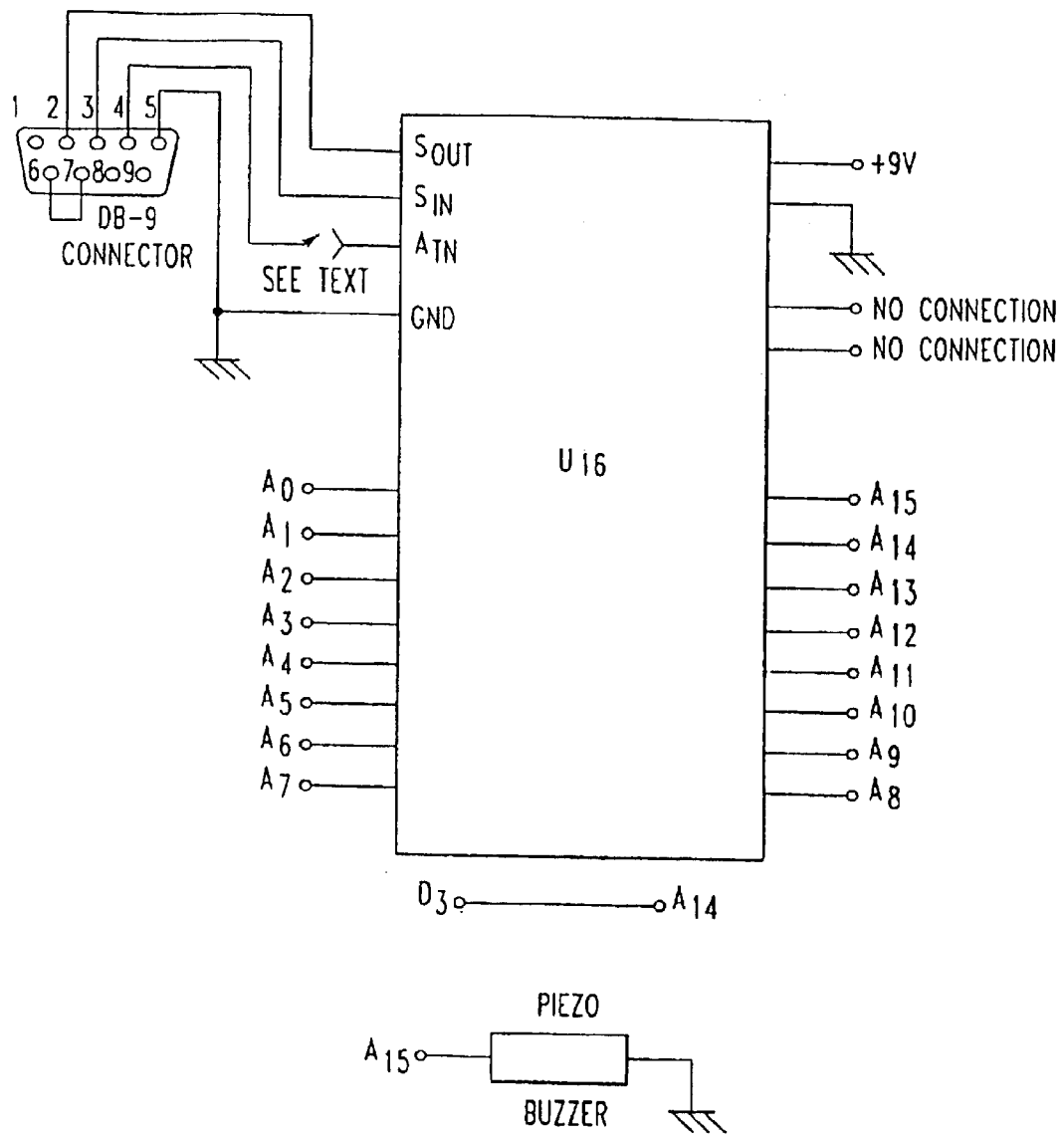

The microcontroller, U16, is a BASIC stamp II from Parallax, Inc. It has a built-in serial interface with a line receiver, "fakes" a line transmitter with a resistor, 16 I/O lines, 26 bytes RAM, 2048 bytes EEPROM, and a BACIC interpreter in ROM. The controller programs in a BASIC dialect. It should be noted: pin 3 of U16 must be connected when programming the microcontroller, but must be disconnected immediately after programming and prior to use. This disconnection is shown in FIG. 33.

To read an impedance, the following steps must be performed by the microcontroller, which is preferably in communication with a host computer running Windows 98 and appropriate software. The microcontroller software is already written, and serves to accept commands from the host computer and return readings as appropriate.

1. Set the D/A converter to output a voltage which causes the VCO to oscillate at the desired frequency. This is within a range of 300 kHz to 1.2 MHZ. This step is performed by sending a 12-bit signal to the D/A converter via the 3-wire serial interface A0, A11, and A12.
2. The frequency output by the VCO should be measured by counting the pulses on the appropriate microcontroller pin (A13) over a fixed period of time. The D/A converter output can be adjusted as necessary to ensure that the correct frequency is produced. (This step can be done either in real time, or more preferably as a pre-operation sequence to produce a frequency calibration curve. The unit will not drift appreciably during a usage session, but might over weeks or months. It also requires this frequency calibration prior to being placed in service. This step can be entirely user-transparent.)
3. The input and output MUX channels (fingers or wrist must be selected. This is done by sending an 8-bit signal to U9 via the 2-wire serial interface A0 and A10.
4. The appropriate frequency divider output (1, 4, 16, 64, 256, 1024, or 4096) must be selected. This is done by sending a 8 bit signal (7 bits are used) to U14 via the 2-wire serial interface A0 and A14.
5. A brief settling time (10 ms is adequate) should occur to allow the capacitor in the signal detector to reach equilibrium with the new measured value.
6. The A/D converter is read. This is accomplished using A0 through A7 for data, A8 and A9 for control. The chip is actually read twice to obtain all ten bits of the result; refer to the manufacturer's documentation. Do not forget to set A0 as an input pin for this step; it is used at other times as an output pin for serial data. The data read by the A/D converter will require numeric adjustment via some calibration curve to represent an actual impedance. This curve will be sensitive to frequency on account of the RC filters and frequency response of the input amplifiers, MUX, and signal detector circuit. A "calibration plug" with fixed impedances in place of a hand piece has been fabricated to allow the system to produce calibration curves for this purpose.
7. A15 is connected to a piezo buzzer to allow the microcontroller to make appropriate noises as desired by the programmer. Alternatively, A15 may be used to drive a small speaker through appropriate circuitry; the microcontroller can generate as many as two audio frequencies at a time on this pin using pulse width modulation.

Many different types of hand units 125 can be used to read and send an individual's signature signal by wiring, or wireless transmission, to a computer, which processes the signal and compares it to a known signature signal stored in the computer's memory, or prepares it for further transmission to a remote location, or both. Upon recognition or identification verification of the individual, an action is allowed, such as access to a computer. Alternatively, the system can require a constant verification signal person operating the hand unit can be sent through a modem either directly or indirectly through the Internet to assure that the individual operating the computer is the verified individual. This assures that the computer is not then turned over to a non-verified third party trying to appropriate the computer for subsequent operations under the authorized individual's name, such as sending or obtaining information or purchasing goods or services. The computer can also keep a log of who accessed a site and when.

Generally, six electrodes are used for hand units. All connections are made through the 9-pin connector that is standard on the back of a computer tower or desktop, although the 25-pin printer port can also be used. The pins used on the 9-pin connector are the same ones for each hand unit. The electrodes can be conductive metallic foil, plastic, or rubber. They can be flat (about 2 cm×2 cm) or molded for finger tips (taking into account the large variations in size of different individuals). A simple flat reversible hand unit can be used for the right or left hand as shown FIGS. 34 and 35. Electrodes are placed in the following regions: 1) heel of the palm (a long electrode strip or a single small electrode movable on a spring); 2) thumb tip; 3) index finger tip; 4) middle finger tip; 5) ring finger tip; 6) little finger tip. The hand unit must be adaptable to large or small hands. It is preferably clear Plexiglas for each surface and has a hollowed out areas for the heel of the palm and for the finger tips. The entire hand area could be hollowed out a little to produce more consistent hand placement. The hand piece is fabricated using brass inserts pressed through plastic sheets for the electrodes.

Keyboard 126 shown in FIG. 36, has electrodes placed at the (T), (7), (9) and (P) keys, and a 4 centimeter strip can be placed on the left end of the space-bar and a palm strip electrode on the lower frame of the keyboard. Conductive rubber keys for the keyboard are preferred. Keyboard 126 is useful only for activation, but not for continuous indication of the presence of an authorized user, since continuous contact with all the electrodes during use is impossible. The wiring from the electrodes on the keyboard can run with the normal keyboard wiring to the computer, or to the 9-pin or 25-pin connections.

Figure 37:
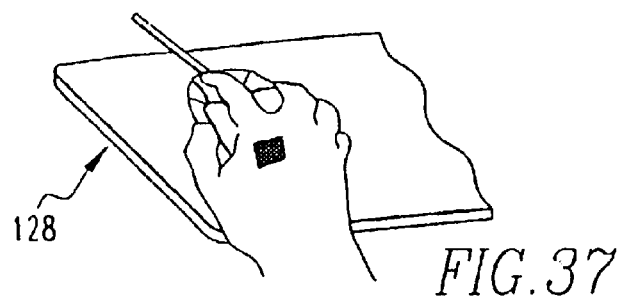
FIG. 37 is a schematic representation of a hand grasping a mouse having sensing electrodes.
Figure 38:
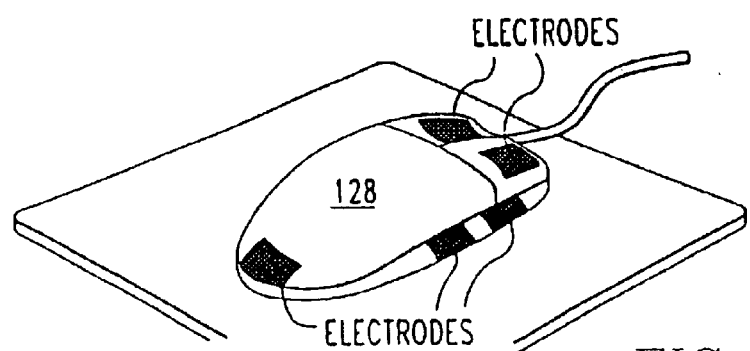
FIG. 38 is a schematic of a mouse having electrodes.

A mouse 128 shown in FIGS. 37 and 38 includes conductive foil strips or imbedded conductive polymers that attach flat to the surface of the mouse for the palm and each finger tip, which allows easy grasping of the mouse. A variation of requiring the user to continuous contact for continuous verification is to require periodic grasping for verification to prevent computer shut down. The keyboard and mouse preferably use Compaq aluminized tape with conductive adhesive for the electrodes. The wiring from the electrodes on the mouse can run with the normal keyboard wiring to the computer, or to the 9-pin or 25-pin connections.

Figure 39:
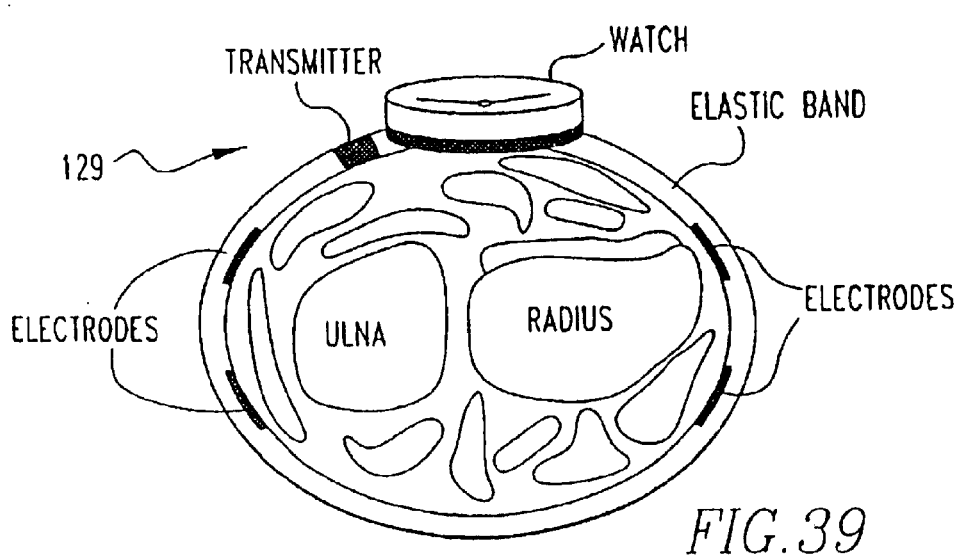
FIG. 39 is a side view of a wrist band having electrodes.

A wrist band 129 shown in FIG. 39, made of elastic material, can be used to simulate a wrist watch. Electrodes of conductive foil are attached to the inside of the band. A transmitter of wrist band 129 transmits the individual's biometric signature obtained by the electrodes by pushing a transmission button or by periodic automatic transmission. The transmission of the signature is received and compared to the individual's stored known signature, and recognition will then be confirmed or denied. For example, the watch could be used in proximity to a receiving and comparing wall unit that controls access to a room. The wall unit transmits a radio signal to the watch, causing the watch to transmit the biometric signal. The wall unit receives and compares the signature with known authorized signatures. If a match occurs, the wall unit unlocks a door. The wrist band could be used with a personal area network (e.g. see "Personal Area Networks: Near-Field Intrabody Communication" by T. G. Zimmerman, Systems Journal, Vol. 35, No. 314, 1996, MIT Media Lab).

Figure 40:
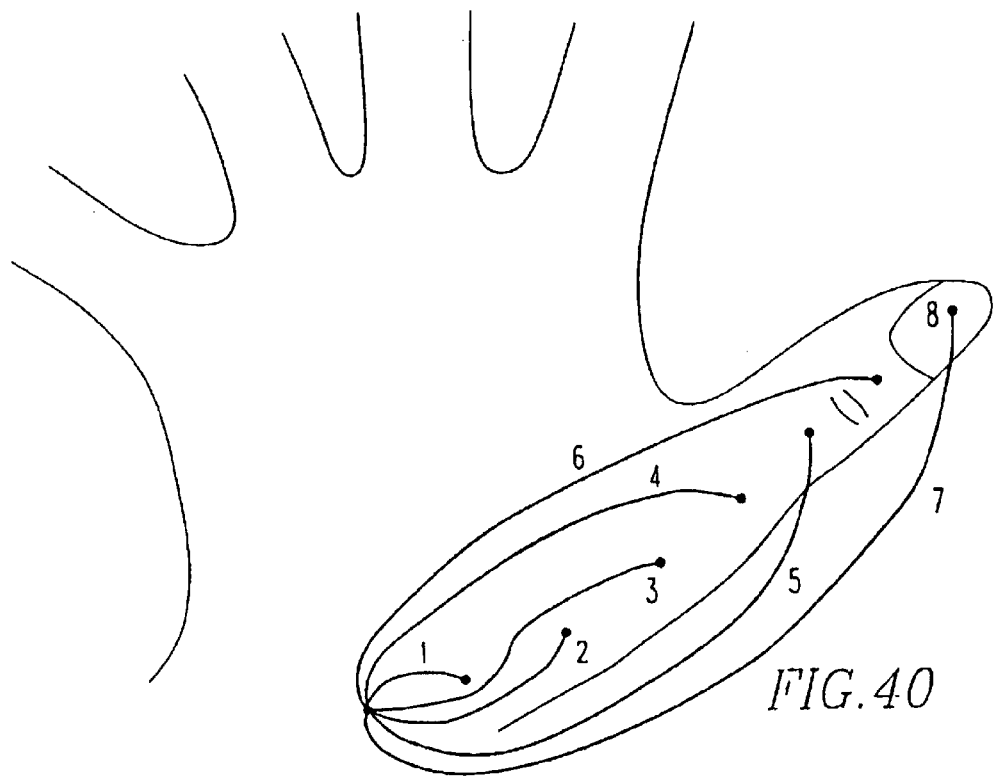
FIG. 40 is a schematic of electrode placement and current path of measurement from the palm to the thumb.
Figure 41:
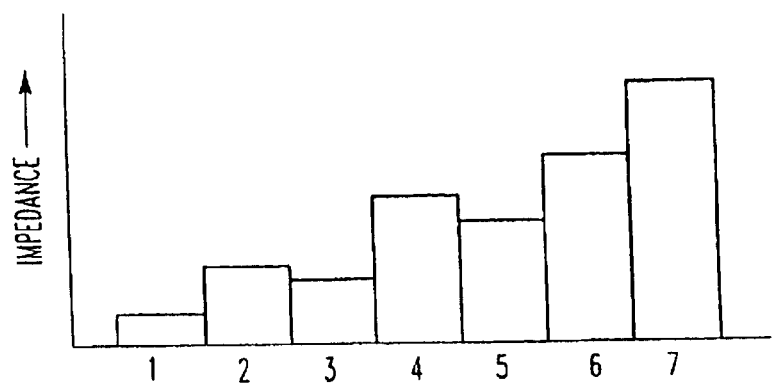
FIG. 41 is a two-dimensional impedance plot corresponding to the electrode placement of FIG. 40.
Figure 42:
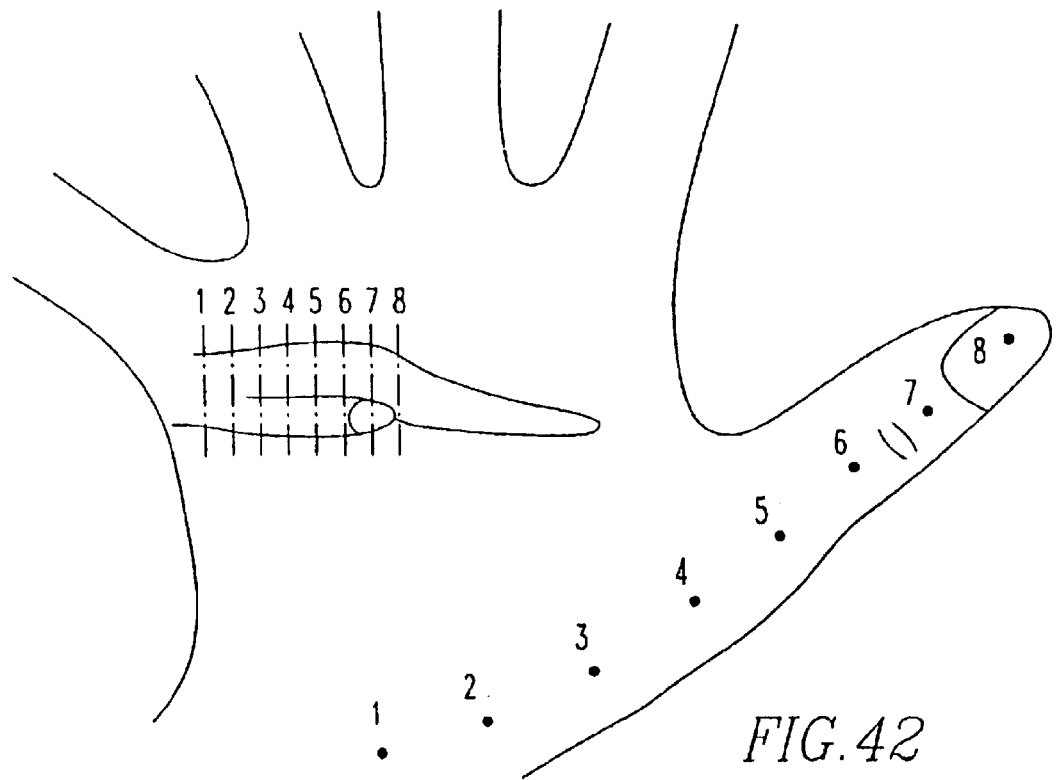
FIG. 42 is a schematic of measurement sites for back-to-front capacitive plate measurements from the palm to the thumb.
Figure 43:
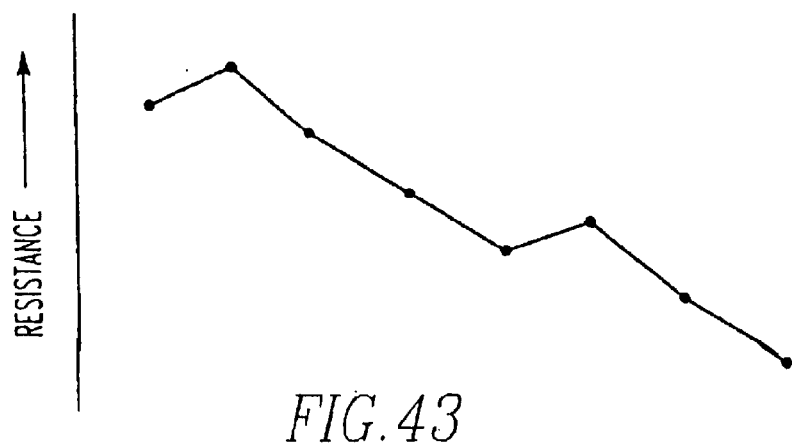
FIG. 43 is a two-dimensional impedance plot regarding resistance at a single frequency corresponding to the measurement sites of FIG. 42.
Figure 44:
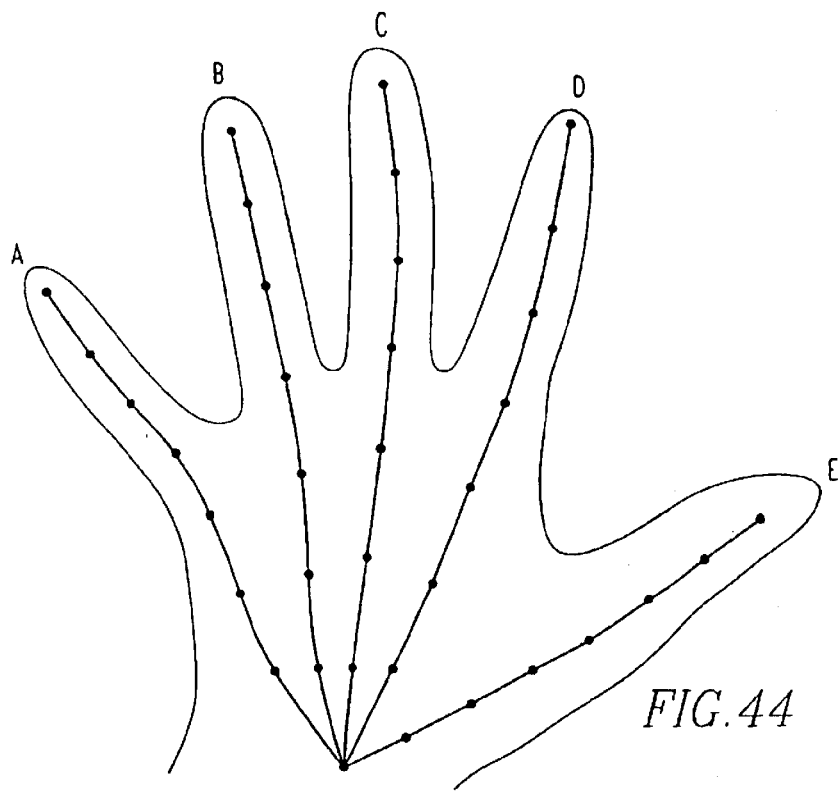
FIG. 44 is a schematic of measurement sites from the palm to each finger-Up.
Figure 45:
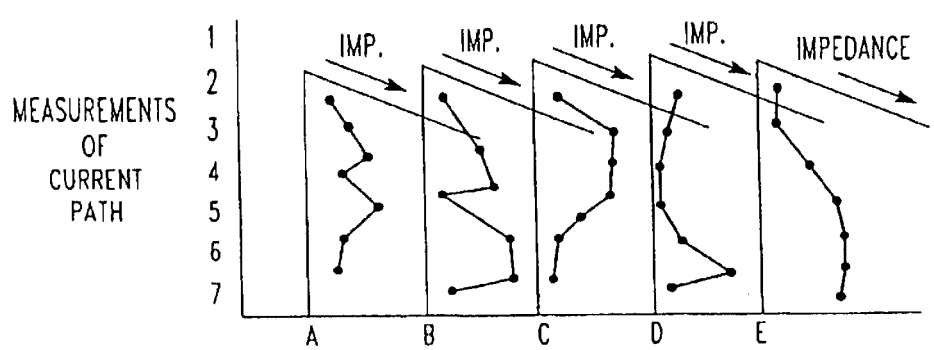
FIG. 45 is a three-dimensional plot at a single frequency regarding measurements from the measurement sites of FIG. 44.
Figure 46:
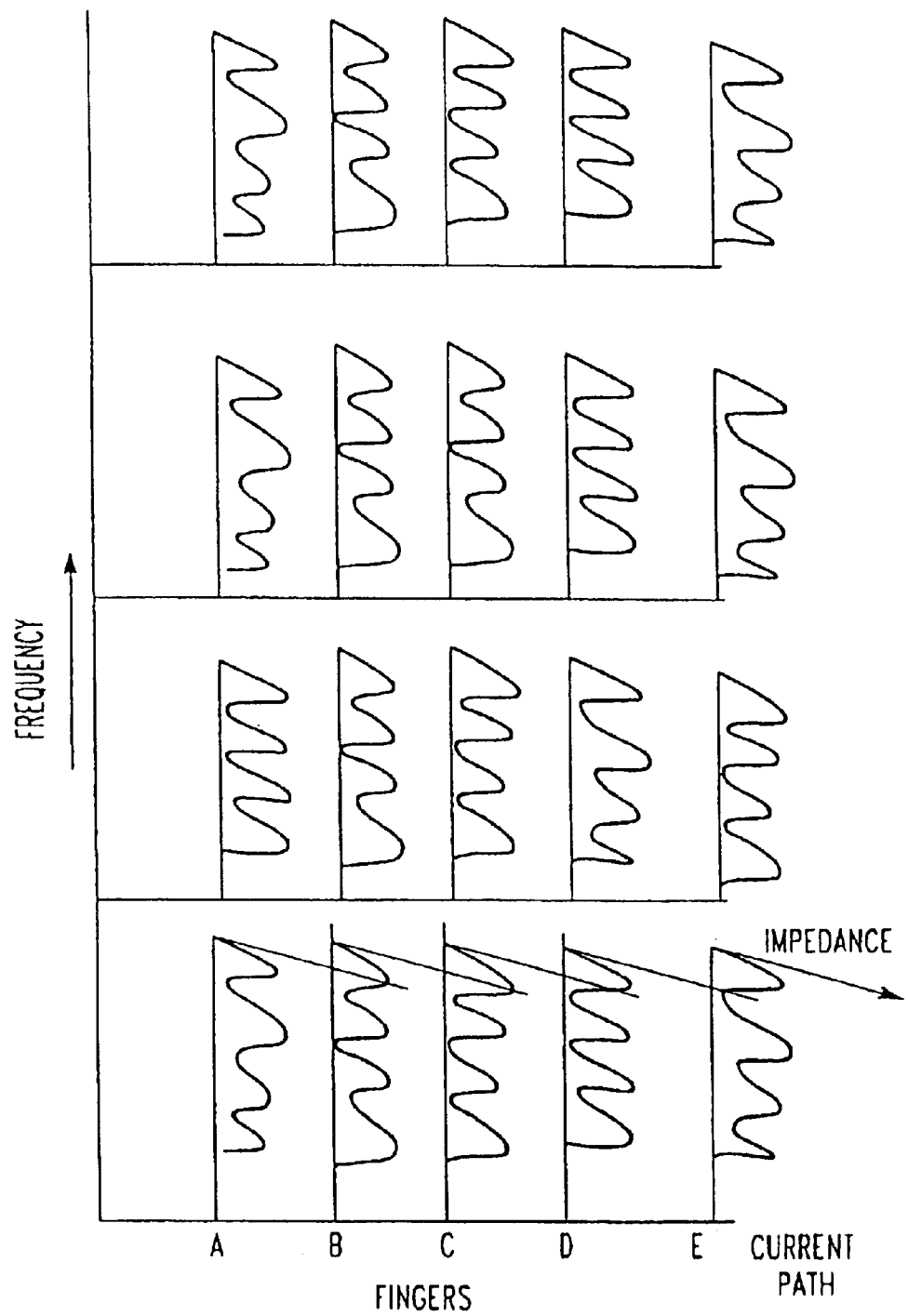
FIG. 46 is a four-dimensional plot at four different frequencies from the palm to each finger-tip.
Figure 47:
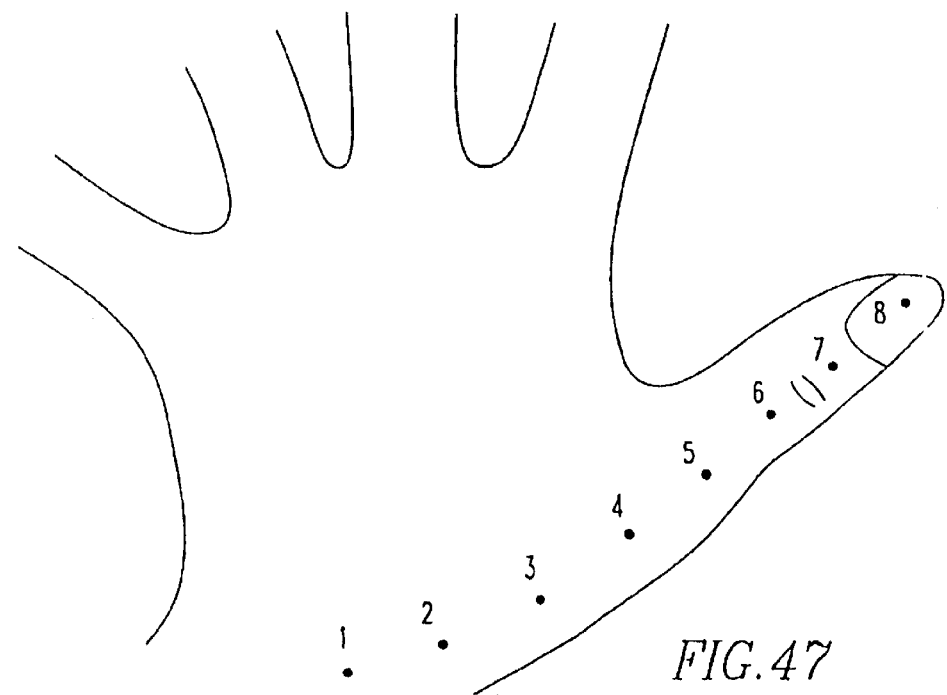
FIG. 47 is a schematic of electrodes for one finger.
Figure 48:
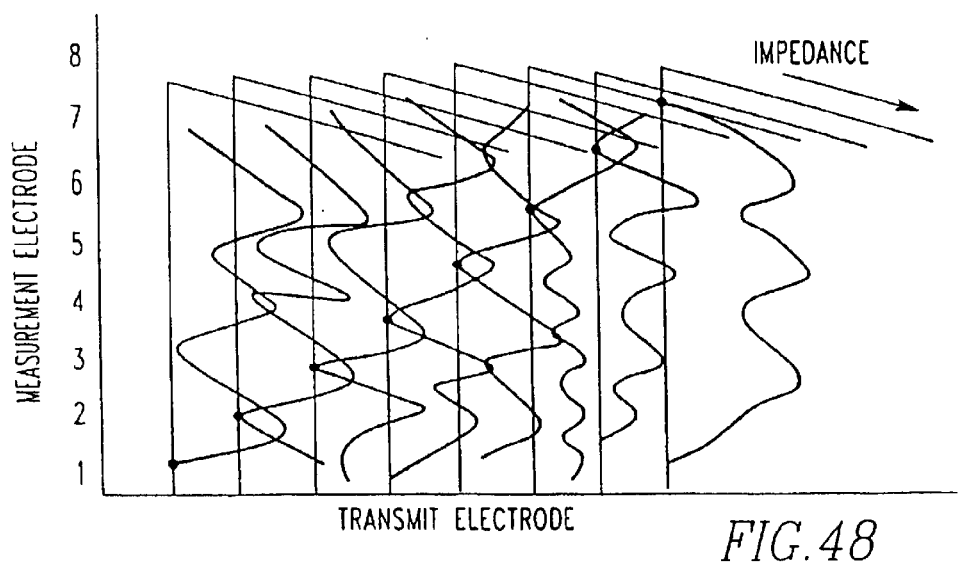
FIG. 48 is a three-dimensional plot at a single frequency from electrode to electrode for one finger as shown in FIG. 47.
Figure 49:
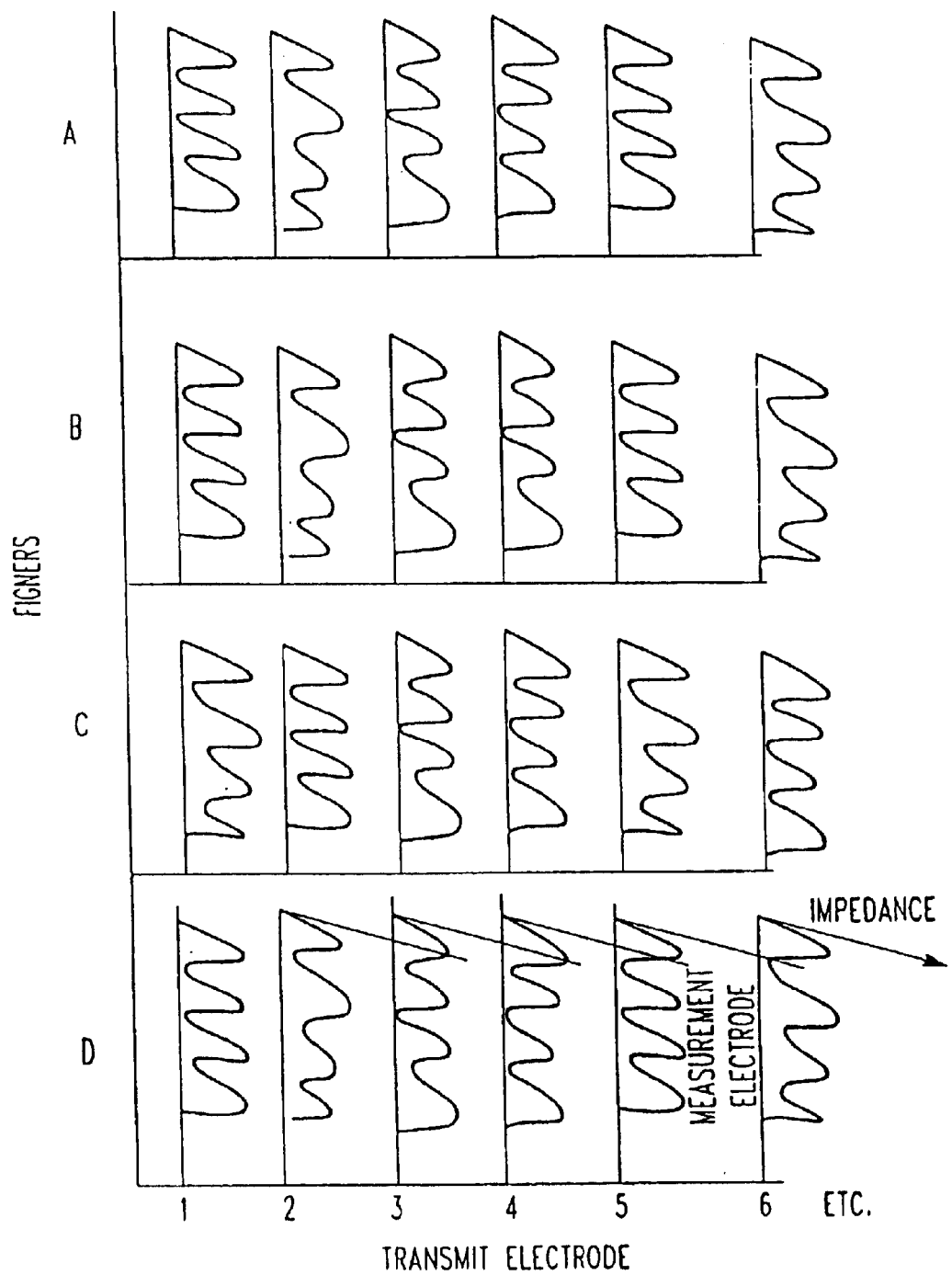
FIG. 49 is a four-dimensional plot at a single frequency from electrode to electrode for each finger.
Figure 55:
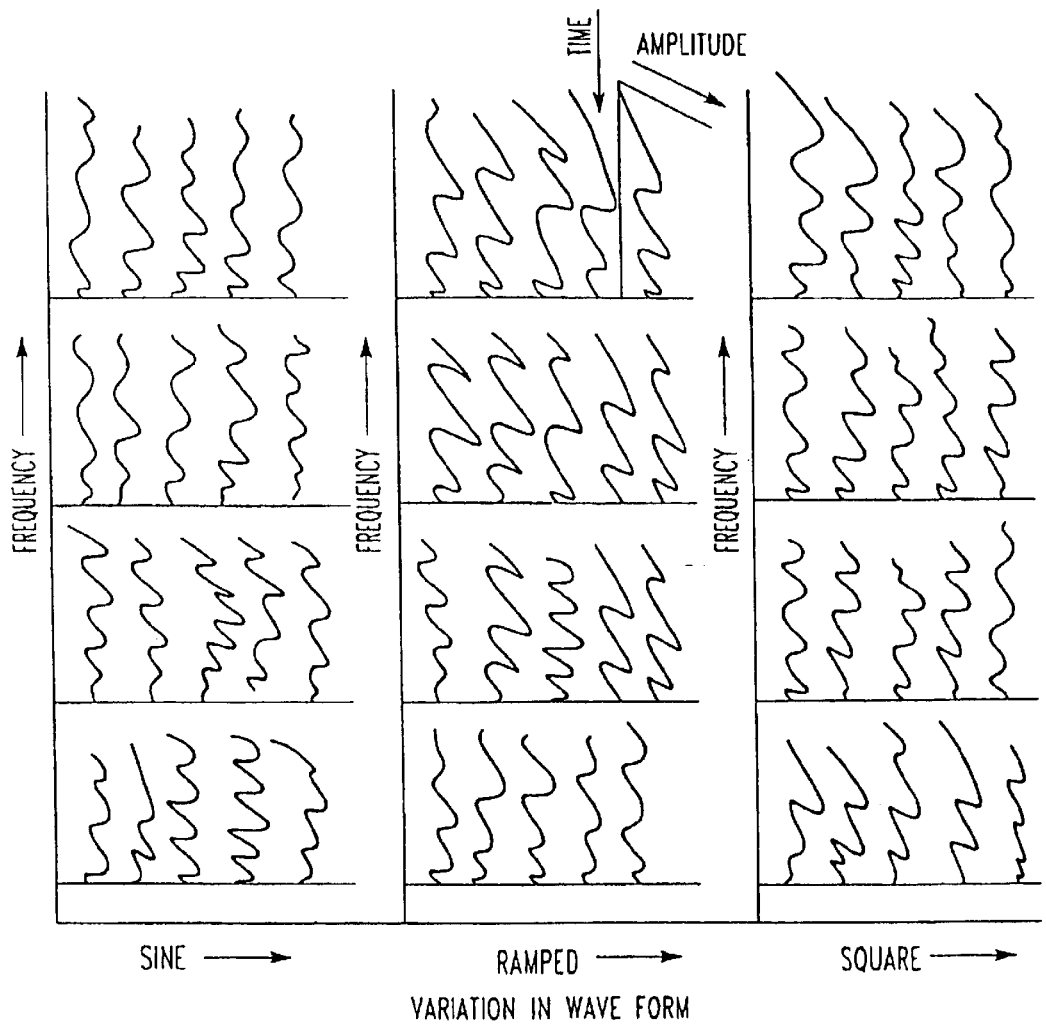
FIG. 55 is a five-dimensional energy plot with sine, square and ramped waveforms at four different frequencies sideways through the thumb.
Figure 56:
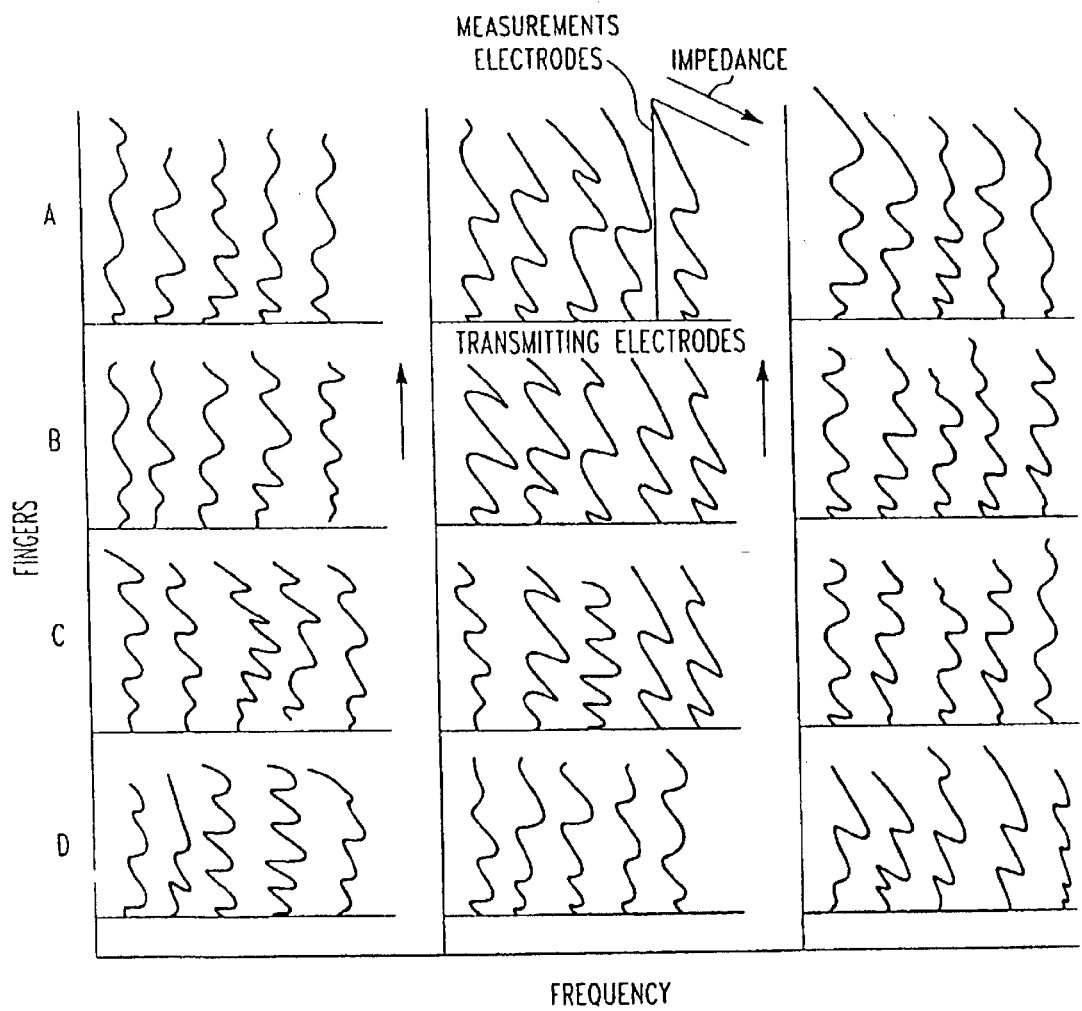
FIG. 56 is a five-dimensional energy plot at three different frequencies from electrode to electrode for each finger.
Figure 57:
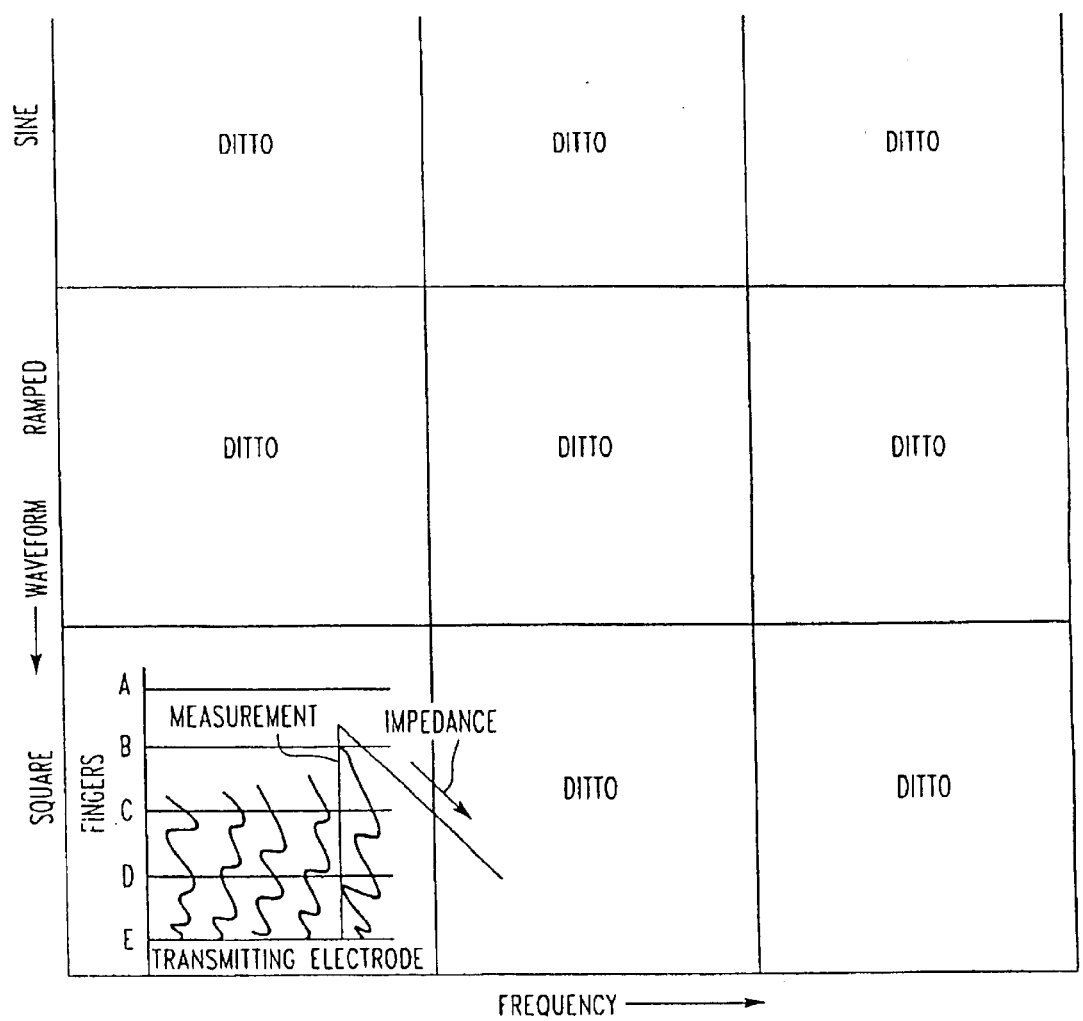
FIG. 57 is six-dimensional energy plot with sine, ramped and square wave forms at three different frequencies from electrode to electrode for each finger.
Figure 58:
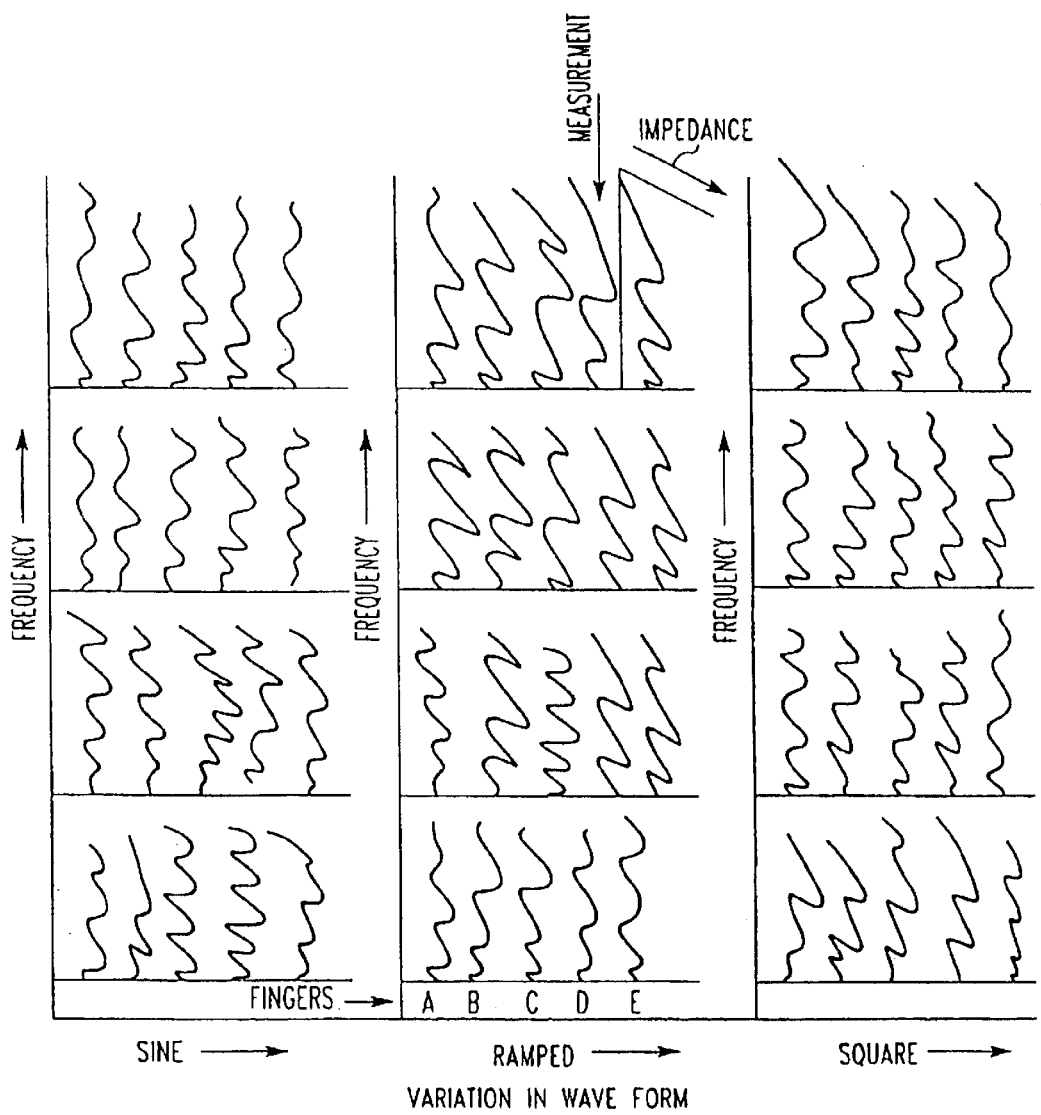
FIG. 58 is a five-dimensional energy plot with sine, square and ramped waveforms at four different frequencies from the palm to each finger-tip.

Referring to FIGS. 40–58, multidimensional matrices such as three- and four-dimensional matrices can formed for recognition purposes. Acoustic biometric scans can produce three-dimensional patterns at one frequency, and four-dimensional patterns at multiple frequencies. The electric/magnetic techniques described herein produced two-dimensional scans at a single frequency and three-dimensional matrices when multiple frequencies are used to test a single body segment. In the electric/magnetic techniques, if there are multiple sensors along the current path, such as shown in FIGS. 40, 42, and 44, there would be 8 different readings for the palm to thumb-tip current at a single frequency. This produces a two-dimensional reading for the thumb and a three-dimensional plot for all five fingers. Extending this to multiple frequencies would yield a four-dimensional plot of the tested body part, as shown in FIGS. 46 and 49. By varying the waveform and switching patterns, five- and six-dimensional matrices, as shown in FIGS. 56–58 are attained.

Figure 50:
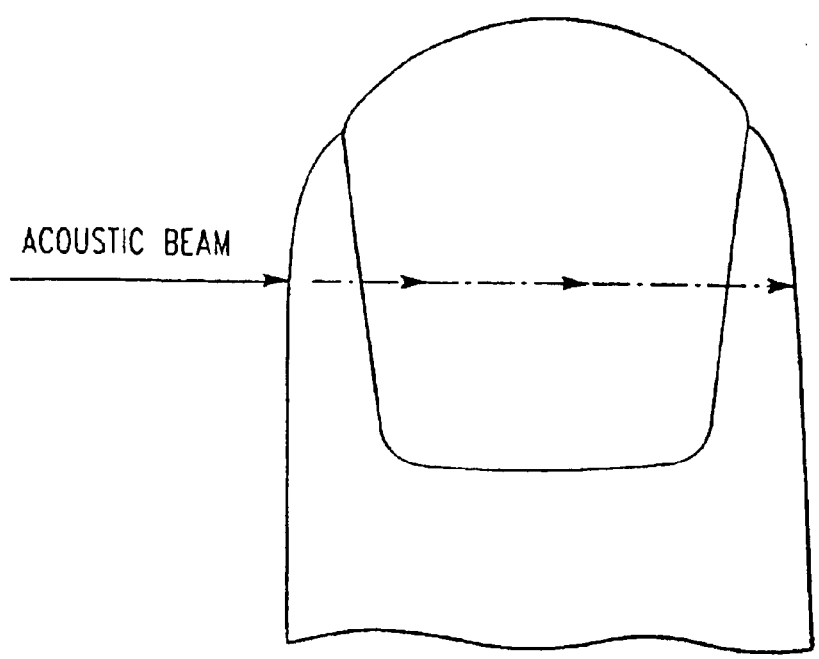
FIG. 50 is a schematic of an acoustic beam at a single frequency passing through the thumb from the side of the thumb.
Figure 51:
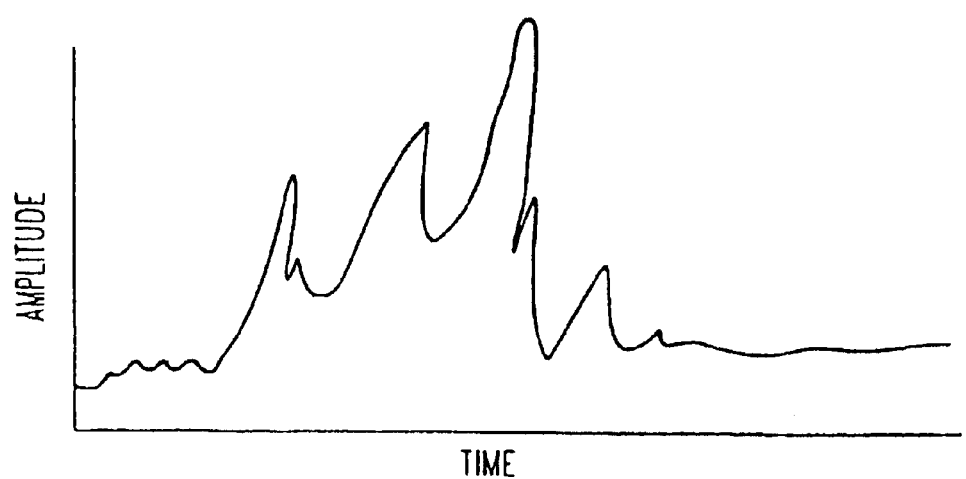
FIG. 51 is a two-dimensional acoustic plot at a single frequency of FIG. 50 energy, charting amplitude versus time.

Scans on the thumb of several individuals at a single frequency resulted in unique signatures for the individuals which allowed for easy identification of the individuals. For a single frequency scan, in its simplest form, a two-dimensional plot was obtained, with amplitude on the Y-axis, and time on the X-axis, as shown in FIGS. 50 and 51. For a multiple frequency scan, a three-dimensional plot was obtained, with frequency on the Z-axis. The mode used to obtain the result was the "radar" type mode, with a single transducer working in what is known as the "pulse-echo mode". Preferably, only one transducer was used, and excellent results were achieved, although more than one transducer could have been used.

In the radar type mode, the acoustic energy was transmitted by the single transducer in contact with the skin of the tested body part. The acoustic energy was released in a well-defined short burst and as the energy passed through the subject organism, portions of it over time were reflected as the energy moved through the soft and hard tissue of the subject organism. The echo or reflection of the energy back to the transducer over time yielded the biometric signature of the subject organism.

Figure 52:
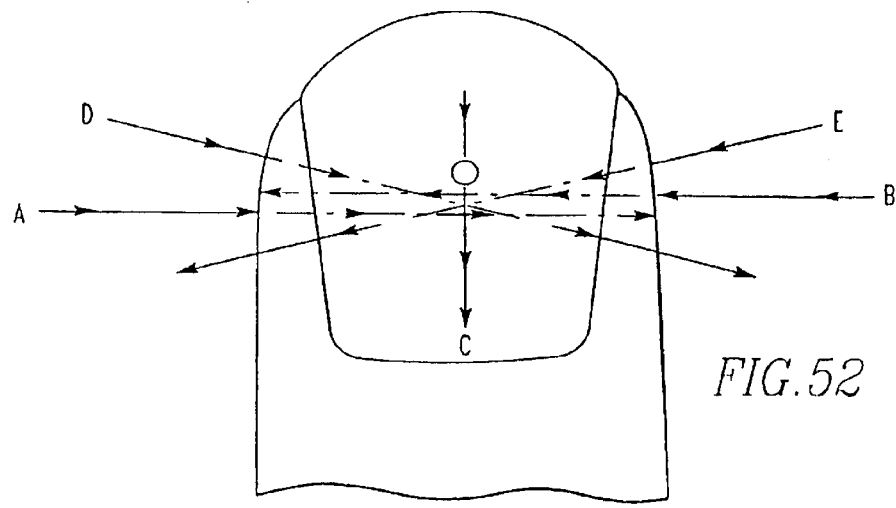
FIG. 52 is a schematic of acoustic energy at a single frequency passing sideways through the thumb, varying the location of the thumb relative to the acoustic energy.
Figure 52A:
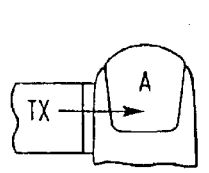
Figure 52B:
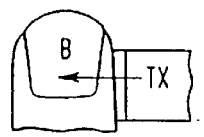
Figure 52C:
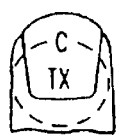
Figure 52D:
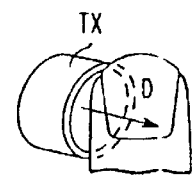
Figure 53:
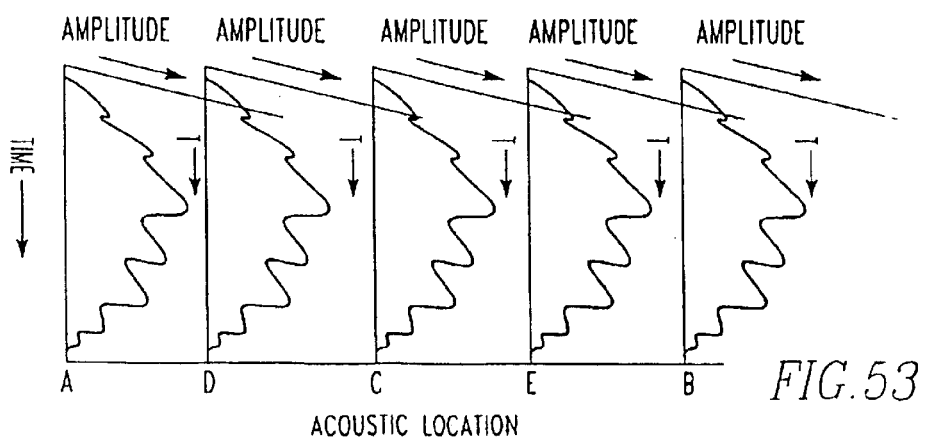
FIG. 53 is a three-dimensional energy plot of FIG. 52.
Figure 54:
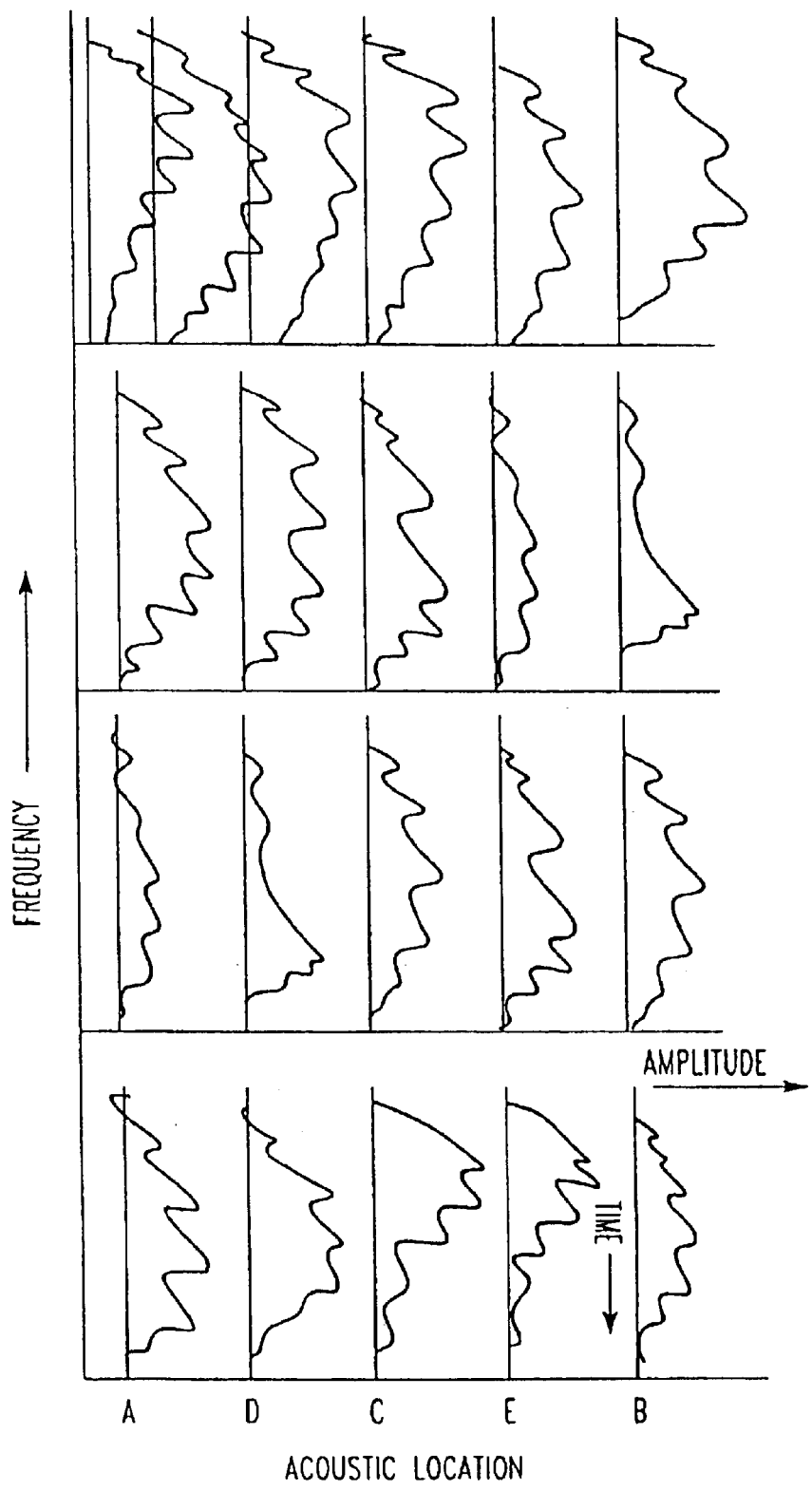
FIG. 54 is a four-dimensional plot of sensed energy at four different frequencies measured sideways through the thumb.

In its more complex and preferable form, three-dimensional scans were produced at a single frequency. One side of the thumb was scanned to the other, for a total of 25–35 scans per person. Each single scale was two-dimensional, and when combined in a group, with location plotted on the Z-axis, yielded a three-dimensional ultrasonic topography of the thumb, as shown in FIGS. 52 and 53. If the three-dimensional ultrasonic topography is extended to multiple frequencies, a four-dimensional plot results, with frequency on the W-axis, as shown in FIG. 54. If waveform is varied, a five-dimensional plot results, as shown in FIG. 55.

Medical frequencies are preferably in the low MHZ range (2.25 MHZ; 0.7 to 1.8 mm wavelength) were used and were able to detect all the detail necessary to obtain a unique signature.

Although the detection of induced current can be used for biometric recognition, the detection of induced current can be used for other purposes, such as for diagnostic purposes including diagnosing bone condition. In a normal bone (FIG. 59), an induced current will flow through the bone since the bone is a conductor, as is well known in the art. See "Radiofrequency Radiation Dosimetry Handbook", Fourth Edition, October, 1986; USAF School of Aerospace Medicine, Aerospace Medical Division (AFSC), Brooks Air Force Base, TX 78235-5301. However, when the bone has a fracture or break in it (FIG. 60), the current flow will be interrupted or reduced by the break or fracture. As shown in FIG. 61, an apparatus for inducing an electric current in the bone, as described above, has a galvanometer which indicated a stoppage of current flow in the bone due to a break. In FIG. 62 the galvanometer indicated expected and normal current flow through a normal bone.

In this case, the detecting mechanism (galvanometer) detects a characteristic of the organism (bone) associated with current induced in the organism.

The present invention pertains to a method for secure communication between an individual at a first location and a second location. The method comprises the steps of sensing a non-visible attribute of an individual, recognizing the individual, and allowing the individual to communicate with the second location.

U.S. patent application Ser. No. 08/974,781, entitled "Method and System For Biometric Recognition Using Unique Internal Distinguishing Characteristics"; incorporated by reference herein, describes a method and apparatus for biometric recognition which utilizes acoustic energy transmitted via a transmitting transducer through an external surface of a body part to the non-visible internal tissue. This acoustic energy is altered by interaction with the discontinuities and inhomogenieties of the internal tissue to comprise a unique acoustic characteristic that is sensed by a receiving transducer. As with electric and/or magnetic characteristics, the acoustic characteristics are unique to an individual and can similarly be used for identification purposes. The transmitting and receiving functions can be accomplished by a single transducer.

The present invention pertains to a method for sensing the electric and/or magnetic properties of an individual living organism comprising the steps of transmitting acoustic energy into the organism, and receiving the electric and/or magnetic energy generated in the organism due to the acoustic energy after it has interacted with the organism.

Impedance and phase angle resonance frequencies can also be used for recognition. An individual can grasp a transducer with the thumb and forefinger to provide a multifrequency scan point of the thumb and forefinger. An organism's body segment has a unique impedance or phase angle resonance frequency that can be used to recognize the organism.

Figure 67:
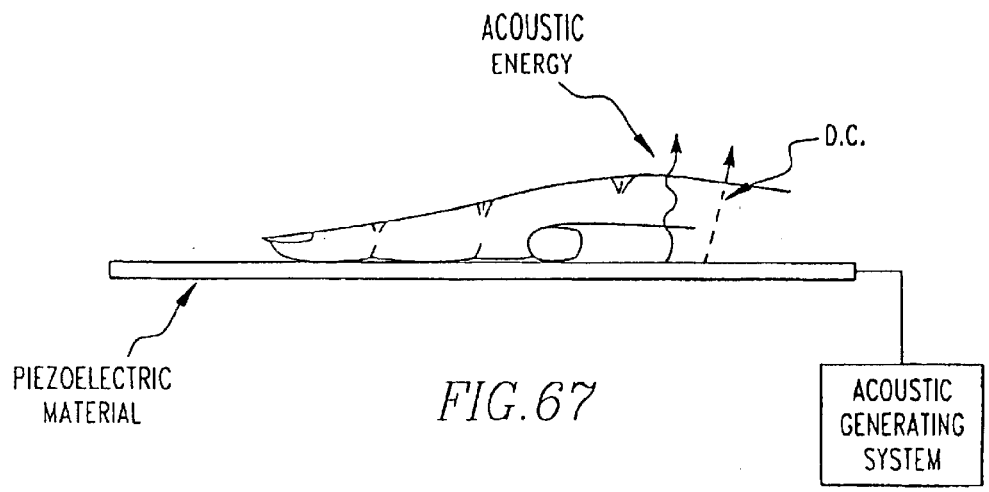
FIG. 67 shows an acoustic mechanism for generation of direct current.
Figure 68:
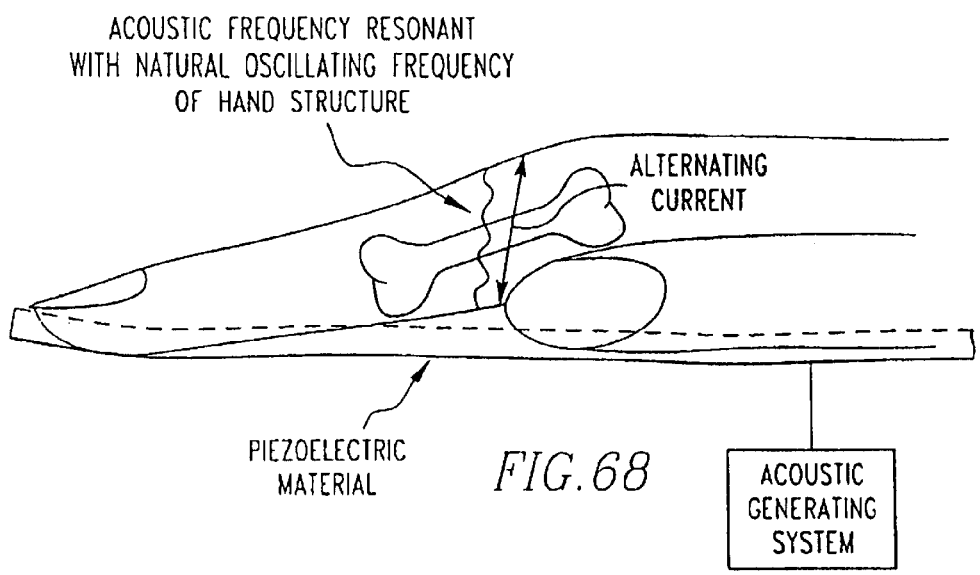
FIG. 68 shows an acoustic apparatus for the generation of alternating current and magnetic fields.
Figure 69:
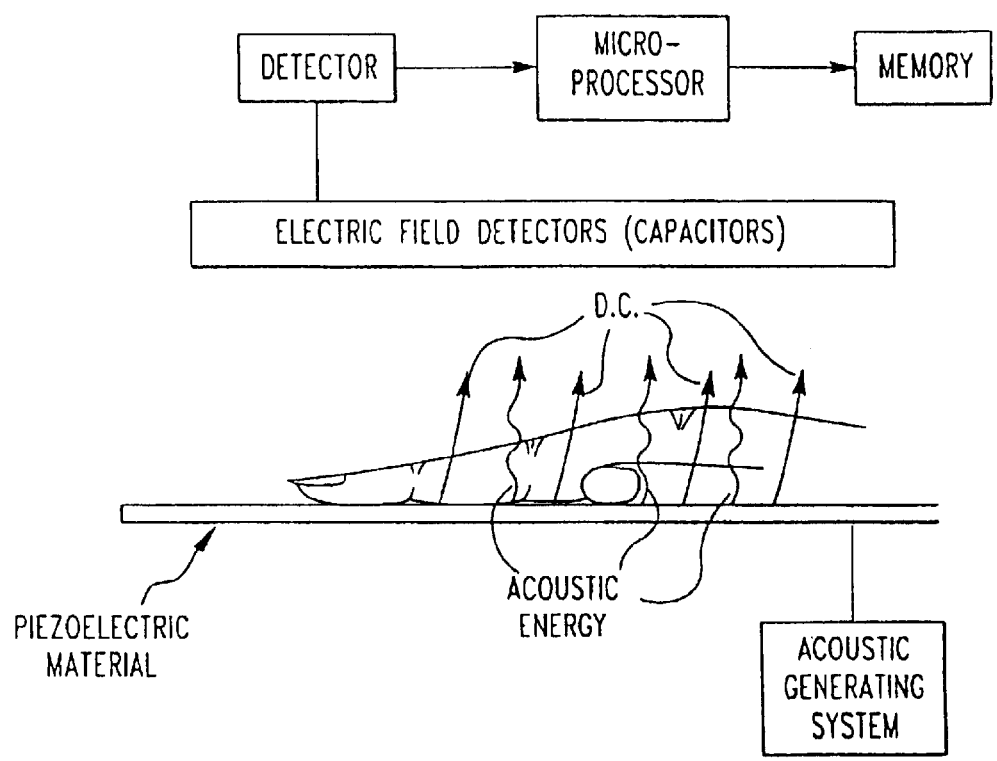
FIG. 69 shows an apparatus for detection of direct current or alternating current induced by acoustic energy.
Figure 70:
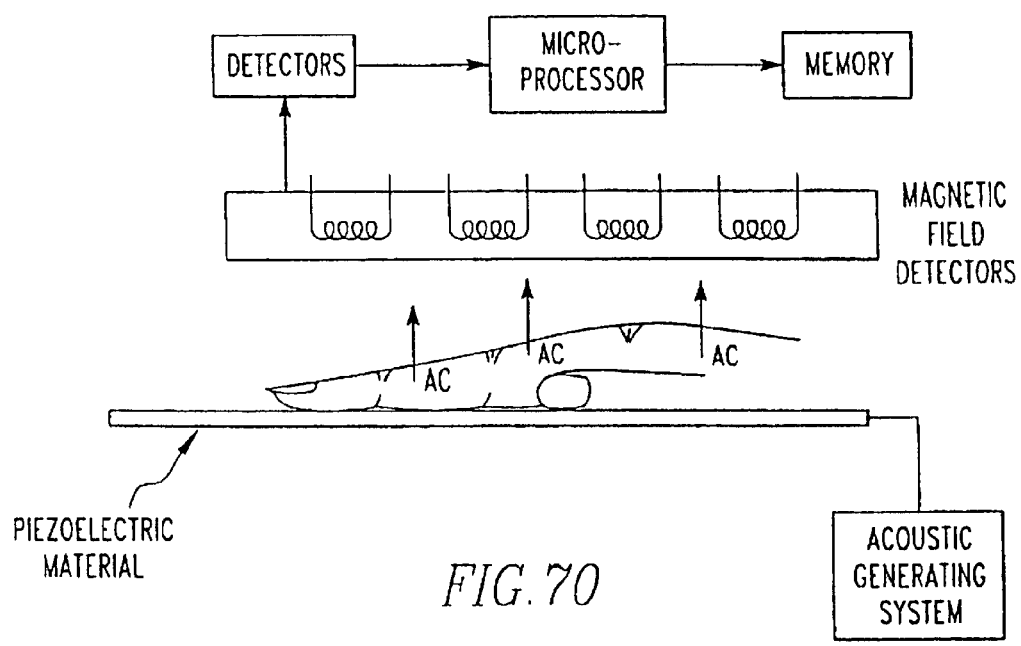
FIG. 70 shows an apparatus for the detection of alternating current induced by acoustic energy.
Figure 71:
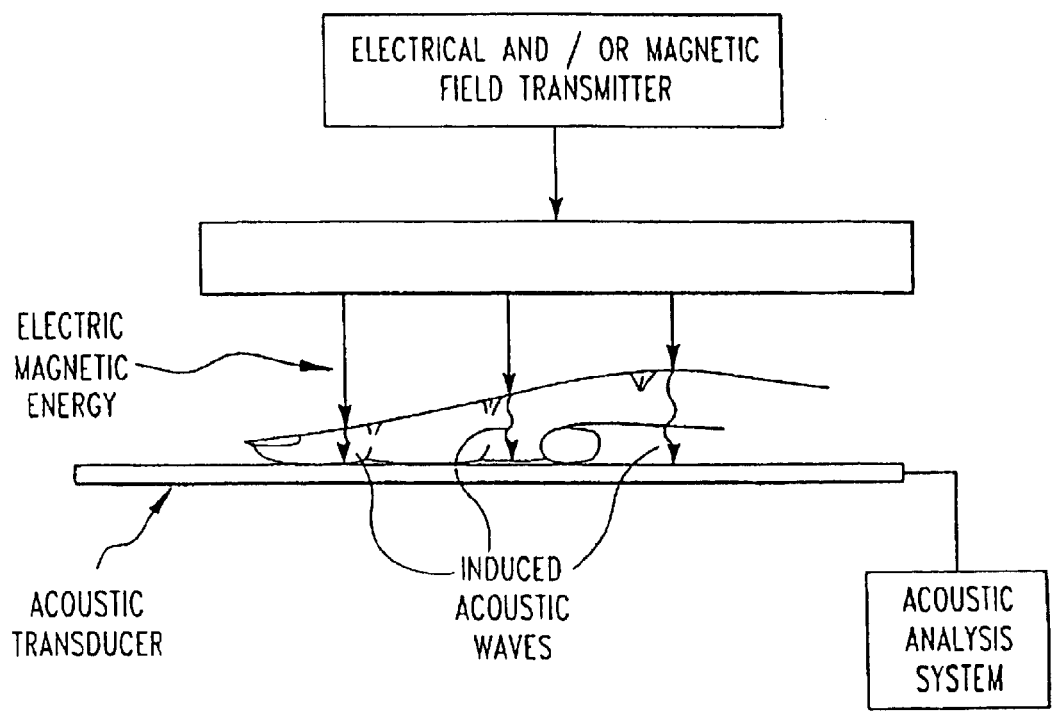
FIG. 71 shows an apparatus for producing an acoustic wave by electric and/or magnetic energy.

FIG. 67 illustrates acoustic generation of direct current. An acoustic generating system provides energy via a piezoelectric material into a body segment, which generates a direct current. The direct current will be generated in the semi-conductor structures. FIG. 68 shows the acoustic generation of alternating current and magnetic fields. An alternating current will be generated in the semi-conductor structures whose natural oscillating frequency matches the acoustic frequency. This will in turn produce a magnetic field. FIG. 69 shows apparatus for detection of direct current or alternating current induced by acoustic energy. The acoustic generating system is connected to the piezoelectric material which sends acoustic energy through a body segment, here a hand. This produces direct current that is detected by electric field detectors, such as capacitors. FIG. 70 shows apparatus for detecting alternating current induced by acoustic energy. At a single frequency the locations are mapped out of the structures producing the alternating current by detection with magnetic field detectors. FIG. 71 depicts an electric and/or magnetic field energy transmitter which induces an acoustic wave. An acoustic analysis system receives the induced acoustic waves detected by an acoustic transducer which result from electric/magnetic energy interacting with the hand.

Referring to FIGS. 75, 76, 77, 78 and 79, an apparatus 199 for authenticating an individual includes a mechanism 135 for recognizing a biometric signature of the individual, including a contact card 170 having electrodes 150 which an individual touches to generate a biometric signature. Authenticating apparatus 199 includes a reader 174 for reading contact card 170 to obtain the biometric signature.

Contact card 170 provides a present biometric signature of a presented individual and reader 174 compares it with a known biometric signature to recognize the individual. Card 170 has a first side 147 and a second side 148, including electrodes 150 which comprise a plurality of finger electrodes 151 disposed on first side 147, and a thumb electrode 153 disposed on the second side 148.

Apparatus 199 includes a contact electrode 173 located in a card insertion groove 175, which contacts a reader contact plate 183 of reader 174 to transfer the present biometric signature to the reader 174. The groove 175 includes a stop 169 for card 170 to align contact electrode 173 and contact plate 183.

Card 170 includes a card memory 172 located on one side that has the known biometric signature. Reader 174 includes a memory reading mechanism 185 in groove 175 that reads the known biometric signature from card memory 172.

Reader 174 includes a generator 177 for generating an electrical signal that is transferred to contact plate 183, to the contact electrode 173, and to the finger electrodes 151 and/or the thumb electrode 153 for generating the present biometric signal.

Reader 174 includes a comparator 163 for comparing the known biometric signature with the present biometric signature. Comparing mechanism 163 preferably is or includes a computer 158. Reader 174 includes a register 160 that stores the present biometric signature and computer 158. Register 160 is connected to contact plate 183.

Alternatively, reader 174 may include a modem 197, remote from reader 174, that sends the present biometric signature to computer 158. Modem 197 is in communication with the contact plate 183. Computer 158 can be mounted in reader 174 to provide a more compact arrangement with signature authentication occurring in the reader and communicated by modem 197.

Figure 80:
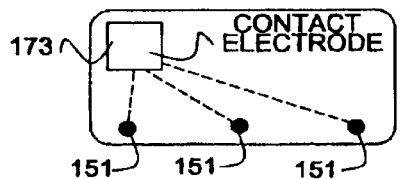
FIG. 80 is a side view of a contact card with magnetic strip.
Figure 81:
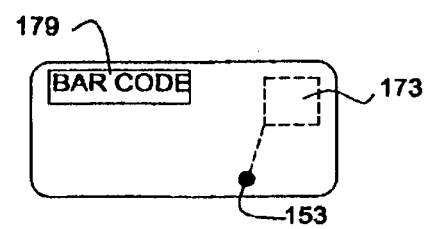
FIG. 81 is a view of the other side of a contact card with magnetic strip.

Card memory 172 may be either a bar code 171, a magnetic strip 179, as shown in FIGS. 80 and 81, or both, as shown in FIGS. 86 and 87. Card memory can also be a microchip memory 189, or a hologram or an optical memory, or any other memory mechanism convenient to mount on a card. The memory reader mechanism 185 would then include a bar code reader 179, as shown in FIGS. 77 and 78, or a magnetic strip reader, or both as represented by the memory reader mechanism is a hologram reader or microchip reader. The reader 174 can include a PIN entering mechanism 195, as shown in FIG. 77, through which a PIN is entered to enable reader 174 to function.

Alternatively, a microchip 189 can be disposed on card 170 as shown in FIGS. 75b, 79a, 79b and 85. Microchip 189 is connected to card memory 172 and contact electrode 173. Microchip 189 controls generator 177 through contact electrode 173 and contact plate 183. Alternatively, the authenticating mechanism 199 may include an antenna 187 and microchip 189 for transmitting the present biometric signal to reader 174 as shown in FIGS. 78a, 88, 89 and 90.

In operation of the invention, recognition of the biometric signature of an organism authorizes an action. Once the organism, preferably a person, is recognized by comparing the person's biometric signature with a known signature, then an action, such as a lock opening or charging a purchase, can occur. For example, the biometric signature of the person can be used in place of a credit card to authorize a purchase.

Figure 72:
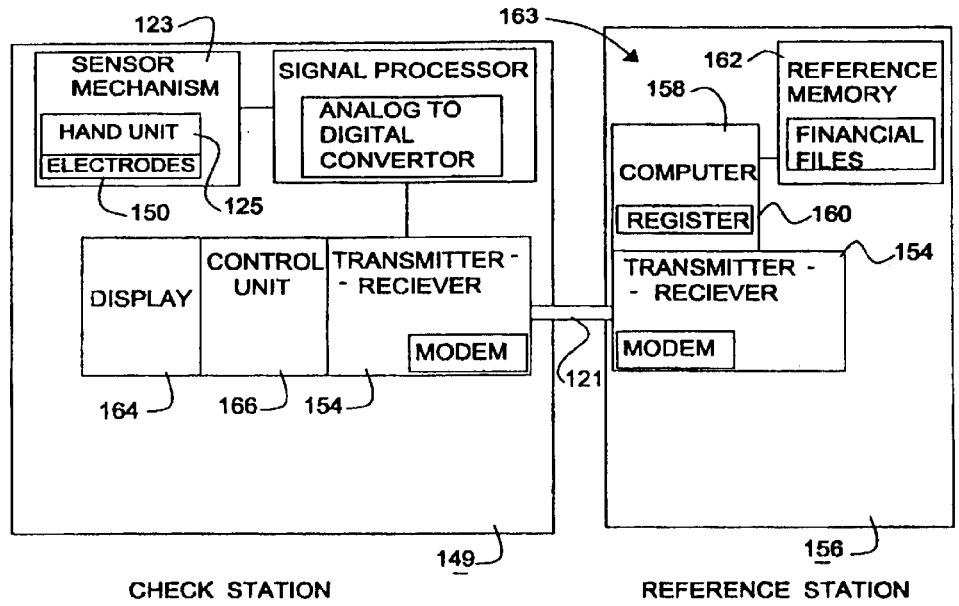
FIG. 72 is a schematic of apparatus for charging a purchase.

Any apparatus which obtains a biometric signature of a person can be used, such as a sensor mechanism 123 having a hand unit 125, as shown in FIG. 72. As described below, the person at a check station 149 simply places the purchaser's hand on hand unit 125 in contact with electrodes 150 to obtain a biometric signature which is converted by a signal processor 152 into a signal having a desired form, such as a digital signal, for transmission over a communication line 121. Signal processor 152, which can be an analog to digital converter, provides the digital biometric to an adjacent transmitter/receiver 154, that is preferably a modem, which communicates over a communication line 121, to a reference station 156 in a manner similar to that used to verify credit cards for transactions. Reference station 156 also has a transmitter/receiver 154, which receives the digital signal and provides it to computer 158, which stores the signal in a register 160, and then searches a reference memory 162 containing a library of known digital signals of biometric signatures of authorized individuals.

When computer 162 locates a corresponding substantially similar authorized biometric signature, a confirmation signal is transmitted. The computer confirmation signal can appear on a display 164, such as a monitor or a printer. If no corresponding biometric signature is found in the reference memory 162, then computer 158 transmits a denial signal to the check station 149.

If the desired action is the purchase of an item, then the purchase cost can be sent with the digital signal of the biometric signature. When computer 158 locates a corresponding biometric signature, the purchase price can be charged to a corresponding file 159 also maintained in reference memory 162, with the person's biometric signature, as shown in FIG. 72. This process is similar to using a credit card to change a purchase, but with an individual's biometric signature replacing the credit card.

Alternatively, when the confirmation of a biometric signature match is sent back to check station 149 from the computer 158, additional personal information, such as the person's name, birth date, or Social Security number can also be sent so that an employee operating check station 149 can further confirm the identity of the individual using the hand unit 125. In medical applications the additional information also include the medical history, including prescriptions in use and allergies.

Various types of cards having different attributes can be used in the identification system:
I. Contact Card—Contact cards must physically contact a card reader. A card may contain memory only, memory and sensors, and memory and/or sensors, and/or microprocessors. Memory mechanisms 172 include but are not limited to:
  A. Data Storage:
    bar code
    magnetic strip
    embedded microchip (smart card)
    hologram
    electric ink
    pi index system
    optical memory
  B. Sensor card systems:
    1. Memory sensor card—Card contains memory 172 and sensors (bar code, magnetic strip, microchip, etc.). The generator control is in the card reader. Biometric analysis can take place in the card reader, or remotely.
    2. Microprocessor sensor card—The card contains a microprocessor as well as memory and sensors. The generator control and analysis can be in the card (microprocessor card), the card reader, or remotely performed.
    3. Sensor card—The card contains sensor(s) only and replaces a hand unit.

Electric/Magnetic Characteristics

Figure 79:
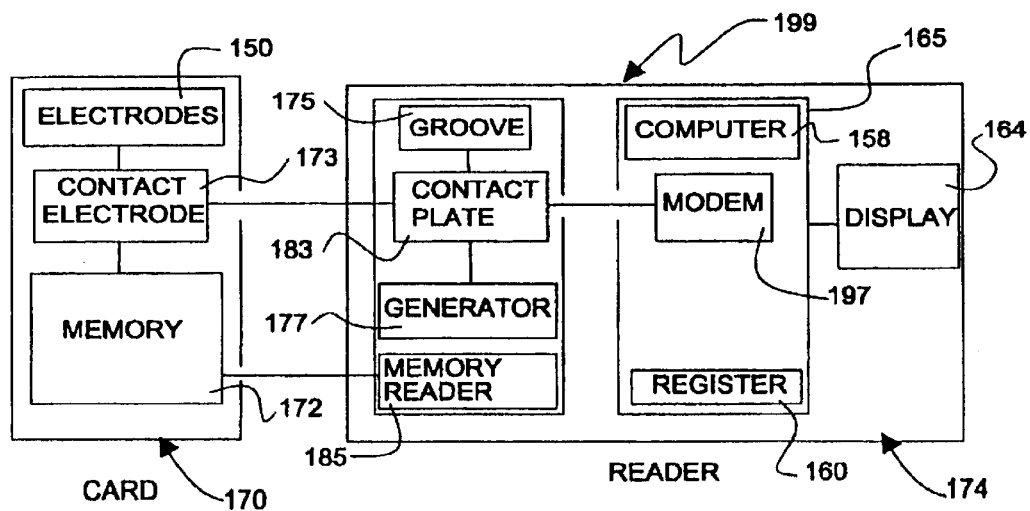
FIG. 79 is a schematic of a contact card and a reader for a contact card with memory.
Figure 79A:
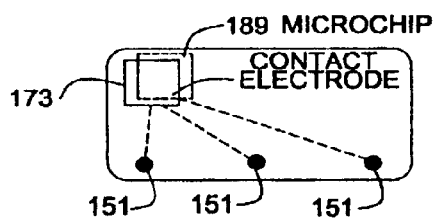
FIG. 79a is a front view of an electrode smart card.
Figure 79B:
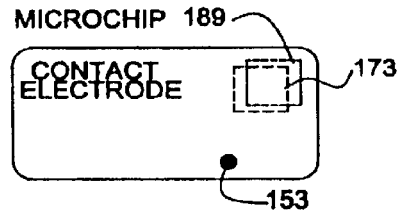
FIG. 79b is a back view of an electrode smart card.

C. Example for Bar Code—Card 170 (FIG. 75 (front) and 76 (back)) bears a bar code 171, which contains information on the impedance pattern. Card 170 also has electrodes 150 (preferably gold plated) for the thumb and three fingers. Connected to a contact electrode 173 (also preferably gold plated). In one embodiment, the card user grasps card 170 on finger electrodes 151 and thumb electrode 153, and swipes card 170 through the reader (FIGS. 77 and 78), which obtains the known impedance pattern from the bar code 171. The user abuts card 170 at the end of slot 175 so that reader 174 generates a signal which is sent through the contact electrode 173 to finger electrodes 151 and/or thumb electrode 153. Reader 174 reads the impedance pattern generated from finger electrodes 151 and/or thumb electrode 153, again via the contact electrode 173. Reader 174 compares the present impedance pattern with the pattern obtained from the bar code 171 on card 170 (FIG. 79). If the present and known biometric impedance patterns are sufficiently similar, the user is approved. Card 170 can be of a type which stores pre-paid credit and does not require connection by modem to another computer.

The system can work like present credit or debit cards that also require processing by modem, as shown in FIG. 79, where card 170 is used to obtain the biometric signature of a person. The user grasps card 170 so electrodes 150 contact the fingers and thumb and swipes card 170 through groove 175 in reader 174, where memory reading mechanism 185 reads the information stored in memory on the card and provides it to computer register 160 located in reader 174. The user resets card 170 at the end of groove 175, with card contact plate 173 in contact with reader contact plate 183 to obtain the user's biometric signature and provide it to computer 158, where it is compared to the biometric signatures stored in register 160, and a recognition or denial signal is sent out to display 164.

In another embodiment, instead of containing the actual electric/magnetic pattern, which comprises the biometric signature, a bar code 171 contains a numerical index, number, pattern, or cipher based on the electric/magnetic pattern. When the electric/magnetic pattern of a presented individual is generated, the reader converts it through a predetermined algorithm into the numerical index, number, pattern, or cypher. The two indices, etc. are then compared, rather than the actual electric/magnetic patterns.

In another embodiment, processing of the actual electric/magnetic pattern or index will occur only if a unique user PIN number is provided.

In another embodiment, the unique user PIN number is used mathematically in the predetermined algorithm to determine the numerical index, number, pattern, or cipher.

In another embodiment, the card's memory contains only the user name and account number information. Obtaining the known impedance pattern and performing the comparison must be done by modem with a remote computer, such as shown in FIG. 22. In this instance, the reader 174 simply generates the current biometric pattern and transmits the resulting electrical measurements to the remote computer.

D. Acoustic Characteristics—The acoustic version of smart card 170 (FIGS. 74a, 75a (front) and 76b (back)) has a microchip 189, which contains information on the acoustic pattern. Card 170 also has a transducer connected to microchip 189. In one embodiment, the card user grasps the transducer, and swipes it through the reader (FIG. 74a), which obtains the known acoustic pattern from the microchip 189 via contact electrode 173 (an acoustic biometric system with an acoustic card is shown in FIG. 77a). The user rests the card 170 at the end of groove 175 for a few seconds to allow reader 174 to generate an electrical signal from generator 177 which is sent though the contact electrode 173 to the transducer. Reader 174 reads the sensed acoustic pattern generated from the transducer, via the contact electrode 173, and compares it with the pattern obtained from the microchip memory 189 on the card 170. If there is a match, the user is approved. Card 170 can be of a type which stores pre-paid credit and does not require connection by modem to another computer. A contactless smart card 170 can be used with a system that communicates through antenna 187a, 187b and transceivers, as shown in FIG. 78a. All of the various embodiments of the electric/magnetic cards can be used with acoustic cards or any other type of sensor card.

E. Magnetic Strip—Card 170 (FIGS. 80 and 81) bears a magnetic strip 129, which contains information on the biometric pattern. Card 170 is swiped through a magnetic. Use of the card is virtually identical to that of the bar code card. The electrical contact electrode must be placed a sufficient distance from the magnetic strip to prevent disruption of the magnetic strip.

F. Memory Microchip (Smart) Card—Card 170 (FIGS. 82 and 83) is embedded with a small (preferably gold plated) contact electrode 173. When card 170 is inserted into a smart card reader (no swiping is necessary; simple insertion is sufficient). The contact electrode 173 contacts the contact plate 183. In one embodiment, the generator control is in the card reader. Contact electrode 173 transfers information to the reader as described above (FIG. 84). Current generation through contact electrode 173 to the sensors(s) takes place, with subsequent reading and analysis of the biometric pattern, as described above.

G. ID card—The card bears a memory with information on the biometric signature of the user whose name appears on the front of the card. The card interacts with a sensor/memory reader, and the present biometric signature is obtained, as above. The card authenticates the identity of the user for completion of an action. This is essentially the same schematic as in FIG. 79.

H. Microprocessor (Smart) Card—In this embodiment, smart card 170 does not need to transfer information to the reader on the known biometric pattern or index. Instead, it may transfer directions to the reader on scanning parameters (FIG. 79). The reader is simply the sensor energy generator and reader, while control of the scanning parameters rests with the smart card. Reader 174 generates the biometric scans in generator 177, and relays the information on the scans to microprocessor 138 on the smart card. The smart card then compares the pattern or index relayed by the reader with the pattern or index in its embedded memory 172. If there is sufficient agreement between the present pattern and the pattern in memory, the card signals to the reader that the user is authorized, and the reader signals approval to the user. The microprocessor may function as a simple memory chip, or may assume one or more functions of the reader, computer, register, generator and/or display.

In one embodiment, the scanning parameter directions contained in the smart card are fixed. In another embodiment, the scanning parameter directions in the smart card can be changed by the user, by insertion of the card into a scanning setter maintained by the user or a commercial enterprise. The user could: 1) program specific frequencies and scanning patterns; 2) choose from one of several scanning programs, the details of which are not known to the user (i.e. the user would choose one scanning program from programs 1 through 100); 3) the user could program the smart card to randomly change its scanning pattern after every use.

In another embodiment, the sensor generator scanning control rests within the microprocessor on the smart card. The reader serves merely as an energy source and possibly a display mechanism for authorization.

I. Hybrid Card—The hybrid card 170 (FIGS. 86 and 87) contains more than one memory system, such as a bar code, magnetic strip, and microchip, all on the same card. It functions as described above, such as either a simple memory card, or as a combined memory/microprocessor card, or as a sensor/memory card.

In another embodiment of the hybrid card 170, the card is very similar to current credit cards and contains a signature line and the familiar magnetic strip. It also contains sensors such as a transducer or electrodes for the fingers and thumb, and a contact plate. The user can use it like a regular credit card at those locations that do not have sensor (acoustic or electric/magnetic) readers. At those locations that do have sensor (acoustic or electric/magnetic readers, the rendering of a written signature is unnecessary.

Figures 88, 89:
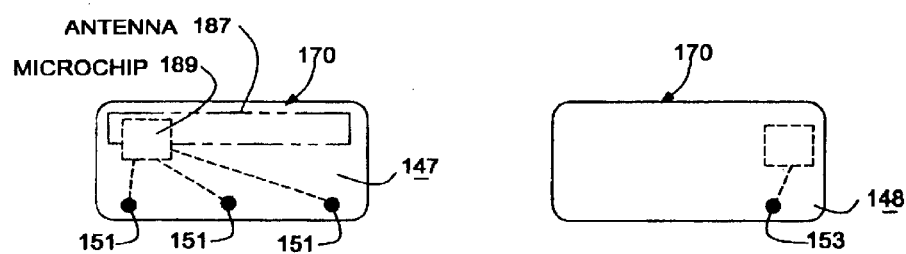
FIG. 88 is a side view of a contactless card.
FIG. 89 is a view of the other side of the card of FIG. 88.
Figure 90:
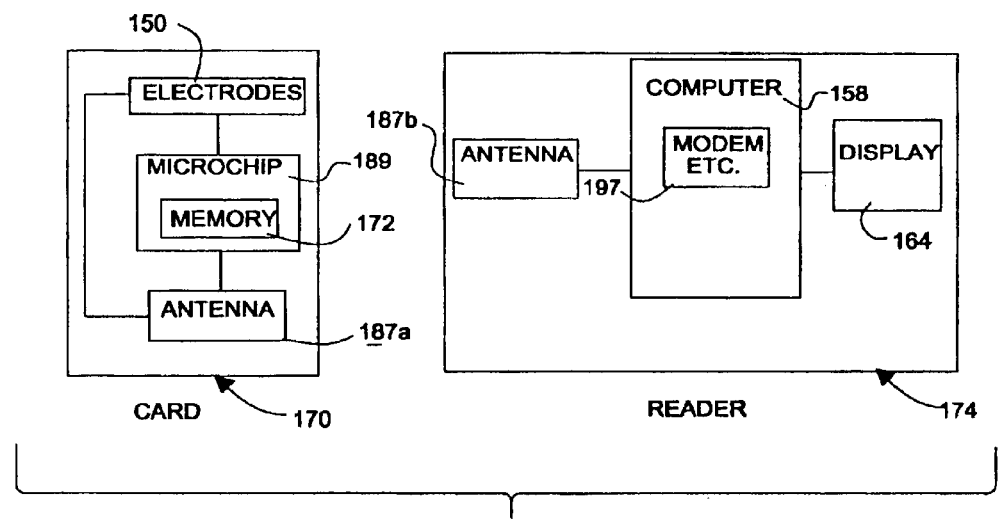
FIG. 90 is a schematic of a contactless card and its reader.

I. Contactless Cards—These cards look just like plastic credit cards, although there is an embedded microchip 189 and an antenna 187 that allow the card 170 to communicate with an antenna/coupler unit without actual physical contact with a reader (FIGS. 88, 89, and 90). The contactless biometric sensor card works much the same way as the contact card. The primary difference is in the coupling between the reader and the card. With the contact card, a contact plate on the card comes in contact with a contact plate on the reader. There is a direct electrical connection which allows reading of the biometric pattern.

In the contactless card 170, its antenna 187 communicates with and obtains power from the antenna in the coupler unit. The EM field generated by the antenna in the coupler unit produces induced current in the card microchip and sensor system which measure the biometric pattern. The microchip communicates the readings via the antennae 187 to the coupler/reader 174. This is a wireless system. The system in the card is called a tag (an electronic device that can communicate with a reader by means of a radio frequency signal.) FIGS. 88 and 89 show what a contactless electric/magnetic sensor card would look like. FIG. 90 shows schematics for a contactless system.

The embodiments described above for sensor cards can be used with other sensor devices such as watchbands, gloves, glasses and other portable or detachable sensor mechanisms.

The present invention pertains to a method for authorizing an action by recognizing a biometric signature of the individual, allowing the action to occur, and, preferably, performing the action.

Exemplary actions include the following:
  I. Financial Transactions
    Banking and payment
    Gaming
    Utilities and metering
    Mass transit and toll
    Payphones
    Healthcare and social services
    Wireless communications
    Pay TV
    Education Travel
Information technology
Access control systems;
II. Information technology
Loyalty and retail systems
Government ID
Identification
Time card systems
Health care and social services
Financial transactions
Access control systems;
III. Access control systems
Locks
Vehicles
Remote controllers
Closed environments
Security
Health care and social services
Information technology
Financial Transactions
Communications
IV. Electronic tagging
House arrest
Locator/Tracking.

Biometric authentications can be done in two modes— identifications or verification. Examples of methods and systems using each mode are discussed in the examples below. It should be understood that an authentication for a particular purpose can sometimes be achieved using either mode. For instance, access to an account at an ATM can be obtained in identification mode by the bank's computer searching for a match to the customer's present biometric pattern. In verification mode, the customer types in his name, and the bank's computer compares the customer's present biometric pattern with only one biometric pattern— the customer's known pattern on file—rather than searching the entire database.

Figure 94:
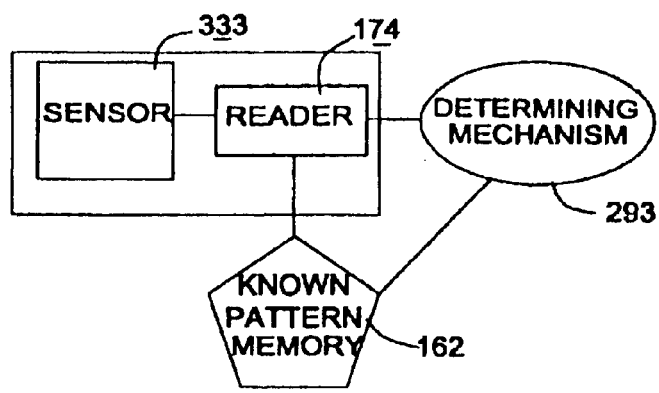
FIG. 94 is a schematic showing a sensor and reader in the same housing.
Figure 95:
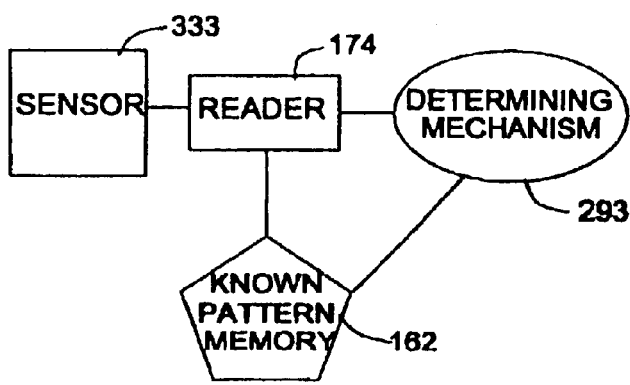
FIG. 95 is a schematic showing a sensor and reader in separate housings.

The authentication determination can be made using a variety of sensor 333 housing arrangements, including but not limited to: (1) Sensor(s) 333 and reader 174 housed in the same unit, as shown in FIG. 94; (2) Sensor(s) 333 and reader 174 housed separately, as shown in FIG. 95, and communication directly through mechanisms including but not limited to contact electrode 183, wire, fiber optic cable, modem 197, and such; and (3) Sensor(s) 333 and reader 174 housed separately, and communicating wirelessly via infrared, radio waves, microwaves, sound waves, contactless, and such. Examples of each sensor housing arrangement are discussed below. It should be understood that authentication for the same purpose can be achieved using different types of sensor housing arrangements. For example, access to an account at an ATM to withdrawal money can be controlled by an authentication device built into the ATM, housing both reader 174 and sensor(s) 333. The customer could insert a separate sensor bank card into the ATM, which communicates with the ATM reader 174 through the contact electrode. Alternatively, the sensor bank card could be a contactless smart card which communicates with the ATM reader 147 wirelessly, via a radio frequency transmission.

Figure 96:
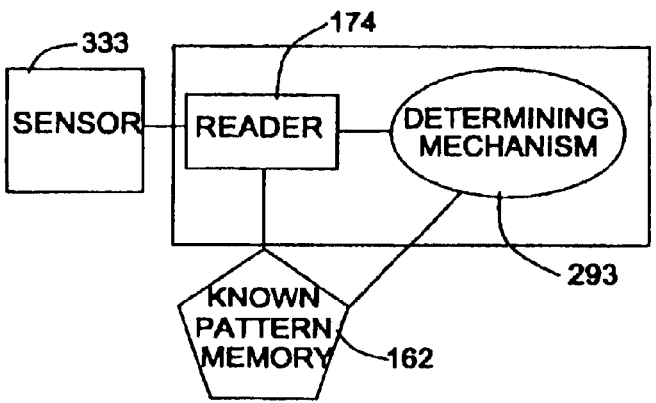
FIG. 96 is a schematic of a reader and determining mechanism in the same housing.
Figure 97:
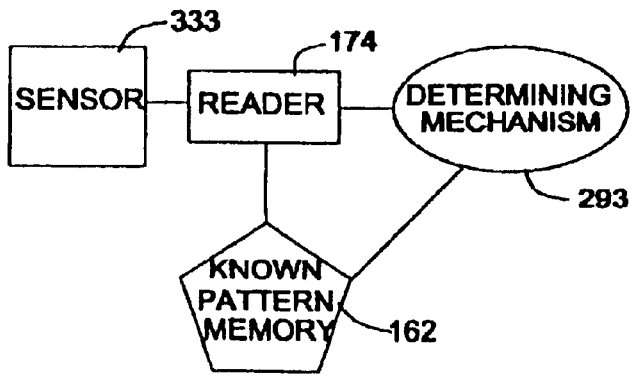
FIG. 97 is a schematic showing a reader and determining mechanism in separate housings.

The authentication determination can be made by a variety of reader 174 housing arrangements, included by not limited to: (1) reader 174 and determining mechanism 293 housed in the same as unit, as shown in FIG. 96; (2) reader 174 and determining mechanism 293 housed separately, as shown in FIG. 97, and communicating directly through means such as wires, fiber optic, cables, modems 197, and such; (3) reader 174 and determining mechanism 293 housed separately, and communicating, wirelessly through means such as infrared (IR), radio waves, microwaves, and such. Examples of each reader 174 housing arrangement are discussed below. It should be understood that authentication for the same purpose can be achieved using different types of reader 174 housing arrangements. For example access to an account at an ATM to withdraw money can be authenticated by a reader 174 and determining mechanism 293 which are both housed in the ATM. A reader 174 in the ATM could communicate by modem 197, with the bank's separately located central computer 158. The reader 174 in the ATM could communicate by microwave transmission with the bank's computer.

Figure 98:
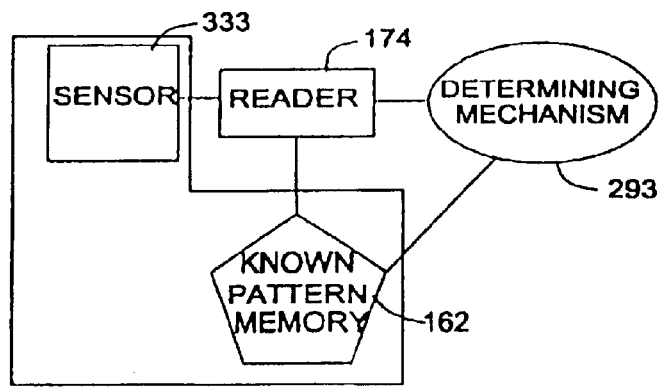
FIG. 98 is a schematic showing a memory and sensor in the same housing.
Figure 99:
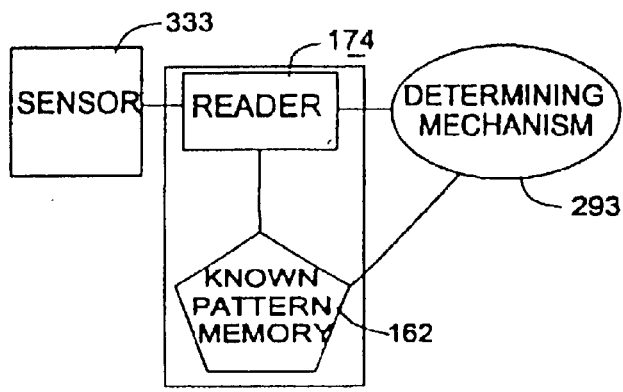
FIG. 99 is a schematic showing a memory and reader in the same housing.
Figure 100:
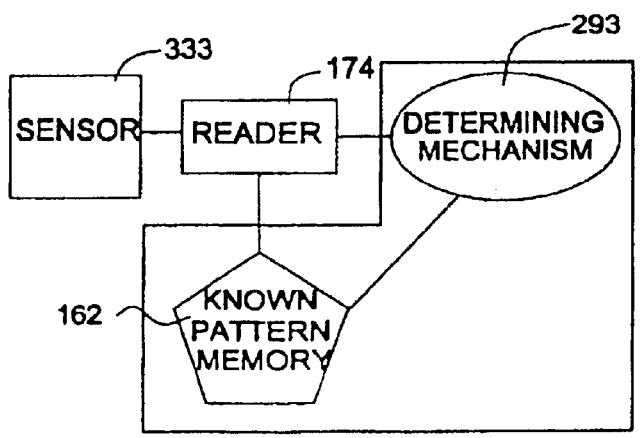
FIG. 100 is a schematic showing a memory and determining mechanism in the same housing.
Figure 101:
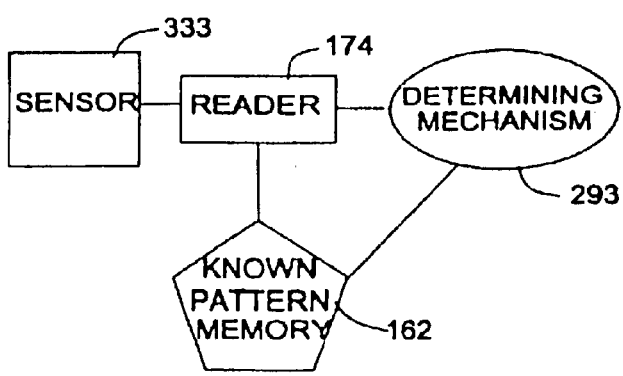
FIG. 101 is a schematic showing a memory and determining mechanism in separate housings.
Figure 102:
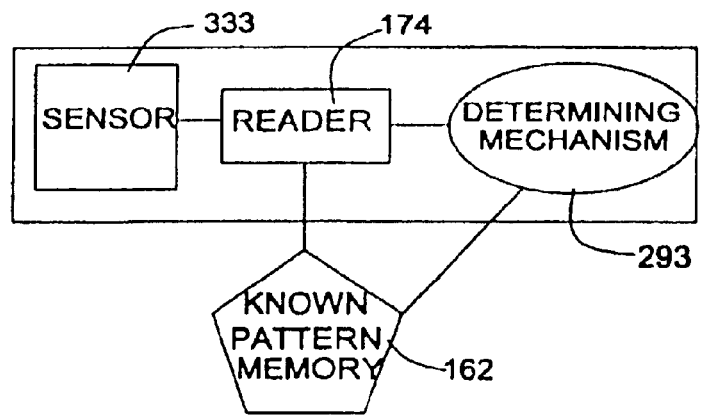
FIG. 102 is a schematic showing a sensor, reader and determining mechanism in the same housing.
Figure 103:
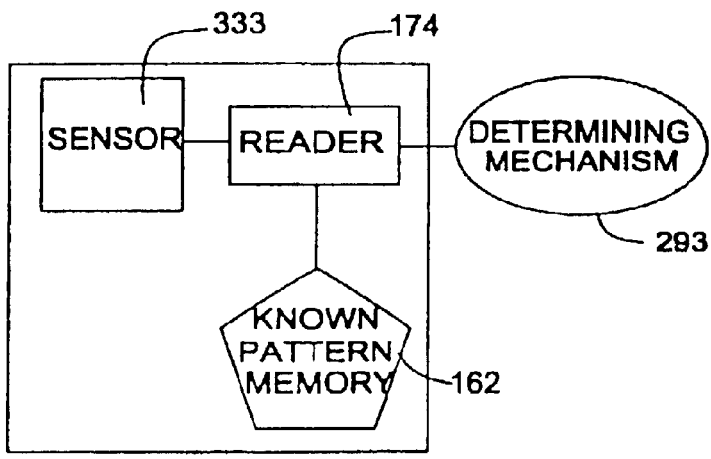
FIG. 103 is a schematic showing a sensor, reader and memory in the same housing.
Figure 104:
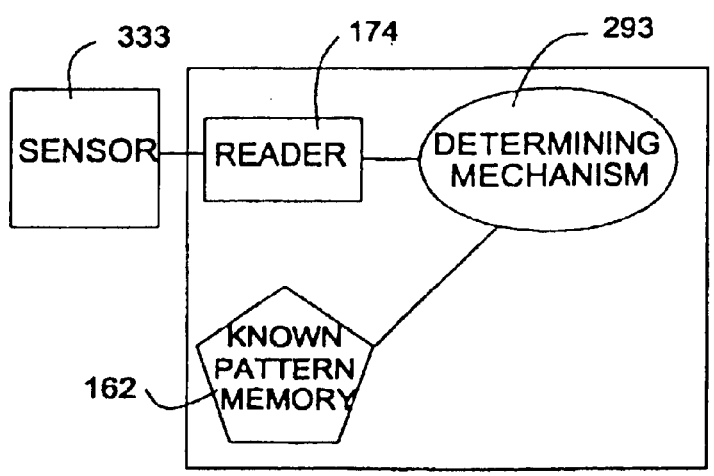
FIG. 104 is a schematic showing a reader, determining mechanism and memory in the same housing.
Figure 105:
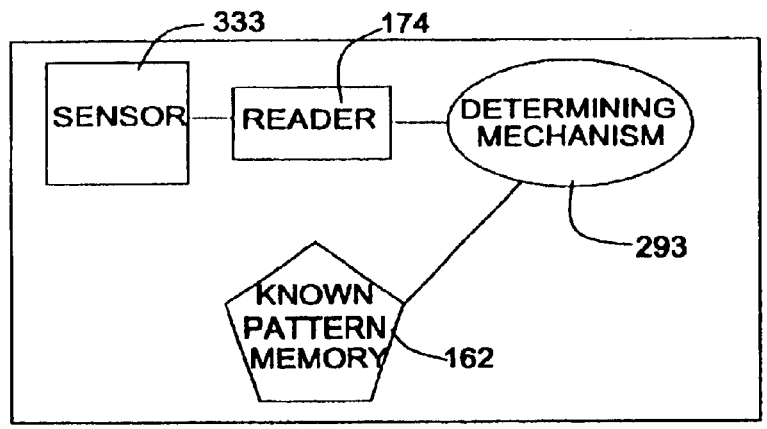
FIG. 105 is a schematic showing a sensor, reader, determining mechanism and memory in the same housing.
Figure 106:
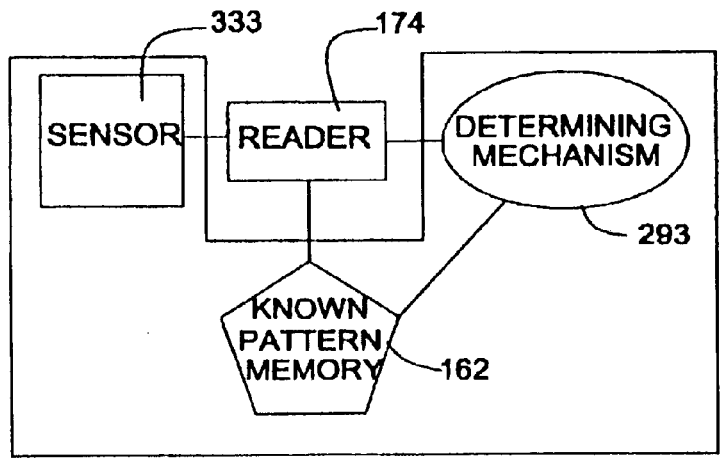
FIG. 106 is a schematic showing a sensor, determining mechanism and memory in the same housing.

Biometric memory storage devices for known biometric patterns can be housed in a wide variety of ways. These can be grouped into four categories:
(1) Memory 162 housed with sensor 333 device, as shown in FIG. 98; (2) Memory 162 housed with reader 174, as shown in FIG. 99; (3) Memory 162 housed with determining mechanism 293, as shown in FIG. 100; (4) Memory housed separately, as shown in FIG. 101. Each general category is discussed in more detail in the examples below. It should be understood that biometric authentication for the same purpose can be accomplished using memory storage devices in more than one memory housing category. For instance, access to an account to withdraw money could be authorized by inserting a simple plastic card with biometric sensor(s) 333 and a magnetic strip memory containing the account number and known biometric pattern into an ATM reader 174. Secondly, the ATM reader 174 could house a memory storage device for all biometric patterns of authorized account users, and make the determination. Thirdly, the ATM reader 174 could send the present pattern to the band's central computer 158, which stores the known biometric pattern and makes the comparison. Finally, the reader 174 could send the present pattern to the bank's central computer 158, which in turn communicates with a separate known biometric pattern memory storage device. There can be a sensor 333, reader 174 and determining mechanism 293 in the same housing, as shown in FIG. 102, a sensor 333, reader 174 and memory in the same housing, as shown in FIG. 103, a reader 174, determining mechanism 293 and memory in the same housing, as shown in FIG. 104, a sensor 333, reader 174, determining mechanism 293, and memory in the same housing, as shown in FIG. 105, or a sensor 333, determining mechanism 293, and memory in the same housing, as shown in FIG. 106.

Biometric authentication can be powered using a wide variety of power systems. These can be grouped in 3 categories: (1) Electrical power from the national power grid, such as from an outlet; (2) Electrical power from batteries (including rechargeable batteries); and (3) Electrical power converted from mechanical energy. Combinations of power systems can (be used. Access to an account to withdraw money could be authorized by an ATM reader 174 powered by direct electrical supply from the utility company power grid, and also by batteries inside the ATM. Reader 174 could be powered by electricity generated mechanically by turning a handle.

Biometric identification or verification can be performed using a wide variety of sensor installation arrangements. These arrangements can be grouped in four general categories: (1) Stationary merchant devices; (2) Portable merchant devices; (3) Stationary customer devices; and (4) Portable customer devices. Installation arrangements in more than one category can be used. Access to an account to withdraw money could be authorized by biometric sensors built into an ATM machine. The sensors could be in a portable reader carried by a personal banker who makes house calls, or in a reader built into the account holder's computer, or in a portable bank card.

The sensors can perform biometric identification or verification using a wide variety of energy fields. These fields can be grouped in four general categories: (1) Acoustic; (2) Electric; (3) Magnetic; and (4) Electromagnetic. Fields in more than one category can be used. Withdrawal of money from the account could be authorized by determining the biometric impedance pattern of the account holders' hand using acoustic fields, electric fields, magnetic fields, or electromagnetic fields.

The sensors can obtain biometric information in two different user modes: touch and touchless. Biometric identification or verification of the same biophysical trait can sometimes be accomplished using either user mode. Withdrawal of money from an account could be authorized by determining the biometric impedance pattern of the account holders' hand using touch electrodes, or using a touchless electric field hand sweep device.

Biometric identification or verification can be performed using sensors having a variety of unique characteristics. These characteristics can be grouped in six general categories: (1) Size; (2) Thickness; (3) Accuracy; (4) Moldability; (5) Flexibility; and (6) Matrices with four or more dimensions. Unique characteristics in more than one category can be used. A multi-frequency reader for plastic cards using thin metal foil electrodes that are 2 mm in diameter, is unique for accuracy, matrices, flexibility, thickness, and size. Different sensor devices that use the same unique characteristic can be used. Access to a bank account at an ATM to withdraw money can be achieved with a flexible smart card fitted with biometric electrodes. Money can also be withdrawn using a biometric wrist watchband fitted with biometric electrodes.

Biometric identification or verification can be performed using sensors housed in a manner to be either operational or non-operational. An example of an operational sensor is an acoustic transducer on the thumb button of a door handle. Depressing the thumb button to open the door activates the biometric system which reads the user's biometric boneprint pattern and, if verified, opens the door. An example of a non-operational sensor is a hand contact plate placed on the wall next to a door. The user places his hand on the hand piece sensor for authentication to unlock the door.

Biometric identification or verification can be used to authorize a wide variety of actions. The actions can be grouped in four general categories: (1) Financial transactions; (2) Information technology; (3) Access control systems; and (4) Electronic tagging. Authorization for a particular action can involve more than one category. Access to an account at an ATM to withdraw money is a financial transaction. It also involves information technology and access control, because the account information is stored in an information storage device with controlled access.

Figure 107:
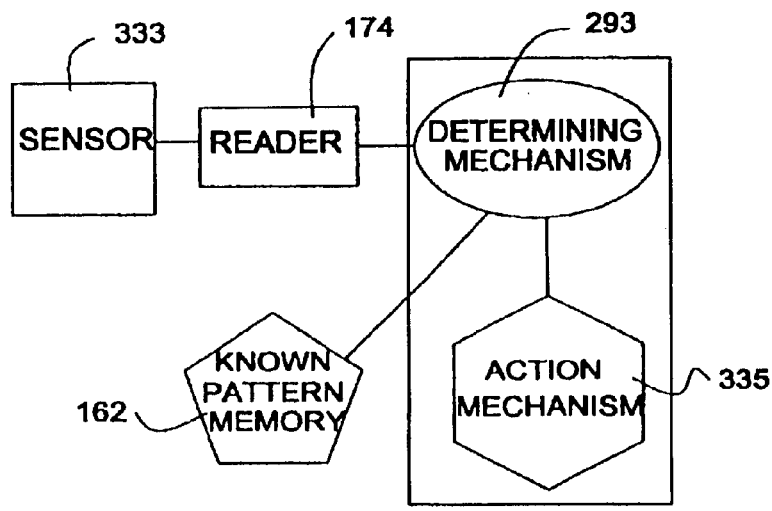
FIG. 107 is a schematic showing a determining mechanism and action mechanism in the same housing.

Authorization of an action is achieved by an action mechanism 335, In communication with the determining mechanism 293. The action mechanism 335 can be: (1) housed with the determining mechanism 293, as shown in FIG. 107; or (2) housed alone. Biometric authentication devices can be housed with or differently from the action mechanism. Authorization to open a door could be achieved by handle electrodes, reader 174, memory 162, determining mechanism 293, and action mechanism 335 (door unlock) all located in the door handle/lock mechanism. Similarly, the electrodes, reader 174, memory 162, and determining mechanism 293 could be installed together in a hand unit in the wall next to the door, in communication with the action mechanism 335 (door unlock) in the door handle/lock mechanism. Thus, one or more mechanisms making up a biometric authentication device or method, such as sensors 333, reader 174, memory 162, determining mechanism 293, or action mechanism 335, can be mounted within the same housing or device.

EXAMPLES

I. Financial Transactions

Figure 111:
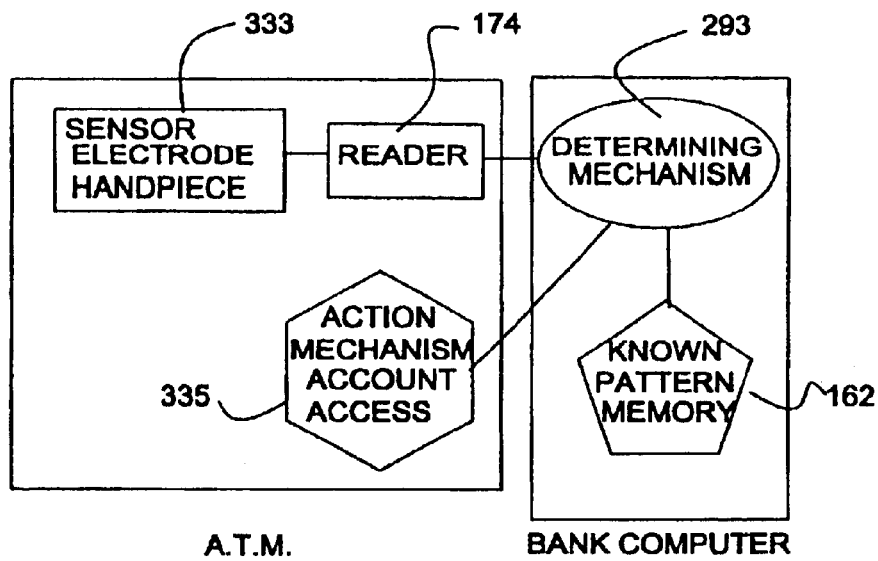
FIG. 111 is a schematic of an ATM with hand piece, where pattern data is communicated to bank computer for comparison.
Figure 112:
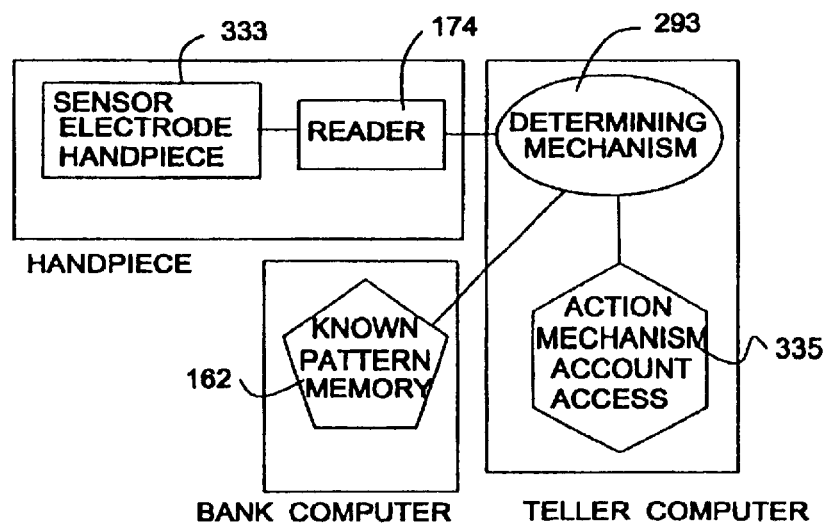
FIG. 112 is a schematic of a teller hand piece, where pattern data and known pattern memory are communicated to a teller computer for comparison.
Figure 113:
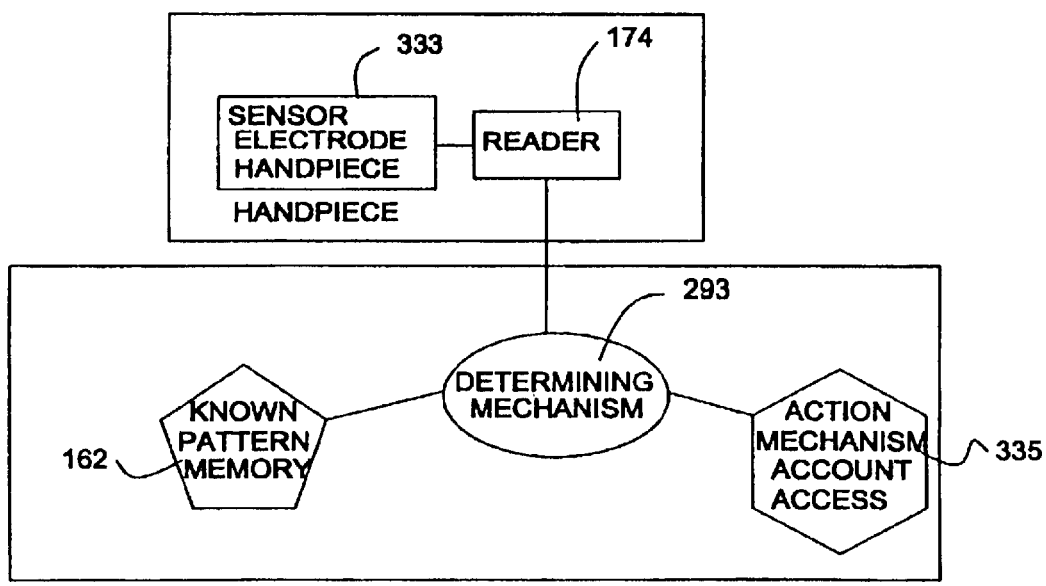
FIG. 113 is a schematic of a teller hand piece, where pattern data is communicated to teller computer for comparison.

A. Banking and payment—ATM tellers can be equipped with hand units with six round electrodes, 1 mm thick×2 mm diameter. Biometric authorization could be required for a bank customer to deposit, withdraw, or transfer funds from a checking, savings, money market, CD, credit card, debit card, stored value card, or other type of account. The hand unit electrodes read the customer's hand biometric pattern. The present pattern data is communicated to the ATM or teller computer 158, as shown in FIGS. 109, 100, 112, 113 or by modem 197 or wireless means to another bank computer 158, for comparison with the known biometric pattern on file, as shown in FIG. 111. This can be done in either identify or verify mode. Matching of the biometric pattern authorizes the customer to proceed with the banking action.

Figure 114:
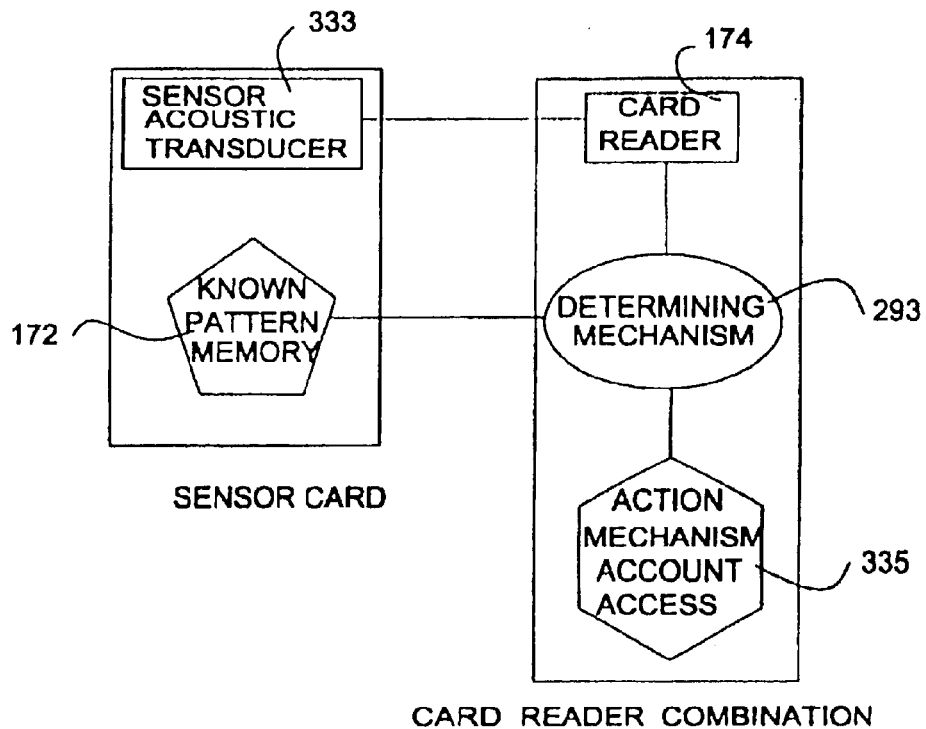
FIG. 114 is a schematic of a bank card with acoustic sensor.

Bank cards 170 with sensors 333 can be used in place of hand units. The biometric pattern might be the acoustic pattern from the bone at the end of the thumb, as shown in FIG. 114. A piezoelectric plastic transducer, 1.5 cm in area, is molded into the flexible card. The banking customer places the card into a contact reader 174, with thumb touching the transducer. The reader 174 obtains the known biometric pattern from the card memory 172 (verify mode) and compares it to the present biometric pattern. The card is credit card sized to be carried by the customer.

Figure 115:
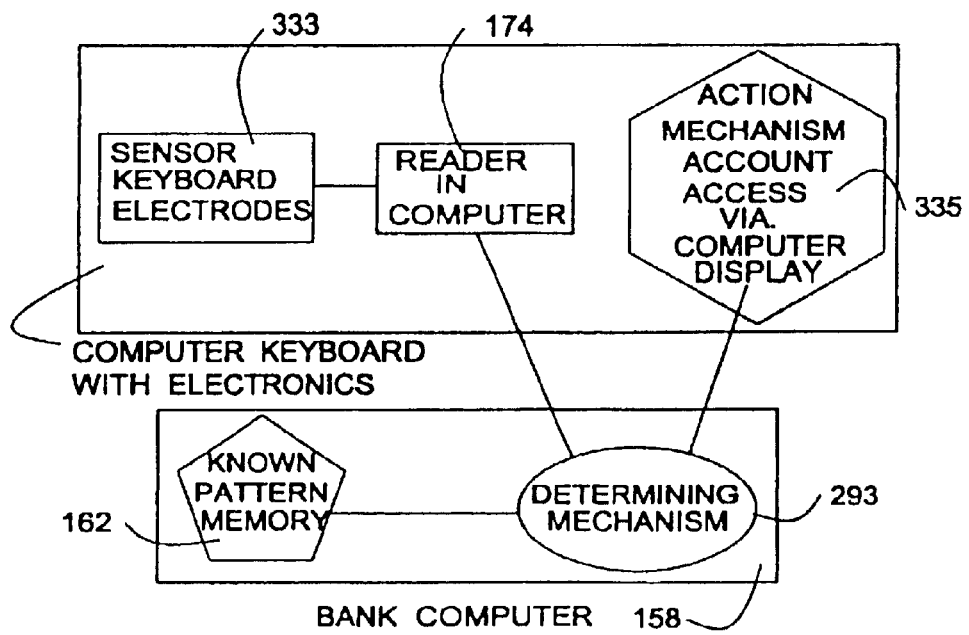
FIG. 115 is a schematic of a home computer having keyboard electrodes.

Suppose an Ohio customer wishes to bank in the Virgin Islands. He establishes a checking account with a Virgin Islands bank, which requires biometric authorization. The bank customer connects via direct computer connection with the Virgin Islands bank computer and sends his present biometric pattern, via touch electrodes molded onto his computer 158 keyboard keys 126, as shown in FIG. 115. The keyboard electrode reader 174 uses 12 different AC frequencies to provide accuracy of one in 10,000,000,000. The bank computer 158 compares the customer's known biometric pattern 162 with the present pattern (verify) to authorize the customer to make electronic payments from his checking account. Alternatively, the customer simply sends his present biometric pattern to the bank computer 158, and it searches its database for a match, to allow him access to his checking account (identify mode).

Figure 116:
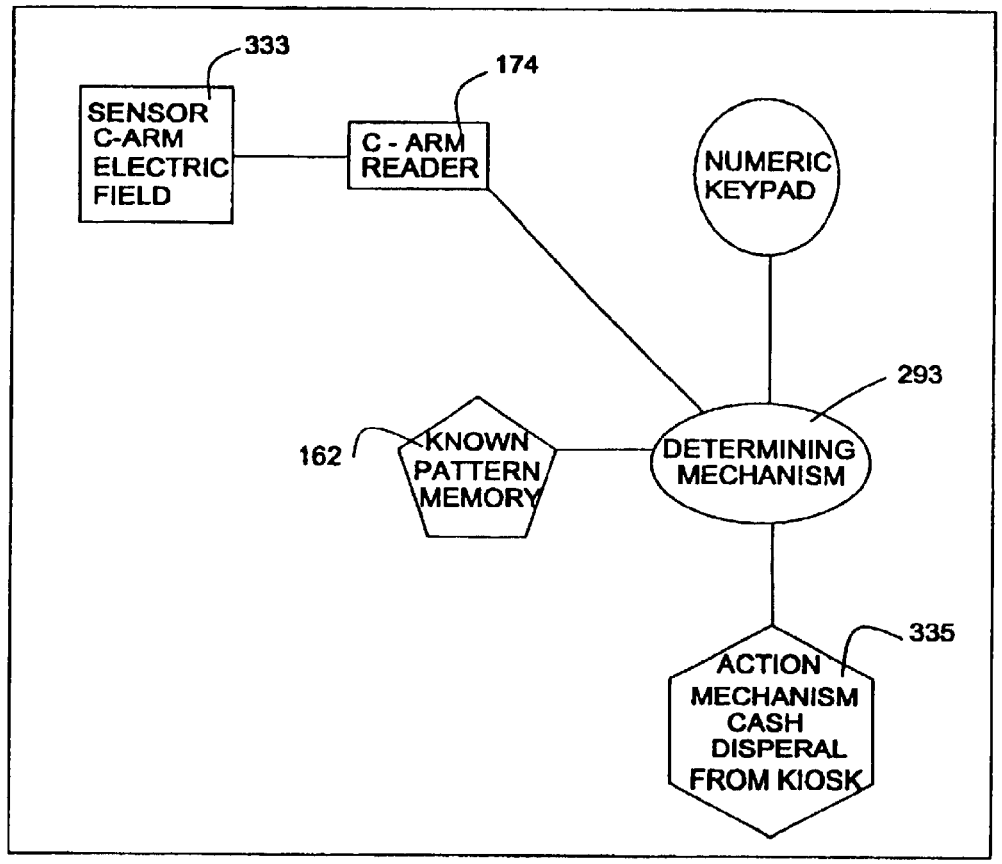
FIG. 116 is a schematic of a kiosk having a touchless C-arm electric sensor.

A person wishes to obtain cash from a credit union kiosk, as shown in FIG. 116. The kiosk is equipped with a number pad and a touchless biometric sensor 333. The sensor 333 is c-shaped, with an electric field between the c arms. The person inputs his birth date on the keypad, allowing the reader 174 memory to restrict its identify search to only patterns with that birth date. The person next sweeps his right hand between the sensor 333 arms. The interruption to the electric field caused by the hand passing through the field produces a present biometric pattern which is matched to the known pattern 162 on file in the kiosk. Upon matching present and known biometric patterns, the person is given access to his accounts. In another embodiment, the apparatus includes two accounts, a mechanism for allowing the financial transaction, such transfer of equities an/or money between the accounts.

Figure 91:
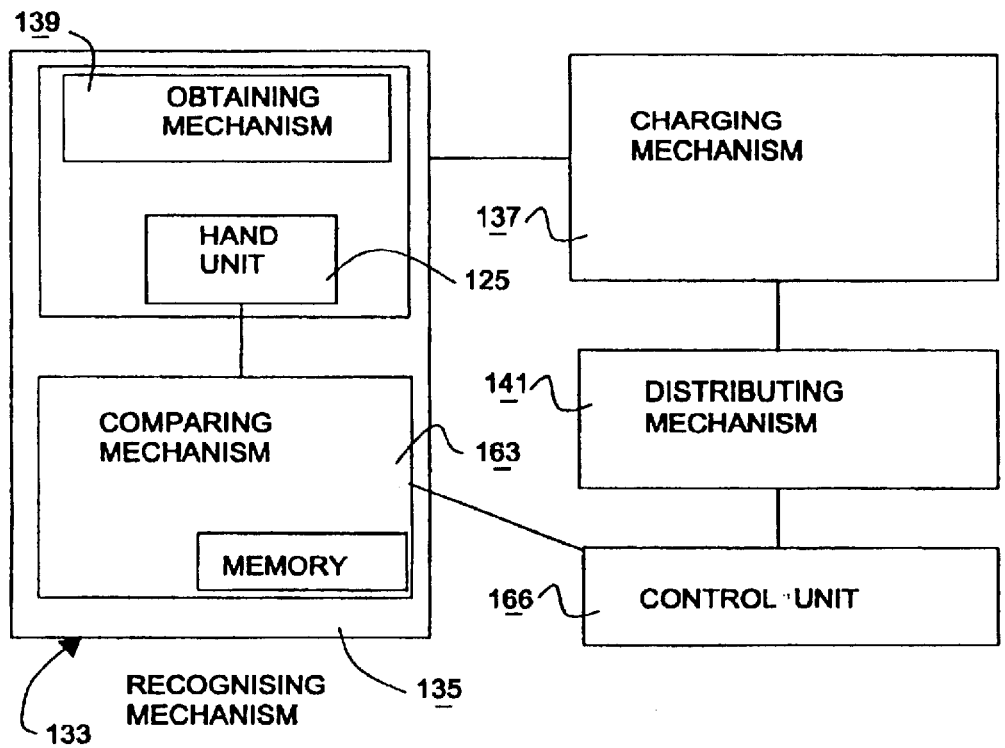
FIG. 91 is a schematic of apparatus for charging a purchase.

FIGS. 91 and 72 illustrate an apparatus 133 for charging a purchase, comprising a mechanism 135 for recognizing a biometric signature of a purchaser, and a mechanism 137 for charging an account of the purchaser with the purchase price connected to the recognizing mechanism 135. The recognizing mechanism 135 includes a mechanism 139 for obtaining a present biometric signature from a purchaser, and a mechanism 163 for comparing a known biometric signature of the purchaser with the presented biometric signature of the purchaser. The comparing mechanism 163 is in communication with the obtaining mechanism 139. The obtaining mechanism 139 preferably includes a hand unit 125 which is adapted to receive the hand of the purchaser to obtain the biometric signature of the purchaser and is in communication with the comparing mechanism 163, which includes a memory in which the known biometric signature of the purchaser is stored.

The account of the purchaser can be a bank account. The apparatus 133 for charging a purchase can include a control unit 166 in communication with the comparing mechanism 163 in which the purchaser identifies an amount of cash to be distributed to the purchaser, and a mechanism 141 for distributing cash disposed adjacent with the obtaining mechanism 139 and in communication with the comparing mechanism 163. The account can be a brokerage account or any other account involving finances. The application described herein can be used for credit cards, debit cards, ATMs, checks, or any system in which a financial transaction and the recognition of an individual in some ways are desirable.

When the biometric signature as a digital signal is sent to the computer 158, the employee can also send the person's name by entering it through a control unit 166 connected to the modem at the check station 149. When the computer 158 receives the name, instead of searching all the digital signals of biometric signatures in the reference memory 162, the computer 158 can search by name the reference memory 162, and when the name is located, the biometric signature that was sent with the name can be compared to the stored known biometric signature with the name in the reference memory 162 to verify the identity of the person submitting the biometric signature.

Figure 73:
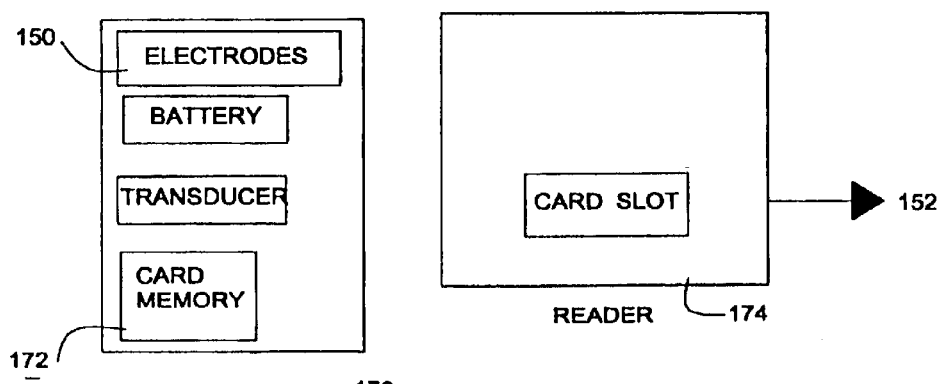
FIG. 73 is a schematic of a card and a reader.

Referring to FIG. 73, an employee at the check station 149 can provide a small sensor unit 170 to a person wishing to receive authorization. The sensor unit 170 has biometric sensors such as at least two preferably several electrodes 150 on it or a transducer, and a sensor unit memory 172. When the person holds the sensor unit 170 and places the person's fingers on the electrodes 150 or transducer, a signal is stored in the sensor unit memory 172. The employee then takes the card 170 back and inserts it into a reader 174 which downloads the biometric signature stored in the sensor unit memory 172. The process regarding confirmation of the biometric signature then proceeds as described above. In the alternative, a portable sensor memory unit can use a touchless sensor system.

Instead of using a communication line 121 to contact a computer 158 at a reference station, there can be a computer 158 at the check station 149 and a reference memory 162 in contact with the computer 158 at the check station 149, as shown in FIG. 74. In this way the need for a communication line 121 is eliminated. The procedure is similar to that described above except that no transmission or reception between remote locations is necessary. The computer 158 will simply search the reference memory 162 at the check station 149 for the biometric signature of the person requesting authorization and either upon finding the biometric signature in the reference memory 162, provide authorization to the person, or upon not finding the biometric signature in the reference memory 162 at the check station 149 can be updated by a CD or DVD or by a communication line downloading the latest list of authorized biometric signatures into the reference memory 162, as is well known to one skilled in the art.

Figure 121:
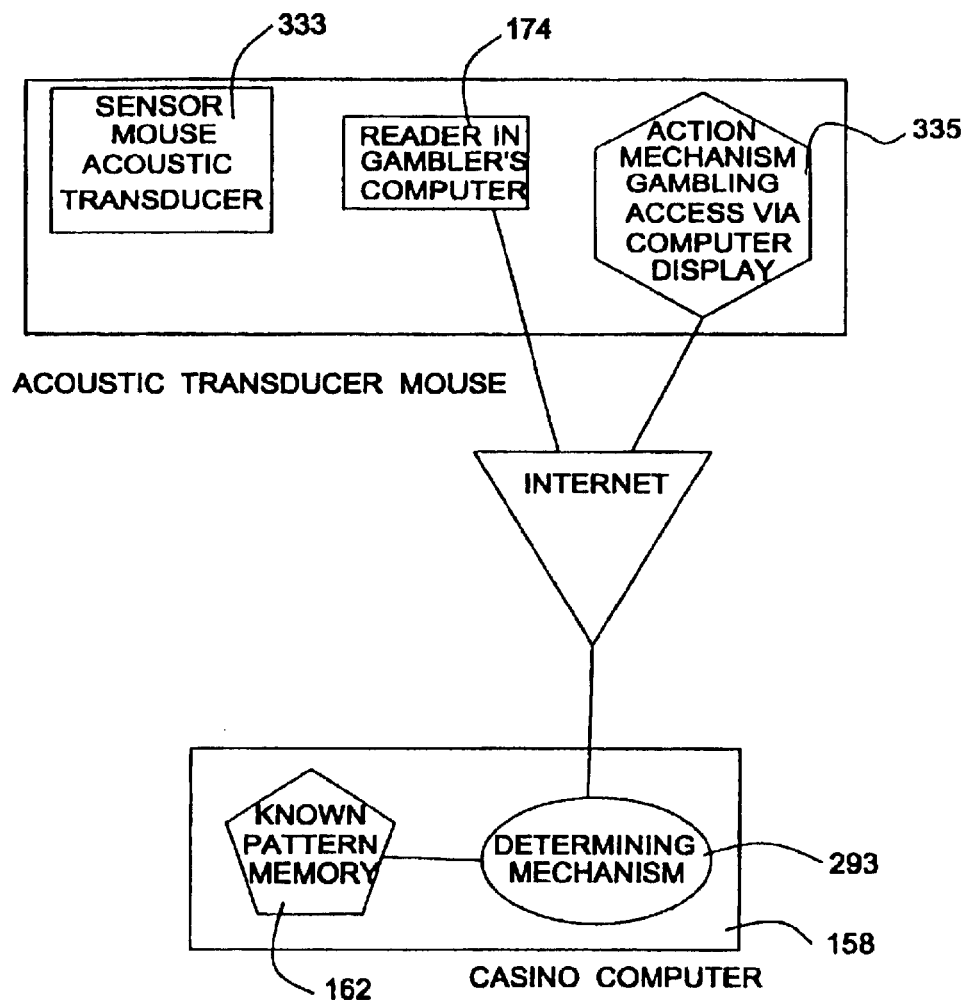
FIG. 121 is a schematic of a home computer with an acoustic transducer mouse.

B. Gaming—An Ohio gambler who wishes to bet in Las Vegas establishes an internet account with a Las Vegas casino which requires biometric authorization to place a bet, as shown in FIG. 121. The gambler connects over the internet with the casino computer 158 and sends his biometric pattern, via his computer 158 mouse with molded, 1 mm thick, touch acoustic index finger transducer, to the casino computer 158. The casino computer 158 compares the gambler's present biometric pattern with the known pattern 162 (in either identify or verify mode) to authorize the placing of the bet.

Figure 117:
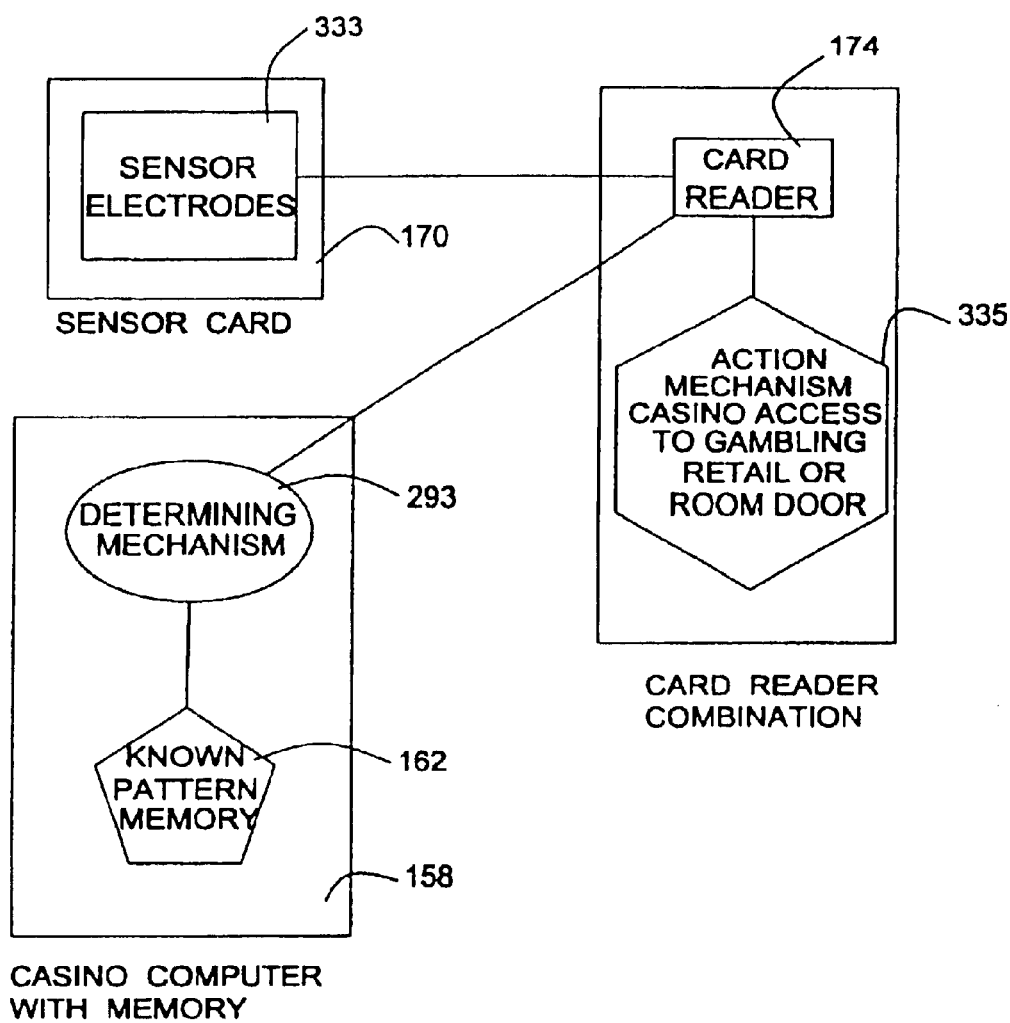
FIG. 117 is a schematic of a casino electrode card with memory in casino computer.
Figure 118:
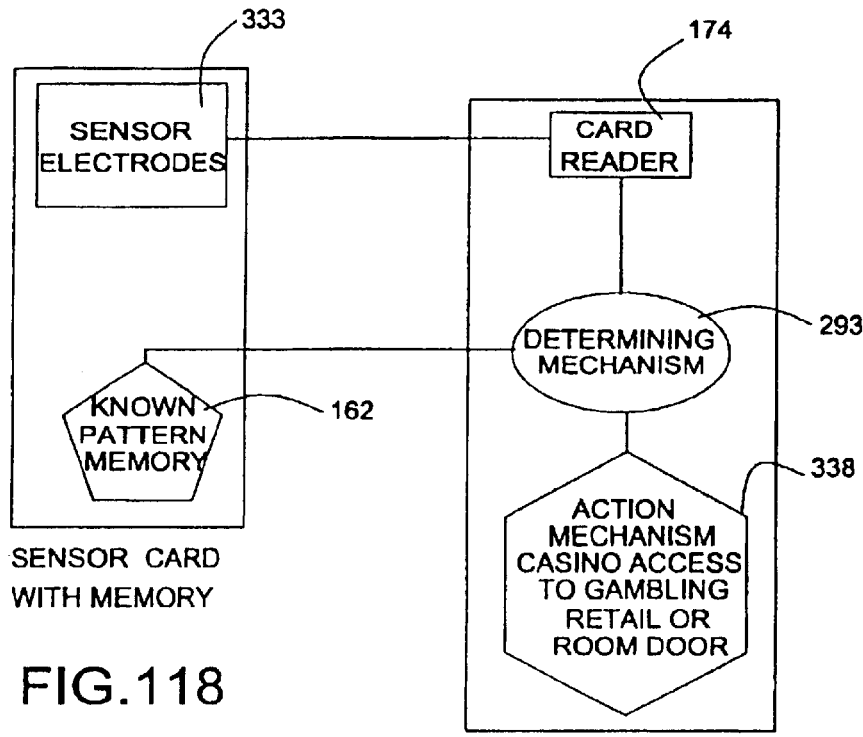
FIG. 118 is a schematic of a casino electrode card with memory in the card.
Figure 119:
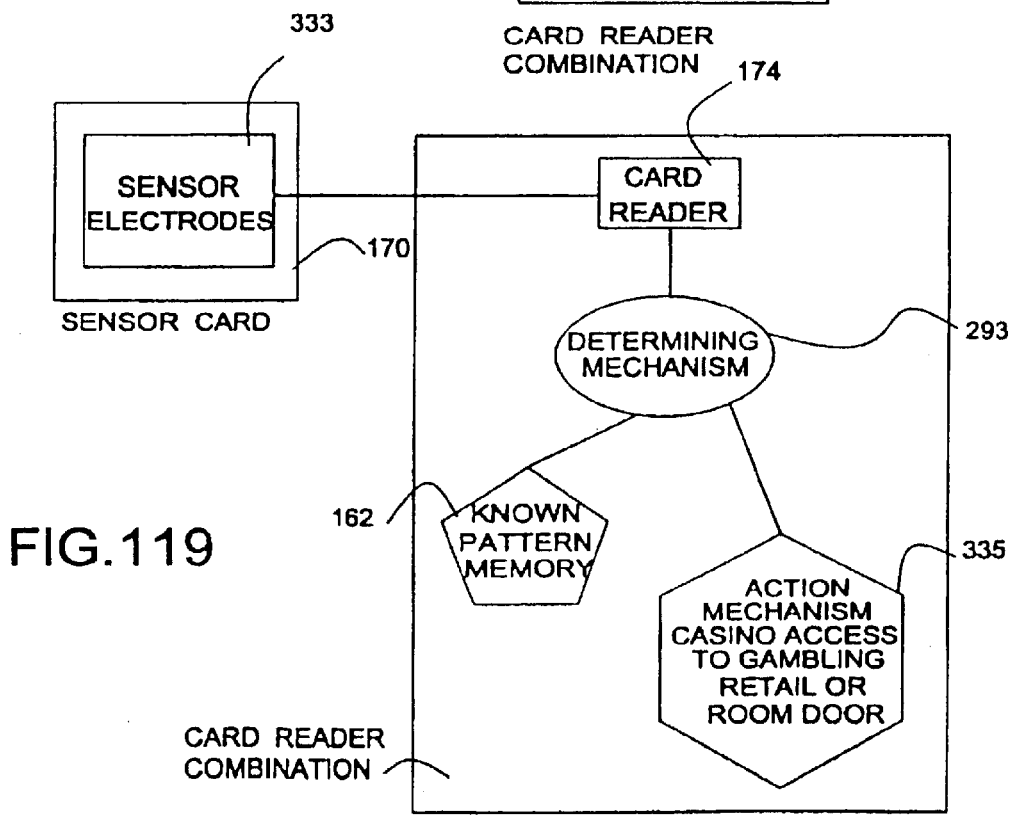
FIG. 119 is a schematic of a casino electrode card with memory with reader.

A casino/hotel flexible card molded with four touch electrodes (2 mm diameter and 0.5 mm thick) can be issued to customers, as shown in FIG. 118. The card also functions as a room key. The casino/hotel card readers 174 use 5 frequencies, with sine and ramped waveforms at each frequency, producing a 4 dimensional biometric matrix. Anywhere the customer goes in the casino/hotel complex, the card can be used to pay for items and bill them to his room account. A line of credit with a dollar limit is also stored in the card for gambling purposes. The gambler wishes to obtain $1,000 of chips to gamble. He places his electrode card, as shown in FIGS. 117 and 118 in an automatic chip dispenser, grasping the electrodes. The reader 174 in the chip dispenser obtains his present biometric pattern and compares it to his known pattern (which is stored either in the casino computer 158, the reader 174, or the card), as shown in FIG. 117, FIG. 119 and FIG. 118, respectively. If the patterns match he is authorized to receive the $1,000 of chips. When the gambler returns to his room, he grasps the electrodes on the card and places the card in a groove on the lock mechanism. The lock mechanism compares his present and known biometric patterns, and upon finding a match, unlocks his door, as shown in FIGS. 117, 118 and 119.

Figure 120:
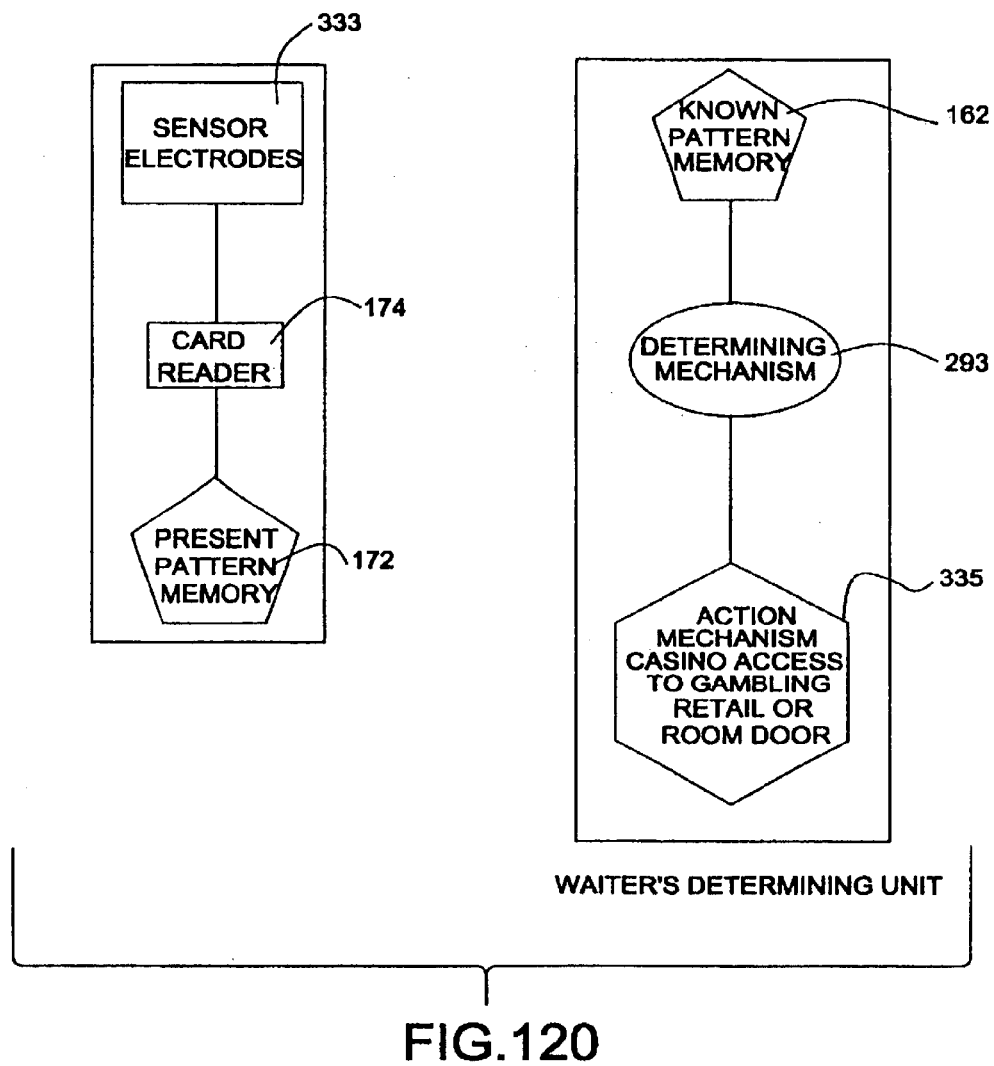
FIG. 120 is a schematic of a casino sensor/reader with present pattern memory in the determining unit.
Figure 122:
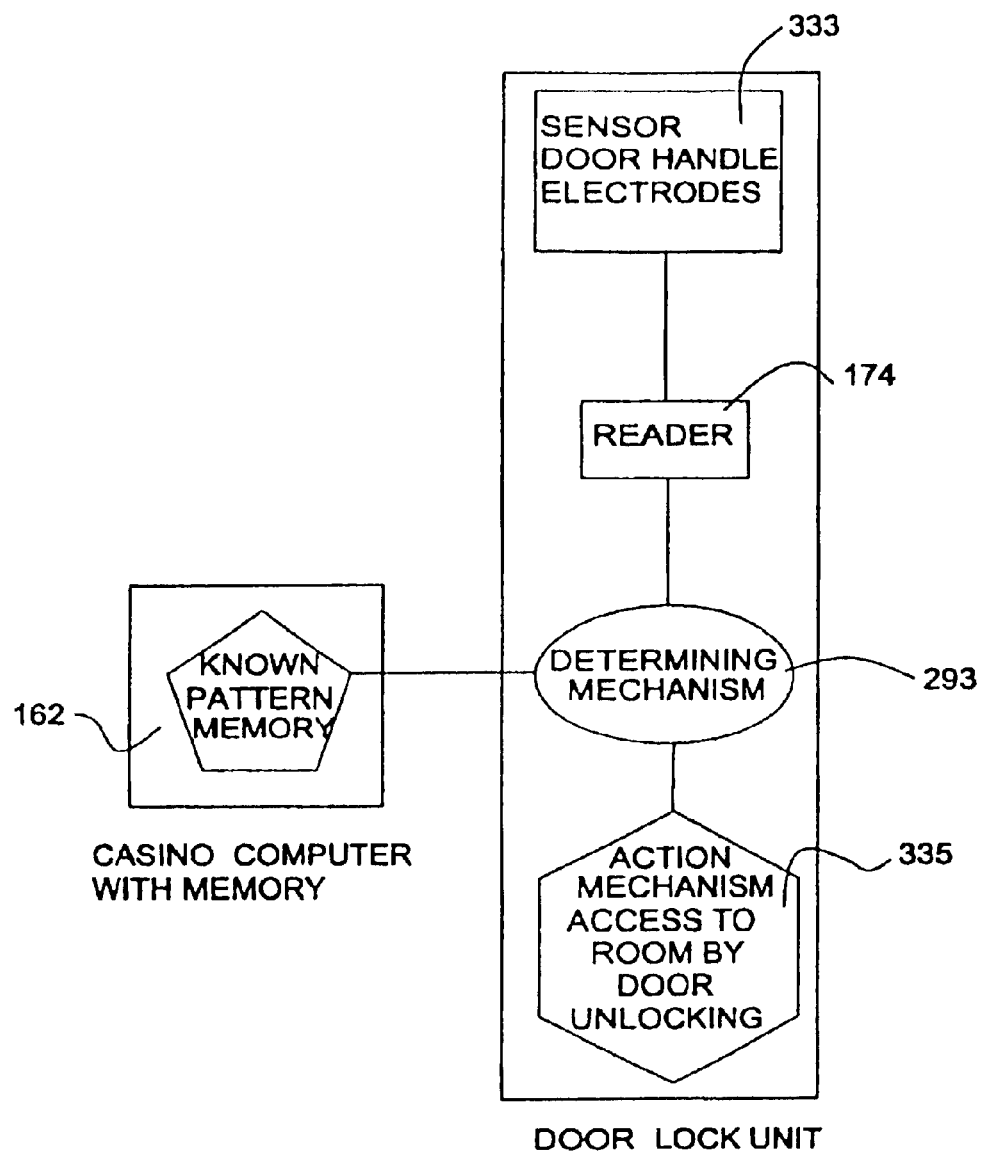
FIG. 122 is a schematic of a casino room door handle.

The gambler eats in the casino restaurant, but has forgotten his electrode card in his other suit. The waiter has a portable touch electrode card with embedded battery and microprocessor, and with electrodes 2 mm in diameter and 0.5 mm thick), as shown in FIG. 120. He brings the portable electrode card to the gambler's table. The gambler grasps the electrodes. The card stores his present biometric pattern. The waiter takes the card back to a determining mechanism 293, which compares (in either identify or verify mode), the gambler's present biometric pattern with his known pattern. The patterns match and the meal is billed to the gambler's account. When he returns to his room, he grasps the door handle (which is also fitted with electrodes) and upon matching biometric patterns enters his room, as shown in FIG. 122.

Figure 123:
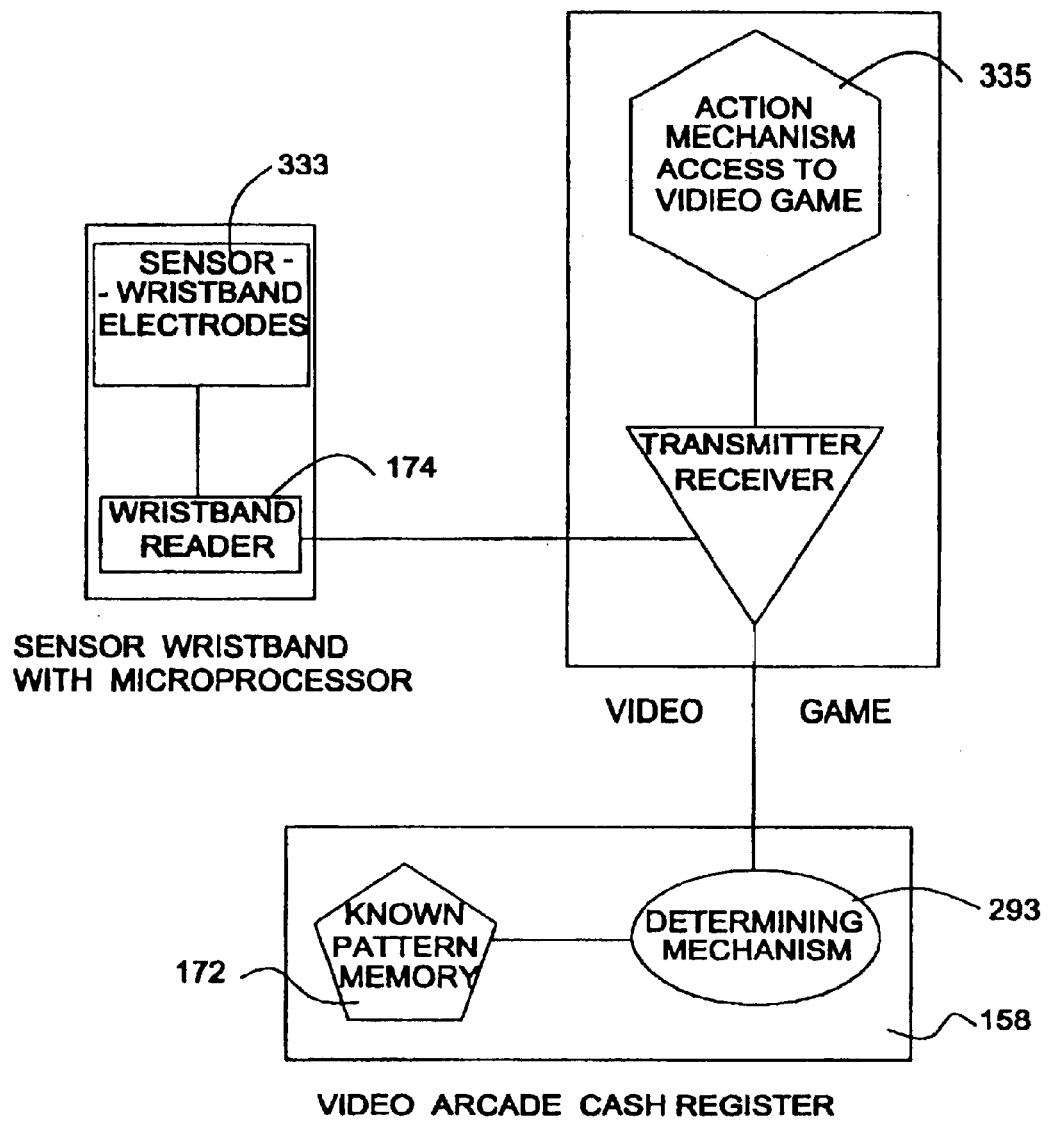

A video arcade issues biometric touch electrode wristbands (with enclosed microprocessor) to all customers entering the arcade, as shown in FIG. 123. Their biometric wristband pattern is stored in the arcade cash register computer 158, which is in communication with all the video games. When a customer wishes to play a game, he holds his wristband near a small RF transmitter/receiver on the front of the game and presses a button. The RF transmitter/ receiver sends energy to the wristband microprocessor, creating induced current flow, which in turn causes the wristband to obtain the biometric wrist pattern and relay the pattern to the transmitter/receiver. This mode is similar the contactless smart cards. The pattern s communicated to the cash register computer 158, which identifies the customer, and bills the game to the customer's account. This way no tokens or coins are needed to play the games. When the customer leaves, their wristband is read at the cash register, and the amount they owe tabulated. The display can alternatively be a diamond emitter display.

Figure 124:
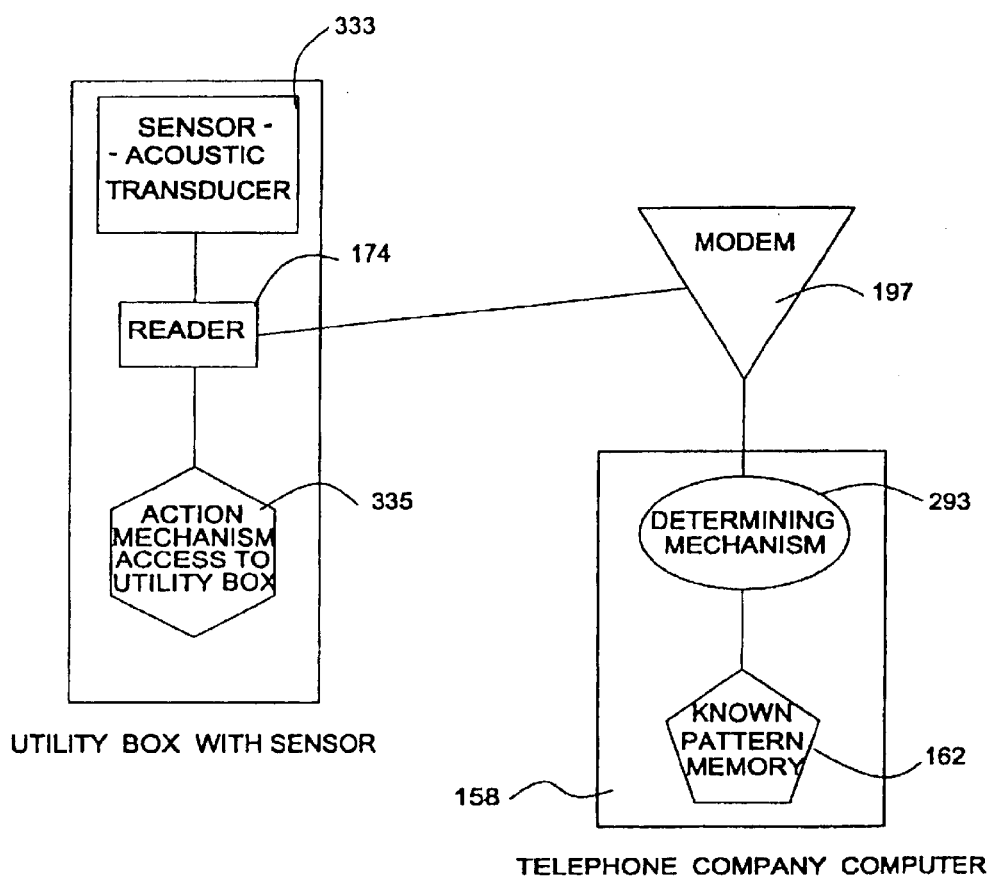
Figure 124A:
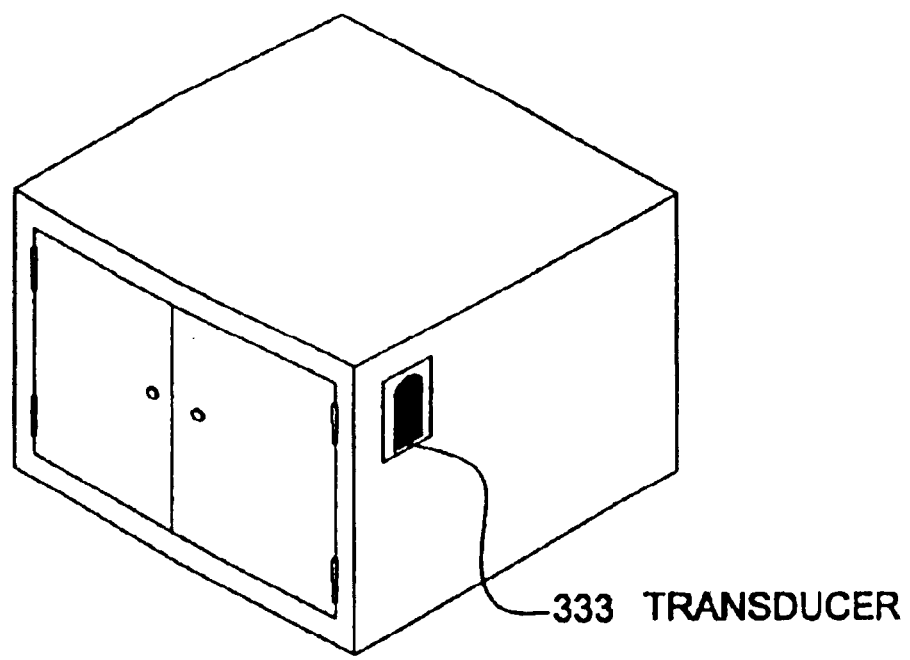

C. Utilities and Metering—An apartment complex has large telephone wire boxes located outside which the telephone company services. The biometric patterns of authorized repair workers are stored by the telephone company. Access to the telephone box is denied to unauthorized people (who might surreptitiously activate their own telephone service). When an authorized repair worker wants to access a box to connect service for a new apartment dweller, he places his middle finger on the touch finger unit on the box, as shown in FIG. 124 and FIG. 124a. The finger units molded (slightly concave) acoustic transducer reads his middle finger boneprint biometric pattern and relays it by modem 197 to the telephone company. The telephone company computer 158 confirms authorization (in either identify or verify mode) and by modem 197 causes a release mechanism to unlock the telephone box.

Figure 125:
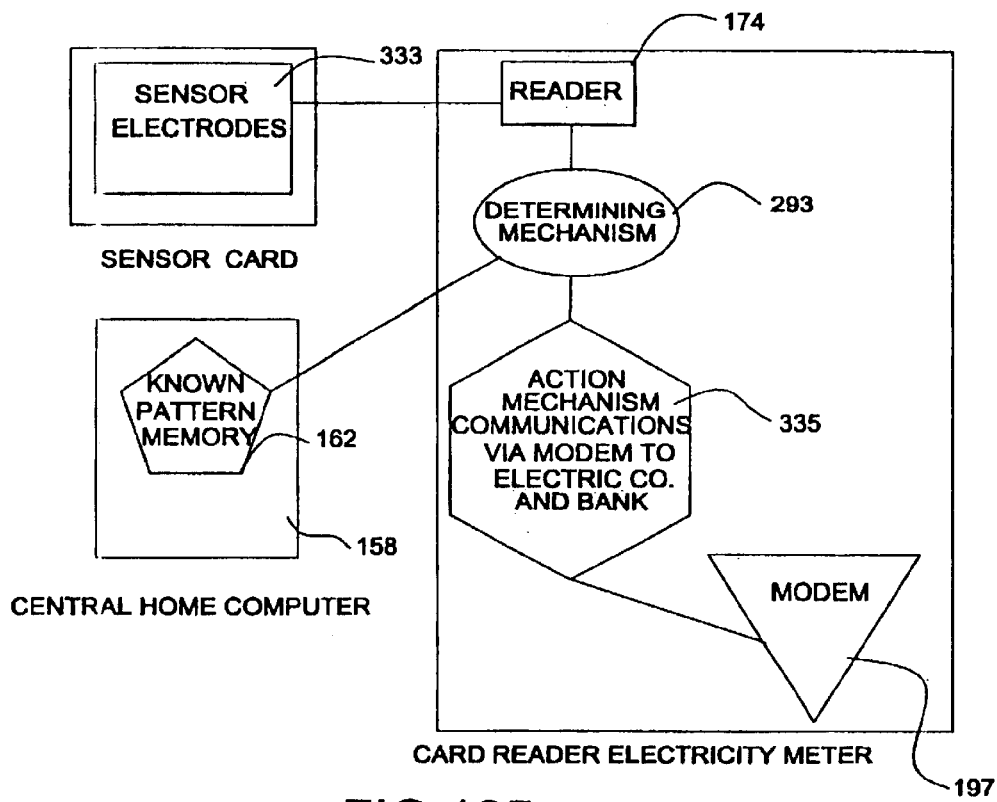

A homeowner builds a house with an electric meter in the utility room. The electric meter is equipped with a touch electrode card reader 174/determining mechanism 293, as shown in FIG. 125. Once a month, the homeowner grasps the card electrodes (nippled gold, 2 mm in diameter) and places it into the reader 174 (five frequencies and two waveforms). The homeowner's known pattern is stored separately in the house's centralized computer 158, with which the reader 174/determining mechanism 293 communicates via microwave (2,450 MHZ) signals. The reader 174/determining mechanism 293 compares the present and known biometric patterns. Upon authorizing the homeowner by matching biometric patterns, the electric meter modems 197 data on the amount of electricity consumed to the electric company computer 158. The modem 197 also sends information to the homeowner's bank debit account and the money for the electricity bill is debited to the electric company. The meter resets to zero.

Figure 126:
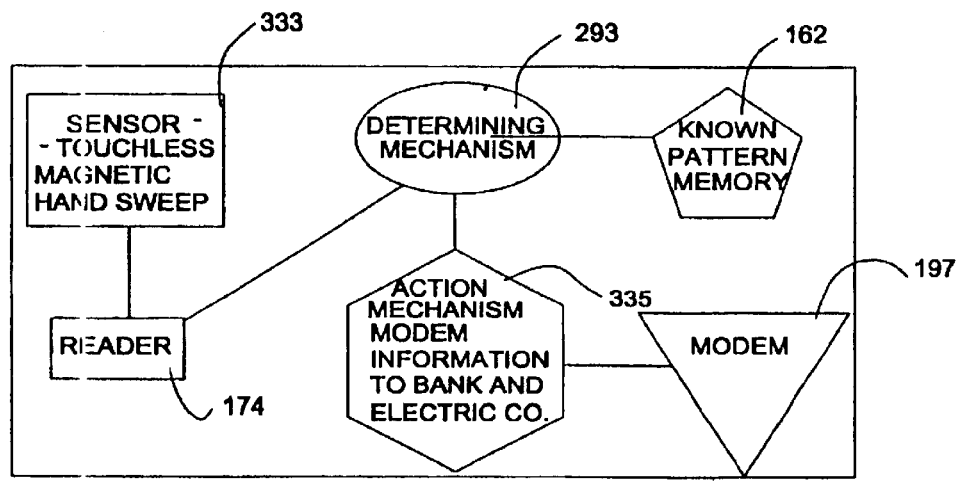

Another homeowner builds a house with an electric meter in the utility room. The electric meter is equipped with a touchless magnetic field hand sweep biometric device housing sensors 333, reader 174, determining mechanism 293, and memory all together, as shown in FIG. 126. The electric meter is equipped with a control panel on the front, with flip up arms containing the magnetic field sweep sensors 333. Once a month, the homeowner flips open the sensor 333 arms at right angles to the control panel, and parallel to each other. The arms are activated in this position. The homeowner sweeps his hand through the magnetic field between the arms and the magnetic field hand sweep biometric device determines his present pattern and compares it to a known pattern for authorization. Upon authorizing the homeowner by matching biometric patterns, the electric meter sends 197 data on the amount of electricity consumed via modem to the electric company computer 158. The modem 197 also sends information to the homeowner's bank debit account and the money for the electricity bill is debited to the electric company. The meter resets to zero.

Figure 127:
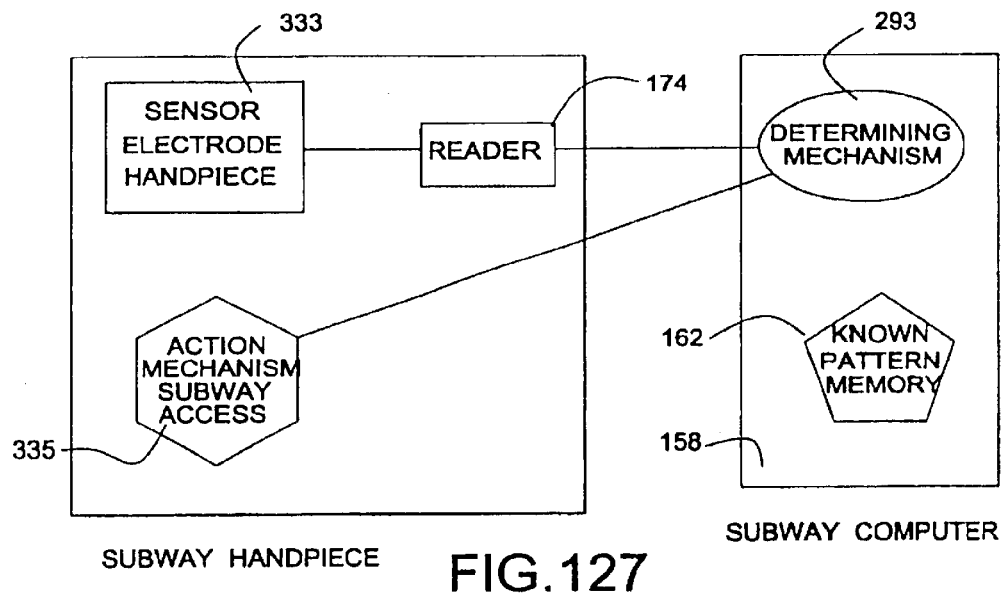

D. Mass Transit and Toll—As shown in FIG. 127, a business person takes the subway to work every day. The business person opens an account with the subway and is billed on a monthly basis. To use the subway, the business person places a hand on a touch hand unit, with 18 electrodes covering the palmar surface of the hand. It reads his biometric pattern using 12 frequencies. The pattern data is communicated to the subway computer 158, or by modem 197 to another subway computer 158, for comparison with the known biometric pattern on file (either identify or verify mode.) Matching the biometric pattern authorizes the business person to proceed onto the subway.

Figure 128:
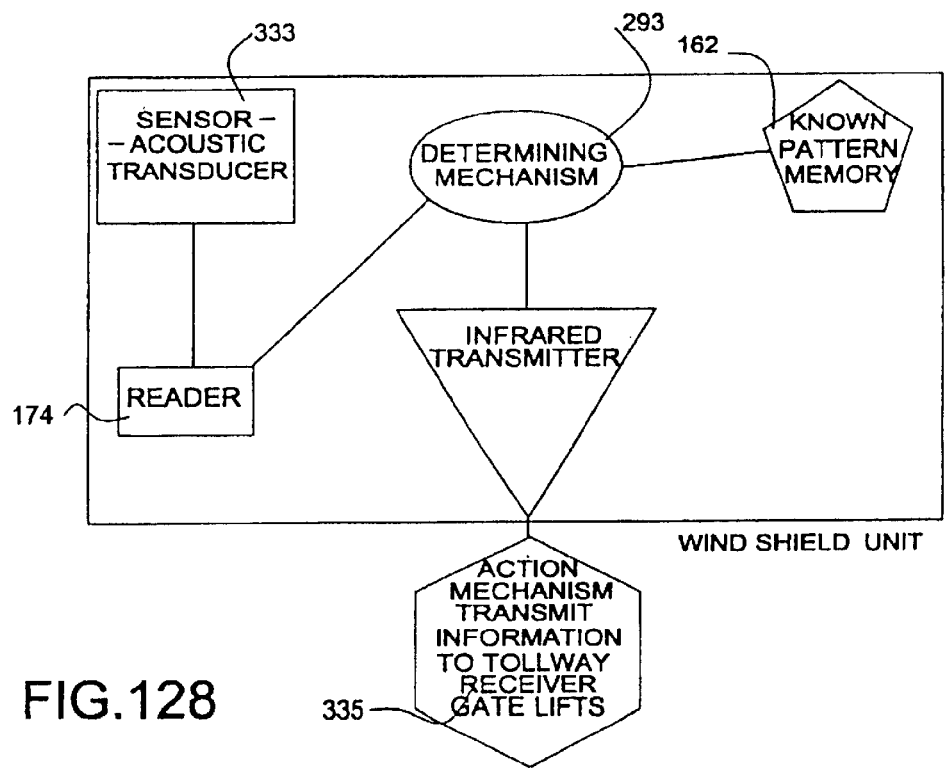

A commuter must take the toll turnpike to work. The toll booths are fitted with IR receivers 335, as shown in FIG. 128. The commuter has a sensor 333/reader 174/determining mechanism 293 unit installed at the upper, driver's side, edge of the windshield. The sensor 333 unit is powered by the car's electrical system (battery). On the outside of the windshield, the sensor 333 unit has a small IR transmitter. Communicating with it on the inside of the windshield, the sensor 333 unit contains an acoustic touch thumb sensor 333, with red, green, and yellow lights. The red light means the sensor 333 is in standby. The green light means the sensor 333 has verified an authorized thumb boneprint and is transmitting an authentication and account information signal. The yellow light means only 5 seconds of transmission remain. A blinking yellow light means the boneprint verification was near selected confidence limits and the user should consider restoring the known biometric pattern to eliminate problems with pattern drift over time. The commuter has an account with the toll turnpike which is paid monthly by automatic credit card billing. Upon reaching a toll booth, the commuter presses his thumb against the thumb sensor 333 inside the windshield. Pressure activates the sensor 333, which obtains the present biometric pattern and compares it to the known biometric pattern stored in the microprocessor chip in the unit. The patterns match. The green light flashes and the IR transmitter transmits an authentication and account information signal, which is received by a receiver mounted in the toll aisle. The amount of the toll is billed to the consumer's account, the gate rises, and the commuter goes to work.

Figure 129:
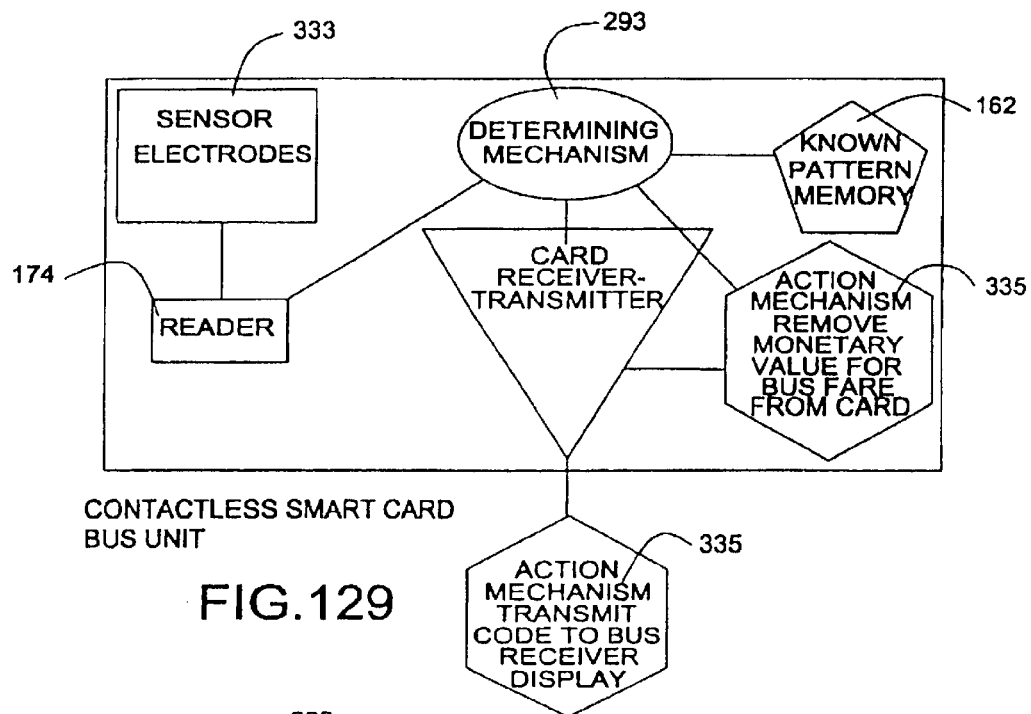

A business person rides the bus to work every day. The person pays for the bus fare with a stored value card in the form of a contactless smart card fitted with 1 mm diameter touch electrodes in scalloped indentations on the card edges, as shown in FIG. 129. Upon entering the bus, the person grasps the card edges, finger and thumb flexion creases on the electrodes, and waves the card over the bus scanner. The scanner powers the card microprocessor 293 wirelessly, which compares the present and known biometric patterns 162. It transmits an authorization code to the scanner as well as account information 335. The bus scanner is powered by the bus battery.

Figure 130:
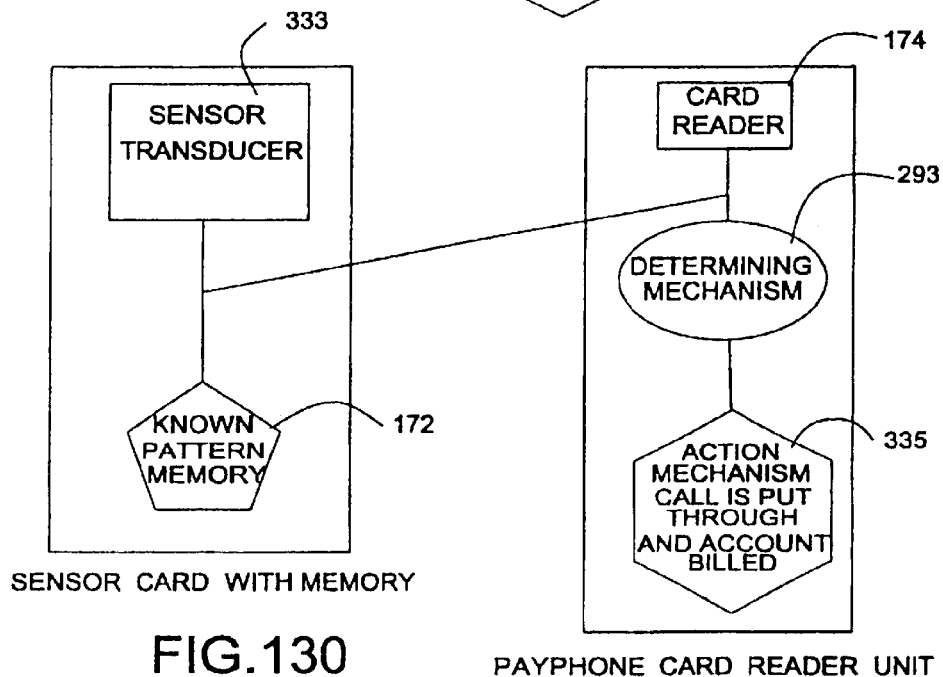

E. Payphones—A traveler wishes to call home using a calling card. The touch calling card is fitted with a transducer and a memory with the known biometric pattern and account information, as shown in FIG. 130. The traveler inserts the transducer card into a unit on the telephone equipped with contact plate, reader 174, and determining mechanism 293. The unit takes the travelers' present biometric pattern, reads the memory 172 from the card, and compares the two. Upon verification, the traveler places the call home, and the account is billed for the call.

Figure 131:
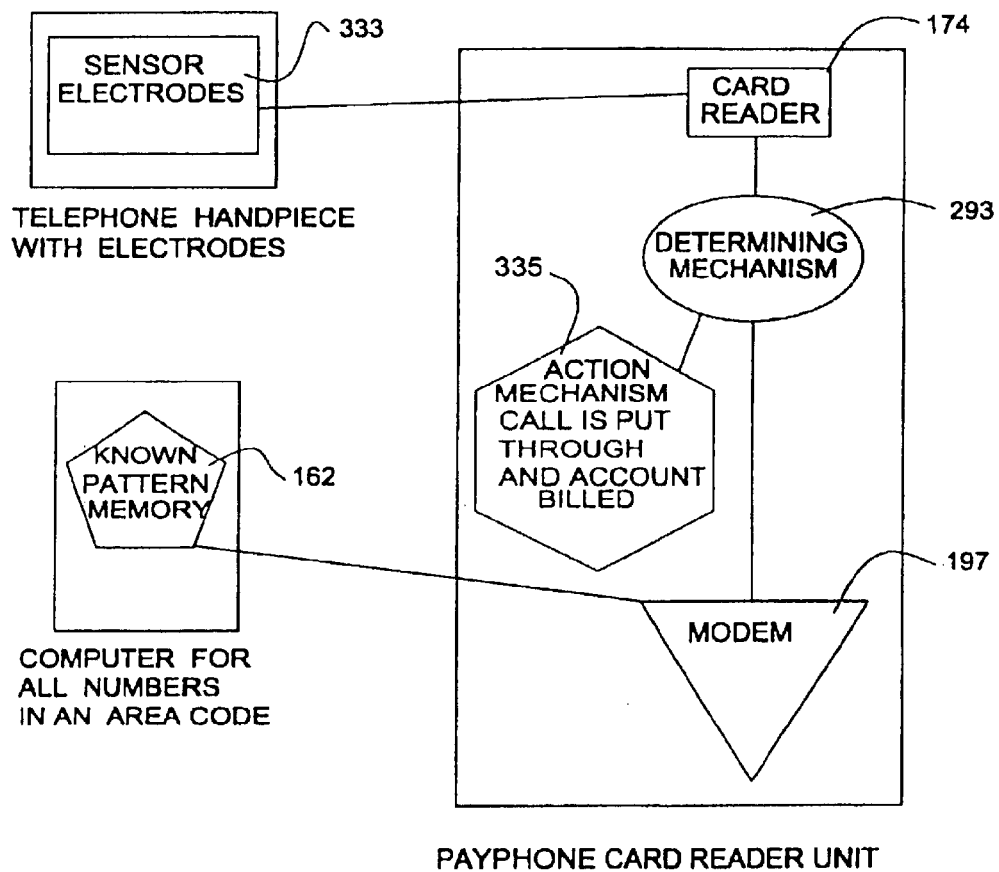
Figures 131A, 131B:
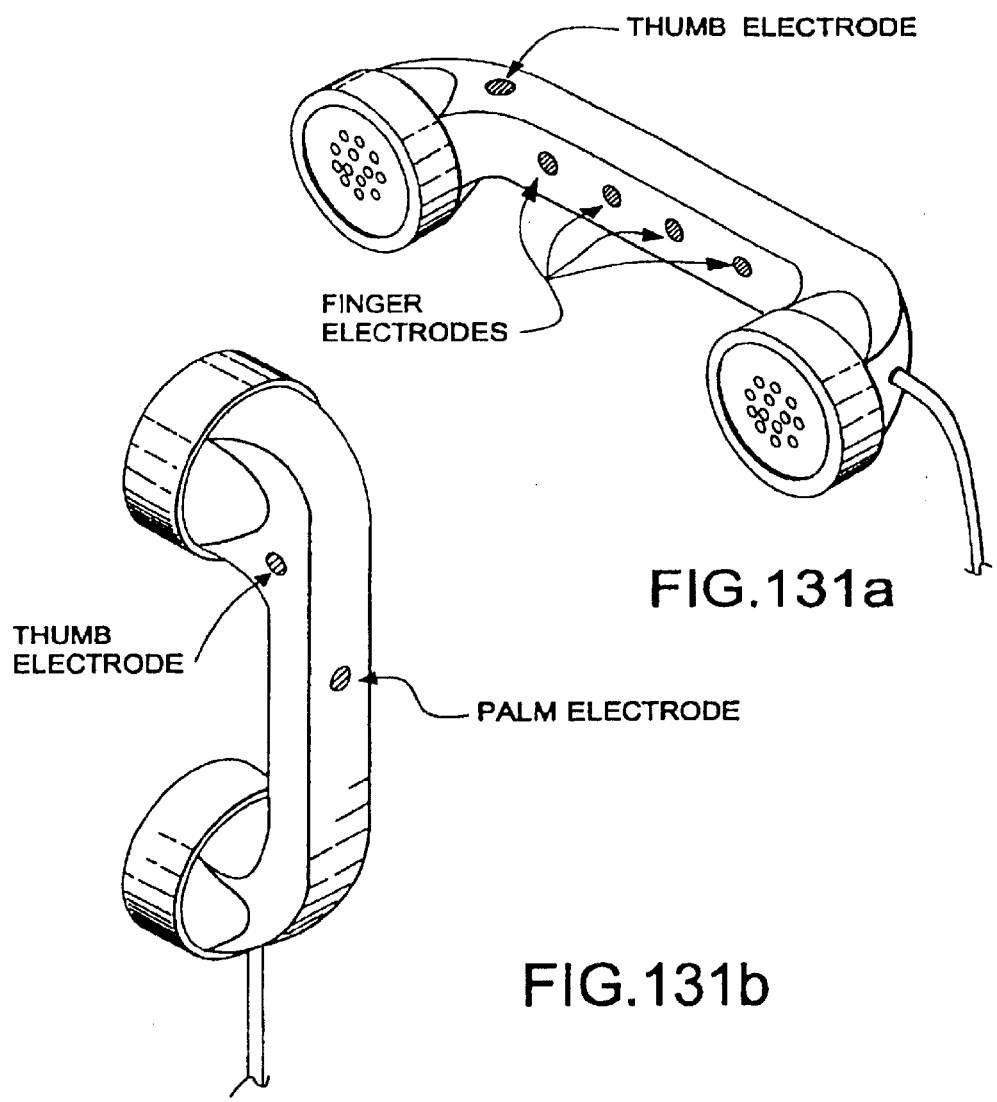

A traveler wishes to call home without using a calling card. The traveler grasps the biometric touch electrodes molded onto the curved surface of the telephone hand piece, dials their home phone number, and hits # # #, as shown in FIG. 131, FIG. 131a and FIG. 131b. The telephone hand piece sensors 333 are connected by wires to a reader 174 and determining mechanism 293 inside the payphone, which obtain the travelers' present biometric pattern. The telephone communicates by modem 197 with a computer 158 for the traveler's area code, which stores known biometric patterns authorized for each phone number. The telephone compares the known and presented biometric patterns to authorize the travelers' call, and the telephone number is billed for the call.

Figure 132:
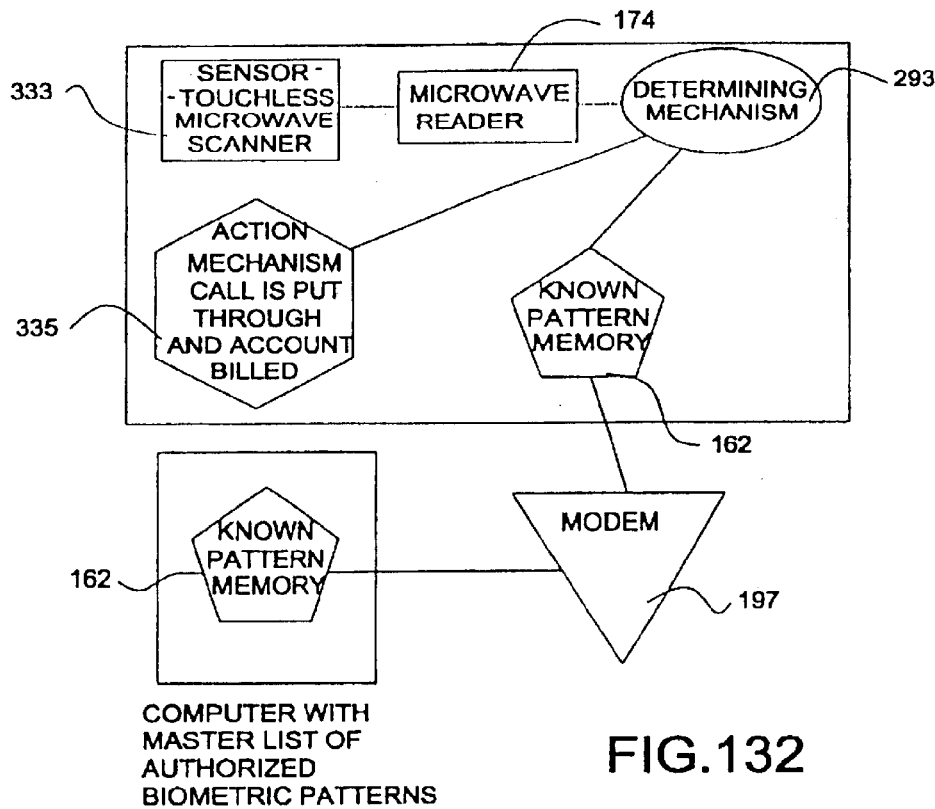
Figure 132A:
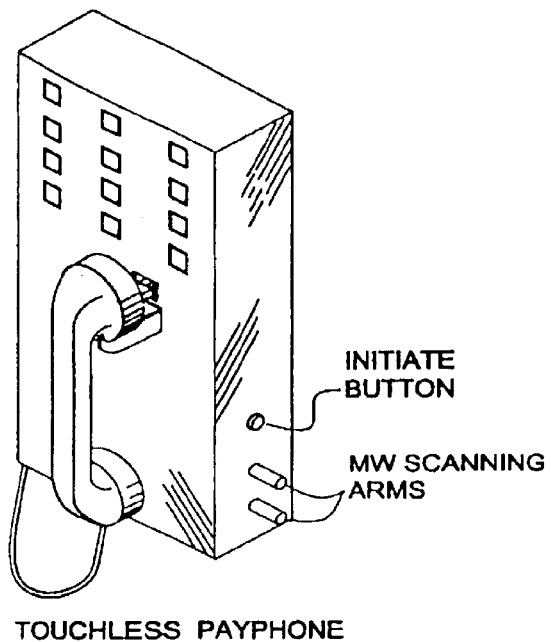

A traveler wishes to call home without using a calling card. The traveler dials the office phone number, and hits # # #. The side of the telephone box is equipped with a small touchless microwave field finger sweep unit, which obtains a biometric pattern based on interruption of the microwave field due to differing dielectric constants in unique tissue configurations in the finger, as show in FIG. 132 and FIG. 132a. The unit contains sensor 333 (transmitter/receiver arms parallel to each other and at right angles to the side of the phone), reader 174, determining mechanism 293 and memory 162. Memory is updated by modem 197 every 8 hours. The traveler presses a button next to the finger sweep unit (activating the transmitter/receiver for 4 seconds) and draws their index finger through the unit transmitter/receiver, between the parallel arms. The unit obtains the travelers' present biometric pattern and compares it to the known biometric patterns registered to the traveler's office phone number. The patterns match, the call is authorized, and the telephone number is billed for the call.

F. Healthcare and Social Services—A medical insurance company makes payments to hospitals and doctors electronically. Only certain people in the company are authorized to approve and initiate the electronic payments. The authorized payers place their hand on an electrode hand piece in the insurance company's financial office, as shown in FIG. 133. The biometric pattern data is communicated to the insurance company's computer 158, for comparison with the known biometric patterns 162 on file. This can be done in either identify or verify mode. Matching of the biometric pattern authorizes the payer to proceed with the electronic payments action 335.

A patient has a medical saving account (MSA). The patient also has a transducer card storing information on the MSA and the patient's biometric pattern, as shown in FIG. 188. The patient goes to the emergency room. To pay the bill, the patient inserts the MSA card into a reader and grasps the transducer. The reader verifies that the patient is authorized and initiates a transfer from the patient's MSA to the emergency room to pay the bill.

A patient has a medical savings account (MSA). The patient also has an electrode card storing information on the MSA and the patient's biometric pattern, as shown in FIG. 134. The patient goes to the emergency room. To pay the bill, the patient inserts the MSA card into a reader 174 and grasps the electrodes. The reader 174 verifies that the patient is authorized and initiates a transfer from the patient's MSA to the emergency room to pay the bill. The patient also has a smart card storing information on the MSA and the patient's biometric patterns for several touch and touchless devices, as shown in FIG. 135. The patient goes to the emergency room. The emergency room uses a touchless sensor 333 of the type measuring electric currents in the fingertips upon sweeping the palm of the hand over an electric field power source. To pay the bill, the patient inserts the MSA card into a reader 174 and sweeps a hand over the sensor 333 device. The reader 174/deter mining mechanism 293 verifies that the patient is authorized and initiates a transfer from the patient's MSA to the emergency room to pay the bill. The hospital's reader 174 is plugged into the wall outlet, as shown in FIG. 188.

G. Wireless Communications—A restaurant maintains accounts for its customers. A patron wishes to place a telephone call, while waiting for dinner. The waiter brings a portable telephone fitted with electrodes in the hand piece to the table, as shown in FIG. 136. The patron grasps the electrodes on the phone, which communicates with the restaurant computer 158 (housing memory, reader 714 and determining mechanism), either identifying or verifying the patron. The patron places the call and their restaurant account is billed for the call.

A lawyer uses a hand-held video phone equipped with a biometric sensor 333 to prevent unauthorized use and powered by rechargeable batteries. The biometric sensor 333 flips up from a recessed area on the side of the video phone, as shown in FIG. 138. It is round and flat, with a gold-plated electrode on each side (2 mm diameter, 0.5 mm thick). Authorization to use the video-phone is obtained by the lawyer flipping up the sensor 333 and grasping the electrodes sequentially between thumb and index finger, thumb and middle finger, and so on.

A lawyer uses a hand-held video-phone equipped with an acoustic biometric sensor to prevent unauthorized use and powered by rechargeable batteries. The transducer is made of piezoelectric polymer molded onto the side of the video-phone, on a pressure activated housing, as shown in FIG. 189. Authorization to use the video-phone is obtained by the lawyer pressing on the transducer sensor with his index finger. The transducer reads his index finger boneprint and compares it to the boneprint on file.

Generally, the biometric system can be used on any type of stationary or portable communications device including, but not limited to, cell phones and handheld phones.

H. Pay TV—Parents of teenaged boys install a lock-out system on the television, plugged into a wall outlet. The lock-out system contains an electrode hand piece and a mechanism to allow only authorized users to view adult channels, as shown in FIGS. 138 and 138a. Only the parents are authorized users. When the teenagers attempt to access the adult channel, they cannot provide the correct biometric pattern and are unable to. The same is applicable to radios, as shown in FIG. 138b.

An army barracks has a rec room with a pay TV. The pay TV is fitted with an electrode card reader 174/determining mechanism 293 device, as shown in FIG. 139. When a soldier wishes to see a pay-per-view movie, an electrode military ID card is inserted into the device. When he grasps the electrodes on the card, the device compares the soldier's present biometric pattern to the pattern on the card, and to the pattern in the military base computer 158. The patterns match, the soldier is shown the movie, and the cost for the pay-per-view movie is deducted from the soldier's pay.

The pay TV could be fitted with a contact card device housing sensors 333, reader 174, and determining mechanism 293, as shown in FIG. 140. When a soldier wishes to see a pay-per-view movie, he inserts his military ID card into the card device. He then holds his hand over the touchless electric field sensor 333, of the type measuring induced currents simultaneously in all the fingers, upon holding the palm of the hand over the electric field source. The device compares the soldier's present biometric pattern to the pattern on the card, and to the pattern in the military base computer 158. The patterns match, the soldier is shown the movie, and the cost for the pay-per-view movie is deducted from the soldier's pay.

The pay TV could be fitted with a transducer card reader/determining mechanism device, as shown in FIG.

190. When a soldier wishes to see a pay-per-view movie, their transducer military ID card is inserted into the device. When he grasps the transducer on the card, the device compares the soldier's present biometric pattern to the pattern on the card, and to the pattern in the military base computer. The patterns match, the soldier is shown the movie, and the cost for the pay-per-view movie is deducted from the soldier's pay.

I. Education—Educational institutions such as Florida State University use a card system. The card has items such as the student's color photo, signature, and university status in memory. The student uses the card for identification on campus; for physical access to dormitories, classrooms, buildings, libraries, and university offices; to check out books at the library; for banking on campus including a personal account, ATM withdrawals, payments for room and board, tuition payments, electronic purse, and pre-paid value for copiers and vending machines and such; for local merchant loyalty programs; to access personal University data; for telecommunications including local and long-distance calls from campus payphones; for bus passes; and for voice messaging. These and other functions can be performed more securely and privately using a biometric signature linked to the student. This is done easily using any of the biometric sensor cards with memory. Other devices include hand pieces at various school locations, biometric sensor door handles, and the student's biometric sensor PC mouse or keyboard.

J. Travel—A business traveler makes frequently flights on FlyHigh Airlines. The airline places hand units at check-in stations for their frequent travelers, as shown in FIG. 141. The travelers places their hands on the hand unit, which reads the biometric pattern. The pattern data is communicated to the airline's hand unit computer 158, or by modem 197 to another airline computer 158, for comparison with the known biometric patterns on file. This can be done in either identify or verify mode. Matching of the biometric pattern authorizes the traveler's check-in to proceed electronically and instantaneously, as shown in FIG. 142. No more long lines.

The airlines could issue memory sticks to travelers, storing biometric and account information. The airline installs touchless "L" shaped hand units at check-in stations for their frequent travelers, as shown in FIG. 143. The hand unit has two surfaces, one horizontal surface parallel to the floor and housing electric field detectors, and another low vertical surface at right angles and facing away from the traveler and housing an electromagnetic transmitter. The traveler sweeps a hand over the horizontal surface. An electric eye in the unit activates the electromagnetic transmitter, and the electric field detectors read the biometric pattern as sequential slices of data. The pattern data is communicated to the airline's hand unit computer 158, or by modem 197 to another airline computer 158, for comparison with the known biometric pattern in the memory stick (verify mode), as shown in FIG. 144. Matching of the biometric patterns authorizes the traveler's check-in to proceed electronically and instantaneously. No more long lines.

The business traveler must leave the country and go through customs. The traveler has an electronic passport containing their personal information and biometric signature, as shown in FIG. 145. The traveler places the electrode card into (contact) or near (contactless) a reader 174/determining mechanism 293 at customs, grasping the electrodes. The reader 174 obtains the known biometric pattern and personal information from the card (verify mode) and the determining mechanism 293 compares it to the traveler's present biometric pattern. The patterns match and the traveler is cleared through customs in a matter of minutes.

The business traveler must leave the country and go through customs. The traveler has an electronic passport containing their personal information and biometric signature stored in a smart card. The traveler holds the scalloped edges of the smart card and holds it over a contactless touchless biometric device at the customs exit, as shown in FIG. 146. The contactless touchless device has a horizontal surface containing a radio transmitter for communicating with the microchip 189 in the underside of the smart card via the antenna 187. A low vertical surface facing away from the traveler houses a microwave transmitter, which emits microwaves at the travelers hand when activated. A second horizontal surface above the traveler's hand contains magnetic coils for detecting induced currents from the microwaves, which produce the biometric pattern. The device obtains the known biometric pattern and personal information from the card (verify mode) and compares it to the traveler's present biometric pattern. The patterns match and the traveler is cleared through customs in a matter of minutes.

K. Brokerage and Equities—A brokerage firm allows on-line trading by its clients. Mobile clients can make trades using a laptop PC and wireless technology, as shown in FIGS. 147, 147a, 147b and 147c. Biometric authorization is provided by a small linear acoustic transducer (1 mm×12 mm) which flips up at right angles with the PC surface, from a flush recess. The client sweeps the palmar surface of the index finger from first crease to fingertip along the acoustic sensor 333. The boneprint signature matches that on file with the brokerage firm, and the client is authorized to complete the trade if a match is made.

A brokerage firm allows on-line trading by its clients. Mobile clients can make trades using a laptop PC and wireless technology, as shown in FIGS. 148, 148a, 148b and 148c. The PC has a small, spring loaded, fingertip-sized flap flush with its side. When the client presses in on the flap with the index finger, an electromagnetic transmitter is activated, to direct electromagnetic energy at the fingertip, parallel with the finger. Electric field detectors in the flap measure the biometric pattern. The electric signature matches that on file with the brokerage firm, and the client is authorized to complete the trade.

II. Information Technology

Successful development of an information society depends on trust between unseen partners. These partners—customers, merchants, employers, banks, databases, governments, and the like—need to know that the identity claimed by the person at the other end is indeed genuine. Authentication of identity can then facilitate rightful access to information in any number of data storage systems and databases.

Three systems now in use attempt to meet this need: public key cryptography, digital certificates, and smart cards. Public key cryptography is a method of scrambling information by using two numbers, called keys, and complex mathematical operations to scramble and unscramble digital data. The "public" key is widely available, while the "private" key is available only to the authorized user of the key. Unfortunately, there is no reliable way to confirm that the person presenting a public key is the authentic user of the matching private key.

Digital certificates were developed to solve this problem. Certificates are data files that contain a person's public key with other information such as the person's name and address, as well as the name and authorization code of the certification authority that issued the certificate. The problem with digital certificates is that anyone who gains access to the private key, through hacking or piracy, can assume the authorized person's identity and engage in fraudulent use of the certificate. Because the digital certificate does not absolutely link itself to a particular individual, it is like a passport without a photograph.

To solve this problem smart card applications were developed, incorporating public key cryptography and digital certificate methods. The private key is stored on the smart card, rather than on the PC hard drive. This protects the private key from piracy and hacking. The problem with smart cards is that private key authentication is linked to a particular card, rather than to a particular person. If stolen, the card can be used to gain unauthorized access.

Biometric linking of one person to the private key is an improvement on these systems. The biometric signature or its index is stored on the card or digital certificate. Presentation of the correct biometric signature is required to access the private key. Even if the card or certificate is stolen, the thief cannot present the correct biometric signature to use it.

A. Loyalty and Retail Systems—Patrons of a retail chain are given points whenever a purchase is made. Points are redeemed for gifts chosen from the retailer's merchandise, as shown in FIG. 149. The points are stored on a microchip 189 card with biometric electrodes. The card, with its valuable accrued points, cannot be used by anyone other than the rightful owner. Payphones or cash registers at the point of sale (POS) are fitted with card readers 174. The customer places the electrode card into (contact) or near (contactless) the reader 174, grasping the electrodes, as shown in FIGS. 150, 149. The biometric signature is communicated to the retailer's cash register computer 158, or by modem 197 to another computer 158, for comparison with the known biometric pattern on file. This can be done in either identify or verify mode. Matching of the biometric pattern authorizes the customer to redeem the valuable points.

At another store, the biometric pattern is determined using a touchless device measuring magnetic properties via reflected electromagnetic waves from the customer's hand, as shown in FIG. 151. The electromagnetic waves are of sufficient frequency, such as infrared or microwaves, to penetrate beneath the skin and obtain an internal biometric pattern. The customer does not even need to carry a card because their account information is located via identify mode. The customer simply places a hand over a transmitter 333/receiver 174 on the cash register 293. The account information appears on a screen 335 for confirmation.

At another store, the biometric pattern is determined using an acoustic device measuring the acoustic properties of the bones in the customer's hand, as shown in FIG. 191. The customer simply places their hand on the acoustic hand piece near the cash register. They are identified by the acoustic handprint and their account information appears on a screen for their confirmation.

B. Government ID—Accurate, up-to-date, and portable information systems have been identified as being key to timely, fraud-proof delivery of government services. Smart cards are proposed for driver's licenses (Argentina and El Salvador already use them). The smart license can store "lasting" information (name, address, license #, citizenship, blood type, etc.) and "passing" information (driving record and outstanding fines). Traffic officers are equipped with either stationary readers 174 on their vehicles or hand-held readers 174 that can be carried to the traffic violator's vehicle, the way ticket books are carried now. The smart license can be fitted with sensors 333 such as electrodes, as shown in FIG. 152. The driver places the electrode license into (contact) or near (contactless) the reader 174, grasping the electrodes. The reader 174 obtains the biometric pattern from the card (verify mode) and authenticates the driver's claimed identity. The traffic offense is updated directly on the smart license and by wire less modem 197 with the main traffic computer 158. Alternatively, the hand-held reader 174 can store all the traffic offenses for later downloading to the traffic computer 158. Alternatively the smart license can contain a transducer or other sensor(s) rather than electrodes, to determine the biometric boneprint of the driver's thumb, as shown in FIG. 192.

The business traveler must leave the country and go through customs. The traveler has an electronic passport containing personal information and biometric signature, as shown in FIG. 153. The traveler places the electrode card into (contact) or near (contactless) a reader 174 at customs, grasping the electrodes. The reader 174 obtains the known biometric pattern and personal information from the card (verify mode) and compares it to the traveler's present biometric pattern. The patterns match and the traveler is cleared through customs in a matter of minutes.

Access to computer 158 databases at the Central Intelligence Agency (CIA) is restricted. Access can be authorized and audited using biometric authentication, as shown in FIG. 154. A hand unit can be installed at doorways to computer 158 terminal rooms. The hand unit uses and acoustic field to produce direct currents in the biological semi-conductor structures of the applicant's hand. These structures are unique and produce biometric patterns for the hand. The hand unit consists of two parallel surfaces, the lower one consisting of a material producing an acoustic field, and the upper surface housing electric field detectors. The person seeking access to the room places a hand on the lower plate. Their DC pattern is detected by the upper surface and compared to their biometric pattern on file.

Access to the most top-secret computer 158 databases at the (CIA) can be restricted and audited using a more secure biometric authentication. A hand unit can be installed at doorways to computer 158 terminal rooms, as shown in FIG. 155. The hand unit uses a multi-frequency acoustic field scan to produce alternating currents in the biological structures of the applicant's hand. These structures are unique and produce biometric patterns for the hand at each frequency, yielding accuracy greater than one in a billion. The hand unit consists of two parallel surfaces, the lower one consisting of a material producing an acoustic field, and the upper surface housing magnetic field detectors. The person seeking access to the room places the hand on the lower plate. Their AC patterns are detected by the upper surface magnetic field sensors and are compared to the biometric pattern on file.

C. Identification—The biggest problems with identification papers and cards are fraud and copying. Use of a biometric signature and a microprocessor (complete with unique serial number, protected area, and cryptographic authentication) in a sensor 333 smart identification card prevent all but the most scientifically sophisticated abuses, as shown in FIG. 156. Customers, merchants, employers, banks, databases, governments, and the like, can know with some assurance that the identity claimed by the person with the card is indeed genuine.

D. Time Card Systems—The first day on the job, a new employee is issued an electrode wristband. The wristband contains a contact plate 173 and an embedded microchip 189, as shown in FIG. 157. The microchip 189 contains data on the employee's biometric wrist signature, digital certificate, public and private keys, and level of access to physical and network facilities. When the employee arrives at work in the morning, and places the wristband in contact with a reader 174 on the wall next to the door. The contact plate 183 in the reader 174 communicates with the contact plate 173 on the wristband, reads the biometric signature and authorizes the employee to enter. The door unlocks. The time of the employee's arrival is archived for the time card system. The same sequence of events occurs when the employee leaves for the day. Similarly, the same system is used whenever the employee attempts to enter rooms or databases in the facility with limited access. The employee's successful entry into limited access areas is archived, as well as the employee's attempted entry into areas for which they are not authorized.

E. Healthcare—A hospital uses electronic medical records. The records are accessible on chart-sized portable PC notepads for use by hospital personnel. The notepads communicate with the various hospital department computers wirelessly. When a nurse wishes to chart information on Mrs. Jones, the nurse activates a notepad, as shown in FIGS. 158, 158a and 158b. Activation is accomplished by providing an authentic biometric signature, through electrodes on the rim of the notepad, in either identify or verify mode. The notepad, based on her authentication, authorizes her to read and write on the charts of only those patients for which she is providing care. Mrs. Jones is one of her patients, and the nurse is authorized to chart her care.

Another hospital uses electronic medical records and personal area networks (PANs) for its doctors. The records are accessible on chart-sized portable PC notepads for use by hospital personnel. Doctors are issued PAN wrist devices coordinating cellular phone, pager, personal digital assistant, and digital watch capabilities, as shown in FIG. 159. The wrist devices display data and communicate only after activation by the doctor's authentic biometric signature, through electrodes on the inside of the wristband, in a simple verify mode. Pages, phone calls, and access to patient care databases are authorized by the biometric wristband. To access an electronic medical record, the doctor holds their wristband near a computer 158 terminal. The wristband PAN and the computer 158 communicate wirelessly, the wristband authenticates the doctor's biometric pattern, and the computer 158 logs the doctor into the database. If a thief steals the doctor's watch and attempts to access the same patient care database, he will be unable to supply the correct biometric signature and will be unsuccessful.

Alternatively, the PAN wristband is fitted with two transducers of flexible piezoelectric polymer on either side of the wristband face. The transducers are thus positioned adjacent to the radius and ulna bone at the wrist. Unique biometric patterns are produced by the bone prints from these bones. The acoustic wristband functions as described above.

In addition to patient medical records, biometric signatures can also be used to access and record healthcare information by patients, third party payers, health care workers, and health care organizations, for managing administrative data such as verifying eligibility of individual claims and benefits, processing claims, obtaining pre-approval, risk management, quality improvement and error reduction, admission and discharge from facilities, and patient tracking within facilities. Use of biometric signatures with electronic medical records can protect patient privacy and health, by authorizing efficient and confidential sharing of information between authorized parties for the delivery and monitoring and payment of healthcare services.

F. Social Services—Biometric signatures can also be used to access and record social services information. A woman is eligible for Aid to Dependent Children, food stamps, and Medicaid. She is given an electrode card with microchip 189 memory, as shown in FIG. 160. When she seeks care at a physician's office, she presents the card which contains data on her Medicaid eligibility status, coverage type, and service limitations. She verifies that she is the true authorized user of the card and services by providing a biometric signature, obtained through the card electrodes.

When the woman goes to the grocery store to buy food, she uses the card to pay for the food. She verifies that she is the authorized user of the card by providing a biometric signature via the card electrodes. The store reader 174 communicates by modem 197 to the food stamp computer 158 and the woman's food stamp account for the month is debited. Alternatively, this can be done as either a credit account, or stored value card.

Alternatively, the sensor card contains a piezoelectric polymer which functions as an acoustic transducer, rather than electrodes, as shown in FIG. 193, to determine the biometric boneprint of the woman's thumb.

Use of biometric signatures for social services can provide eligibility verifications, allow high precision on benefits, restrict purchases to essential items, prevent fraud, improve efficiency, improve service delivery to truly needy beneficiaries, allow data tracking and surveys, and eliminate the need for monthly mailings.

G. Financial Transactions—Electronic commerce requires safe, portable, and simple systems which allow only authorized transactions. Businesses, financial institutions, and customers alike need to know that the entity on the other end of the modem 197 is legitimate. For example, an on-line service provider, such as USA On-Line (UOL), can function as a secure electronic commerce authority. UOL would use encrypted keys and biometric signatures to identify or verify the users. A customer would provide their biometric signature through sensors placed on their keyboard 128, mouse 126, laptop frame, wristband, glove, card 170, internet phone, virtual screen glasses, or other device. The computer 158 servicing the merchant would be authorized daily, and after an interruption of operations by a valid biometric signature.

For example, a customer desiring well-controlled access to his private electronic records uses a biometric glove, as shown in FIGS. 161, 161a and 161b. He wears the glove continuously while accessing his electronic records and biometric signatures are assessed randomly and repeatedly throughout his access. The glove fits over the palm of his hand and over two-thirds of each finger, leaving the fingertip free. The palmar surface of the glove contains a multi-frequency magnetic field generating mechanism. The back surface of the glove contains sensors 333 for detecting acoustic fields, in contact with the back of the hand and fingers. The multi-frequency magnetic field produces an acoustic pattern unique at each frequency, which serves as the biometric identifier. The glove communicates with a reader 174 unit in the device with which he accesses his electronic records.

To avoid repetitive typing of account information, consumers can store their account information on a simple electrode card. The customer simply inserts their electrode card into a reader 174 in or connected to their Internet device. Instead of entering a PIN code to unlock the card, the customer's own biometric signature serves as the code to unlock the card and authorize the transaction.

Figure 108:
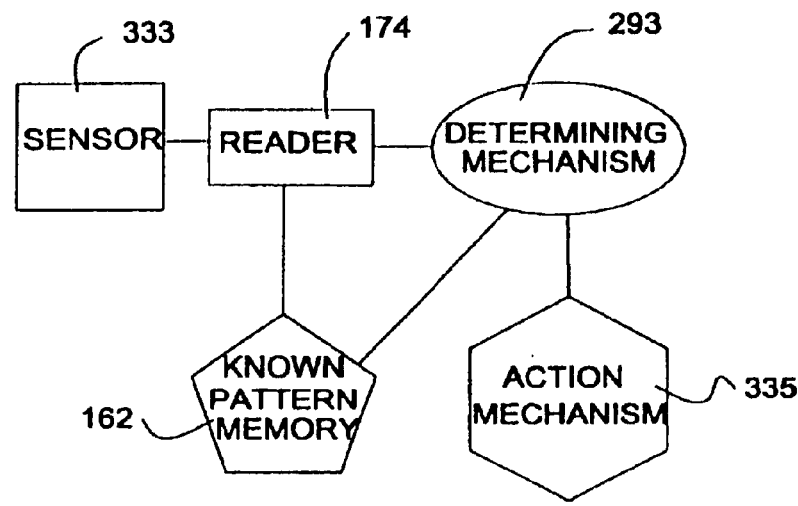
FIG. 108 is a schematic showing a determining mechanism and action mechanism in separate housing.
Figure 109:
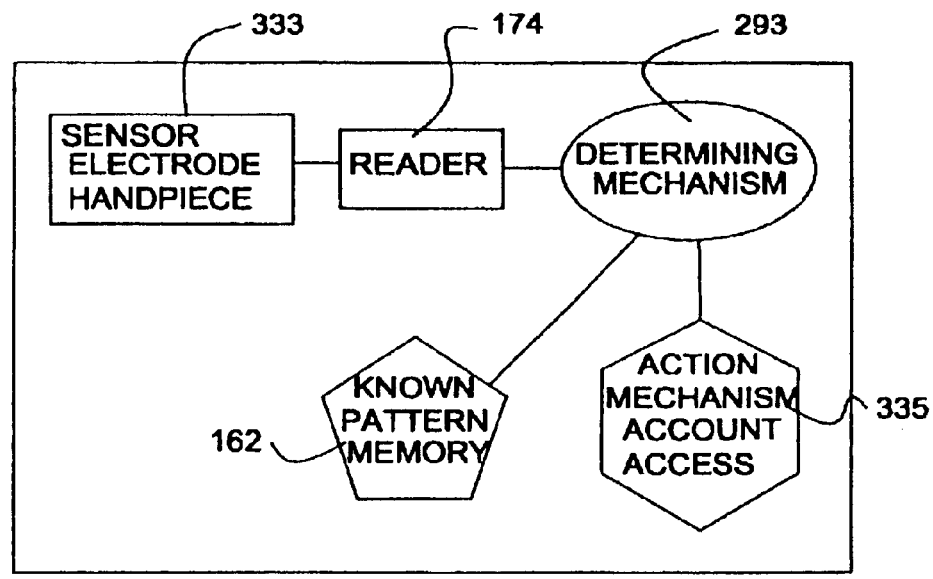
FIG. 109 is a schematic of an ATM with hand piece and memory.
Figure 110:
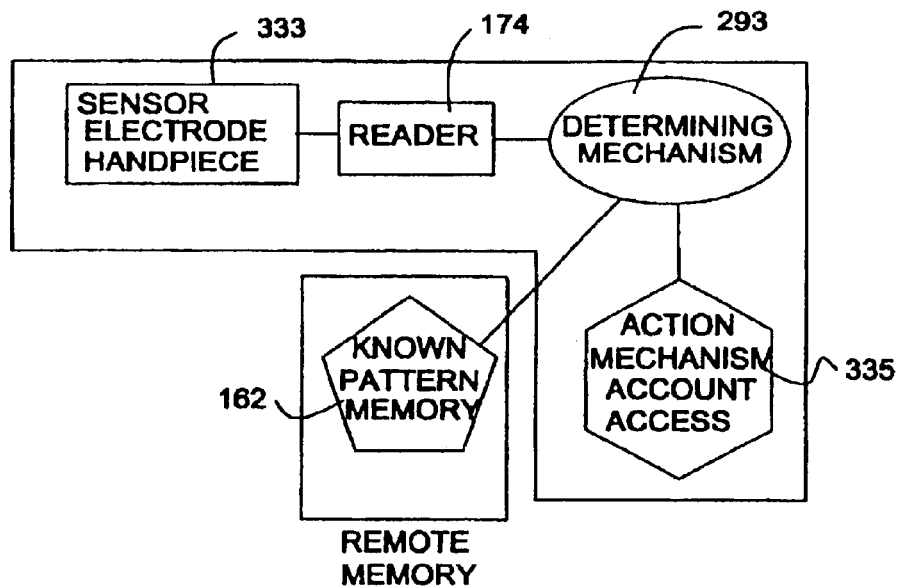
FIG. 110 is a schematic of an ATM with hand piece and memory accessed by modem.

H. Software Licensing—Software copying and piracy are significant problems for software developers. In spite of written licensing agreements, purchasers of software are often able to give copies to friends and associates. Schemes that make the software computer-specific, deprive the purchaser of the ability to rightfully move the software to a new computer 158. Consequently, software merchants lose a great deal of income from unauthorized copying of their programs. Biometric signatures can eliminate this problem and allow software merchants to sell user-specific software, as shown in FIG. 108. The software is written to run only after an authorized biometric signature is entered via sensor 335 mouse, keyboard, card, hand piece, joystick, or other such device. When the computer 158 is turned on and the system and programs booted, the authorized biometric signature is required to initiate the software. The software can also require re-entry of an authorized biometric signature, for instance, every 4 hours, to prevent defeat of the user-specific requirement by leaving the computer 158 running continuously. When the authorized user buys a new computer 158, the software can be loaded on to the new one by reloading the biometric signature.

For instance, Windows 2005 could require biometric authentication to function properly. The authentication is obtained by a sensor 333 recessed in the mouse employing electromagnetic transmission to the index finger, leading in turn to an acoustic-electric effect detected via an acoustic sensor 333 pad. On a right handed mouse, the left button cover flips up at a 45 degree angle revealing the sensor 333 assembly, as shown in FIGS. 162a, 162b and 162c. The lid contains an antenna for transmitting electromagnetic energy. The bottom, palmar surface of the sensor 333 assembly, inside the mouse, contains a piezoelectric polymer molded slightly concavely to fit the index finger comfortably. The sensor 333 assembly is pressure activated. To operate, the user flips up the button cover and slides their index finger in, touching against the bottom surface. By clicking the assembly with the index finger, the biometric scanner is activated and their biometric pattern is read and compared to that on file within the Windows 2005 operating system.

Alternatively, the mouse contains either simple electrodes to obtain an electric/magnetic biometric signature, or a transducer placed under the thumb or fingers to obtain a boneprint biometric signature, as shown in FIG. 194. A biometric system with electrodes or a transducer placed on a "smart quill" type pen, such as that offered by British Telecom Labs in Ipswich, England, can be used to control usage and operation of such a pen.

III. Access Control Systems

Access control systems involve access to three main things—physical areas, physical objects, and virtual areas. Physical areas include real estate and installations such as homes, offices, apartments, hospitals, factories, military bases, stores, prisons, rooms, hallways, and such. Physical objects include personal property, both tangible and intangible, such as watercraft, aircraft, land vehicles, weapons, cabinets, furniture, appliances, tools, computer 158, hardware, briefcases, documents and files representing intangible personal property, and such. Virtual areas include all manner of intangible personal property, computer 158 software, and electronic data systems, with their databases, information, and communication systems.

A. Locks—Customarily, access to areas and objects is controlled using locks 211. Locks 211 traditionally are operated by any number of mechanisms including keys, timers, combinations, passwords, numbers, or electronically. Lock 211 operation is linked to a particular mechanism, rather than a particular person.

Biometric locks 211 are linked to a particular person. Biometric locks 211 are operated by the correct biometric pattern, rather than by a traditional lock 211 operating mechanism, such as a key or code. A biometric lock 211 can be discrete, composite, multiple, or optional. Discrete biometric locks 211 use the biometric pattern to totally replace the traditional lock 211 operating mechanism (such as a key or code). In the discrete biometric lock 211, the biometric pattern is the only mechanism operating the lock 211. An example of a discrete biometric lock 211 is a door handle containing biometric electrodes which unlock the door, only when an authorized person places their hand on the door handle electrodes and provides their biometric impedance pattern, as shown in FIGS. 163, 163a, 163b, 163c and 163d, the latter being a car door type handle. Similarly, handles with acoustic transducers are shown in FIGS. 163e, 163f, 163g and 163h.

A composite biometric lock 211 requires both a biometric pattern and a traditional lock 211 operating mechanism, as shown in FIG. 164. An example of a composite biometric lock 211 is a door handle containing biometric electrodes and a numerical keypad. The lock 211 opens only after the correct numerical code is keyed in AND an authorized person places their hand on the door handle electrodes and provides their biometric impedance pattern.

A multiple biometric lock 211 requires two or more biometric patterns to operate the lock 211. An example of a multiple biometric lock 211 is a door handle containing biometric electrodes and an acoustic boneprint scanner, as shown in FIG. 165. The lock 211 opens only after an authorized person places their hand on the door handle sensors 333 and their thumb on the thumb flap, and simultaneously provides their electric finger AND acoustic boneprint biometric patterns.

An optional biometric lock 211 requires successful use of at least one, of two or more lock operating mechanisms (one or more of which is biometric). An example of an optional composite biometric lock 211 is a door handle containing biometric electrodes and a keyhole, as shown in FIG. 166. The lock 211 opens after an authorized person either opens the lock 211 with a metal key, or places their hand on the door handle electrodes and provides their biometric patterns. An example of an optional multiple biometric lock 211 is a door handle containing biometric electrodes and a boneprint scanner, as shown in FIG. 167. The lock 211 opens after an authorized person either places their hand on the door handle electrodes and provides their electric biometric patterns, or places their thumb on the boneprint scanner and provides their biometric boneprint pattern.

Lastly, a composite multiple biometric lock 211 is considered. This lock 211 contains at least one traditional lock operating mechanism, as shown in FIG. 168. It also contains two or more biometric lock 211 operating mechanisms. An example of a composite multiple biometric lock 211 is a door handle containing biometric electrodes, a boneprint scanner, and a keyhole. The keyhole is accessible only after an authorized person places their hand on the door handle sensors 333 and simultaneously provides their electrical and boneprint biometric patterns. Alternatively, the composite multiple biometric lock can be optional. For instance, the keyhole can be accessible after an authorized person either places their hand on the transducers, and provides at least one valid biometric pattern.

Figure 92A:
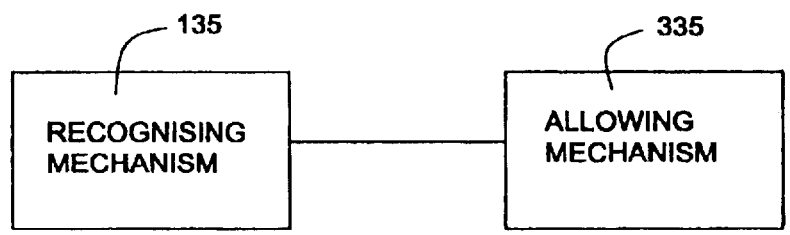
FIGS. 92 and 92a are schematics of apparatus for authorizing an action.
Figure 92:
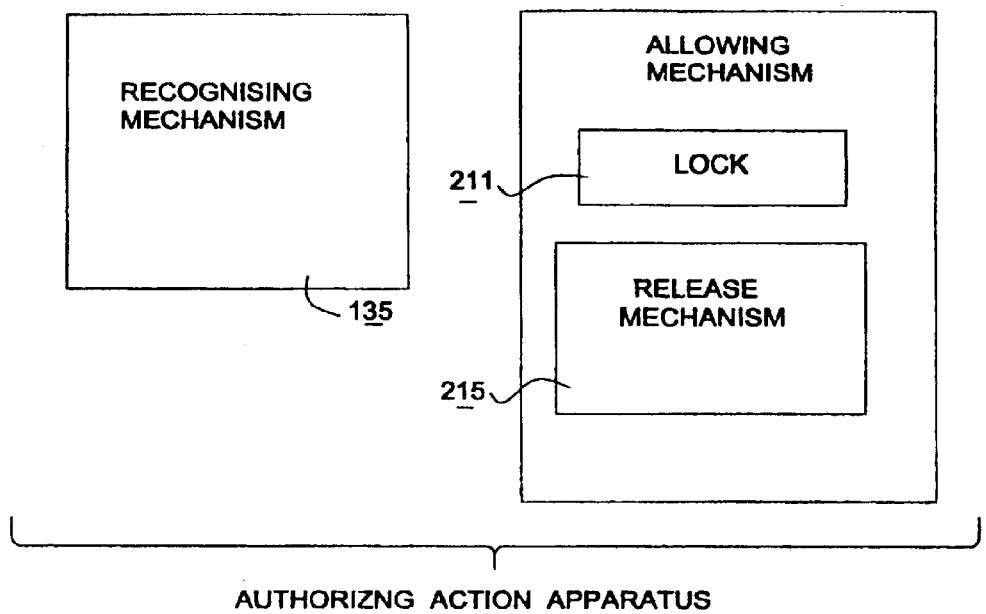

B. Closed Environments—Closed environments are simply those areas or objects which are not openly available to everyone. Preferably, the action is accessing an area as shown in FIG. 92, and the allowing mechanism includes a mechanism for allowing access to the area. The allowing mechanism preferably includes a lock 211 and a release mechanism 215 connected to the recognizing mechanism 135 and the lock 211. The recognizing mechanism 135 produces a recognizing signal when the individual is recognized which is received by the release mechanism 215 and causes the release mechanism 215 to open the lock 211.

Referring to FIG. 92, in an area where there is controlled access, for instance by a door or a window into a room, or a gate into a fenced field, or a safe, there is some form of a lock 211, which prevents the door or the window or the gate to open when it is locked, as is well known in the art. By introducing the mechanism for recognizing a biometric signature of an individual, any one of which is described herein, and a release mechanism 215 connected to the recognizing mechanism 135 and the lock 211, access to the area is controlled. The biometric signature is used for recognizing the individual by the recognizing mechanism 135 which causes a recognizing signal to be sent to the release mechanism 215. The release mechanism 215 can be some type of a motor which moves the lock 211, or simply an electric current that flows through a coil that creates a magnetic field which causes a lock 211 to open. Basically, any type of release mechanism 215 in conjunction with a lock 211, as is well known in the art can be used. Such a combination is simply connected with the recognizing mechanism 135, which serves as the controller for determining when the release mechanism 215 should operate.

For instance, a defense contractor wishes to restrict access to certain laboratories. Electronic locks 211 are installed on the doors to the laboratories, as shown in FIG. 169. To enter, an authorized laboratory technician places his hand in the hand unit installed on the wall next to the door. The hand unit has two parallel surfaces—one against the wall and another five inches away from the wall. The surface against the wall contains acoustic field sensors 333, while the surface five inches away from the wall contains multi-frequency magnetic field transmitters. The technician places their hand on the acoustic field sensors 333 and presses gently to activate the sensor 333/reader 174 device. Magnetic field transmitters utilize the acousto-electric effect to produce unique acoustic patterns at different frequencies, thereby producing a biometric signature. The sensor 333/reader 174 relays it by modem 197 to the laboratory computer 158. The laboratory computer 158 confirms authorization (in either identify or verify mode) and by modem 197 causes a release mechanism to unlock the door. The laboratory computer 158 also records the date, time, and identity of the technician entering the lab.

Figure 93:
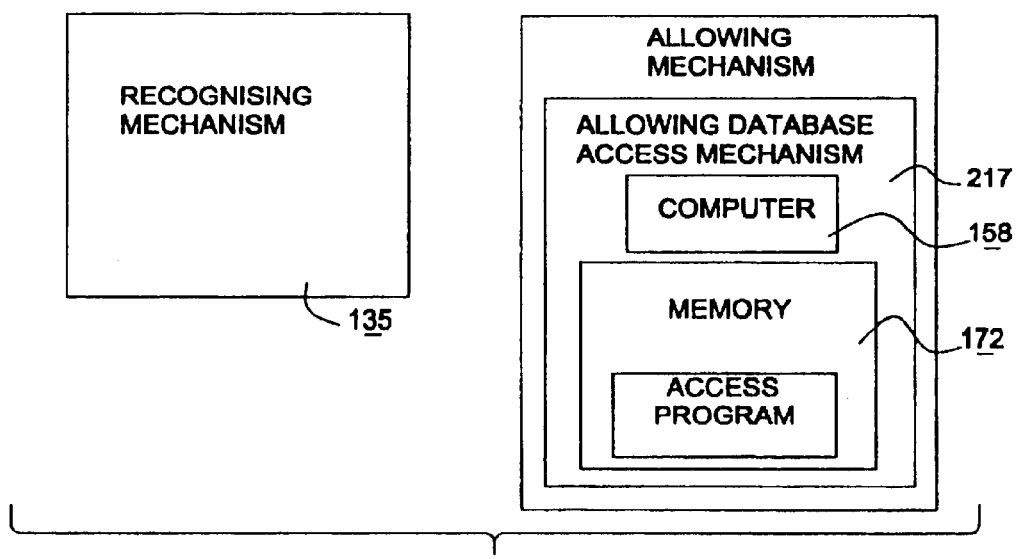
FIG. 93 is a schematic of an alternative embodiment of apparatus for authorizing an action.

An office area in the defense contractor's facility is open to all employees. The company does want to know who enters the office. When employees wish to enter the office, they grasp the door handle, making contact with the biometric electrodes, as shown in FIGS. 170 and 170a. The door handle is a curved vertical handle, with a thumb flap positioned above it on the door. It is normally operated by grasping the curved portion with the fingers, and pressing down on the thumb flap with the thumb. The electrode door handle is fitted with electrodes (tetrapolar, 1 mm diameter, nippled and molded with the handle surface) in the thumb flap for the thumb, and on the curved portion for the fingertips. Current is generated at the thumb and read at the fingertip electrodes. The biometric signature is identified, the door unlocks admitting the employee, and the company database records the date, time, and identity of the employee entering the office. In an alternate preferred embodiment as shown in FIG. 93, the area is a database and the allowing mechanism includes a mechanism 217 for allowing access to data in the database connected to the recognizing mechanism 135. The recognizing mechanism 135 producing a recognizing signal when the individual is recognized which is received by the allowing access mechanism and causes the allowing access mechanism to allow the individual to access the data base. The allowing access mechanism preferably includes a computer 158, a memory 172 and an access program stored in the memory.

C. Data Processing—Similarly, as shown in FIG. 93, the area can be a data base having data stored in it. The database can be connected with a computer 158 having a memory 172 and a program stored in the memory 172 which, when activated, the program causes the computer 158 to be able to access the data in the data base. The program would be activated by the recognizing mechanism 135 recognizing an individual through the individual's biometric signature and the recognizing mechanism 135 producing a recognizing signal which is provided to the computer 158 and which is received and processed by the computer 158 with the program. The program, upon receiving the recognizing signal, is activated, causing the computer 158 to be able to access the database. In this case, the biometric signature is the substitute for a password that has to be entered into the computer 158. The well-known techniques of using a password for access to databases or other aspects of the computer 158 would be exactly the same, except that the signal in which the password is provided to the computer 158 now becomes the recognizing signal from the recognizing mechanism 135.

A computer 158 database in the defense contractor's facility is accessed on a need to know basis only. Each employee is given access to various portions of the computer 158 system, based on their work. When an employee logs on, their biometric signature is authenticated. When an employee attempts to access a restricted database, their biometric signature is again required. Access to a restricted database requires a second biometric signature via an electric field/acoustic hand piece, as shown in FIGS. 171, 171a and 171b. The hand piece is a shell device which fits on the side of the monitor. The inside surface closest to the monitor has an acoustic field receiver such as a piezoelectric ceramic or polymer sheet. The outside of the shell, furthest away from the monitor contains a set of capacitors for generating an electric field. To access the restricted database, the employee slides their hand into the shell, placing the palm of their hand against the side of the monitor (against the piezoelectric surface.) A barrier between the capacitors and the piezoelectric surface prevents contact between the person's hand and the capacitors. The employee presses gently against the acoustic sensor 333, activating the electric field. The electric field is converted in the hand via the acousto-electric effect into a unique acoustic field pattern, which serves as the biometric signature. Alternatively, the sensor is a sole acoustic hand piece mounted on the side of the monitor, which provides an acoustic print of the employee's hand.

D. Security—A homeowner has biometric sensor door handles installed on the home's doors. When the homeowner wishes to enter the home, he grasps the door handle, making contact with the biometric sensors 333. The correct biometric signature is identified or verified and the door unlocks, admitting the homeowner.

The homeowner also has a cabin in the mountains, without electricity. The cabin is protected by a similar electrode door handle system that is powered by mechanically produced electricity. In one embodiment, the homeowner turns a handle crank to charge a capacitor, as is well known by those skilled in the art for powering portable radios and telephones. In another embodiment, a handle winds a large spring, as in the Baylis generator, producing electricity to power the biometric door lock 211, as shown in FIG. 172.

The homeowner also owns a defensive weapon, to encase an intruder in a sticky goo that limits the intruder's movement. See U.S. patent application Ser. No. 09/183,923, incorporated by reference herein. The homeowner does not want a would-be assailant to use the homeowner's weapon on the homeowner. The goo weapon handle is fitted with electrodes (tetrapolar, 1 mm diameter, nippled and molded with the handle surface) for the thumb, and third, fourth, and fifth fingers; or a thumb transducer, as shown in FIG. 173. Identification or verification of the homeowner's authorized biometric signature is required to activate the weapon. Alternatively, the sensor can be a transducer on the weapon handle.

A large military facility restricts vehicular access to areas, using guards and checkpoints. Those with authorization to travel in the facility are given touch electrode wristbands with a contact electrode, as shown in FIG. 174. When the vehicle approaches the checkpoint, the occupants hold out the wristband and the guard places it in contact with a portable contact device (reader 174/determining mechanism 293/memory). An authorized biometric signature is obtained from the wrist electrodes, communicated via the contact electrode to the reader 174 device, and the vehicle is allowed to proceed.

E. Healthcare and Social Services—Access to the controlled substances storage cabinet in a hospital pharmacy is restricted to a small group of pharmacists. The cabinet contains a hand piece, as shown in FIG. 175. When the authorized pharmacist needs to add or remove controlled drugs, he places his hand on the hand piece, making contact with the electrodes. The present biometric signature is identified from the small list of authorized users' known signatures, and the cabinet unlocks. The cabinet microprocessor records the date, time, and identity of the pharmacist entering the cabinet.

In another hospital, access to the controlled substances storage cabinet in a hospital pharmacy is controlled by biometric PAN cards, as shown in FIG. 176. The cabinet lock 211 communicates wirelessly with the biometric PAN card. When an authorized pharmacist needs to add or remove controlled drugs, he grips the PAN card on the edge electrodes, and hold it up to the cabinet. The PAN card transmits via transmitter 229 the biometric signature to the receiver 223 of the cabinet lock 211. The present biometric signature is identified from the small list of authorized users' known signatures, and the cabinet unlocks. The cabinet microprocessor records the date, time, and identity of the pharmacist entering the cabinet.

Electronic records are used in a large nursing home. Doctors access the records using a forehead-mounted headset fitted with virtual screen glasses in "see through" mode, as shown in FIGS. 177, 177a and 177b. This allows the doctor to examine and talk to the patient while simultaneously seeing the patient records. Access to the patient record database is granted by biometric signature recognition in the form of a biometric signature of the forehead. This can be accomplished with electrodes or with an acoustic transducer positioned on the inner surface of the headset in contact with the forehead. The virtual screen glasses utilize a PAN system to communicate with the central records computer 158. The central records computer 158 also stores the known biometric patterns of the doctors.

D. Information Technology—A telecommunications company maintains a computerized switching system. Physical components are periodically added to and maintained in the system hardware. Access to the hardware is biometrically restricted to authorized individuals. This is accomplished with electromagnetically induced currents, as shown in FIGS. 178 and 178a. The authorized individuals are issued contactless smart cards, with electrodes in scalloped area on the card edges. The individual holds the smart card on the scalloped edges, over the antenna/coupler unit on the outside of the hardware. The antenna/coupler unit transmits electromagnetic energy wirelessly to the antenna in the smart card. The hand also acts as an antenna, producing induced currents which are read by the electrodes in the scalloped edges, producing a biometric signature.

A homeowner has a flat-screen portable TV, and a portable radio, both of which are powered by electricity generated from stored human mechanical energy. The mechanical energy can also be obtained from a small dynamic device powered by means of a crank. Biometric locks 211 on the devices via acoustic boneprint restrict use to authorized users only, as shown in FIG. 179.

G. Financial Transactions—ATM machines must be periodically emptied of banking documents and refilled with cash. Access to the machines is limited to the bank employees servicing the machines. Rightful limited access can be further assured by using biometric locks 211 on the ATM machines. Each ATM worker carries a transducer card, as shown in FIG. 180. To unlock the ATM, the worker inserts the transducer card into the reader 174 on the ATM, and presses their thumb on the transducer pad. The ATM reader 174 communicates by modem 197 with the bank computer 158, which identifies the worker from a small list of authorized workers and unlocks the machine. The date, time, ATM location, and identity of the ATM worker is recorded.

The bank learns that the ATM worker concealed his true identity and is actually a convicted felon. The ATM worker's authorization is immediately removed from the list of authorized workers. The ATM worker is ordered to return his transducer card to the bank. The ATM worker attempts to open an ATM to steal the contents. The ATM identifies the worker, keeps the ATM locked, and informs the police and the bank of the worker's location. Alternatively, each ATM worker carries an electrode card, as shown in FIG. 195, which functions similarly in relation to the ATM as the transducer card.

H. Vehicles—The door handles and steering wheel of a land, water, or aircraft are fitted with electrodes (1 mm diameter, tetrapolar). The doors will not unlock until the biometric pattern of an authorized user is entered via the door handle, as shown in FIGS. 181, 182, 182a and 182b. Similarly, entry of the authorized biometric signature via the steering wheel allows the vehicle motor to start. Automobile drivers no longer need to carry car keys to unlock the car or start the engine. The car will not unlock and the electrical system will not function for a thief, but only for the rightful owner upon identification.

The metal key to a vehicle contains an acoustic pad on the bow or head. When the key is inserted in the ignition, the metal tip on the key conducts current from the dashboard reader 174, to obtain the boneprint of the driver's thumb, as shown in FIGS. 183, 183a and 183b. The driver is identified and the ignition is unlocked. Based on the driver's profile, driving characteristics are controlled such a maximum speed, and access to adult establishments via a global positioning system.

I. Remotely Operated Devices—Numerous devices are operated by remote control, such as vehicle ignitions, vehicles unlocking devices, televisions, radios, garage doors, and the like. The remote control unit can be fitted with sensors 333 such as electrodes or transducers, as shown in FIG. 187. Verification of an authorized biometric signature is required to operate the remote control.

IV. Electronic Tagging Systems

A. House Arrest—A convicted felon is sentenced to house arrest. The felon wears an ankle band fitted with biometric electrodes, as shown in FIG. 197. The ankle band communicates wirelessly with an antenna/coupler device connected to the felon's telephone, which communicates by modem 197 with a law enforcement computer 158. The biometric ankle band periodically communicates the felon's biometric pattern via the antenna coupler and modem 197 to the authorities, thereby confirming that the felon remains under house arrest.

B. Tracking—Using one of the techniques disclosed herein, the biometric signature and information about an individual are obtained by inserting a controller PAN touch sensor card 170 and transmitting the sensed biometric signature to a recognizing mechanism. The biometric signature of the individual is recognized and the individual's location or position is ascertained using a GPS.

Living, metabolizing organisms manipulate energy in many different forms, including acoustic, magnetic, electric, and electromagnetic. Living organisms produce energy which can be detected. The energy pattern which a specific organism produces is unique for that organism.

Detecting an Organism's Energy Pattern

The energy pattern of an organism can be detected actively or passively. In FIG. 11, the energy pattern of the organism is detected by looking at how the organism's energy pattern interacts with the energy provided. By applying a known energy pattern, and examining how the known energy pattern is changed by the organism, the organism's inherent energy pattern is detected. In a passive system, as shown in FIGS. 200 and 207, the organism's inherent energy pattern is detected, without applying an outside energy field. Regardless of whether the electric and/or magnetic properties actively or passively is detected, the same properties are still being detected.

For an example of a passive detection system, a stationary, pressure activated, curved detector band is used, against which the individual presses their forehead. The detector band is fitted with E-field probes with pseudo vector information. See "E-Field Probe With Pseudo-Vector Information" by K. Pokovic. T. Schmid, J. Frohlich, N. Chavannes and N. Kuster; Swiss Federal Institute of Technology (ETH), CH-8092, Zurich, Switzerland. This probe type allows precise measurement of electric field strength distributions in complex environments, giving information about the field amplitude as well as the field polarization at any measured location. By putting several probes in the detector band, a measurement can be taken at several locations.

When the individual presses their forehead against the detector band, they say their name out load. The electroencephalographic pattern produced when a person pronounces their own name will be unique based on the electrical patterns produced in multiple areas of the brain such as the motor areas, sensory areas, speech centers, and emotional centers. This will produce a unique pattern of electric field amplitudes and polarizations at the detector band.

The electrical activity of the brain is usually divided into three categories: 1) spontaneous potentials such as alpha and beta rhythms, 2) evoked or event related potentials, and 3) single neuron potential recorded with microelectrodes. *Electric Fields of the Brain: The Neurophysics of EEF*. P. L. Nunez and R. D. Katznelson, Oxford Univ. Press, 1981. The primary structures of the brain are the brainstem, midbrain (thalamus), cerebellum, and cerebrum (including cerebral cortex). The cortex is vital to much of our conscious experience. It is believed to produce most of the electrical potentials measured on the scalp.

Traditionally, scalp (cortex) potentials are described by their amplitude, frequency, and spatial characteristics. *Electric Fields of the Brain: The Neurophysics of EEF*. P. L. Nunez and R. D. Katznelson, Oxford Univ. Press, 1981. The unique characteristics of scalp potentials from any particular individual depend on the nature, location, and patterns in the electrical current sources in the cortex. The unique characteristics from an individual also depend on the electrical and structural geometric properties of the individual's brain, skull, and scalp as well.

In the embodiment described above, the spontaneous and event related potentials produced by the cortex is measured, and transmitted through the geometric structures of the brain (two hemispheres), skull, and scalp. The background spontaneous potential will tend to vary for an individual from day to day, depending on their mood and state of health, however, the spontaneous potential produced by a person truthfully stating their own name will be a significant EEG marker. If the same person pronounces two different words, the event potentials will be different because the muscle sequences required to say the two names will be different. Thus, an individual will have one event potential when the individual says one name, and a different one when the individual says a second name. The combined spontaneous and event related potentials will thus be unique for an individual truthfully stating their own name.

Now what if two people have the same name? Their combined spontaneous and event related potentials will still be different because no two people have the identical set of memories and neuromotor connections. Also, since the cortex produced electric field must be transmitted through their differing brains, skulls, and scalps, even if their spontaneous and event related potentials were identical, the field detected at the scalp (forehead) would be different and unique.

Scalp measurements vary depending on the strength of the electric field and distance between it and the sensors. They range from about 0.1 to 200 $\mu$V at the scalp and are around 500 $\mu$V in the cortex itself. Various probe and data processing techniques can also be used such as bipolar recordings, average reference recording, linked-ears reference, spectral analysis, Laplace derivations, frequency-wavenumber spectra, orthogonal and/or Bessel functions in temporal and/or spatial domains, Fourier transforms, and multichannel preprocessing by matrix operations.

The above embodiment could be combined with an active electric/magnetic and/or acoustic forehead sensor system, or with a voice recognition system. It can also be incorporated into a portable forehead mounted system such as we have already described for the active systems. In regard to another embodiment of the hand unit, otherwise referred to as the Hand Pad Biometric Impedance System (HBIS), the following description is provided.

Elements of the HBIS

1. Dolch Computer, Inc. portable computer, the FieldPAC.
2. National Instruments Data Acquisition Board (DAQ board model PCI-MIN-16E-1)
3. Hand Pad Electronics Box
   a. connection to DAQ board through shielded cable
   b. Six electrodes built into top of box for placement of hand
   c. External connector with pins that connect directly to the electrodes through extension wires d. Active circuitry for ensuring constant current through a variable load over a wide range of frequencies 4. Software
   a. LabVIEW runtime engine for executing LabVIEW graphical code, version 5.1.
   b. Biometric Recognition, source code that interfaces with the user and controls the Hand Pad box (via the DAQ board) so as to automatically conduct impedance measurements of the hand according to user specifications (3 and 5 finger versions)
   c. NI-DAQ driver software to interface between the DAQ board and the LabVIEW executable
   d. Configuration software to control DAQ board settings and associate it with a device number.

Active Circuitry for Ensuring Constant Current in a Variable Load

With reference to FIG. 199, active circuitry means use of an operational amplifier (OA). Constant current is achieved when OA is used in a negative feedback arrangement. The current path is from the analog output (AO) through the input resistor R1, and through the feedback impedance R2 or some finger of the hand, and to the output terminal of the OA (returning to the DAQ board via the signal ground (SG) via the +−15V power connections to the OA). No significant current enters the (+) or (−) terminals of the OA because they are high impedance.

Negative feedback means that the input terminals have equal voltage. Since the (+) terminal is fixed to ground (SG) then the (−) terminal must also be 0 volts all the time. Hence the current in the circuit is uniquely determined by the voltage of AO ($V_{AO}$) divided by R1)Ohm's Law). $I=V_{AO}/R1$. Since this current does not split, it must travel through the hand regardless of its impedance. Hence the voltage at the palm (=output voltage of OA and =to voltage across hand) is determined (Ohm's Law): $V_{palm}$ $I*Z_{hand}$. The equation for $Z_{hand}$ needs only $V_{AO}$ which is set by the software, $V_{palm}$ which is measured at channel 6 of the analog input, and R1 which is fixed and known.

Other Elements of the Electronics

+5V power is sensed at AI channel 1 to be certain that there is a good connection between the computer and the hand pad box. +5V power is sensed at AI channel 0 to be certain that the fuse is intact. Fused +5V power is used to provide power to the OA via a dc to dc converter and to drive all relay switches. The connector board on which the circuit was built originally came with at 0.8 amp 5 mm×20 mm fuse. I have used 0.5 amp and 1.0 amp fuses. Do not use greater than 1 amp fuses as damage to the DAQ board may result.

Digital output (DO, +5V—high, 0V=low) lines control transistors (Q) that turn on or off relay switches. Transistors are switches themselves but are not suitable for bipolar signals such as ac sinewaves. Relay switches are used to send current through one finger at a time.

An additional switch is used to put the active circuit in a constant voltage mode. This feature has been disabled in Biometric Recognition because constant voltage mode is unreliable compared to constant current mode. However, this feature is still available in the test program. One digital line controls a pair of relay switches that reverse the position of R1 and the hand impedance. R1 becomes the feedback resistor and a current sensing resistor. The voltage across the hand is constant if AO is constant (meaning the peak voltage).

When data is not actively being taken another switch sets R2 as the feedback resistor. If there is no feedback resistance, then the output of OA will saturate, i.e. it will go to the maximum magnitude voltage (+ or −15 volts) in an attempt to control the voltage at the (−) input terminal and make it 0V. Once finite feedback resistance is restored after the OA has saturated, it takes time (longer than relay switching time) for it to recover to a stable operating mode. In this case double Zener (Z) diodes at the OA output clamp the voltage to between + and −10.2 volts to protect the inputs on the DAQ board.

The driving AO voltage is sampled at AI channel 7. The AO voltage is reliable and need not be double checked, but AI chan 7 is sampled in differential mode, i.e., with respect to the virtual ground at the (−) terminal, not the signal ground (SG). Therefore any significant differences between A0 and A17 mean that there is no virtual ground and the OA is not operating in stable mode. Data measurements are thus disregarded.

Stray capacitance is a nuisance. It provides a point for the current to split and bypass the rest of the circuit, especially at high frequencies. Capacitive impedance in parallel with $Z_{hand}$ allows a smaller effective feedback impedance. Hence, even fixed resistors appear to lose resistance as the frequency increases.

Another issue is phasing. AO drives a sinewave that attempts to put a sinewave voltage on the (−) terminal. The OA output responds by driving a negative sinewave (alternatively, a wave 180° out of phase) that cancels the response at (−) terminal thereby making it a constant 0V. When there is capacitance in the feedback, the 180° phasing is upset and a small sinewave ripple appears on the virtual ground. It grows at higher frequencies and no longer operates in a stable feedback mode.

Part of the source of this parallel capacitance is the pair of wires leading to AI chan 6 and AI chan 14. Placing shielding around the wires in the electronics box alleviates the problem by diverting the capacitance from across the hand to ground. This simply becomes a demand for more current from OA, which can supply up to 30 mA compared to the 10s of $\mu A$ in the feedback circuit (which is limited by R1). Similarly, pairs of wires leading to the external connector (and to an external hand pad if one should be connected) introduce stray capacitance. These too have also been shielded. Nevertheless, there is still the characteristic roll off in fixed resistance impedance versus frequency. As long as the intrinsic capacitance of the hand is less than the stray capacitance, the stray capacitance should not be an influence.

The user selects a set of fingers and frequencies to measure. The program synthesizes a sinewave that is sent to the analog output (AO) which then drives the active circuitry. Sampling at the AI channels is done so that 12 points per cycle and 4 cycles are collected. The AI waveform is Fourier analyzed to determine the amplitude at the measurement frequency.

The most difficult part of the program has been how to decide what amplitude to use for the AO sinewave. The maximum amplitude that can be used is 10 V which is also the maximum voltage that can be sampled at the AI input. The AO amplitude must be chosen to maximize the AI amplitude in order to defeat the noise that hampers precise reproducibility needed for identification and verification functions.

The choice for AO amplitude must take into consideration what is meant by "constant current". Originally it meant the same current for all frequencies, fingers, and impedance. This meant that the AO signal had to be tiny in order to measure the highest impedance (so as not to exceed the AI limit), but then the AI signal was too small for all other measurements. Then the AO amplitude was a function of the frequency assuming that the hand impedance decreased as the frequency increased.

Constant current is taken to mean only that the current is constant in each of the fingers of the hand for a single frequency measurement of the hand. The hand impedance is regarded as only one measurement and individual finger impedances are only elements of the measurement. The current in the hand then may be different for two people measuring at the same frequency. It may be different for the same person measuring at the same frequency on different occasions, although this difference is expected to be slight.

The method to choose the AO amplitude is based on maximizing the A1 signal. The fingers are crudely measured with only one $\mu$amp of current. The finger with the highest impedance is used to determine AO so that the AI amplitude is 9.5 V (near maximum but not quite). AO is fixed and the current is constant and the measurement proceeds more carefully. For each finger as many 4 cycle measurements are taken as possible in the allotted dwell time. The mean of these measurements is the finger impedance and their standard deviation is the statistical error. For impedances greater than R1, AO is less than 9.5 V.

For impedances less than R1 then AO=9.5 V and the current is constant all the time, all frequencies, all hands. In this case AI is always less than 9.5 V and as much signal as possible that can be obtained is measured. It makes sense to make R1 as small as possible, but on the other hand AO must be made tiny to measure large impedances and the quality of sinewave synthesis begins to suffer. The <V between digital points is 2.5 mV. The result is that R1 should be between 10 k$\Omega$ and 200 k$\Omega$.

An apparatus for accessing an area comprises a mechanism 293 for determining a biometric signature of an individual, as shown in FIG. 201. The apparatus comprises a door having door handle in which electrodes 333 are so placed to obtain the biometric signature of the individual when the individual grabs or touches the handle, and a lock. The apparatus comprises a reader 174 for reading the biometric signature of the individual from the electrodes 333. The reader 174 is connected to the determining mechanism 293 and the electrodes 333. The apparatus has a memory 162 containing a known biometric signature of the individual. The determining mechanism 293 is connected to the memory 162 and compares the known biometric signature of the individual with the presented biometric signature of the individual obtained from the electrodes 333. A mechanism 335 unlocks the lock when the presented biometric signature is recognized.

The apparatus can include a numerical keypad in which an entry code is entered, as shown in FIG. 202. The keypad 397 is connected to the determining mechanism 293. The memory 162 has a predetermined entry code associated with the individual. The unlocking mechanism 335 unlocks the lock when the determining mechanism 293 recognizes the presented biometric signature and receives a predetermined entry code associated with the individual from the keypad 397.

The door handle preferably has a thumb flap having an acoustic transducer 333 for obtaining (with the other electrodes) the biometric signature of the individual, as shown in FIG. 203. The lock may have a key slot for receiving a key, as shown in FIG. 206, and can or cannot include the acoustic transducer. The unlocking mechanism 335 unlocks the lock when the presented biometric and the key is inserted in the key slot. The transducer 333 preferably obtains a thumb biometric signature of the individual, and includes a thumb flap reader 174 connected to the transducer in the thumb flap, and a thumb flap memory 162 having a known biometric thumb signature connected to the determining mechanism 293, as shown in FIG. 205.

Preferably, the determining mechanism 293 includes an electrode determining mechanism 293 connected to the memory 162 and the reader 174 for comparing the known and with the presented biometric signatures of the individual obtained from the sensors 333, a thumb flap determining mechanism 293 connected to the thumb flap memory 162 and the thumb flap reader 174.

A method for accessing an area comprises the steps of grabbing or touching a door handle or a door in which sensors 333 are disposed to obtain the biometric signature of the individual. The biometric signature is sensed by the sensors, compared with a known biometric signature, and the door is unlocked when the presented biometric signature matches the known biometric signature. Preferably, the unlocking step includes the additional step of entering an entry code into a numerical keypad. The unlocking step preferably includes touching an acoustic transducer of a thumb flap of the door handle. In other embodiments, other mechanisms for entering a predetermined entry code may be used, such as bar codes, magnetic strips, etc.

Preferably, the step of unlocking can include inserting a key into a key slot of a lock, obtaining a thumb biometric signature of the individual by touching an acoustic transducer of a thumb flap of the door handle.

Preferably, the method of authorizing an action or recognizing an individual is performed as part of the customary operation of a device.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. Apparatus for authenticating a specific individual, by including means for measuring unique, internal electric or magnetic or acoustic properties of a plurality of different body parts of said specific individual, and means for calculating a ratio of said measurements to generate a present biometric signature, and means for comparing said present biometric signature with at least one known biometric signature, said apparatus including a card having a plurality of electrodes for engagement with said body parts to generate said present biometric signature, a reader for reading the present biometric signature generated by the card, and a comparator for comparing the present and known biometric signatures to authenticate the individual if the biometric signatures match.

2. The apparatus of claim 1, including a database of known biometric signatures representing a class of individuals, wherein the comparator has means for comparing the present biometric signature with the known biometric signatures in said database to authenticate said specific individual as a member of said class of individuals.

3. The apparatus of claim 2, wherein the comparator includes means for authorizing an action when said specific individual is authenticated.

4. The apparatus of claim 1, wherein the card includes first and second sides, and plurality of sensors comprising finger electrodes on the first side and a thumb electrode on the second side.

5. The apparatus of claim 4, wherein the plurality of sensors include a contact electrode which contacts the reader to transfer the present biometric signature to the reader.

6. The apparatus of claim 5, wherein the reader includes a groove for card insertion, and a reader contact plate in the groove that contacts the contact electrode.

7. The apparatus of claim 6, wherein the card includes a card memory containing the known biometric signature and the reader includes a memory reading mechanism that reads the known biometric signature from the card memory.

8. The apparatus of claim 7, wherein the memory reading mechanism is located in the groove, and the card memory is located on one of the sides of the card for reading by the memory reading mechanism.

9. The apparatus of claim 8, wherein the reader includes a generator which generates an electrical signal that is transferred to the contact plate, the contact electrode and the finger electrodes and/or the thumb electrode for generating the present biometric signature.

10. The apparatus of claim 9, wherein the comparator includes a register which stores the present biometric signature, and a microprocessor for comparing the signatures.

11. The apparatus of claim 9, wherein the microprocessor is remote from the reader and the reader includes a modem, which communicates the present biometric signature to the microprocessor.

12. The apparatus of claim 9, wherein the card memory is a bar code, magnetic strip, microchip, or hologram.

13. The apparatus of claim 12, wherein the comparator includes a PIN entering mechanism through which a PIN is entered into the reader, as a prerequisite to reading the biometric signature of the card memory.

14. Apparatus for authorizing an action by a specific individual, comprising
   means for measuring unique, internal electric or magnetic or acoustic properties of a plurality of different body parts of said specific individual,
   means for calculating a ratio of said measurements to generate a present biometric signature,
   a database containing known biometric signatures representing a class of individuals, and
   a comparator for comparing the present biometric signature and the known biometric signatures in said database to determine if said individual is a member of said class of individuals, and for authorizing an action by said specific individual when identified as a member of said class.

15. The apparatus of claim 14, wherein each of a plurality of the known biometric signatures in said database is identified with an associated PIN, said apparatus includes means for inputting a PIN in association with a present biometric signature, and said comparator compares said present biometric signature and associated PIN with said plurality of said known biometric signatures and PINs to identify said specific individual as a specific member of said class.

16. The apparatus of claim 14, wherein the comparator includes means for authorizing an action when said specific individual is authenticated.

17. The apparatus of claim 14, wherein the signature generating means include a touch mechanism which the individual touches to obtain the present biometric signature.

18. The apparatus of claim 14, wherein the signature generating mechanism includes a touchless mechanism having a zone in which the body parts of the individual are placed to obtain the present biometric signature.

19. The apparatus of claim 18, wherein the touchless mechanism includes electric and/or magnetic field producing means for producing electric and/or magnetic fields in the zone for the sensor mechanism to obtain the present biometric signature.

20. The apparatus of claim 18, wherein the touchless mechanism includes acoustic field producing means for producing an acoustic field in the zone to obtain the present biometric signature.

21. The apparatus of claim 18, wherein the touchless mechanism includes a touchless electric field sensor for measuring induced current in the individual to obtain the biometric signature, and a card having a memory that stores a known biometric signature of the individual, and wherein the sensor mechanism has a reader for obtaining the known biometric signature from the card.

22. The apparatus of claim 14, including a touch electrode wristband having the electrodes that includes means to communicate the biometric signature to the sensor mechanism.

23. The apparatus of any of claims 3 or 16, wherein the action is accessing an area.

24. The apparatus of any of claims 3 or 16, wherein the action is accessing a database.

25. The apparatus of any of claims 3 or 16, wherein the action is authorizing a financial transaction.

26. The apparatus of any of claims 3 or 16, wherein the action is accessing a locked device.

27. The apparatus of any of claims 3 or 16, wherein the action is enabling access to transportation.

28. The apparatus of any of claims 3 or 16, wherein the action is accessing telecommunications equipment.

29. An apparatus as described in any of claims 3 or 16, wherein the action is boarding a transportation vehicle.

30. The apparatus of any of claims 3 or 16, including an electronic passport having known biometric signature of the individual, and a passport reader which reads the known biometric signature to allow the individual through customs when authenticated.

31. The apparatus of any of claims 3 or 16, herein the action is administering government benefits or funds, and including a memory having an account of the individual, which includes funds/benefits values, and the mechanism includes means for adjusting the funds/benefits values in the account when the of the individual is authenticated.

32. The apparatus of any of claims 3 or 16, wherein the action is accessing a room having an access door having a handle and a lock including means to unlock the door when individual is authenticated.

33. The apparatus of claim 32, wherein the handle includes a touch mechanism for obtaining the biometric signature of the individual.

34. The apparatus of claim 32, including a touchless mechanism having a zone in which the door handle is disposed and in which the body parts of the individual are placed to obtain the biometric signature.

35. The apparatus of claim 32, including a card reader and a contact card with electrodes grasped by the individual for engaging the card reader to provide the biometric signature of the individual.

36. The apparatus of any of claims 3 or 16, wherein the action is accessing electronic records stored in a memory, and including a foreheads mounted headset fitted with virtual screen glasses having a see-through mode, which allows the individual to jointly view a patient and the electronic records through the glasses, said headset having sensors for obtaining the biometric signature of the individual, a transmitter for transmitting the biometric signature to the comparator, and a receiver which receives the electronic records when the individual is authenticated.

37. The apparatus of claim 25, wherein the action is accessing an ATM machine.

38. The apparatus of any of claims 3 or 16, wherein the action is monitoring the location of the individual.

39. The apparatus of claim 38, including a receiver, an alarm, and a touch mechanism for obtaining the present biometric signature of the individual, the touch mechanism comprising an ankle or wrist band including the touch mechanism and a transmitter communicating with the comparator, and means for actuating the alarm if the comparator does not receive the present biometric signature from the transmitter at a predetermined time.

40. The apparatus of any of claims 3 or 16, wherein the action is tracking the individual, and the signature generating means includes a first transmitter/receiver and a GPS carried by the individual, and the comparator has an associated second transmitter/receiver in communication with the first transmitter/receiver for receiving information including the biometric signature of the individual from the first transmitter/receiver to identify and ascertain the position of the individual.

41. A method of authorizing an action by a specific individual, comprising the steps of measuring unique, internal electric or magnetic or acoustic properties of a plurality of different body parts of said specific individual, calculating a ratio of said measurements to generate a present biometric signature, providing a database containing known biometric signatures representing a class of individuals, comparing the present biometric signature and the known biometric signatures in said database to determine if said individual is a member of said class of individuals, and authorizing the action by said specific individual when identified as a member of said class.

42. The method of claim 41, including the steps of providing a mechanism touchable by said body parts, and touching said mechanism to provide the present biometric signature.

43. The method of claim 41, including the steps of providing a touchless mechanism having a sensor area, and inserting said body parts into said sensor area to provide the present biometric signature.

44. The method of any of claims 41–43, wherein the authorized action is access to a restricted area by the individual.

45. The method of any of claims 41–43, wherein the authorized action is access to a locked device.

46. The method of any of claims 41–43, wherein the authorized action is a financial transaction.

47. The method of any of claims 41–43, wherein the authorized action is access to a database.

48. The method of any of claims 41–43, wherein the authorized action is access to a transportation vehicle.

49. The method of any of claims 41–43, wherein the authorized action is access to a tollway.

50. The method of any of claims 41–43, wherein the action is recording a traffic offense on the individual's driver license, including the step of providing the individual with a driver license containing a memory having the stored biometric signature, comparing a present biometric signature with the stored signature, and recording the offense in said memory when the individual is identified.

51. The method of any of claims 41–43, wherein the authorized action is administering a government benefit.

52. The method of any of claims 41–43, wherein the authorized action is accessing medical records, and wherein the body parts are located in the head of the individual, including the steps of sensing the present biometric signature with a head-mounted device, and enabling access to said medical records when the individual is identified.

53. The method of any of claims 41–43, wherein the authorized action is monitoring location of the individual, including the steps of providing the individual with a sensing device having a transmitter and a GPS, and transmitting the present biometric signature and position to a remote location for comparison with a stored signature to determine the location of the individual.

54. Apparatus for authorizing an action by a specific individual, comprising means for measuring unique, Internal electric or magnetic or acoustic properties of a plurality of different body parts of said specific individual, means for calculating a ratio of said measurements to generate a present biometric signature, a database containing known biometric signatures representing a class of individuals, means for comparing the present biometric signature and the known biometric signatures in said database to determine if said individual is a member of said class of individuals, and means for authorizing the action by said specific individual when identified as a member of said class.

* * * * *